US006406884B1

(12) United States Patent
Bossone

(10) Patent No.: US 6,406,884 B1
(45) Date of Patent: Jun. 18, 2002

(54) SECRETED PROTEINS AND USES THEREOF

(75) Inventor: Steven Bossone, Lexington, MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 09/336,536

(22) Filed: Jun. 18, 1999

(51) Int. Cl.[7] ................................................ C12P 21/02
(52) U.S. Cl. .................... 435/69.1; 530/350; 536/23.5; 435/320.1; 435/325; 435/363; 435/361; 435/252.3; 435/6
(58) Field of Search ........................ 530/350; 536/23.5; 435/320.1, 325, 252.3, 363, 361, 69.1, 6

(56) References Cited

U.S. PATENT DOCUMENTS 5,272,057 A 12/1993 Smulson et al. ............... 435/6
5,459,039 A 10/1995 Modrich et al. ............... 435/6

FOREIGN PATENT DOCUMENTS

WO WO 98/39446 A2 9/1998
WO WO 98/49304 A1 11/1999

OTHER PUBLICATIONS

Hashimoto et al., EST Database, Accession No. AA088083, Feb. 1997.*

Marra et al., EST Database, Accession No. W97427, Jul. 1996.*

Altschul SF et al., "Gapped BLAST and PSI–BLAST: a new generation of protein database search programs", Nucleic Acids Res. Sep. 1, 1997 ;25(17):3389–402.

Altschul SF et al., "Basic local alignment search tool", J Mol Biol. Oct. 5, 1990;215(3):403–10.

Arkin AP and Youvan DC, "An algorithm for protein engineering: simulations of recursive ensemble mutagenesis", Proc Natl Acad Sci U S A. Aug. 15, 1992;89(16):7811–5.

Barany F, "Genetic disease detection and DNA amplification using cloned thermostable ligase", Proc Natl Acad Sci. U S A. Jan 1, 1991;88(1):189–93.

Cotton RG et al., "Reactivity of cytosine and thymine in single–base–pair mismatches with hydroxylamine and osmium tetroxide and its application to the study of mutations", Proc Natl Acad Sci U S A. Jun. 1988;85(12):4397–401.

Cotton RG, "Current methods of mutation detection", Mutat Res. Jan. 1993;285(1):125–44.

Delagrave S et al., "Recursive ensemble mutagenesis", Protein Eng. Apr. 1993;6(3):327–31.

Gibbs RA et al., "Detection of single DNA base differences by competitive oligonucleotide priming", Nucleic Acids Res. Apr. 11, 1989;17(7):2437–48.

Hayashi K, "PCR–SSCP; a method for detection of mutations", Genet Anal Tech Appl. Jun. 1992;9(3):73–9.

Heath JK et al., "The human A33 antigen is a transmembrane glycoprotein and a . . . member of the immunoglobulin superfamily", Proc Natl Acad Sci U S A. Jan. 21, 1997;94(2):469–74.

Hsu IC et al., "Detection of DNA point mutations with DNA mismatch repair enzyme", Carcinogenesis. Aug. 1994;15(6):1657–62.

Karlin S and Altschul SF, "Methods for assessing the statistical significance of molecular sequence features by using general scoring schemes", Proc Natl Acad Sci U S A. Mar. 1990;87(6):226–3.

Karlin S and Altschul SF, "Applications and statistics for multiple high–scoring segments in molecular sequences", Proc Natl Acad Sci U S A. Jun. 15, 1993;90(12):5873–7.

Keen J et al., "Rapid detection of single base mismatches as heteroduplexes on Hydrolink gels", Trends Genet. Jan. 1991;7(1):5.

Myers RM et al., "Detection of single base substitutions by ribonuclease cleavage at mismatches in RNA:DNA duplexes", Science. Dec. 13, 1985;230(4731):1242–6.

Nielsen H et al., "Identification of prokaryotic and eukaryotic signal peptides and prediction of their cleavage sites", Protein Eng. Jan. 1997;10(1):1–6.

Orita M et al., "Detection of polymorphisms of human DNA by gel electrophoresis as single–strand conformation polymorphisms", Proc Natl Acad Sci U S A. Apr. 1989;86(8):2766–70.

Pearson WR and Lipman DJ, "Improved tools for biological sequence comparison", Proc Natl Acad Sci U S A. Apr. 1988;85(8):2444–8.

Rosenbaum V and Riesner D, "Temperature–gradient gel electrophoresis. Thermodynamic analysis of nucleic acids and proteins in purified form and in cellular extracts", Biophys Chem. May 9, 1987; 29(2–3):235–46.

(List continued on next page.)

*Primary Examiner*—Lorraine Spector
*Assistant Examiner*—Eileen B. O'Hara
(74) *Attorney, Agent, or Firm*—Pennie & Edmonds LLP

(57) ABSTRACT

The invention provides isolated nucleic acid molecules, designated TANGO 281, which encode proteins downregulated in megakaryocytes that fail to express the gata-1 transcription factor (a factor critical for blood cell formulation) and can, therefore, represent direct or indirect gata-1 targets. The invention also provides antisense nucleic acid molecules, expression vectors containing the nucleic acid molecules of the invention, host cells into which the expression vectors have been introduced, and non-human transgenic animals in which a nucleic acid molecule of the invention has been introduced or disrupted. The invention still further provides isolated polypeptides, fusion polypeptides, antigenic polypeptides and antibodies. Diagnostic, screening and therapeutic methods utilizing compositions of the invention are also provided.

26 Claims, 78 Drawing Sheets

OTHER PUBLICATIONS

Figure 2:
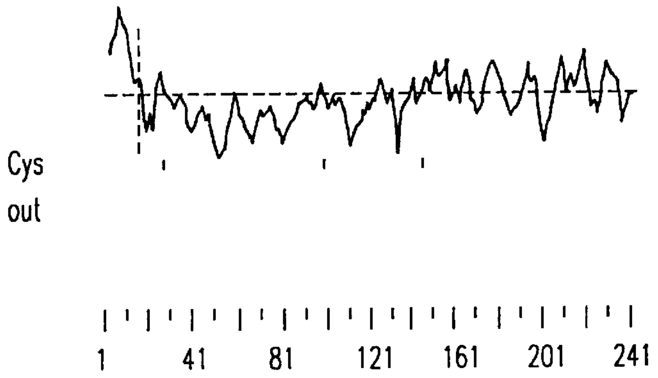

Saiki RK et al., "Genetic analysis of amplified DNA with immobilized sequence–specific oligonucleotide probes", Proc Natl Acad Sci U S A. Aug. 1989;86(16):6230–4.

Saiki RK et al., "Analysis of enzymatically amplified beta–globin and HLA–DQ alpha DNA with allele–specific oligonucleotide probes", Nature. Nov. 13–19, 1986;324(6093):163–6.

Torelli A and Robotti CA, "Advance and Adam: two aligorithms for the analysis of global similarity between homologous informational sequences", Comput Appl Biosci. Feb. 1994;10(1):3–5.

Nuc Patent Database Accession No. V34245.

pfam.wust.edu/cgi–bin/getdesc?name=PSBH (Pfam 4.3 St. Louis) Accession No. PF00737. Photosystem II 10 kDa phosphoprotein. Database [Online]. Accessed on: Jan. 21, 2000.

www.ncbi.nim.nih.gov (National Center for Biotechnology Information) Genbank Accession No. Q15848. 30 Kd Adipocyte Complement–related Protein Precursor (Acrp30) (Adipose Most Abundant Gene Transcript 1). Database [Online]. Last update: Jul. 15, 1998. Accessed on: Jan. 22, 2000.

www.ncbi.nim.nih.gov (National Center for Biotechnology Information) Genbank Accession No. A1417523. tg79a12.x1 Soares _NhHMPu_S1 *Homo sapiens cDNA clone Image:2114974 3' similar to SW:ACR3*_Human Q15848 30 Kd Adipocyte Complement–related Protein Precursor; mRNA sequence. Database [Online]. Last update: Mar. 30, 2000. Accessed on: Jan. 21, 2000, Release date: Feb. 9, 1999.

www.ncbi.nim.nih.gov (National Center for Biotechnology Information) Genbank Accession No. A1083823. qf18c08.x1 NCI_CGAP_Brn25 *Homo sapiens* cDNA clone Image:1750382 3', mRNA sequence. Database [Online]. Last update: Aug. 17, 1998. Accessed on: Jan. 21, 2000. Release date: Aug. 17, 1998.

www.ncbi.nim.nih.gov (National Center for Biotechnology Information) Genbank Accession No. AI085548. qf24c09.x1 NCI_CGAP_Bm25 *Homo sapiens* cDNA clone Image:1750960 3', mRNA sequence. Database [Online]. Last update: Nov. 10, 1998. Accessed on: Jan. 21, 2000. Release date: Aug. 17, 1998.

www.ncbi.nim.nih.gov (National Center for Biotechnology Information) Genbank Accession No. AI083824. qf18c09.x1 NCI_CGAP_Brn25 *Homo sapiens* cDNA clone Image:1750384 3', mRNA sequence. Database [Online]. Last update: Aug. 17, 1998. Accessed on: Jan. 21, 2000. Release date: Aug. 17, 1998.

www.ncbi.nim.nih.gov (National Center for Biotechnology Information) Genbank Accession No. W92687. zd92f04.s1 Soares_fetal_heart _NbHH19W *Homo sapiens* cDNA clone Image:356959 3', mRNA sequence. Database [Online]. Last update: Nov. 25, 1996. Accessed on: Jan. 21, 2000. Release date: Jul. 16, 1996.

www.ncbi.nim.nih.gov (National Center for Biotechnology Information) Genbank Accession No. W92830. zd92f04.r1 Soares_fetal_heart_NbHH19W *Homo sapiens* cDNA clone Image:356959 5', mRNA sequence. Database [Online]. Last update: Nov. 25, 1996. Accessed on: Jan. 21, 2000. Release date: Jul. 16, 1996.

www.ncbi.nim.nih.gov (National Center for Biotechnology Information) Genbank Accession No. AA775561. zf25h01.s1 Soares_fetal_heart_NbHH91W *Homo sapiens* cDNA clone Image:378001 3', mRNA sequence. Database [Online]. Last update: Feb. 5, 1998. Accessed on: Jan. 21, 2000. Release date: Feb. 5, 1998.

www.ncbi.nim.nih.gov (National Center for Biotechnology Information) Genbank Accession No. M91217. HUMRT-PGEB Subtracted human retinal pigment epithelium (RPE) *Homo sapiens* cDNA, mRNA sequence. Database [Online]. Last update: Oct. 29, 1992. Accessed on: Jan. 21, 2000.

www.ncbi.nim.nih.gov (National Center for Biotechnology Information) Genbank Accession No. AI393090. tg25g10.x1 NCI_CGAP_CLL1 *Homo sapiens* cDNA clone Image:2109858 3', mRNA sequence. Database [Online]. Last update: Mar. 30, 1999. Accessed on: Jan. 21, 2000. Release date: Feb. 4, 1999.

www.ncbi.nim.nih.gov (National Center for Biotechnology Information) Genbank Accession No. AI481222. vh21h07.x1 Soares mouse mammary gland NbMMG Mus musculus cDNA clone Image:876157 3' similar to SW:CA28_Human P25067 Collagen Alpha 2(VIII) Chain:, mRNA sequence. Database [Online]. Last update: Mar. 9, 1999. Accessed on: Jan. 21, 2000. Release date: Mar.5, 1999.

www.ncbi.nim.nih.gov (National Center for Biotechnology Information) Genbank Accession No. AI019893. ua93g09.ri Soares mouse mammary gland NbMMG Mus musculus cDNA clone Image:1365088 5', mRNA sequence. Database [Online]. Last update: Jun. 16, 1998. Accessed on: Jan. 21, 2000. Release date: Jun. 16, 1998.

www.ncbi.nim.nih.gov (National Center for Biotechnology Information) Genbank Accession No. AA510952. vg34c03.r1 Soares mouse mammary gland NbMMG Mus musculus Complement–Related Protein ACRP30. mRNA sequence. Database [Online]. Last update: Jul. 8, 1997. Accessed on: Jan. 21, 2000. Release date: Jul. 8, 1997.

www.ncbi.nim.nih.gov (National Center for Biotechnology Information) Genbank Accession No. AI614058. vg34c03.y1 Soares mouse mammary gland NbMMG Mus musculus cDNA clone Image:863236 5' similar to SW:CA1A_Human Q03692 Collagen Alpha 1(X) Chain Precursor. mRNA sequence. Database[Online]Last update: Apr. 21, 1999. Accessed on:Jan. 21, 2000. Release date:Apr. 16, 1999.

www.ncbi.nim.nih.gov (National Center for Biotechnology Information) Genbank Accession No. AF086482. *Homo sapiens* full length insert cDNA clone ZD92F04. Database [Online]. Last update: Aug. 29, 1998. Accessed on: Jan. 21, 2000. Release date: Aug. 29, 1998.

www.ncbi.nim.nih.gov (National Center for Biotechnology Information) Genbank Accession No. AI078144. oz30b06.x1 Soares_total_fetus_Nb2HF8_9w *Homo sapiens* cDNA clone Image:1676819 3' similar to TR:Q99784 Neuronal Olfactomedin–Related ER Localized Protein. mRNA sequence. Database [Online]. Last update: Oct. 1, 1998. Accessed on: Jan. 21, 2000. Release date: Aug. 10, 1998.

www.ncbi.nim.nih.gov (National Center for Biotechnology Information) Genbank Accession No. AA576955. nm82d01.s1 NCI_CGAP_Co9 *Homo sapiens* cDNA clone Image:1074721 3', mRNA sequence. Database [Online]. Last update: Sep. 12, 1997. Accessed on: Jan. 21, 2000. Release date: Sep. 3, 1997.

www.ncbi.nim.nih.gov (National Center for Biotechnology Information) Genbank Accession No. AI115209. ui47e03.x1 Sugano mouse embryo mewa Mus musculus cDNA clone Image:1885564 3', mRNA sequence. Database [Online]. Last update: Sep. 2, 1998. Accessed on: Jan. 21, 2000. Release date: Sep. 2, 1998.

www.ncbi.nim.nih.gov (National Center for Biotechnology Information) Genbank Accession No. AI315556. uj30a10.x1 Sugano mouse kidney mkia Mus musculus cDNA clone Image:1921434 3', mRNA sequence. Database [Online]. Last update: Dec. 17, 1998. Accessed on: Jan. 21, 2000. Release date: Dec. 17, 1998.

www.ncbi.nim.nih.gov (National Center for Biotechnology Information) Genbank Accession No. G26877. human STS SHGC–31969. Database [Online]. Last update: Jun. 14, 1996. Accessed on: Jan. 21, 2000. Release date: Jun. 14, 1996.

www.ncbi.nim.nih.gov (National Center for Biotechnology Information) Genbank Accession No. AI050418. Cell Surface A33 Antigen Precursor. Database [Online]. Last update: Jul. 15, 1998. Accessed on: Jan. 21, 2000.

www.ncbi.nim.nih.gov (National Center for Biotechnology Information) Genbank Accession No. U79725. Human A33 antigen precursor mRNA, complete cds. Database [Online]. Last update: Feb. 4, 1997. Accessed on: Jan. 21, 2000. Release date: Feb. 4, 1997.

www.ncbi.nim.nih.gov (National Center for Biotechnology Information) Genbank Accession No. NM_000442. *Homo sapiens* platelet/endothelial cell adhesion molecule (CD31 antigen) (PECAM1) mRNA. Database [Online]. Last update: Mar. 19, 1999. Accessed on: Jan. 21, 2000.

www.ncbi.nim.nih.gov (National Center for Biotechnology Information) Genbank Accession No. W52782. zd13h06.r1 Soares_fetal_heart_NbHH19W *Homo sapiens* cDNA clone Image:340571 5', mRNA sequence. Database [Online]. Last update: Oct. 15, 1996. Accessed on: Jan. 21, 2000. Release date: May 31, 1996.

www.ncbi.nim.nih.gov (National Center for Biotechnology Information) Genbank Accession No. AA707399. zj27g05.s1 Soares_fetal_liver_spleen_1NFLS_S1 *Homo sapiens* cDNA clone Image:451544 3', mRNA sequence. Database [Online]. Last update: Dec. 24, 1997. Accessed on: Jan. 21, 2000. Release date: Dec. 24, 1997.

www.ncbi.nim.nih.gov (National Center for Biotechnology Information) Genbank Accession No. AA780017. zj88g03.s1 Soares_fetal_liver_spleen_1NFLS_S1 *Homo sapiens* cDNA clone Image:462004 3', mRNA sequence. Database [Online]. Last update: Feb. 5, 1998. Accessed on: Jan. 21, 2000. Release date: Feb. 5, 1998.

www.ncbi.nim.nih.gov (National Center for Biotechnology Information) Genbank Accession No. AA520297. TgESTzz38c12.r1 TgME49 invivo Bradyzoite cDNA size selected *Toxoplasma gondii* cDNA clone tgzz38c12.r1 5', mRNA sequence. Database [Online]. Last update: Jul. 16, 1997. Accessed on: Jan. 21, 2000. Release date: Jul. 16, 1997.

www.ncbi.nim.nih.gov (National Center for Biotechnology Information) Genbank Accession No. AA519102. TgESTzz33f04.r1 TgME49 invivo Bradyzoite cDNA size selected *Toxoplasma gondii* cDNA clone tgzz33f04.r1 5', mRNA sequence. Database [Online]. Last update: Jul. 16, 1997. Accessed on: Jan. 21, 2000. Release date: Jul. 16, 1997.

www.ncbi.nim.nih.gov (National Center for Biotechnology Information) Genbank Accession No. AI169176. EST215010 Normalized rat kidney, Bento Soares Rattus sp. cDNA clone RKIO45 3' end, mRNA sequence. Database [Online]. Last update: Jan. 31, 1999. Accessed on: Jan. 21, 2000. Release date: Oct. 6, 1998.

www.ncbi.nim.nih.gov (National Center for Biotechnology Information) Genbank Accession No. AA946254. EST201753 Normalized rat lung, Bento Soares Rattus sp. cDNA clone RLUBC90 3' end, mRNA sequence. Database [Online]. Last update: May 1, 1998. Accessed on: Jan. 21, 2000. Release date: May 1, 1998.

www.ncbi.nim.nih.gov (National Center for Biotechnology Information) Genbank Accession No. AI556026. UI–R–C2p–qz–g–07–0–UI.s1 UI–R–C2p *Rattus norvegicus* cDNA clone UI–R–C2p–qz–g–07–0–UI 3', mRNA sequence. Database [Online]. Last update: Mar. 23, 1999. Accessed on: Jan. 21, 2000. Release date: Mar. 23, 1999.

www.ncbi.nim.nih.gov (National Center for Biotechnology Information) Genbank Accession No. AA198884. mu16f04.r1 Soares 2NbMT Mus musculus cDNA clone Image:639583 5', mRNA sequence. Database [Online]. Last update: Feb. 9, 1997. Accessed on: Jan. 21, 2000. Release date: Jan. 23, 1997.

www.ncbi.nim.nih.gov (National Center for Biotechnology Information) Genbank Accession No. AI573744. uj65c04.y1 Sugano mouse liver mlia Mus musculus cDNA clone Image:1924806 5', mRNA sequence. Database [Online]. Last update: Mar. 29, 1999. Accessed on: Jan. 21, 2000. Release date: Mar. 29, 1999.

www.ncbi.nim.nih.gov (National Center for Biotechnology Information) Genbank Accession No. AA145626. ms07e11.r1 Stratagene mouse skin (#937313) Mus musculus cDNA clone Image:606284 5', mRNA sequence. Database [Online]. Last update: Feb. 12, 1997. Accessed on: Jan. 21, 2000. Release date: Dec. 5, 1996.

* cited by examiner

```
GTCGACCCACGCGTCCGGGACTGGGGTGACGGCAGGGCAGGGGGCGCCTGGCCGGGGAGAAGCGCGGGGGCTGGAGCAC       79

CACCAACTGGAGGGTCCGGAGTAGCGAGCGCCCCGAAGGAGGCCATCGGGGAGCCGGGAGGGGGGACTGCGAGAGGACC      158

                               M   R   P   L   L   V   L   L   L   L   G   L       12
 CCGGCGTCCGGGCTCCCGGTGCCAGCGCT ATG AGG CCA CTC CTC GTC CTG CTG CTC CTG GGC CTG     223

 A   A   G   S   P   P   L   D   D   N   K   I   P   S   L   C   P   G   H   P     32
GCG GCC GGC TCG CCC CCA CTG GAC GAC AAC AAG ATC CCC AGC CTC TGC CCG GGG CAC CCC   283

 G   L   P   G   T   P   G   H   H   G   S   Q   G   L   P   G   R   D   G   R     52
GGC CTT CCA GGC ACG CCG GGC CAC CAT GGC AGC CAG GGC TTG CCG GGC CGC GAT GGC CGC   343

 D   G   R   D   G   A   P   G   A   P   G   E   K   G   E   G   G   R   P  G     72
GAC GGC CGC GAC GGC GCG CCC GGG GCT CCG GGA GAG AAA GGC GAG GGC GGG AGG CG GGA    403

 L   P   G   P   R   G   D   P   G   P   R   G   E   A   G   P   A   G   P   T     92
CTG CCG GGA CCT CGA GGG GAC CCC GGG CCG CGA GGA GAG GCG GGA CCC GCG GGG CCC ACC   463

 G   P   A   G   E   C   S   V   P   P   R   S   A   F   S   A   K   R   S   E    112
GGG CCT GCC GGG GAG TGC TCG GTG CCT CCG CGA TCC GCC TTC AGC GCC AAG CGC TCC GAG   523

 S   R   V   P   P   P   S   D   A   P   L   P   F   D   R   V   L   V   N   E    132
AGC CGG GTG CCT CCG CCG TCT GAC GCA CCC TTG CCC TTC GAC CGC GTG CTG GTG AAC GAG   583

 Q   G   H   Y   D   A   V   T   G   K   F   T   C   Q   V   P   G   V   Y   Y    152
CAG GGA CAT TAC GAC GCC GTC ACC GGC AAG TTC ACC TGC CAG GTG CCT GGG GTC TAC TAC   643
```

FIG.1A

```
 F   A   V   H   A   T   V   Y   R   A   S   L   Q   F   D   L   V   K   N   G   172
TTC GCC GTC CAT GCC ACC GTC TAC CGG GCC AGC CTG CAG TTT GAT CTG GTG AAG AAT GGC  703

 E   S   I   A   S   F   F   Q   F   F   G   G   W   P   K   P   A   S   L   S   192
GAA TCC ATT GCC TCT TTC TTC CAG TTT TTC GGG GGG TGG CCC AAG CCA GCC TCG CTC TCG  763

 G   G   A   M   V   R   L   E   P   E   D   Q   V   W   V   Q   V   G   V   G   212
GGG GGG GCC ATG GTG AGG CTG GAG CCT GAG GAC CAA GTG TGG GTG CAG GTG GGT GTG GGT  823

 D   Y   I   G   I   Y   A   S   I   K   T   D   S   T   F   S   G   F   L   V   232
GAC TAC ATT GGC ATC TAT GCC AGC ATC AAG ACA GAC AGC ACC TTC TCC GGA TTT CTG GTG  883

 Y   S   D   W   H   S   S   P   V   F   A   *   244
TAC TCC GAC TGG CAC AGC TCC CCA GTC TTT GCT TAG  919

TGCCCACTGCAAAGTGAGCTCATGCTCTCACTCCTAGAAGGAGGGTGTGAGGCTGACAACCTGGTCATCCAGGAGGGCT  998

GGCCCCCCTGGAATATTGTGAATGACTAGGGAGGTGGGGTAGAGCACTCTCCGTCCTGCTGCTGGCAAGGAATGGGAAC  1077

AGTGGCTGTCTGCGATCAGGTCTGGCAGCATGGGGCAGTGGCTGGATTTCTGCCCAAGACCAGAGGAGTGTGCTGTGCT  1156

GGCAAGTGTAAGTCCCCCAGTTGCTCTGGTCCAGGAGCCCACGGTGGGGTGCTCTCTTCCTGGTCCTCTGCTTCTCTGG  1235

ATCCTCCCCACCCCCTCCTGCTCCTGGGGCCGGCCCTTTTCTCAGAGATCACTCAATAAACCTAAGAACCCTCCAAAAA  1314

AAAAAAAAAAAAAAAGGGCGGCCGC  1339
```

FIG.1B

MRPLLVLLLLGLAAGSPPLDDNKIPSLCPGHPGLPGTPGHHGSQGLPGRDGRDGRDGAPG
APGEKGEGGRPGLPGPRGDPGPRGEAGPAGPTGPAGECSVPPRSAFSAKRSESRVPPPSD
APLPFDRVLVNEQGHYDAVTGKFTCQVPGVYYFAVHATVYRASLQFDLVKNGESIASFFQ
FFGGWPKPASLSGGAMVRLEPEDQVWVQVGVGDYIGIYASIKTDSTFSGFLVYSDWHSSP
VFA

```
GTCGACCCACGCGTCCGCGCTGTGAAGCCAGCAAGGAGCAACCAGAAGCTAGGAGTCAGTCAGCAAGGACAGGGGCTGC  79

                                                     M   R   P   L   L   A     6
CTGCCTACAGACTACAAGAGAGGTTCCTGGAGTCTGAGCCTCCGGGGTCACCACC ATG AGG CCA CTT CTT GCC  152

 L   L   L   L   G   L   V   S   G   S   P   P   L   D   D   N   K   I   P   S    26
CTT CTG CTT CTG GGT CTG GTG TCA GGC TCT CCT CCT CTG GAC GAC AAC AAG ATC CCC AGC  212

 L   C   P   G   Q   P   G   L   P   G   T   P   G   H   H   G   S   Q   G   L    46
CTG TGT CCC GGG CAG CCC GGC CTT CCA GGC ACA CCA GGT CAC CAT GGC AGC CAA GGC CTG  272

 P   G   R   D   G   R   D   G   R   D   G   A   P   G   A   P   G   E   K   G    66
CCT GGC CGT GAC GGC CGT GAT GGC CGC GAC GGT GCA CCC GGA GCT CCG GGA GAG AAA GGC  332

 E   G   G   R   P   G   L   P   G   P   R   G   E   P   G   P   R   G   E   A    86
GAG GGC GGG AGA CCG GGA CTA CCT GGC CCA CGT GGG GAG CCC GGG CCG CGT GGA GAG GCA  392

 G   P   M   G   A   I   G   P   A   G   E   C   S   V   P   P   R   S   A   F   106
GGG CCC ATG GGG GCT ATC GGG CCT GCG GGG GAG TGC TCG GTA CCC CCA CGA TCA GCC TTC  452

 S   A   K   R   S   E   S   R   V   P   P   P   A   D   T   P   L   P   F   D   126
AGT GCC AAG CGA TCC GAG AGC CGG GTA CCT CCG CCA GCC GAC ACA CCC CTA CCT TTC GAC  512

 R   V   L   L   N   E   Q   G   H   Y   D   P   T   T   G   K   F   T   C   Q   146
CGT GTG CTG CTA AAT GAG CAG GGC CAT TAC GAC CCC ACT ACT GGC AAG TTC ACC TGC CAA  572
```

FIG.3A

```
 V   P   G   V   Y   Y   F   A   V   H   A   T   V   Y   R   A   S   L   Q   F   166
GTG CCT GGC GTC TAC TAC TTT GCT GTG CAC GCC ACT GTC TAC CGG GCC AGC TTG CAG TTT  632

 D   L   V   K   N   G   Q   S   I   A   S   F   F   Q   Y   F   G   G   W   P   186
GAT CTT GTC AAA AAC GGG CAG TCC ATC GCC TCT TTC TTC CAG TAT TTT GGG GGG TGG CCC  692

 K   P   A   S   L   S   G   G   A   M   V   R   L   E   P   E   D   Q   V   W   206
AAG CCA GCC TCG CTC TCA GGG GGT GCG ATG GTA AGG CTA GAA CCT GAG GAC CAG GTG TGG  752

 V   Q   V   G   V   G   D   Y   I   G   I   Y   A   S   I   K   T   D   S   T   226
GTG CAG GTG GGC GTG GGT GAT TAC ATT GGC ATC TAT GCC AGC ATC AAG ACA GAC AGT ACC  812

 F   S   G   F   L   V   Y   S   D   W   H   S   S   P   V   F   A   *           244
TTC TCT GGA TTT CTC GTC TAT TCT GAC TGG CAC AGC TCC CCA GTC TTC GCT TAA          866

AACACAGTGAACCCGGAGCTGGCACTTGCTCCTCAGTGGAGGGTGTGACACTAACCCGCGCAGCGCATACCAGGAGGGC  945

TGGCCCCCTGGAATATTGTGAATGACTTAGGAAGAGAGGGAGCCACTTCCAGTCCCACTGCTGGCAATGAATGGAGACA  1024

GGCTGTCTGAGGTCAAGACAGCGTGGAGCAGTGGCTGGGTTTCTGCCCAGGACTTTAGAATGCAGTAGGCTGGCAGCTG  1103

TGGGTCCTGGCCCAGGACTCCAAGGTGGGATGCTCCATTCCTAGTCCTGTGTCCCCTCTAGGTCCCTGACTCCATCTCT  1182

GCTGCTCCCAGGGCAGGCCTTTTTCTCAGAGGTCACTTAATAAACCTAAAATCCTCAAAAAAAAAAAAAAAGGGCGGCC  1261

GC                                                                               1263
```

FIG.3B

>mT253
MRPLLALLLLGLVSGSPPLDDNKIPSLCPGQPGLPGTPGHHGSQGLPGRDGRDGRDGAPG
APGEKGEGGRPGLPGPRGEPGPRGEAGPMGAIGPAGECSVPPRSAFSAKRSESRVPPPAD
TPLPFDRVLLNEQGHYDPTTGKFTCQVPGVYYFAVHATVYRASLQFDLVKNGQSIASFFQ
YFGGWPKPASLSGGAMVRLEPEDQVWVQVGVGDYIGIYASIKTDSTFSGFLVYSDWHSSP
VFA

```
ALIGN calculates a global alignment of two sequences
 version 2.0uPlease cite: Myers and Miller, CABIOS (1989)
> hT253 a.a.                                    243 aa vs.
> mT253 a.a.                                    243 aa
scoring matrix: pam120.mat, gap penalties: -12/-4
93.8% identity;        Global alignment score: 1239
                10        20        30        40        50        60        70
inputs MRPLLVLLLLGLAAGSPPLDDNKIPSLCPGHPGLPGTPGHHGSQGLPGRDGRDGRDGAPGAPGEKGEGGR
       :::::.::::::..::::::::::::::::.:::::::::::::::::::::::::::::::::::::::
       MRPLLALLLLGLVSGSPPLDDNKIPSLCPGQPGLPGTPGHHGSQGLPGRDGRDGRDGAPGAPGEKGEGGR
                10        20        30        40        50        60        70

                80        90       100       110       120       130       140
inputs PGLPGPRGDPGPRGEAGPAGPTGPAGECSVPPRSAFSAKRSESRVPPPSDAPLPFDRVLVNEQGHYDAVT
       ::::::::.::::::::: :..::::::::::::::::::::::::::.:.::::::::.:::::::..:
       PGLPGPRGEPGPRGEAGPMGAIGPAGECSVPPRSAFSAKRSESRVPPPADTPLPFDRVLLNEQGHYDPTT
                80        90       100       110       120       130       140

               150       160       170       180       190       200       210
inputs GKFTCQVPGVYYFAVHATVYRASLQFDLVKNGESIASFFQFFGGWPKPASLSGGAMVRLEPEDQVWVQVG
       ::::::::::::::::::::::::::::::::.:::::::.:::::::::::::::::::::::::::::
       GKFTCQVPGVYYFAVHATVYRASLQFDLVKNGQSIASFFQYFGGWPKPASLSGGAMVRLEPEDQVWVQVG
               150       160       170       180       190       200       210

               220       230       240
inputs VGDYIGIYASIKTDSTFSGFLVYSDWHSSPVFA
       :::::::::::::::::::::::::::::::::
       VGDYIGIYASIKTDSTFSGFLVYSDWHSSPVFA
               220       230       240
```

FIG.5

```
ALIGN calculates a global alignment of two sequences
 version 2.0uPlease cite: Myers and Miller, CABIOS (1989)
> hT253 a.a.                                        243 aa vs.
> SwissProt Q15848 - (untitled)                     244 aa
scoring matrix: pam120.mat, gap penalties: -12/-4
38.7% identity;      Global alignment score: 262

               10        20        30        40        50        60
inputs MRPL-LVLLLLGLAA---GSPPLDDNKIPSL----CPG-HPGLPGTPGHHGSQGLPGRDGRDGRDGAPGA
       :  :  ::::::.:..      .    .  .  .  .:     : :  .:.:: :::.:..: ::::  :  :. :.
       MLLLGAVLLLLALPGHDQETTTQGPGVLLPLPKGACTGWMAGIPGHPGHNGAPGRDGRDGTPGEKGEKGD
               10        20        30        40        50        60        70

              70        80        90       100       110       120       130
inputs PGEKGEGGRPGLPGPRGDPGPRGEAGPAGPTGPAGECSVPPRSAFSAKRSESRVPPPSDAPLPFDRVLVN
       ::  :  :  :  :  :  :. :::: .:  :  : .:: .   :::::.   :. :  :  . :. : ... :
       PGLIGPKGDIGETGVPGAEGPRGFPGIQGRKGEPGEGAYVYRSAFSVGL-ETYVTIP-NMPIRFTKIFYN
               80        90       100       110       120       130

             140       150       160       170       180       190       200
inputs EQGHYDAVTGKFTCQVPGVYYFAVHATVYRASLQFDLVKNGESIASFFQFFGGWPKPASLSGGAMVRLEP
       .:.:::. :::: :..::.:::: : :::  ... .: :.. ..   .. .      . .  ::......::
       QQNHYDGSTGKFHCNIPGLYYFAYHITVYMKDVKVSLFKKDKAMLFTYDQYQE-NNVDQASGSVLLHLEV
     140       150       160       170       180       190       200

             210       220       230       240
inputs EDQVWVQV-GVGDYIGIYASIKTDSTFSGFLVYSDWHSSPVFA
        ::::.:: : :.  :.::.  .::::.::::.:   :..   .
       GDQVWLQVYGEGERNGLYADNDNDSTFTGFLLY---HDT---N
       210       220       230       240
```

FIG.6A

```
ALIGN calculates a global alignment of two sequences
 version 2.0uPlease cite: Myers and Miller, CABIOS (1989)
> mT253 a.a.                                      243 aa vs.
> SwissProt Q15848 - (untitled)                   244 aa
scoring matrix: pam120.mat, gap penalties: -12/-4
38.3% identity;      Global alignment score: 264

                10        20                 30         40        50        60
inputs MRPLLALLLLGLVSGSPPLDDNKIPSL--------CPG-QPGLPGTPGHHGSQGLPGRDGRDGRDGAPGA
       :  : :.:::  ..:  .   .. :..        : :  .:.:: :::.:..:  ::::  :  :. :.
       MLLLGAVLLLLALPGHDQETTTQGPGVLLPLPKGACTGWMAGIPGHPGHNGAPGRDGRDGTPGEKGEKGD
                10        20        30        40        50        60        70

               70        80        90       100       110       120       130
inputs PGEKGEGGRPGLPGPRGEPGPRGEAGPMGAIGPAGECSVPPRSAFSAKRSESRVPPPADTPLPFDRVLLN
       ::  :  :  :  :  :. ::::  .:  :  : .:: .  :::::.   :. :  :  . :. : ... :
       PGLIGPKGDIGETGVPGAEGPRGFPGIQGRKGEPGEGAYVYRSAFSVGL-ETYVTIP-NMPIRFTKIFYN
                80        90       100       110        120        130

              140       150       160       170       180       190       200
inputs EQGHYDPTTGKFTCQVPGVYYFAVHATVYRASLQFDLVKNGQSIASFFQYFGGWPKPASLSGGAMVRLEP
       .:.::: .:::: :.::.:::: : :::  ... .: :.....   .. .     . .  :.......::
       QQNHYDGSTGKFHCNIPGLYYFAYHITVYMKDVKVSLFKKDKAMLFTYDQYQE-NNVDQASGSVLLHLEV
      140       150       160      170       180       190        200

              210       220       230       240
inputs EDQVWVQV-GVGDYIGIYASIKTDSTFSGFLVYSDWHSSPVFA
        ::::.:: : :.  :.::.  .::::.:::.:   :..    .
       GDQVWLQVYGEGERNGLYADNDNDSTFTGFLLY---HDT---N
       210       220       230       240
```

FIG.6B

```
ALIGN calculates a global alignment of two sequences
 version 2.0uPlease cite: Myers and Miller, CABIOS (1989)
> hT253 n.a.                                        1339 aa vs.
> adipocyte n.a. (AI417523)                          653 aa
scoring matrix: pam120.mat, gap penalties: -12/-4
29.1% identity;      Global alignment score: -1168

               10        20        30        40        50        60        70
inputs GTCGACCCACGCGTCCGGGACTGGGGTGACGGCAGGGCAGGGGGCGCCTGGCCGGGGAGAAGCGCGGGGG
        :  .      :::.:  : .:::     :.. :.   ::::       :. :..: :.  :..:   ::  ::.
       TTTTTT----GCAT--GTAACTTTTTTATTGA---GGCA-----CAACAAGGCATTGTAACTTGCCTGGA
                   10          20           30              40        50

               80        90       100       110       120       130       140
inputs CTGGAGCACCACCAACTGGAGGGTCCGGAGTAGCGAGCGCCCCGAAGGAGGCCATCGGGGAGCCGGGAGG
       :: :::        .:.:       :.:. ::: .:::      :::          ::  .:  .:.:  ...
       CTTGAG--------GCAGT------CAGTTTAGTAAGCT----GAA---------CGTTAATACAGTTAA
         60                       70        80                      90

              150       160       170       180       190       200       210
inputs GGGGACTGCGAGAGGACCCCGGCGTCCGGGCTCCCGGTGCCAGCGCTATGAGGCCACTCCTCGTCCTGCT
       ::. . .:                             ::: :.:. :::.    :: ::          .:.
       GGATTAAG----------------------------TGCAAACAATATA----CATTC--------ACA
     100                                   110       120

              220       230       240       250       260       270       280
inputs GCTCCTGGGCCTGGCGGCCGGCTCGCCCCCACTGGACGACAACAAGATCCCCAGCCTCTGCCCGGGGCAC
       :::   ::.   ::.:::.  ::::             ::..:: :::  .:       ::     :::: :.
       GCT--TGA--CTAGCGA--GGCT------------ACATCA-CAATTTATAAAG----TGCCAGA-----
      130           140                    150        160          170

              290       300       310       320       330       340       350
inputs CCCGGCCTTCCAGGCACGCCGGGCCACCATGGCAGCCAGGGCTTGCCGGGCCGCGATGGCCGCGACGGCC
              ::  ::    :: ..      .:: ::   ::   :::::          ..:   :.:
       -------TT--AGT---GCTAA------TTGTCATTCA--GCTTG---------ATTTTTCAC-------
                          180             190                  200
```

FIG.7A

```
              360       370       380       390       400       410       420
inputs GCGACGGCGCGCCCGGGGCTCCGGGAGAGAAAGGCGAGGGCGGGAGGCCGGGACTGCCGGGACCTCGAGG
                         ::: ::.::..:::  :.:... : .:::        .::   .::::
       ------------------CTCAGGAAGGAAAA--CAAAAAAGTAAGG--------ACC---TCCTC----
                            210         220       230

              430       440       450       460       470       480       490
inputs GGACCCCGGGCCGCGAGGAGAGGCGGGACCCGCGGGGCCCACCGGGCCTGCCGGGGAGTGCTCGGTGCCT
                 :: : :::::.
       ----------CCTCTAGGAA--------------------------------------------------
               240

              500       510       520       530       540       550       560
inputs CCGCGATCCGCCTTCAGCGCCAAGCGCTCCGAGAGCCGGGTGCCTCCGCCGTCTGACGCACCCTTGCCCT
                                   :.:.:. :.  : :::                 ....:: .
       ----------------------------CAAAAAACATTTTCCT-----------------AAACCAA
                                  250       260                       270

              570       580       590       600       610       620       630
inputs TCGACCGCGTGCTGGTGAACGAGCAGGGACATTACGACGCCGTCACCGGCAAGTTCACCTGCCAGGTGCC
       ::.. :         .:::  :.::::..:::  :::  .  :: :::        .:: ::.  :...:
       TCAGTC--------ATGA--GGGCAAAGAC--TACTTTTCCTTCA--------ATC-CCA--CTAAT---
                    280         290         300                 310

              640       650       660       670       680       690       700
inputs TGGGGTCTACTACTTCGCCGTCCATGCCACCGTCTACCGGGCCAGCCTGCAGTTTGATCTGGTGAAGAAT
       :.:..          :.::.:::                            ::: ::            :
       TAGAA----------CACCATCC----------------------------TTTTAT-----------T
        320                                              330

              710       720       730       740       750       760       770
inputs GGCGAATCCATTGCCTCTTTCTTCCAGTTTTTCGGGGGGTGGCCCAAGCCAGCCTCGCTCTCGGGGGGGG
       : :.:..: .:    .:: .::: :::.:                :..:
       GTCAATACTGT----ACTGACTTTCAAT----------------CTTG---------------------
        340           350       360
```

FIG.7A-1

```
                780       790       800       810       820       830       840
inputs CCATGGTGAGGCTGGAGCCTGAGGACCAAGTGTGGGTGCAGGTGGGTGTGGGTGACTACATTGGCATCTA
          ::.:..:::.: :  ::::::::..::                : .:..:.:
       --ATAAAGAAGAT--AGCCTGAAAAC--------------GTAGAATAT--------------------
             370           380                        390

                850       860       870       880       890       900       910
inputs TGCCAGCATCAAGACAGACAGCACCTTCTCCGGATTTCTGGTGTACTCCGACTGGCACAGCTCCCCAGTC
       : :::::..:.                     :::. :..:                    .::::::.::
       TTCCAGCTACT-----------------TCCATAAAT--------------------TGCTCCCCTGT-
         400                           410                             420

                920       930       940       950       960       970       980
inputs TTTGCTTAGTGCCCACTGCAAAGTGAGCTCATGCTCTCACTCCTAGAAGGAGGGTGTGAGGCTGACAACC
                                                                   ::.:::..
       -----------------------------------------------------------GCAGACGT--
                                                                     430

                990      1000      1010      1020      1030      1040      1050
inputs TGGTCATCCAGGAGGGCTGGCCCCCCTGGAATATTGTGAATGACTAGGGAGGTGGGGTAGAGCACTCTCC
            :.:::  ..  :::: : ::::::::                :::  ::..::.: .:::   :
       -----AACCATAT---CTGGTCTCCCTGGAA----------------GAGCTGAAGAATTGCATGAT--
              440          450                        460        470

               1060      1070      1080      1090      1100      1110      1120
inputs GTCCTGCTGCTGGCAAGGAATGGGAACAGTGGCTGTCTGCGATCAGGTCTGGCAGCATGGGGCAGTGGCT
              ::::.:::         : ..:: :::    :::: :: ::    :   :: ::: :: :: .::::
       -------TGCTAGCA-------GTTTCA-TGG---TCTG-GAGCA---C---CATCATTGG-CATAGGCT
              480               490            500             510        520

               1130      1140      1150      1160      1170      1180      1190
inputs GGATTTCTGCCCAAGACCAGAGGAGTGTGCTGTGCTGGCAAGTGTAAGTCCCCCAGTTGCTCTGGTCCAG
       :...      ::::::::.           ::    :.  :.. ..:.::       :::: .:   .: :::
       GATA------CCAAGACCT----------CTT--CATTCTTCANTGAG-------GTTG-AC--ATACAG
                    530                   540       550                 560
```

FIG.7A-2

```
              1200      1210      1220      1230      1240      1250      1260
inputs GAGCCCACGGTGGGGTGCTCTCTTCCTGGTCCTCTGCTTCTCTGGATCCTCCCCACCCCCTCCTGCTCCT
        .:: ::          ::.:: ::.:  : : :.:.: : ...:.            :  .. .: :
       TGGCACAT----------TCACTGCCAG--CTTTTACATGTGAAAAA-------------TGAAAAACGT
           570                  580       590                    600

              1270      1280      1290      1300      1310      1320      1330
inputs GGGGCCGGCCCTTTTCTCAGAGATCACTCAATAAACCTAAGAACCCTCCAAAAAAAAAAAAAAAAAAAAG
       .: :::.      :::.:. .:  ::   :.:::: :::        :::::. ..:.:. :::
       AGTGCCA------TTCACTTGG--CA---ATTAAATCTA--------CCAAAGCTGAGATCAAA------
      610              620            630               640       650

inputs GGCGGCCGC

       ---------
```

FIG.7A-3

```
ALIGN calculates a global alignment of two sequences
 version 2.0uPlease cite: Myers and Miller, CABIOS (1989)
> mT253 n.a.                                       1263 aa vs.
> adipocyte n.a. (AI417523)                         653 aa
scoring matrix: pam120.mat, gap penalties: -12/-4
30.4% identity;      Global alignment score: -840

                10        20        30        40        50        60        70
inputs GTCGACCCACGCGTCCGCGCTGTGAAGCCAGCAAGGAGCAACCAGAAGCTAGGAGTCAGTCAGCAAGGAC
        :                 : :      .:::.: :.:..    ..  .. ::: ::  :::::::: :
       TT-----------------TTT------TGCATGTAACTT----TTTTATTGAGGCA--CAACAAGG-C
                                        10            20        30

                80        90       100       110       120       130       140
inputs AGGGGCTGCCTGCCTACAGACTACAAGAGAGGTTCCTGGAGTCTGAGCCTCCGGGGTCACCACCATGAGG
       :  :                ..:::           : ::::::                      :.:::::
       ATTG-------------TAACT----------TGCCTGGA---------------------CTTGAGG
      40                                 50                               60

               150       160       170       180       190       200       210
inputs CCACTTCTTGCCCTTCTGCTTCTGGGTCTGGTGTCAGGCTCTCCTCCTCTGGACGACAACAAGATCCCCA
       : .             ::.: ::            .:: ::          :::.:::. :: :
       CAG----------TCAGTTT----------AGTAAG-----------CTGAACGTTAATA---------
                      70                                80        90

               220       230       240       250       260       270       280
inputs GCCTGTGTCCCGGGCAGCCCGGCCTTCCAGGCACACCAGGTCACCATGGCAGCCAAGGCCTGCCTGGCCG
         :.:: .    ::.            ::  . ::: :: :  .:       .::  :: .:: :: ::.:: :
       --CAGTTA--AGGA----------TTAAGTGCAAACAATAT-------ACATTCACAGCTTGACTAGC-G
                   100                  110              120       130       140
```

FIG.7B

```
           290       300       310       320       330       340       350
inputs TGACGGCCGTGATGGCCGCGACGGTGCACCCGGAGCTCCGGGAGAGAAAGGCGAGGGCGGGAGACCGGGA

       AGGCTAC-------------------------ATCACAATTTATAAAGTGC-----CAGATTA---GTG
                                       150       160            170

           360       370       380       390       400       410       420
inputs CTACCTGGCCCACGTGGGGAGCCCGGGCCGCGTGGAGAGGCAGGGCCCATGGGGGCTATCGGGCCTGCGG

       CTAATTGTCATTCA---------------GCTTGATTTTTCA----CCTCAGGAA------GGAAAACAA
        180       190                     200           210            220

           430       440       450       460       470       480       490
inputs GGGAGTGCTCGGTACCCCCACGATCAGCCTTCAGTGCCAAGCGATCCGAGAGCCGGGTACCTCCGCCAGC

       AAAAGTA---AGGACCTCCTC------CCT-------CTAG-GAACAAAAAAC-ATTTTCCTA-------
               230             240              250        260

           500       510       520       530       540       550       560
inputs CGACACACCCCTACCTTTCGACCGTGTGCTGCTAAATGAGCAGGGCCATTACGACCCCACTACTGGCAAG

       -----------AACCAATCAGTCATGAG-GGCAAAGACTACTTTTCCTT--CAATCCCACTAAT---TAG
                    270       280       290       300        310

           570       580       590       600       610       620       630
inputs TTCACCTGCCAAGTGCCTGGCGTCTACTACTTTGCTGTGCACGCCACTGTCTACCGGGCCAGCTTGCAGT

       AACACCATCCTTTTA--TTG--------TCAATACTGT-------ACTGACTT-----------------
     320       330                 340              350

           640       650       660       670       680       690       700
inputs TTGATCTTGTCAAAAACGGGCAGTCCATCGCCTCTTTCTTCCAGTATTTTGGGGGGTGGCCCAAGCCAGC

       -------------------------------TCAATCTT-----GATAAAGAAGATAGCC---------
                                        360            370
```

FIG.7B-1

```
                710       720       730       740       750       760       770
inputs CTCGCTCTCAGGGGGTGCGATGGTAAGGCTAGAACCTGAGGACCAGGTGTGGGTGCAGGTGGGCGTGGGT
                  :....::..:..     :: ..::.:     :          :.:
       -----------TGAAAACGTAGAA-----TATTTCCAG-----C---------TAC---------------
                380       390            400

                780       790       800       810       820       830       840
inputs GATTACATTGGCATCTATGCCAGCATCAAGACAGACAGTACCTTCTCTGGATTTCTCGTCTATTCTGACT
         :: :::... . ::     ::  :  :.. .::::. .:::.: :::::    ::::  :        ::
       --TTCCATAAATTGCT---CC--C--CTGTGCAGACGTAACCATATCTGG---TCTC--C--------CT
           410            420            430       440          450

                850       860       870       880       890       900       910
inputs GGCACAGCTCCCCAGTCTTCGCTTAAAACACAGTGAACCCGGAGCTGGCACTTGCTCCTCAGTGGAGGGT
       :: : ::::      ::. :: ::.:.:..                :::.::: :: :          : :::
       GGAAGAGCTGA--AGAATT-GCATGATT---------------GCTAGCAGTTTC----------ATGGT
           460          470                      480       490

                920       930       940       950       960       970       980
inputs GTGACACTAACCCGCGCAGCGCATACCAGGAGGGCTGGCCCCCTGGAATATTGTGAATGACTTAGGAAGA
                                 :.:::      :: ::          .: :.::.:.:::: .::
       -------------------------CTGGA------GCACC----------ATCATTGGCATAGGCTGA
                                  500                        510       520

                990      1000      1010      1020      1030      1040      1050
inputs GAGGGAGCCACTTCCAGTCCCACTGCTGGCAATGAATGGAGACAGGCTGTCTGAGGTCAAGACAGCGTGG
                  :.:::.  ::.:: :. :..             ::.       ::::::  .::::
       -----------TACCAAGACCTCTTCATTCTT----------CAN------TGAGGT--TGACA------
                      530       540                        550

               1060      1070      1080      1090      1100      1110      1120
inputs AGCAGTGGCTGGGTTTCTGCCCAGGACTTTAGAATGCAGTAGGCTGGCAGCTGTGGGTCCTGGCCCAGGA
       ..::::::::. . : .:::::   ..::::   :.::              ::::...  ::.    :..:
       TACAGTGGCACATTCACTGCC---AGCTTT----TACA-------------TGTGAAAAATGA---AAAA
      560       570            580                        590       600
```

FIG.7B-2

```
                1130      1140      1150      1160      1170      1180      1190
inputs CTCCAAGGTGGGATGCTCCATTCCTAGTCCTGTGTCCCCTCTAGGTCCCTGACTCCATCTCTGCTGCTCC
       :   ...:::       ::::::                 .::.::         : ::  :. . :: :
       C---GTAGTG-------CCATTC-----------------ACTTGG--------CAAT---TAAATCTAC
              610                              620                 630

                1200      1210      1220      1230      1240      1250      1260
inputs CAGGGCAGGCCTTTTTCTCAGAGGTCACTTAATAAACCTAAAATCCTCAAAAAAAAAAAAAAAGGGCGGC
       ::..::.:            :::                       :::::
       CAAAGCTG------------AGA-----------------------TCAAA-------------------
       640                                          650

inputs CGC

       ---
```

FIG.7B-3

```
GTCGACCCACGCGTCCGCGGACGCGTGGGTGAGGGGAAGAGGCTGACTGTACGTTCCTTCTACTCTGGCACCACTCTCC      79

          M   G   P   S   T   P   L   L   I   L   F   L   L   S   W   S   G           17
AGGCTGCC ATG GGG CCC AGC ACC CCT CTC CTC ATC TTG TTC CTT TTG TCA TGG TCG GGA         138

 P   L   Q   G   Q   Q   H   H   L   V   E   Y   M   E   R   R   L   A   A   L        37
CCC CTC CAA GGA CAG CAG CAC CAC CTT GTG GAG TAC ATG GAA CGC CGA CTA GCT GCT TTA      198

 E   E   R   L   A   Q   C   Q   D   Q   S   S   R   H   A   A   E   L   R   D        57
GAG GAA CGG CTG GCC CAG TGC CAG GAC CAG AGT AGT CGG CAT GCT GCT GAG CTG CGG GAC      258

 F   K   N   K   M   L   P   L   L   E   V   A   E   K   E   R   E   A   L   R        77
TTC AAG AAC AAG ATG CTG CCA CTG CTG GAG GTG GCA GAG AAG GAG CGG GAG GCA CTC AGA      318

 T   E   A   D   T   I   S   G   R   V   D   R   L   E   R   E   V   D   Y   L        97
ACT GAG GCC GAC ACC ATC TCC GGG AGA GTG GAT CGT CTG GAG CGG GAG GTA GAC TAT CTG      378

 E   T   Q   N   P   A   L   P   C   V   E   F   D   E   K   V   T   G   G   P       117
GAG ACC CAG AAC CCA GCT CTG CCC TGT GTA GAG TTT GAT GAG AAG GTG ACT GGA GGC CCT      438

 G   T   K   G   K   G   R   R   N   E   K   Y   D   M   V   T   D   C   G   Y       137
GGG ACC AAA GGC AAG GGA AGA AGG AAT GAG AAG TAC GAT ATG GTG ACA GAC TGT GGC TAC      498

 T   I   S   Q   V   R   S   M   K   I   L   K   R   F   G   G   P   A   G   L       157
ACA ATC TCT CAA GTG AGA TCA ATG AAG ATT CTG AAG CGA TTT GGT GGC CCA GCT GGT CTA      558

 W   T   K   D   P   L   G   Q   T   E   K   I   Y   V   L   D   G   T   Q   N       177
TGG ACC AAG GAT CCA CTG GGG CAA ACA GAG AAG ATC TAC GTG TTA GAT GGG ACA CAG AAT      618

 D   T   A   F   V   F   P   R   L   R   D   F   T   L   A   M   A   A   R   K       197
GAC ACA GCC TTT GTC TTC CCA AGG CTG CGT GAC TTC ACC CTT GCC ATG GCT GCC CGG AAA      678
```

FIG.8A

```
 A   S   R   V   R   V   P   F   P   W   V   G   T   G   Q   L   V   Y   G   G    217
GCT TCC CGA GTC CGG GTG CCC TTC CCC TGG GTA GGC ACA GGG CAG CTG GTA TAT GGT GGC   738

 F   L   Y   F   A   R   R   P   P   G   R   P   G   G   G   G   E   M   E   N    237
TTT CTT TAT TTT GCT CGG AGG CCT CCT GGA AGA CCT GGT GGA GGT GGT GAG ATG GAG AAC   798

 T   L   Q   L   I   K   F   H   L   A   N   R   T   V   V   D   S   S   V   F    257
ACT TTG CAG CTA ATC AAA TTC CAC CTG GCA AAC CGA ACA GTG GTG GAC AGC TCA GTA TTC   858

 P   A   E   G   L   I   P   P   Y   G   L   T   A   D   T   Y   I   D   L   A    277
CCA GCA GAG GGG CTG ATC CCC CCC TAC GGC TTG ACA GCA GAC ACC TAC ATC GAC CTG GCA   918

 A   D   E   E   G   L   W   A   V   Y   A   T   R   E   D   D   R   H   L   C    297
GCT GAT GAG GAA GGT CTT TGG GCT GTC TAT GCC ACC CGG GAG GAT GAC AGG CAC TTG TGT   978

 L   A   K   L   D   P   Q   T   L   D   T   E   Q   Q   W   D   T   P   C   P    317
CTG GCC AAG TTA GAT CCA CAG ACA CTG GAC ACA GAG CAG CAG TGG GAC ACA CCA TGT CCC  1038

 R   E   N   A   E   A   A   F   V   I   C   G   T   L   Y   V   V   Y   N   T    337
AGA GAG AAT GCT GAG GCT GCC TTT GTC ATC TGT GGG ACC CTC TAT GTC GTC TAT AAC ACC  1098

 R   P   A   S   R   A   R   I   Q   C   S   F   D   A   S   G   T   L   T   P    357
CGT CCT GCC AGT CGG GCC CGC ATC CAG TGC TCC TTT GAT GCC AGC GGC ACC CTG ACC CCT  1158

 E   R   A   A   L   P   Y   F   P   R   R   Y   G   A   H   A   S   L   R   Y    377
GAA CGG GCA GCA CTC CCT TAT TTT CCC CGC AGA TAT GGT GCC CAT GCC AGC CTC CGC TAT  1218

 N   P   R   E   R   Q   L   Y   A   W   D   D   G   Y   Q   I   V   Y   K   L    397
AAC CCC CGA GAA CGC CAG CTC TAT GCC TGG GAT GAT GGC TAC CAG ATT GTC TAT AAG CTG  1278

 E   M   R   K   K   E   E   E   V   *     407
GAG ATG AGG AAG AAA GAG GAG GAG GTT TGA   1308
```

FIG.8B

GGAGCTAGCCTTGTTTTTTGCATCTTTCTCACTCCCATACATTTATATTATATCCCCACTAAATTTCTTGTTCCTCATT 1387

CTTCAAATGTGGGCCAGTTGTGGCTCAAATCCTCTATATTTTTAGCCAATGGCAATCAAATTCTTTCAGCTCCTTTGTT 1466

TCATACGGAACTCCAGATCCTGAGTAATCCTTTTAGAGCCCGAAGAGTCAAAACCCTCAATGTTCCCTCCTGCTCTCCT 1545

GCCCCATGTCAACAAATTTCAGGCTAAGGATGCCCCAGACCCAGGGCTCTAACCTTGTATGCGGGCAGGCCCAGGGAGC 1624

AGGCAGCAGTGTTCTTCCCCTCAGAGTGACTTGGGGAGGGAGAAATAGGAGGAGACGTCCAGCTCTGTCCTCTCTTCCT 1703

CACTCCTCCCTTCAGTGTCCTGAGGAACAGGACTTTCTCCACATTGTTTTGTATTGCAACATTTTGCATTAAAAGGAAA 1782

ATCCACTGCTAAAAAAAAAAAAAAAAAAAAAAAAAAAAAGGGCGGCCGC 1831

FIG.8C

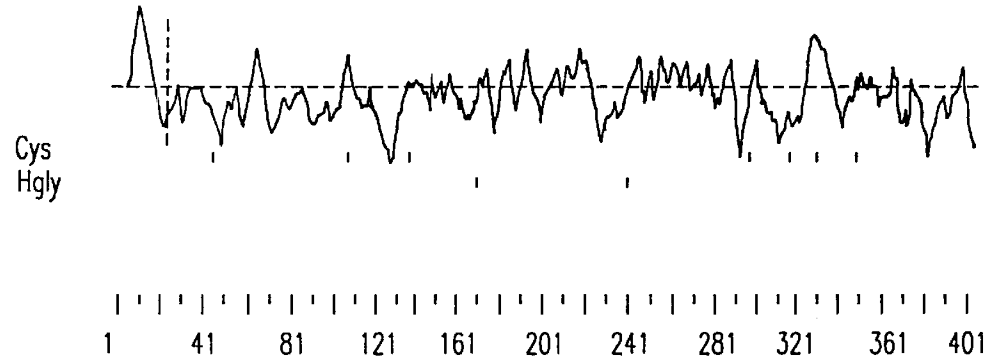

MGPSTPLLILFLLSWSGPLQGQQHHLVEYMERRLAALEERLAQCQDQSSRHAAELRDFKN
KMLPLLEVAEKEREALRTEADTISGRVDRLEREVDYLETQNPALPCVEFDEKVTGGPGTK
GKGRRNEKYDMVTDCGYTISQVRSMKILKRFGGPAGLWTKDPLGQTEKIYVLDGTQNDTA
FVFPRLRDFTLAMAARKASRVRVPFPWVGTGQLVYGGFLYFARRPPGRPGGGGEMENTLQ
LIKFHLANRTVVDSSVFPAEGLIPPYGLTADTYIDLAADEEGLWAVYATREDDRHLCLAK
LDPQTLDTEQQWDTPCPRENAEAAFVICGTLYVVYNTRPASRARIQCSFDASGTLTPERA
ALPYFPRRYGAHASLRYNPRERQLYAWDDGYQIVYKLEMRKKEEEV

FIG.9

```
                              M   G   P   S   A   P   L   L   L   L   F   F    12
GTCGACCCACGCGTCCGACTTAAGGCTGCC ATG GGG CCC AGT GCT CCT CTG CTG CTC CTC TTC TTT  66

 L   S   W   T   G   P   L   Q   G   Q   Q   H   H   L   V   E   Y   M   E   R    32
TTG TCA TGG ACG GGA CCC CTT CAG GGA CAG CAG CAC CAC CTT GTG GAG TAC ATG GAA CGC  126

 R   L   A   A   L   E   E   R   L   A   Q   C   Q   D   Q   S   S   R   H   A    52
CGA CTA GCT GCC TTA GAG GAA CGG CTG GCC CAA TGC CAG GAT CAG AGT AGT CGG CAT GCT  186

 A   E   L   R   D   F   K   N   K   M   L   P   L   L   E   V   A   E   K   E    72
GCC GAG CTT CGG GAC TTC AAA AAC AAG ATG TTG CCT CTC CTG GAG GTG GCA GAG AAG GAG  246

 R   E   T   L   R   T   E   A   D   S   I   S   G   R   V   D   R   L   E   R    92
CGG GAG ACC CTC AGA ACT GAA GCA GAC TCC ATC TCA GGA AGA GTG GAC CGT CTT GAA AGG  306

 E   V   D   Y   L   E   T   Q   N   P   A   L   P   C   V   E   L   D   E   K   112
GAG GTA GAC TAT CTG GAG ACA CAG AAC CCA GCT TTG CCC TGT GTA GAG CTG GAT GAG AAG  366

 V   T   G   G   P   G   A   K   G   K   G   R   R   N   E   K   Y   D   M   V   132
GTG ACT GGA GGT CCT GGA GCC AAA GGC AAG GGC CGA AGA AAT GAG AAA TAC GAT ATG GTG  426

 T   D   C   S   Y   T   V   A   Q   V   R   S   M   K   I   L   K   R   F   G   152
ACG GAC TGT AGC TAC ACA GTC GCT CAG GTG AGG TCA ATG AAG ATC CTG AAG CGG TTT GGT  486

 G   S   V   G   L   W   T   K   D   P   L   G   P   A   E   K   I   Y   V   L   172
GGT TCA GTT GGC CTA TGG ACC AAG GAT CCG CTG GGG CCA GCA GAG AAG ATC TAC GTG TTA  546

 D   G   T   Q   N   D   T   A   F   V   F   P   R   L   R   D   F   T   L   A   192
GAC GGC ACC CAG AAC GAC ACG GCT TTT GTC TTC CCA AGG CTG CGT GAC TTC ACC CTT GCC  606
```

FIG.10A

M A A R K A S R I R V P F P W V G T G Q 212

ATG GCT GCC CGG AAA GCT TCC CGA ATT CGG GTG CCC TTC CCC TGG GTA GGC ACG GGG CAG 666

L V Y G G F L Y Y A R R P P G G P G G G 232

CTG GTG TAC GGT GGC TTC CTT TAT TAT GCT CGA AGG CCT CCT GGA GGA CCT GGA GGG GGT 726

G E L E N T L Q L I K F H L A N R T V V 252

GGT GAA TTG GAG AAC ACT CTG CAG CTG ATC AAA TTT CAC TTG GCA AAC CGA ACA GTG GTG 786

D S S V F P A E S L I P P Y G L T A D T 272

GAT AGC TCA GTG TTC CCT GCA GAG AGC CTG ATA CCC CCC TAC GGC CTG ACA GCA GAT ACA 846

Y I D L A A D E E G L W A V Y A T R D D 292

TAT ATC GAC CTG GCA GCT GAT GAG GAG GGC CTG TGG GCT GTC TAT GCC ACT CGA GAT GAT 906

D R H L C L A K L D P Q T L D T E Q Q W 312

GAC AGG CAT TTG TGT CTA GCC AAG TTA GAC CCA CAG ACA CTT GAC ACA GAG CAG CAG TGG 966

D T P C P R E N A E A A F V I C G T L Y 332

GAC ACA CCA TGT CCC AGA GAG AAC GCA GAG GCT GCG TTT GTC ATC TGT GGG ACC CTG TAC 1026

V V Y N T R P A S R A R I Q C S F D A S 352

GTT GTC TAT AAC ACC CGC CCT GCC AGT AGG GCT CGT ATT CAG TGT TCC TTC GAT GCC AGT 1086

G T L A P E R A A L S Y F P R R Y G A H 372

GGT ACT CTC GCC CCT GAA AGG GCA GCA CTC TCC TAT TTT CCA CGC CGA TAT GGT GCC CAT 1146

A S L R Y N P R E R Q L Y A W D D G Y Q 392

GCC AGC CTT CGC TAT AAC CCC CGT GAG CGC CAG CTG TAT GCC TGG GAT GAT GGC TAC CAG 1206

I V Y K L E M K K K E E E V * 407

ATT GTC TAC AAA TTG GAG ATG AAG AAG AAG GAG GAG GAA GTT TAA 1251

FIG.10B

GCAGCTAGCCTTGTGCTCTTGATTCTTATGCCCAGACATTTATATTCCTGTGAGCTCTCCTGCAGTTCATCCTTCAAAA 1330

CGAAGGCCAGTGGTGGTAGCTCATATACCCTAATTTCTAAAGGACAACCAAATTCTCAAGCCCCTCTGTTTTATGCAGA 1409

ACTCCAGATCCTGGGTAGCATTTTAGAACTGAACAGCAAACAAACACCCTAAATCTTCACTCCTGCCTTATGTCCACAA 1488

AGTTTAGTTCCAAACTCAGAGCCCTGTCCTTTGGAGAGGGTCAACCCCAGACAGCAGGCGACAGCATTCTTGCCCTCAG 1567

TATGACCGAAGGGAGAGAACTCAGAGACAAAGCTGCCCTCCCTCCCTTCCCCCTCCAGTGTAGGGGAGAATGGGGCTTT 1646

CCCCACATCACTTTGTATGGTAACAGTTTGCATTAAAAGGAAAACCCACCAAAAAAAAAAAAAAAGGGCGGCCGC 1721

FIG.10C

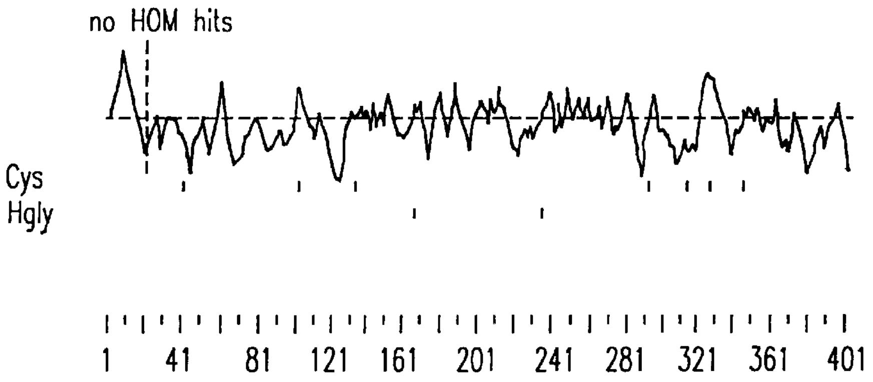

>mT257
MGPSAPLLLLFFLSWTGPLQGQQHHLVEYMERRLAALEERLAQCQDQSSRHAAELRDFKN
KMLPLLEVAEKERETLRTEADSISGRVDRLEREVDYLETQNPALPCVELDEKVTGGPGAK
GKGRRNEKYDMVTDCSYTVAQVRSMKILKRFGGSVGLWTKDPLGPAEKIYVLDGTQNDTA
FVFPRLRDFTLAMAARKASRIRVPFPWVGTGQLVYGGFLYYARRPPGGPGGGGELENTLQ
LIKFHLANRTVVDSSVFPAESLIPPYGLTADTYIDLAADEEGLWAVYATRDDDRHLCLAK
LDPQTLDTEQQWDTPCPRENAEAAFVICGTLYVVYNTRPASRARIQCSFDASGTLAPERA
ALSYFPRRYGAHASLRYNPRERQLYAWDDGYQIVYKLEMKKKEEEV

FIG.11

```
ALIGN calculates a global alignment of two sequences
 version 2.0uPlease cite: Myers and Miller, CABIOS (1989)
> hT257 a.a.                                    406 aa vs.
> mT257a.a.                                     406 aa
scoring matrix: pam120.mat, gap penalties: -12/-4
94.1% identity;        Global alignment score: 2097

                10        20        30        40        50        60        70
inputs MGPSTPLLILFLLSWSGPLQGQQHHLVEYMERRLAALEERLAQCQDQSSRHAAELRDFKNKMLPLLEVAE
       ::::.:::.::.:::.:::::::::::::::::::::::::::::::::::::::::::::::::::::::
       MGPSAPLLLLFFLSWTGPLQGQQHHLVEYMERRLAALEERLAQCQDQSSRHAAELRDFKNKMLPLLEVAE
                10        20        30        40        50        60        70

                80        90       100       110       120       130       140
inputs KEREALRTEADTISGRVDRLEREVDYLETQNPALPCVEFDEKVTGGPGTKGKGRRNEKYDMVTDCGYTIS
       ::::.:::::.:::::::::::::::::::::::::::.::::::::.:::::::::::::::::.::..
       KERETLRTEADSISGRVDRLEREVDYLETQNPALPCVELDEKVTGGPGAKGKGRRNEKYDMVTDCSYTVA
                80        90       100       110       120       130       140

               150       160       170       180       190       200       210
inputs QVRSMKILKRFGGPAGLWTKDPLGQTEKIYVLDGTQNDTAFVFPRLRDFTLAMAARKASRVRVPFPWVGT
       :::::::::::::..::::::::..::::::::::::::::::::::::::::::::::::.::::::::
       QVRSMKILKRFGGSVGLWTKDPLGPAEKIYVLDGTQNDTAFVFPRLRDFTLAMAARKASRIRVPFPWVGT
               150       160       170       180       190       200       210

               220       230       240       250       260       270       280
inputs GQLVYGGFLYFARRPPGRPGGGGEMENTLQLIKFHLANRTVVDSSVFPAEGLIPPYGLTADTYIDLAADE
       ::::::::::.:::::: :::::.::::::::::::::::::::::::::.:::::::::::::::::::
       GQLVYGGFLYYARRPPGGPGGGGELENTLQLIKFHLANRTVVDSSVFPAESLIPPYGLTADTYIDLAADE
               220       230       240       250       260       270       280

               290       300       310       320       330       340       350
inputs EGLWAVYATREDDRHLCLAKLDPQTLDTEQQWDTPCPRENAEAAFVICGTLYVVYNTRPASRARIQCSFD
       ::::::::::.:::::::::::::::::::::::::::::::::::::::::::::::::::::::::::
       EGLWAVYATRDDDRHLCLAKLDPQTLDTEQQWDTPCPRENAEAAFVICGTLYVVYNTRPASRARIQCSFD
               290       300       310       320       330       340       350

               360       370       380       390       400
inputs ASGTLTPERAALPYFPRRYGAHASLRYNPRERQLYAWDDGYQIVYKLEMRKKEEEV
       :::::.:::::.:::::::::::::::::::::::::::::::::::::.::::::
       ASGTLAPERAALSYFPRRYGAHASLRYNPRERQLYAWDDGYQIVYKLEMKKKEEEV
               360       370       380       390       400
```

FIG.12

```
ALIGN calculates a global alignment of two sequences
 version 2.0uPlease cite: Myers and Miller, CABIOS (1989)
> hT257 a.a.                                  406 aa vs.
> Patent Protein W75120 - (untitled)          355 aa
scoring matrix: pam120.mat, gap penalties: -12/-4
86.9% identity;        Global alignment score: 1681

               10        20        30        40        50        60        70
inputs MGPSTPLLILFLLSWSGPLQGQQHHLVEYMERRLAALEERLAQCQDQSSRHAAELRDFKNKMLPLLEVAE
       ::::::::::::::::::::::::::::::::::::::::::::::::::::::::::::::::::::::
       MGPSTPLLILFLLSWSGPLQGQQHHLVEYMERRLAALEERLAQCQDQSSRHAAELRDFKNKMLPLLEVAE
               10        20        30        40        50        60        70

               80        90       100       110       120       130       140
inputs KEREALRTEADTISGRVDRLEREVDYLETQNPALPCVEFDEKVTGGPGTKGKGRRNEKYDMVTDCGYTIS
       ::::::::::::::::::::::::::::::::::::::::::::::::::::::::::::::::::::::
       KEREALRTEADTISGRVDRLEREVDYLETQNPALPCVEFDEKVTGGPGTKGKGRRNEKYDMVTDCGYTIS
               80        90       100       110       120       130       140

              150       160       170       180       190       200       210
inputs QVRSMKILKRFGGPAGLWTKDPLGQTEKIYVLDGTQNDTAFVFPRLRDFTLAMAARKASRVRVPFPWVGT
       ::::::::::::::::::::::::::::::::::::::::::::::::::::::::::::::::::::::
       QVRSMKILKRFGGPAGLWTKDPLGQTEKIYVLDGTQNDTAFVFPRLRDFTLAMAARKASRVRVPFPWVGT
              150       160       170       180       190       200       210

              220       230       240       250       260       270       280
inputs GQLVYGGFLYFARRPPGRPGGGGEMENTLQLIKFHLANRTVVDSSVFPAEGLIPPYGLTADTYIDLAADE
       ::::::::::::::::::::::::::::::::::::::::::::::::::::::::::::::::::::::
       GQLVYGGFLYFARRPPGRPGGGGEMENTLQLIKFHLANRTVVDSSVFPAEGLIPPYGLTADTYIDLAADE
              220       230       240       250       260       270       280

              290       300       310       320       330       340       350
inputs EGLWAVYATREDDRHLCLAKLDPQTLDTEQQWDTPCPRENAEAAFVICGTLYVVYNTRPASRARIQCSFD
       ::::::::::::::::::::::::::::::::::::::::::::::::::::::::::::::::::::::
       EGLWAVYATREDDRHLCLAKLDPQTLDTEQQWDTPCPRENAEAAFVICGTLYVVYNTRPASRARIQCSFD
              290       300       310       320       330       340       350

              360       370       380       390       400
inputs ASGTLTPERAALPYFPRRYGAHASLRYNPRERQLYAWDDGYQIVYKLEMRKKEEEV
       ::: .
       ASGPX---------------------------------------------------
```

FIG.13

```
version 2.0uPlease cite: Myers and Miller, CABIOS (1989)
> T257 n.a.                                     1832 aa vs.
> ac02146                                       1925 aa
scoring matrix: pam120.mat, gap penalties: -12/-4
93.5% identity;          Global alignment score: 9158

                10        20        30        40        50        60
inputs GTCGACCCACGCGTCC---GCGGACGCGTGGG--TGAGGGGAAGAGGCTGACTGTACGTTCCTTCTACTC
          ::: ::: :::   :: .:: :  :::  :::::::::.::::::::::::::::::::::::
       -----CCC-CGCCTCCAAAGCTAACCCTCGGGCTTGAGGGGAAGANGCTGACTGTACGTTCCTTCTACTC
                  10        20        30        40        50        60

          70        80        90       100       110       120       130
inputs TGGCACCACTCTCCAGGCTGCCATGGGGCCCAGCACCCCTCTCCTCATCTTGTTCCTTTTGTCATGGTCG
       ::::::::::::::::::::::::::::::::::::::::::::::::::::::::::::::::::::::
       TGGCACCACTCTCCAGGCTGCCATGGGGCCCAGCACCCCTCTCCTCATCTTGTTCCTTTTGTCATGGTCG
          70        80        90       100       110       120       130

         140       150       160       170       180       190       200
inputs GGACCCCTCCAAGGACAGCAGCACCACCTTGTGGAGTACATGGAACGCCGACTAGCTGCTTTAGAGGAAC
       ::::::::::::::::::::::::::::::::::::::::::::::::::::::::::::::::::::::
       GGACCCCTCCAAGGACAGCAGCACCACCTTGTGGAGTACATGGAACGCCGACTAGCTGCTTTAGAGGAAC
         140       150       160       170       180       190       200

         210       220       230       240       250       260       270
inputs GGCTGGCCCAGTGCCAGGACCAGAGTAGTCGGCATGCTGCTGAGCTGCGGGACTTCAAGAACAAGATGCT
       ::::::::::::::::::::::::::::::::::::::::::::::::::::::::::::::::::::::
       GGCTGGCCCAGTGCCAGGACCAGAGTAGTCGGCATGCTGCTGAGCTGCGGGACTTCAAGAACAAGATGCT
         210       220       230       240       250       260       270

          280       290       300       310       320       330       340
inputs -GCCACTGCTGGAGGTGGCAGAGAAGGAGCGGGAGGCACTCAGAACTGAGGCCGACACCATCTCCGGGAG
        :::::::::::::::::::::::::::::::::::::::::::::::::::::::::::::::::::::
       NGCCACTGCTGGAGGTGGCAGAGAAGGAGCGGGAGGCACTCAGAACTGAGGCCGACACCATCTCCGGGAG
          280       290       300       310       320       330       340

          350       360       370       380       390       400       410
inputs AGTGGATCGTCTGGAGCGGGAGGTAGACTATCTGGAGACCCAGAACCCAGCTCTGCCCTGTGTAGAGTTT
       ::::::::::::::::::::::::::::::::::::::::::::::::::::::::::::::::::::::
       AGTGGATCGTCTGGAGCGGGAGGTAGACTATCTGGAGACCCAGAACCCAGCTCTGCCCTGTGTAGAGTTT
          350       360       370       380       390       400       410

          420       430       440       450       460       470       480
inputs GATGAGAAGGTGACTGGAGGCCCTGGGACCAAAGGCAAGGGAAGAAGGAATGAGAAGTACGATATGGTGA
       ::::::::::::::::::::::::::::::::::::::::::::::::::::::::::::::::::::::
       GATGAGAAGGTGACTGGAGGCCCTGGGACCAAAGGCAAGGGAAGAAGGAATGAGAAGTACGATATGGTGA
          420       430       440       450       460       470       480
```

FIG.14A

```
      490       500       510       520       530       540       550
inputs CAGACTGTGGCTACACAATCTCTCAAGTGAGATCAATGAAGATTCTGAAGCGATTTGGTGGCCCAGCTGG
       ::::::::::::::::::::::::::::::::::::::::::::::::::::::::::::::::::::::
       CAGACTGTGGCTACACAATCTCTCAAGTGAGATCAATGAAGATTCTGAAGCGATTTGGTGGCCCAGCTGG
          490       500       510       520       530       540       550

          560       570       580       590       600       610       620
inputs TCTATGGACCAAGGATCCACTGGGGCAAACAGAGAAGATCTACGTGTTAGATGGGACACAGAATGACACA
       ::::::::::::::::::::::::::::::::::::::::::::::::::::::::::::::::::::::
       TCTATGGACCAAGGATCCACTGGGGCAAACAGAGAAGATCTACGTGTTAGATGGGACACAGAATGACACA
          560       570       580       590       600       610       620

          630       640       650       660       670       680       690
inputs GCCTTTGTCTTCCCAAGGCTGCGTGACTTCACCCTTGCCATGGCTGCCCGGAAAGCTTCCCGAGTCCGGG
       ::::::::::::::::::::::::::::::::::::::::::::::::::::::::::::::::::::::
       GCCTTTGTCTTCCCAAGGCTGCGTGACTTCACCCTTGCCATGGCTGCCCGGAAAGCTTCCCGAGTCCGGG
          630       640       650       660       670       680       690

          700       710       720       730       740       750       760
inputs TGCCCTTCCCCTGGGTAGGCACAGGGCAGCTGGTATATGGTGGCTTTCTTTATTTTGCTCGGAGGCCTCC
       ::::::::::::::::::::::::::::::::::::::::::::::::::::::::::::::::::::::
       TGCCCTTCCCCTGGGTAGGCACAGGGCAGCTGGTATATGGTGGCTTTCTTTATTTTGCTCGGAGGCCTCC
          700       710       720       730       740       750       760

          770       780       790       800       810       820       830
inputs TGGAAGACCTGGTGGAGGTGGTGAGATGGAGAACACTTTGCAGCTAATCAAATTCCACCTGGCAAACCGA
       ::::::::::::::::::::::::::::::::::::::::::::::::::::::::::::::::::::::
       TGGAAGACCTGGTGGAGGTGGTGAGATGGAGAACACTTTGCAGCTAATCAAATTCCACCTGGCAAACCGA
          770       780       790       800       810       820       830

          840       850       860       870       880       890       900
inputs ACAGTGGTGGACAGCTCAGTATTCCCAGCAGAGGGGCTGATCCCCCCCTACGGCTTGACAGCAGACACCT
       ::::::::::::::::::::::::::::::::::::::::::::::::::::::::::::::::::::::
       ACAGTGGTGGACAGCTCAGTATTCCCAGCAGAGGGGCTGATCCCCCCCTACGGCTTGACAGCAGACACCT
          840       850       860       870       880       890       900

          910       920       930       940       950       960       970
inputs ACATCGACCTGGCAGCTGATGAGGAAGGTCTTTGGGCTGTCTATGCCACCCGGGAGGATGACAGGCACTT
       ::::::::::::::::::::::::::::::::::::::::::::::::::::::::::::::::::::::
       ACATCGACCTGGCAGCTGATGAGGAAGGTCTTTGGGCTGTCTATGCCACCCGGGAGGATGACAGGCACTT
          910       920       930       940       950       960       970

          980       990      1000      1010      1020      1030      1040
inputs GTGTCTGGCCAAGTTAGATCCACAGACACTGGACACAGAGCAGCAGTGGGACACACCATGTCCCAGAGAG
       ::::::::::::::::::::::::::::::::::::::::::::::::::::::::::::::::::::::
       GTGTCTGGCCAAGTTAGATCCACAGACACTGGACACAGAGCAGCAGTGGGACACACCATGTCCCAGAGAG
          980       990      1000      1010      1020      1030      1040
```

FIG.14B

```
            1050      1060      1070      1080      1090      1100      1110
inputs AATGCTGAGGCTGCCTTTGTCATCTGTGGGACCCTCTATGTCGTCTATAACACCCGTCCTGCCAGTCGGG
       ::::::::::::::::::.:::::::::::::::::::::::::::::::::::::::::::::::::::
       AATGCTGAGGCTGCCTTTNTCATCTGTGGGACCCTCTATGTCGTCTATAACACCCGTCCTGCCAGTCGGG
            1050      1060      1070      1080      1090      1100      1110

            1120      1130      1140      1150      1160      1170      1180
inputs CCCGCATCCAGTGCTCCTTTGATGCCAGCGGCACCCTGACCCCTGAACGGGCAGCACTCCCTTATTTTCC
       ::::::::::::::::::::::::::::::: ::::::::::::::::::::::::::::::::::::::
       CCCGCATCCAGTGCTCCTTTGATGCCAGCGG-ACCCTGACCCCTGAACGGGCAGCACTCCCTTATTTTCC
            1120      1130      1140       1150      1160      1170      1180

            1190      1200      1210      1220      1230      1240      1250
inputs CCGCAGATATGGTGCCCATGCCAGCCTCCGCTATAACCCCCGAGAACGCCAGCTCTATGCCTGGGATGAT
       ::::::::::::::::::::::::::::::::::::::::::::::::::::::::::::::::::::::
       CCGCAGATATGGTGCCCATGCCAGCCTCCGCTATAACCCCCGAGAACGCCAGCTCTATGCCTGGGATGAT
             1190      1200      1210      1220      1230      1240      1250

            1260      1270      1280      1290      1300      1310      1320
inputs GGCTACCAGATTGTCTATAAGCTGGAGATGAGGAAGAAAGAGGAGGAGGTTTGAGGAGCTAGCCTTGTTT
        :::::::::::::::::::::::::::::::::::::::::::::::::::::::::::::::::::::
       CGCTACCAGATTGTCTATAAGCTGGAGATGAGGAAGAAAGAGGAGGAGGTTTGAGGAGCTAGCCTTGTTT
             1260      1270      1280      1290      1300      1310      1320

            1330      1340      1350      1360      1370      1380      1390
inputs TTTGCATCTTTCTCACTCCCATACATTTATATTATATCCCCACTAAATTTCTTGTTCCTCATTCTTCAAA
       ::::::::::::::::::::::::::::::::::::::::::::::::::::::::::::::::::::::
       TTTGCATCTTTCTCACTCCCATACATTTATATTATATCCCCACTAAATTTCTTGTTCCTCATTCTTCAAA
             1330      1340      1350      1360      1370      1380      1390

            1400      1410      1420      1430      1440      1450      1460
inputs TGTGGGCCAGTTGTGGCTCAAATCCTCTATATTTTTAGCCAATGGCAATCAAATTCTTTCAGCTCCTTTG
       ::::::::::::::::::::::::::::::::::::::::::::::::::::::::::::::::::::::
       TGTGGGCCAGTTGTGGCTCAAATCCTCTATATTTTTAGCCAATGGCAATCAAATTCTTTCAGCTCCTTTG
             1400      1410      1420      1430      1440      1450      1460

            1470      1480      1490      1500      1510      1520      1530
inputs TTTCATACGGAACTCCAGATCCTGAGTAATCCTTTTAGAGCCCGAAGAGTCAAAACCCTCAATGTTCCCT
       ::::::::::::::::::::::::::::::::::::::::::::::::::::::::::::::::::::::
       TTTCATACGGAACTCCAGATCCTGAGTAATCCTTTTAGAGCCCGAAGAGTCAAAACCCTCAATGTTCCCT
             1470      1480      1490      1500      1510      1520      1530

            1540      1550      1560      1570      1580      1590      1600
inputs CCTGCTCTCCTGCCCCATGTCAACAAATTTCAGGCTAAGGATGCCCCCAGACCCAGGGCTCTAACCTTGT
       ::::::::::::::::::::::::::::::::::::::::::::::: ::::::::::::::::::::::
       CCTGCTCTCCTGCCCCATGTCAACAAATTTCAGGCTAAGGATGCCCC-AGACCCAGGGCTCTAACCTTGT
             1540      1550      1560      1570      1580       1590      1600
```

FIG.14C

```
          1610      1620      1630      1640      1650      1660      1670
inputs ATGCGGGCAGGCCCAGGGAGCAGGCAGCAGTGTTCTTCCCCTCAGAGTGACTTGGGGAGGGAGAAATAGG
       ::::::::::::::::::::::::::::::::::::::::::::::::::::::::::::::::::::::
       ATGCGGGCAGGCCCAGGGAGCAGGCAGCAGTGTTCTTCCCCTCAGAGTGACTTGGGGAGGGAGAAATAGG
           1610      1620      1630      1640      1650      1660      1670

          1680      1690      1700      1710      1720      1730      1740
inputs AGGAGACGTCCAGCTCTGTCCTCTCTTCCTCACTCCTCCCTTCAGTGTCCTGAGGAACAGGACTTTCTCC
       ::::::::::::::::::::::::::::::::::::::::::::::::::: :::::::::::::::::
       AGGAGACGTCCAGCTCTGTCCTCTCTTCCTCACTCCTCCCTTCAGTGTCCTCAGGAACAGGACTTTCTCC
           1680      1690      1700      1710      1720      1730      1740

          1750      1760      1770      1780      1790      1800      1810
inputs ACATTGTTTTGTATTGCAACATTTTGCATTAAAAGGAAAATCCACTGCTAAAAAAAAAAAAAAAAAAAAA
       ::::::::::::::::::::::::::::::::::::::::::::: .. .:::::::::::::::::::::
       ACATTGTTTTGTATTGCAACATTTTGCATTAAAAGGAAAATCCANAAAAAAAAAAAAAAAAAAAAAAAAA
           1750      1760      1770      1780      1790      1800      1810

          1820                                              1830
inputs AAAAAAAAGG----------------------------------------GCGGCCGC-----------
       ::::::::..                                        ::::::::
       AAAAAAAAAAAAAAAAAAAAAAAAAAAAAAAAAAAAAAAAAAAAAAAAACTGCGGCCGCTGTCCCTTCTG
           1820      1830      1840      1850      1860      1870      1880

inputs -------------------------------------------

       TCGTCTTCTCGCAGCCGTACCCTTCTGTCGTCTTCTCGCAGCC
           1890      1900      1910      1920
```

FIG.14D

```
ALIGN calculates a global alignment of two sequences
 version 2.0uPlease cite: Myers and Miller, CABIOS (1989)
> mT257a.a.                                 406 aa vs.
> Patent Protein W75120 - (untitled)        355 aa
scoring matrix: pam120.mat, gap penalties: -12/-4
81.8% identity;         Global alignment score: 1599

                10        20        30        40        50        60        70
inputs MGPSAPLLLLFFLSWTGPLQGQQHHLVEYMERRLAALEERLAQCQDQSSRHAAELRDFKNKMLPLLEVAE
       ::::.:::.::.:::.::::::::::::::::::::::::::::::::::::::::::::::::::::::
       MGPSTPLLILFLLSWSGPLQGQQHHLVEYMERRLAALEERLAQCQDQSSRHAAELRDFKNKMLPLLEVAE
                10        20        30        40        50        60        70

                80        90       100       110       120       130       140
inputs KERETLRTEADSISGRVDRLEREVDYLETQNPALPCVELDEKVTGGPGAKGKGRRNEKYDMVTDCSYTVA
       ::::.::::::.::::::::::::::::::::::::::.::::::::::.:::::::::::::::.::..
       KEREALRTEADTISGRVDRLEREVDYLETQNPALPCVEFDEKVTGGPGTKGKGRRNEKYDMVTDCGYTIS
                80        90       100       110       120       130       140

               150       160       170       180       190       200       210
inputs QVRSMKILKRFGGSVGLWTKDPLGPAEKIYVLDGTQNDTAFVFPRLRDFTLAMAARKASRIRVPFPWVGT
       :::::::::::::..:::::::::..::::::::::::::::::::::::::::::::::.:::::::::
       QVRSMKILKRFGGPAGLWTKDPLGQTEKIYVLDGTQNDTAFVFPRLRDFTLAMAARKASRVRVPFPWVGT
               150       160       170       180       190       200       210

               220       230       240       250       260       270       280
inputs GQLVYGGFLYYARRPPGGPGGGGELENTLQLIKFHLANRTVVDSSVFPAESLIPPYGLTADTYIDLAADE
       ::::::::::.:::::: ::::::.:::::::::::::::::::::::::.:::::::::::::::::::
       GQLVYGGFLYFARRPPGRPGGGGEMENTLQLIKFHLANRTVVDSSVFPAEGLIPPYGLTADTYIDLAADE
               220       230       240       250       260       270       280

               290       300       310       320       330       340       350
inputs EGLWAVYATRDDDRHLCLAKLDPQTLDTEQQWDTPCPRENAEAAFVICGTLYVVYNTRPASRARIQCSFD
       ::::::::::.:::::::::::::::::::::::::::::::::::::::::::::::::::::::::::
       EGLWAVYATREDDRHLCLAKLDPQTLDTEQQWDTPCPRENAEAAFVICGTLYVVYNTRPASRARIQCSFD
               290       300       310       320       330       340       350

               360       370       380       390       400
inputs ASGTLAPERAALSYFPRRYGAHASLRYNPRERQLYAWDDGYQIVYKLEMKKKEEEV
       ::: .
       ASGPX---------------------------------------------------
```

FIG.15

```
ALIGN calculates a global alignment of two sequences
 version 2.0uPlease cite: Myers and Miller, CABIOS (1989)
> mT257 n.a.                                   1721 aa vs.
> Patent Nucleotide V34217 - (untitled)        1890 aa
scoring matrix: pam120.mat, gap penalties: -12/-4
76.2% identity;      Global alignment score: 6493
                               10                         20
inputs GT----------------CGACCCAC---GCGTCC--------------GACTTAAGG------------
       :.                :: :::::   :: :::              :.:::.:::
       GAGCAGGAGAGAAGGCACCGCCCCACCCCGCCTCCAAAGCTAACCCTCGGGCTTGAGGGGAAGAGGCTGA
               10        20        30        40        50        60        70

                                              30        40        50
inputs ------------------------------------CTGCCATGGGGCCCAGTGCTCCTCTGCTGCTCCT
                                           :::::::::::::::: .: ::::: ::  :: :
       CTGTACGTTCCTTCTACTCTGGCACCACTCTCCAGGCTGCCATGGGGCCCAGCACCCCTCTCCTCATCTT
               80        90       100       110       120       130       140

      60        70        80        90       100       110       120
inputs CTTCTTTTTGTCATGGACGGGACCCCTTCAGGGACAGCAGCACCACCTTGTGGAGTACATGGAACGCCGA
        ::: :::::::::::.:::::::::: ::.:::::::::::::::::::::::::::::::::::::::
       GTTCCTTTTGTCATGGTCGGGACCCCTCCAAGGACAGCAGCACCACCTTGTGGAGTACATGGAACGCCGA
              150       160       170       180       190       200       210

     130       140       150       160       170       180       190
inputs CTAGCTGCCTTAGAGGAACGGCTGGCCCAATGCCAGGATCAGAGTAGTCGGCATGCTGCCGAGCTTCGGG
       :::::::: ::::::::::::::::::::.:::::::: :::::::::::::::::::: ::::: ::::
       CTAGCTGCTTTAGAGGAACGGCTGGCCCAGTGCCAGGACCAGAGTAGTCGGCATGCTGCTGAGCTGCGGG
              220       230       240       250       260       270       280
```

FIG.16A

```
       200       210       220       230       240       250       260
inputs ACTTCAAAAACAAGATGTTGCCTCTCCTGGAGGTGGCAGAGAAGGAGCGGGAGACCCTCAGAACTGAAGC
       :::::::.::::::::: ::::.:: :::::::::::::::::::::::::::.: ::::::::::::.::
       ACTTCAAGAACAAGATGCTGCCACTGCTGGAGGTGGCAGAGAAGGAGCGGGAGGCACTCAGAACTGAGGC
              290       300       310       320       330       340       350

       270       280       290       300       310       320       330
inputs AGACTCCATCTCAGGAAGAGTGGACCGTCTTGAAAGGGAGGTAGACTATCTGGAGACACAGAACCCAGCT
        :::.::::::: ::.:::::::: ::::: ::. ::::::::::::::::::::: :::::::::::
       CGACACCATCTCCGGGAGAGTGGATCGTCTGGAGCGGGAGGTAGACTATCTGGAGACCCAGAACCCAGCT
              360       370       380       390       400       410       420

       340       350       360       370       380       390       400
inputs TTGCCCTGTGTAGAGCTGGATGAGAAGGTGACTGGAGGTCCTGGAGCCAAAGGCAAGGGCCGAAGAAATG
        ::::::::::::: : :::::::::::::::::: :::::.::::::::::::::  ::::.::::
       CTGCCCTGTGTAGAGTTTGATGAGAAGGTGACTGGAGGCCCTGGGACCAAAGGCAAGGGAAGAAGGAATG
              430       440       450       460       470       480       490

       410       420       430       440       450       460       470
inputs AGAAATACGATATGGTGACGGACTGTAGCTACACAGTCGCTCAGGTGAGGTCAATGAAGATCCTGAAGCG
       ::::.::::::::::::::.:::::.::::::::.:: ::::.::::.:::::::::::: ::::::::
       AGAAGTACGATATGGTGACAGACTGTGGCTACACAATCTCTCAAGTGAGATCAATGAAGATTCTGAAGCG
              500       510       520       530       540       550       560

       480       490       500       510       520       530       540
inputs GTTTGGTGGTTCAGTTGGCCTATGGACCAAGGATCCGCTGGGGCCAGCAGAGAAGATCTACGTGTTAGAC
       .::::::::  ::: ::: ::::::::::::::::::.::::::: :.:::::::::::::::::::::
       ATTTGGTGGCCCAGCTGGTCTATGGACCAAGGATCCACTGGGGCAAACAGAGAAGATCTACGTGTTAGAT
              570       580       590       600       610       620       630
```

FIG.16B

```
       550       560       570       580       590       600       610
inputs GGCACCCAGAACGACACGGCTTTTGTCTTCCCAAGGCTGCGTGACTTCACCCTTGCCATGGCTGCCCGGA
       :: :: ::::: :::::.:: :::::::::::::::::::::::::::::::::::::::::::::::::
       GGGACACAGAATGACACAGCCTTTGTCTTCCCAAGGCTGCGTGACTTCACCCTTGCCATGGCTGCCCGGA
               640       650       660       670       680       690       700

       620       630       640       650       660       670       680
inputs AAGCTTCCCGAATTCGGGTGCCCTTCCCCTGGGTAGGCACGGGGCAGCTGGTGTACGGTGGCTTCCTTTA
       :::::::::::.: ::::::::::::::::::::::::::.:::::::::::.:: :::::::: :::::
       AAGCTTCCCGAGTCCGGGTGCCCTTCCCCTGGGTAGGCACAGGGCAGCTGGTATATGGTGGCTTTCTTTA
               710       720       730       740       750       760       770

       690       700       710       720       730       740       750
inputs TTATGCTCGAAGGCCTCCTGGAGGACCTGGAGGGGGTGGTGAATTGGAGAACACTCTGCAGCTGATCAAA
       ::.::::::.::::::::::::.:::::::.::.::::::::..::::::::::: :::::::.::::::
       TTTTGCTCGGAGGCCTCCTGGAAGACCTGGTGGAGGTGGTGAGATGGAGAACACTTTGCAGCTAATCAAA
               780       790       800       810       820       830       840

       760       770       780       790       800       810       820
inputs TTTCACTTGGCAAACCGAACAGTGGTGGATAGCTCAGTGTTCCCTGCAGAGAGCCTGATACCCCCCTACG
       :: ::: :::::::::::::::::::::: ::::::::.:::::.::::::.: ::::: ::::::::::
       TTCCACCTGGCAAACCGAACAGTGGTGGACAGCTCAGTATTCCCAGCAGAGGGGCTGATCCCCCCCTACG
               850       860       870       880       890       900       910

       830       840       850       860       870       880       890
inputs GCCTGACAGCAGATACATATATCGACCTGGCAGCTGATGAGGAGGGCCTGTGGGCTGTCTATGCCACTCG
       :: :::::::::: :: :: :::::::::::::::::::::::.:: :: ::::::::::::::::: ::
       GCTTGACAGCAGACACCTACATCGACCTGGCAGCTGATGAGGAAGGTCTTTGGGCTGTCTATGCCACCCG
               920       930       940       950       960       970       980
```

FIG.16C

```
       900       910       920       930       940       950       960
inputs AGATGATGACAGGCATTTGTGTCTAGCCAAGTTAGACCCACAGACACTTGACACAGAGCAGCAGTGGGAC
       .:: ::::::::::: ::::::::.::::::::::: :::::::::: ::::::::::::::::::::::
       GGAGGATGACAGGCACTTGTGTCTGGCCAAGTTAGATCCACAGACACTGGACACAGAGCAGCAGTGGGAC
              990      1000      1010      1020      1030      1040      1050

       970       980       990      1000      1010      1020      1030
inputs ACACCATGTCCCAGAGAGAACGCAGAGGCTGCGTTTGTCATCTGTGGGACCCTGTACGTTGTCTATAACA
       :::::::::::::::::::: ::.:::::::: ::::::::::::::::::: :: :: :::::::::
       ACACCATGTCCCAGAGAGAATGCTGAGGCTGCCTTTGTCATCTGTGGGACCCTCTATGTCGTCTATAACA
             1060      1070      1080      1090      1100      1110      1120

      1040      1050      1060      1070      1080      1090      1100
inputs CCCGCCCTGCCAGTAGGGCTCGTATTCAGTGTTCCTTCGATGCCAGTGGTACTCTCGCCCCTGAAAGGGC
       :::: ::::::::: :::: :: :: ::::: ::::: :::::::: :: :: :: .:::::::: ::::
       CCCGTCCTGCCAGTCGGGCCCGCATCCAGTGCTCCTTTGATGCCAGCGG-ACCCTGACCCCTGAACGGGC
             1130      1140      1150      1160      1170      1180

      1110      1120      1130      1140      1150      1160      1170
inputs AGCACTCTCCTATTTTCCACGCCGATATGGTGCCCATGCCAGCCTTCGCTATAACCCCCGTGAGCGCCAG
       ::::::: : :::::::: ::: :::::::::::::::::::::: ::::::::::::.::.:::::::
       AGCACTCCCTTATTTTCCCCGCAGATATGGTGCCCATGCCAGCCTCCGCTATAACCCCCGAGAACGCCAG
      1190      1200      1210      1220      1230      1240      1250

      1180      1190      1200      1210      1220      1230      1240
inputs CTGTATGCCTGGGATGATGGCTACCAGATTGTCTACAAATTGGAGATGAAGAAGAAGGAGGAGGAAGTTT
       :: ::::::::::::::::::::::::::::::::: ::. :::::::::.:::::.::::::::.::::
       CTCTATGCCTGGGATGATGGCTACCAGATTGTCTATAAGCTGGAGATGAGGAAGAAAGAGGAGGAGGTTT
      1260      1270      1280      1290      1300      1310      1320
```

FIG.16D

```
       1250      1260        1270      1280      1290          1300      1310
inputs AAGCAGCTAGCCTTGTGCT---CTTGATTCTTATGCCCAGACATTTATATT-----CCTGTGAGCTCTCC
        .:: ::::::::::::  :   :.: .:::: :  :::: :::::::::::     :: .  :. : ::
       GAGGAGCTAGCCTTGTTTTTTTGCATCTTTCTCACTCCCATACATTTATATTATATCCCCACTAAATTTCT
       1330      1340      1350      1360      1370      1380      1390

               1320      1330      1340      1350      1360      1370
inputs TGCAGTTCATCCTTCAAAACGAAGGCCAGTGGTGGTAGCTCATATACCCTAATTTCTAA----AGGACAA
       :: .  :::: ::::::::. :..:::::::: ::::   ::::.:: : :::..:: :.:    : :.:::
       TGTTCCTCATTCTTCAAAT-GTGGGCCAGTTGTGG---CTCAAATCCTCTATATTTTTAGCCAATGGCAA
       1400      1410        1420      1430         1440      1450      1460

         1380        1390      1400      1410      1420        1430      1440
inputs CCAAATTCTCA-AGCCCCTCTGTTTTATGCAGAACTCCAGATCCTGGGTAG-CATTTTAGAACTGAACAG
        :::::::: . ::: ::: ::::: ::.:.:::::::::::::::.:::. : ::::::::.:  .: ::
       TCAAATTCTTTCAGCTCCTTTGTTTCATACGGAACTCCAGATCCTGAGTAATCCTTTTAGAGCCCGA-AG
         1470      1480      1490      1500      1510      1520      1530

          1450      1460            1470      1480      1490
inputs CAAACAAACACCCTAAAT------CTTCACTCCTGCCTTATGTCCACAAAGTT-------TAGTT---CC
        ..  :::: : :.:..:        :: :.::::::::  ::::: ::::: ::        ..:.:   ::
       AGTCAAAACCCTCAATGTTCCCTCCTGCTCTCCTGCCCCATGTCAACAAATTTCAGGCTAAGGATGCCCC
          1540      1550      1560      1570      1580      1590      1600

       1500      1510      1520      1530      1540      1550      1560
inputs AAACTCAGAGCCCTGTCCTTTGGAGAGGGTCAACCCCAGACAGCAGGCGACAGCATTCTTGCCCTCAGTA
       :.:: :::.:: ::..::::  ..: ::: ::. :::::. :::::::..::: .::::: :::::::..
       AGACCCAGGGCTCTAACCTTGTATGCGGG-CAGGCCCAGGGAGCAGGCAGCAGTGTTCTTCCCCTCAGAG
          1610      1620      1630       1640      1650      1660      1670
```

FIG.16E

```
          1570       1580      1590             1600         1610      1620
inputs TGACC-GAAGGGAGAGAACTCAGAGA-------CAAAGCTGCCCTC----CCTCCCTTCCCCCTCCAGTG
       ::::  :..:.:.::::: : .:::.        ::.  ::: ::::    :::: :: : :::: :::::
       TGACTTGGGGAGGGAGAAATAGGAGGAGACGTCCAGCTCTGTCCTCTCTTCCTCACTCCTCCCTTCAGTG
          1680      1690      1700      1710      1720      1730      1740

         1630      1640      1650      1660      1670      1680      1690
inputs TAGGGGAGAATGGGGCTTTCCCCACATCACTTTGTATGGTAACAGTTTGCATTAAAAGGAAAACCCAC--
       :   :..::: .::.::::: :::::: . ::::::: : :::: :::::::::::::::::: ::::
       TCCTGAGGAACAGGACTTTCTCCACATTGTTTTGTATTGCAACATTTTGCATTAAAAGGAAAATCCACTG
          1750      1760      1770      1780      1790      1800      1810

          1700      1710                                                1720
inputs CAAAAAAAAAAAAAAAAGGG--------------CGGC----------------------------CG
       ::::::::::::::::...               ::::                            :.
       CAAAAAAAAAAAAAAAAAAAAAAAAAAAAAAAAACGGCACGAGGGGGGGTCCCGTACCCAATNGCCCTCA
          1820      1830      1840      1850      1860      1870      1880

inputs C------
       :
       CATGCAT
          1890
```

FIG.16F

```
GTCGACCCACGCGTNCNTCCAGCGTNCGGAGCCGCCCTGGGTGTCAGCGGCTCGGCTCCCGCGCACGCTCCGGCCGTCG    79

                                                                             M      1
CGCAGCCTCGGCACCTGCAGGTCCGTGCGTCCCGCGGCTGGCGCCCCTGACTCCGTCCCGGCCAGGGAGGGCC ATG    155

 I   S   L   P   G   P   L   V   T   N   L   X   R   F   L   F   L   G   L   S     21
ATT TCC CTC CCG GGG CCC CTG GTG ACC AAC TTG NTG CGG TTT TTG TTC CTG GGG CTG AGT   215

 A   L   A   P   P   S   R   A   Q   L   Q   L   H   L   P   A   N   R   L   Q     41
GCC CTC GCG CCC CCC TCG CGG GCC CAG CTG CAA CTG CAC TTG CCC GCC AAC CGG TTG CAG   275

 A   V   E   E   G   E   S   G   A   S   A   W   Y   T   L   H   R   E   V   S     61
GCG GTG GAG GAG GGG GAA AGT GGT GCT TCA GCA TGG TAC ACC TTG CAC AGG GAG GTG TCT   335

 S   S   Q   P   W   E   V   P   F   V   M   W   F   F   K   Q   K   E   K   E     81
TCA TCC CAG CCA TGG GAG GTG CCC TTT GTG ATG TGG TTC TTC AAA CAG AAA GAA AAG GAG   395

 D   Q   V   L   S   Y   I   N   G   V   T   T   S   K   P   G   V   S   L   V    101
GAT CAG GTG TTG TCC TAC ATC AAT GGG GTC ACA ACA AGC AAA CCT GGA GTA TCC TTG GTC   455

 Y   S   M   P   S   R   N   L   S   L   R   V   E   G   L   Q   E   K   D   S    121
TAC TCC ATG CCC TCC CGG AAC CTG TCC CTG CGG GTG GAG GGT CTC CAG GAG AAA GAC TCT   515
```

FIG.17A

```
 G   P   Y   S   C   S   V   N   V   Q   D   K   Q   G   K   S   R   G   H   S    141
GGC CCC TAC AGC TGC TCC GTG AAT GTG CAA GAC AAA CAA GGC AAA TCT AGG GGC CAC AGC   575

 I   K   T   L   E   L   N   V   L   V   P   P   A   P   P   S   C   R   L   Q    161
ATC AAA ACC TTA GAA CTC AAT GTA CTG GTT CCT CCA GCT CCT CCA TCC TGC CGT CTC CAG   635

 G   V   P   H   V   G   A   N   V   T   L   S   C   Q   S   P   R   S   K   P    181
GGT GTG CCC CAT GTG GGG GCA AAC GTG ACC CTG AGC TGC CAG TCT CCA AGG AGT AAG CCC   695

 A   V   Q   Y   Q   W   D   R   Q   L   P   S   F   Q   T   F   F   A   P   A    201
GCT GTC CAA TAC CAG TGG GAT CGG CAG CTT CCA TCC TTC CAG ACT TTC TTT GCA CCA GCA   755

 L   D   V   I   R   G   S   L   S   L   T   N   L   S   S   S   M   A   G   V    221
TTA GAT GTC ATC CGT GGG TCT TTA AGC CTC ACC AAC CTT TCG TCT TCC ATG GCT GGA GTC   815

 Y   V   C   K   A   H   N   E   V   G   T   A   Q   C   N   V   T   L   E   V    241
TAT GTC TGC AAG GCC CAC AAT GAG GTG GGC ACT GCC CAA TGT AAT GTG ACG CTG GAA GTG   875

 S   T   G   P   G   A   A   V   V   A   E   A   V   V   G   T   L   V   G   L    261
AGC ACA GGG CCT GGA GCT GCA GTG GTT GCT GAA GCT GTT GTG GGT ACC CTG GTT GGA CTG   935

 G   L   L   A   G   L   V   L   L   Y   H   R   R   G   K   A   L   E   E   P    281
GGG TTG CTG GCT GGG CTG GTC CTC TTG TAC CAC CGC CGG GGC AAG GCC CTG GAG GAG CCA   995

 A   N   D   I   K   E   D   A   I   A   P   R   T   L   P   W   P   K   S   S    301
GCC AAT GAT ATC AAG GAG GAT GCC ATT GCT CCC CGG ACC CTG CCC TGG CCC AAG AGC TCA  1055
```

FIG.17B

```
 D   T   I   S   K   N   G   T   L   S   S   V   T   S   A   R   A   L   R   P    321
GAC ACA ATC TCC AAG AAT GGG ACC CTT TCC TCT GTC ACC TCC GCA CGA GCC CTC CGG CCA  1115

 P   H   G   P   P   R   P   G   A   L   T   P   T   P   S   L   S   S   Q   A    341
CCC CAT GGC CCT CCC AGG CCT GGT GCA TTG ACC CCC ACG CCC AGT CTA TCC AGC CAG GCC  1175

 L   P   S   P   R   H   A   H   D   R   W   G   P   P   S   T   N   I   P   H    361
CTG CCC TCA CCA AGA CAT GCC CAC GAC AGA TGG GGC CCA CCC TCA ACC AAT ATC CCC CAT  1235

 P   W   W   G   F   F   L   W   L   *    371
CCC TGG TGG GGT TTT TTC CTT TGG CTT TGA  1265

GCCGCATGGGTGCTGNGCCTGTGATGGNGCCTGCCCAGAGTCAAGCTGGCTCTCTGGTATGATGACCCCACCACTCATT    1344

GGCTAAAGGATTTGGGGTCTCTCCTTCCTATAAGGGTCACCTCTAGCACAGAGGCCTGAGTCATGGGAAAGAGTCACAC    1423

TCCTGACCCTTAGTACTCTGCCCCCACCTCTCTTTACTGTGGGAAAACCATCTCAGTAAGACCTAAGTGTCCAGGAGAC    1502

AGAAGGAGAAGAGGAAGTGGATCTGGAATTGGGAGGAGCCTCCACCCACCCCTGACTCCTCCTTATGAAGCCAGCTGCT    1581

GAAATTAGCTACTCACCAAGAGTGAGGGGCAGAGACTTCCAGTCACTGAGTCTCCCAGGCCCCCTTGATCTGTACCCCA    1660

CCCCTATCTAACACCACCCTTGGCTCCCACTCCAGCTCCCTGTATTGATATAACCTGTCAGGCTGGCTTGGTTAGGTTT    1739

TACTGGGGCAGAGGATAGGGAATCTCTTATTAAAACTAACATGAAATATGTGTTGTTTTCATTTGCAAATTTAAATAAA    1818

GATACATAATGTTTGTATGAGATAAGAAAAAAAAAAAAAAAGGGCGGCCGC    1869
```

FIG.17C

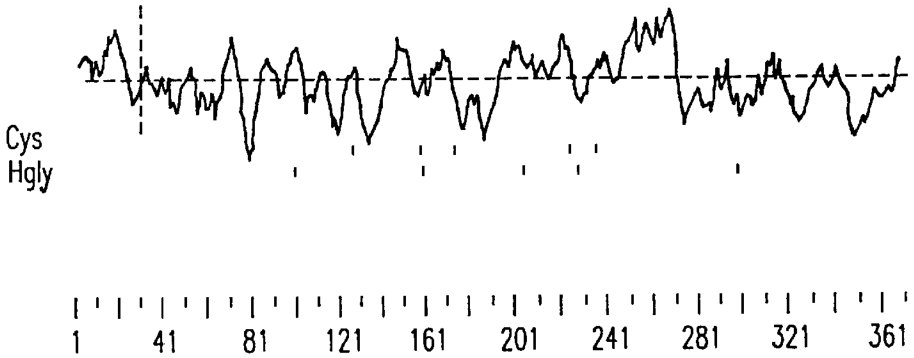

MISLPGPLVTNLXRFLFLGLSALAPPSRAQLQLHLPANRLQAVEEGESGASAWYTLHREV
SSSQPWEVPFVMWFFKQKEKEDQVLSYINGVTTSKPGVSLVYSMPSRNLSLRVEGLQEKD
SGPYSCSVNVQDKQGKSRGHSIKTLELNVLVPPAPPSCRLQGVPHVGANVTLSCQSPRSK
PAVQYQWDRQLPSFQTFFAPALDVIRGSLSLTNLSSSMAGVYVCKAHNEVGTAQCNVTLE
VSTGPGAAVVAEAVVGTLVGLGLLAGLVLLYHRRGKALEEPANDIKEDAIAPRTLPWPKS
SDTISKNGTLSSVTSARALRPPHGPPRPGALTPTPSLSSQALPSPRHAHDRWGPPSTNIP
HPWWGFFLWL

FIG.18

```
GTCGACCCACGCGTCCGGTGCACATTCGGGTTGCCGCCGCTCACCCACAACACCTGTAGACACCGTGTGTCCAACTCTC   79

                            M   I   L   Q   A   G   T   P   E   T   S   L   L    13
CCTGAGTACTCCGGGCCAAGGAGGGCC ATG ATT CTT CAG GCT GGA ACC CCC GAG ACC AGC TTG CTG  145

 R   V   L   F   L   G   L   S   T   L   A   A   F   S   R   A   Q   M   E   L    33
CGG GTT TTG TTC CTG GGA CTG AGT ACC CTT GCT GCC TTC TCC CGA GCT CAG ATG GAG TTG  205

 H   V   P   P   G   L   N   K   L   E   A   V   E   G   E   E   V   V   L   P    53
CAC GTG CCC CCG GGC CTC AAC AAA TTG GAA GCG GTA GAG GGA GAA GAA GTG GTG CTC CCC  265

 A   W   Y   T   M   A   R   E   E   S   W   S   H   P   R   E   V   P   I   L    73
GCC TGG TAC ACG ATG GCA CGG GAG GAG TCG TGG TCC CAC CCC CGG GAG GTG CCC ATC CTG  325

 I   W   F   L   E   Q   E   G   K   E   P   N   Q   V   L   S   Y   I   N   G    93
ATC TGG TTC TTG GAA CAA GAA GGG AAG GAA CCA AAC CAG GTG TTG TCT TAC ATT AAT GGA  385

 V   M   T   N   K   P   G   T   A   L   V   H   S   I   S   S   R   N   V   S   113
GTC ATG ACA AAT AAA CCT GGA ACA GCC CTG GTC CAC TCT ATC TCT TCA CGG AAT GTG TCC  445

 L   R   L   G   A   L   Q   E   G   D   S   G   T   Y   R   C   S   V   N   V   133
CTG CGC CTG GGG GCA CTC CAG GAG GGA GAC TCT GGG ACT TAC CGC TGT TCT GTC AAT GTG  505

 Q   N   D   E   G   K   S   I   G   H   S   I   K   S   I   E   L   K   V   L   153
CAG AAT GAT GAA GGC AAA AGT ATA GGC CAC AGC ATC AAA AGC ATA GAG CTC AAA GTG CTG  565
```

FIG.19A

```
 V   P   P   A   P   P   S   C   S   L   Q   G   V   P   Y   V   G   T   N   V    173
GTT CCT CCA GCT CCT CCA TCC TGT AGT TTA CAG GGT GTA CCC TAT GTC GGG ACC AAT GTG   625

 T   L   N   C   K   S   P   R   S   K   P   T   A   Q   Y   Q   W   E   R   L    193
ACC CTG AAC TGC AAG TCC CCA AGG AGT AAA CCT ACT GCT CAG TAC CAG TGG GAG AGG CTG   685

 A   P   S   S   Q   V   F   F   G   P   A   L   D   A   V   R   G   S   L   K    213
GCC CCA TCC TCC CAG GTC TTC TTT GGA CCA GCC TTA GAT GCT GTT CGT GGA TCT TTA AAG   745

 L   T   N   L   S   I   A   M   S   G   V   Y   V   C   K   A   Q   N   R   V    233
CTC ACT AAC CTT TCC ATT GCC ATG TCT GGA GTC TAT GTC TGC AAG GCT CAA AAC AGA GTG   805

 G   F   A   K   C   N   V   T   L   D   V   M   T   G   S   K   A   A   V   V    253
GGC TTT GCC AAG TGC AAC GTG ACC TTG GAC GTG ATG ACA GGG TCC AAG GCT GCA GTG GTC   865

 A   G   A   V   V   G   T   F   V   G   L   V   L   I   A   G   L   V   L   L    273
GCT GGA GCA GTT GTG GGC ACT TTT GTT GGG TTG GTG CTG ATA GCT GGG CTG GTC CTG TTG   925

 Y   Q   R   R   S   K   T   L   E   E   L   A   N   D   I   K   E   D   A   I    293
TAC CAG CGC CGG AGC AAG ACC TTG GAA GAG CTG GCC AAT GAT ATC AAG GAA GAT GCC ATT   985

 A   P   R   T   L   P   W   T   K   G   S   D   T   I   S   K   N   G   T   L    313
GCT CCC CGG ACC TTG CCT TGG ACC AAA GGC TCA GAC ACA ATC TCC AAG AAT GGG ACA CTT  1045

 S   S   V   T   S   A   R   A   L   R   P   P   K   A   A   P   P   R   P   G    333
TCT TCG GTC ACC TCA GCA CGA GCT CTG CGG CCA CCC AAG GCT GCT CCT CCA AGA CCT GGC  1105
```

FIG.19B

```
 T   F   T   P   T   P   S   V   S   S   Q   A   L   S   S   P   R   L   P   R    353
ACA TTT ACT CCC ACA CCC AGT GTC TCT AGC CAG GCC CTG TCC TCA CCA AGA CTG CCC AGG  1165

 V   D   E   P   P   P   Q   A   V   S   L   T   P   G   G   V   S   S   S   A    373
GTA GAT GAA CCC CCA CCT CAG GCA GTG TCC CTG ACC CCA GGT GGG GTT TCT TCT TCT GCT  1225

 L   S   R   M   G   A   V   P   V   M   V   P   A   Q   S   Q   A   G   S   L    393
CTG AGC CGC ATG GGT GCT GTG CCT GTG ATG GTG CCT GCA CAG AGT CAG GCT GGG TCT CTT  1285

 V   *                                                                            395
GTG TGA                                                                          1291

TAGCCCAGGCACTCATTAGCTACATCTGGTATCTGACCTTTCTGTAAAGGTCTCCTTGTGGCACAGAGGACTCAATCTT  1370

GGGAGGATGCCCACATTCTAGACCTCCAGTCCTTTGCTCCTACCTCCTTCTATTGTTGGAATACTGGGCCTCAGTAAGA  1449

CTAAAATCTGGGTCAAAGGACAAAAGGAGGAAATGGACCTGAGGTAGGGGGTTGGGAGTGAGGAGGCTTCACTTCCTCC  1528

CTGCTTCTCCCTGAAGCCAGATGAATGCTGCGGAAGATCGGCTACCCTCCAAGGGCTCTGGAGGAGACTGCCAGTCAGT  1607

GATGCCCCTGGCTCTGTGATCTGTACAACACCCTTATCTAATGCTGTCCTTTGCCGTTCGCTCCATCTCCCTGTATTAA  1686

TATAACCTGTCCTGCTGGCTTGGCTGGGTTTTGTTGTAGCAGGGGGATAGGAAAGACATTTTAAAATCTGACTTGAAAT  1765

TGATGTTTTTGTTTTTATTTTGCAAATTTCAATAAAGATACATCGCATTTGCATGGAAAAAAAAAAAAAAAGGGCGGCC  1844

GC                                                                               1846
```

FIG.19C

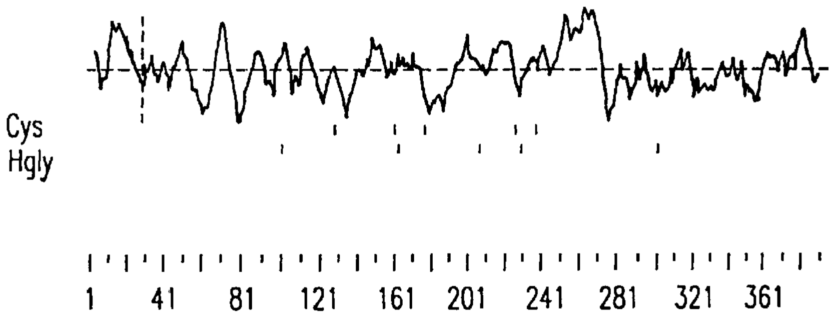

>mT258
MILQAGTPETSLLRVLFLGLSTLAAFSRAQMELHVPPGLNKLEAVEGEEVVLPAWYTMAR
EESWSHPREVPILIWFLEQEGKEPNQVLSYINGVMTNKPGTALVHSISSRNVSLRLGALQ
EGDSGTYRCSVNVQNDEGKSIGHSIKSIELKVLVPPAPPSCSLQGVPYVGTNVTLNCKSP
RSKPTAQYQWERLAPSSQVFFGPALDAVRGSLKLTNLSIAMSGVYVCKAQNRVGFAKCNV
TLDVMTGSKAAVVAGAVVGTFVGLVLIAGLVLLYQRRSKTLEELANDIKEDAIAPRTLPW
TKGSDTISKNGTLSSVTSARALRPPKAAPPRPGTFTPTPSVSSQALSSPRLPRVDEPPPQ
AVSLTPGGVSSSALSRMGAVPVMVPAQSQAGSLV

FIG.20

```
ALIGN calculates a global alignment of two sequences
 version 2.0uPlease cite: Myers and Miller, CABIOS (1989)
> hT258a.a.                                   370 aa vs.
> mT258 a.a.                                  394 aa
scoring matrix: pam120.mat, gap penalties: -12/-4
62.8% identity;        Global alignment score: 1085

               10        20        30          40        50        60
inputs MISLPGPLVTNLXRFLFLGLSALAPPSRAQLQLHLPA--NRLQAVEEGESGASAWYTLHREVSSSQPWEV
       ::  .:   :.:.: ::::::.::. ::::..::.:.  :.:.:::  :   .::::. :: : :.:.::
       MILQAGTPETSLLRVLFLGLSTLAAFSRAQMELHVPPGLNKLEAVEGEEVVLPAWYTMAREESWSHPREV
               10        20        30        40        50        60        70

       70       80         90       100       110       120       130
inputs PFVMWFFKQKEKE-DQVLSYINGVTTSKPGVSLVYSMPSRNLSLRVEGLQEKDSGPYSCSVNVQDKQGKS
       :...::. :  :: .::::::::: :.:::..:: :..:::.:::. .::: ::: : ::::::. .:::
       PILIWFLEQEGKEPNQVLSYINGVMTNKPGTALVHSISSRNVSLRLGALQEGDSGTYRCSVNVQNDEGKS
               80        90       100       110       120       130       140

       140       150       160       170       180       190       200
inputs RGHSIKTLELNVLVPPAPPSCRLQGVPHVGANVTLSCQSPRSKPAVQYQWDRQLPSFQTFFAPALDVIRG
        :::::..::.:::::::::: ::::: ::.::::.:.::::::..::::.:  :: :.::.::::..::
       IGHSIKSIELKVLVPPAPPSCSLQGVPYVGTNVTLNCKSPRSKPTAQYQWERLAPSSQVFFGPALDAVRG
              150       160       170       180       190       200       210

       210       220       230       240       250       260       270
inputs SLSLTNLSSSMAGVYVCKAHNEVGTAQCNVTLEVSTGPGAAVVAEAVVGTLVGLGLLAGLVLLYHRRGKA
       :: ::::: .:.:::::::.: :: :.:::::.: ::. ::::: :::::.::: :.:::::::.::.:.
       SLKLTNLSIAMSGVYVCKAQNRVGFAKCNVTLDVMTGSKAAVVAGAVVGTFVGLVLIAGLVLLYQRRSKT
              220       230       240       250       260       270       280

       280       290       300       310       320        330       340
inputs LEEPANDIKEDAIAPRTLPWPKSSDTISKNGTLSSVTSARALRPPHG-PPRPGALTPTPSLSSQALPSPR
       ::: :::::::::::::::: :.:::::::::::::::::::::: . :::::..:::::.:::::.:::
       LEELANDIKEDAIAPRTLPWTKGSDTISKNGTLSSVTSARALRPPKAAPPRPGTFTPTPSVSSQALSSPR
              290       300       310       320       330       340       350

                             350       360       370
inputs HAH---------------------DRWGPPSTNIPHPWWGFFLWL
       ..                      .: :. .. .: .  .  : .
       LPRVDEPPPQAVSLTPGGVSSSALSRMGAVPVMVPAQSQAGSL-V
              360       370       380       390
```

FIG.21

```
ALIGN calculates a global alignment of two sequences
 version 2.0uPlease cite: Myers and Miller, CABIOS (1989)
> hT258a.a.                                     370 aa vs.
> SwissProt Q99795 - (untitled)                 319 aa
scoring matrix: pam120.mat, gap penalties: -12/-4
23.0% identity;        Global alignment score: -102

                10        20        30        40        50        60
inputs MISLPGPLVTNLXRFLFLGLSALAPPSRAQLQLHLPANRLQAVEEG-ESGASAWYTLHREVSSSQPWEVP
       :..   :.. .:.  . . ..:..  .   .. :. . ..  ..      ...:..  : .
       MVGKMWPVLWTLCA-VRVTVDAISVETPQDV-LRASQGKSVTLPCTYHTSTSSREGLIQWDKLLLTHTER
                10         20        30         40        50        60

      70        80        90       100       110       120       130
inputs FVMWFFKQKEKEDQVLSYINGVTTSKPGVSLVYSMPSRNLSLRVEGLQEKDSGPYSCSVNVQDKQGKSRG
        :.: : .:.        ::.:    :  ::.  .     . :. .. :   :.: : :::.. .      :
       VVIWPFSNKN-------YIHG-ELYKNRVSISNNAEQSDASITIDQLTMADNGTYECSVSLMSDLE---G
       70                80         90       100       110       120

     140       150       160       170       180         190       200
inputs HSIKTLELNVLVPPAPPSCRLQGVPHVGANVTLSCQSPRSKPAVQYQWDR--QLPSFQTFFAPALDVIRG
       ..     . : :::::. : :  ..:    .:.:. :.::: . :. :: : :    :    : .  :: .
       NTKSRVRLLVLVPPSKPECGIEGETIIGNNIQLTCQSKEGSPTPQYSWKRYNILNQEQPLAQPASGQ---
       130       140       150       160       170       180       190

       210       220       230       240        250       260       270
inputs SLSLTNLSSSMAGVYVCKAHNEVGTAQCNVTLEVSTGP-GAAVVAEAVVGTLVGLGLLAGLVLLYHRRGK
       ..:: :.:.. .: :.: . :: ::  ::.:..: . . ..:. .  .::....: ... ..      :::
       PVSLKNISTDTSGYYICTSSNEEGTQFCNITVAVRSPSMNVALYVGIAVGVVAALIIIGIIIYCCCCRGK
          200       210       220       230       240       250       260

        280       290       300       310       320       330       340
inputs ALEEPANDIKEDAIAPRTLPWPKSSDTISKNGTLSSVTSARALRPPHGPPRPGALTPTPSLSSQALPSPR
        .. ..: ::::                           :. : .   : :  :   .    .. . :
       --DDNTED-KEDA-------------------------RPNREAYEEP-PEQLRELSREREEE-DDYR
           270                                  280        290        300

        350       360       370
inputs HAHDRWGPPSTNIPHPWWGFFLWL
       .. .:  . . . :.       :
       QEEQR--STGRESPDH-----LDQ
              310
```

FIG.22

```
ALIGN calculates a global alignment of two sequences
 version 2.0uPlease cite: Myers and Miller, CABIOS (1989)
> hT258 n.a.                                 1869 aa vs.
> GenBank U79725 - Human A33 antigen precursor mR  2793 aa
scoring matrix: pam120.mat, gap penalties: -12/-4
40.6% identity;        Global alignment score: 1182

                         10              20
inputs GTCGACCC-----------ACGCGTNCNT------CCAG---------------C------------
         : ::::           .:  :  .:.:      ::.:               :
       --CTACCCCTTTGTGAGCAGTCTAGGACTTTGTACACCTGTTAAGTAGGGAGAAGGCAGGGGAGGTGGCT
                 10        20        30        40        50        60

                         30                                  40         50
inputs ----------GTNC-----GGAG-----------CCGC------CCT-------GGGTGTCA-GCG-GC
                  :..:     :::.            :: :       :::       .::::.:: . : ::
       GGTTTAAGGGGAACTTGAGGGAAGTAGGGAAGACTCCTCTTGGGACCTTTGGAGTAGGTGACACATGAGC
       70        80        90        100       110       120       130

            60             70             80             90
inputs TCGGCTCCCGCGCAC--GC---TCCGGCCGT----CGCGC-AGCCT---CGGCA----C----C------
        :.:: :: :: :::  ::    :::.:: :.    : :.: .:::.   :.::.     :    :
       CCAGCCCCAGCTCACCTGCCAATCCAGCTGAGGAGCTCACCTGCCAATCCAGCTGAGGCTGGGCAGAGGT
       140       150       160       170       180       190       200

                                 100                110          120
inputs -------------------TGCAGG----TCC----GTGC--GTCCCG---CGGCTGGCGCC----CCTG
                           ::::::    :::    : ::  : :: :   : ::::  ::     ::.:
       GGGTGAGAAGAGGGAAAATTGCAGGGACCTCCAGTTGGGCCAGGCCAGAAGCTGCTGTAGCTTTAACCAG
       210       220       230       240       250       260       270

       130                 140                    150
inputs AC---TCCGTCC----------CGGCCAGGGA------------GGGC---------------CATGA
       ::    :: :.::          : ::::: ::            ::::               ::::.
       ACAGCTCAGACCTGTCTGGAGGCTGCCAGTGACAGGTTAGGTTTAGGGCAGAGAAGAAGCAAGACCATGG
       280       290       300       310       320       330       340

                 160                  170          180
inputs TTT-----------CC-----------CTCCCGGGGCC--CCTGGTGACCAAC------------TTGN
       :              ::           :.: : : ::   :  ::::::::..:                : :.
       TGGGGAAGATGTGGCCTGTGTTGTGGACACTCTGTGCAGTCAGGGTGACCGTCGATGCCATCTCTGTGGA
       350       360       370       380       390       400       410

      190           200                210          220
inputs TGC------GGTTTTTGTTC--------CTGGGGCTGAGTG---CCCT-C---GCGCC--CC--------
       ..:       ::.  :: :::         :.:::. .:::::   :::: :    ::.::  ::
       AACTCCGCAGGACGTTCTTCGGGCTTCGCAGGGAAAGAGTGTCACCCTGCCCTGCACCTACCACACTTCC
       420       430       440       450       460       470       480
```

FIG.23A

```
        230                 240                250                    260
inputs -CCTC-------GCGGGCC-----CA---------GCTGCAACT-GCACTTGC-----------CCGCC
        ::::       : ::: :     ::         ::: :. :: .:.:.:.:            :  :
       ACCTCCAGTCGAGAGGGACTTATTCAATGGGATAAGCTCCTCCTCACTCATACGGAAAGGGTGGTCATCT
      490       500       510       520       530       540       550

           270       280                     290       300       310       320
inputs AACCGGTTGCAGGCGGTGG---------AGGAGGG---GGAAAGTGGTGCTTCAGCATGGTACACCTTGC
       ..::: :: ::..:.....        .::.:.:    ..:::..  :: :::::::.     :: .:::
       GGCCGTTTTCAAACAAAAACTACATCCATGGTGAGCTTTATAAGAATCGCGTCAGCATATCCAACAATGC
      560       570       580       590       600       610       620

                330       340                   350            360
inputs A---CAGGGAGGTGTCTTCATC-CCA-----------GCCATGGGAGG----TGC-CCTT--TGTGATGT
       .   :::    :.:: :: :::: :::          .:::::: .:.     :: :::.  .:::.: :
       TGAGCAGTCCGATGCCTCCATCACCATTGATCAGCTGACCATGGCTGACAACGGCACCTACGAGTGTTCT
      630       640       650       660       670       680       690

     370             380         390       400                410
inputs GGTTCT------TCAAAC--AGAAAGAAAAGGAGGATCAGGTGT---------TGTCCT-----------
       :  ::       :::.::  .::..: :: .  ...::: ::::          :::::
       GTCTCGCTGATGTCAGACCTGGAGGGCAACACCAAGTCACGTGTCCGCCTGTTGGTCCTCGTGCCACCCT
      700       710       720       730       740       750       760

                                             420        430       440
inputs ---------------ACATCAA---------------TGGGGTCA-CAACAAGCAAACCTG--GAGTATC
                      .:::::.:               ::::..:: ::.: :::.:::::  .:  :.
       CCAAACCAGAATGCGGCATCGAGGGAGAGACCATAATTGGGAACAACATCCAGCTGACCTGCCAATCAAA
      770       780       790       800       810       820       830

      450       460                            470                    480
inputs CTTGGTCTACTCCATGCCCTC------------------------CCGGAA------------CCTGTC
         .:: :: :.:::. :::::                        :: :::             :::: :
       GGAGGGCT-CACCAACCCCTCAGTACAGCTGGAAGAGGTACAACATCCTGAATCAGGAGCAGCCCCTGGC
      840       850       860       870       880       890       900

                   490        500         510        520
inputs CCTGC-------GGGT-GGAGGGTCTCC-AGGAGAAAGACTC---TGGCCC---------CTACAGCTG-
       ::.::       .::: .:    :::::: .:.::::...:::   .:.: :             ::::: :::
       CCAGCCAGCCTCAGGTCAGCCTGTCTCCCTGAAGAATATCTCCACAGACACATCGGGTTACTACATCTGT
      910       920       930       940       950       960       970

      530       540       550           560        570
inputs --CTCCGTGAATGTGCAAGACAAACAAG---GCAA-ATCTAGG-GGCCA-CAG---------CAT---CA
         ::::.  ::::.: :.:. : .::.    :::: :::. :: ::::. :::             :::   :.
       ACCTCCAGCAATGAGGAGGGGACGCAGTTCTGCAACATCACGGTGGCCGTCAGATCTCCCTCCATGAACG
      980       990       1000      1010      1020      1030      1040
```

FIG.23B

```
        580                     590         600                     610            620
inputs AAACC---TTAG-----AACTCAATGTAC-TGGTT-----CCTC-----CA---GCTCCTCCATC--CTG
        ...::    :..:     :.: :..:: .: :::::       ::::     ::    ::. :. ::::  :::
       TGGCCCTGTATGTGGGCATCGCGGTGGGCGTGGTTGCAGCCCTCATTATCATTGGCATCATCATCTACTG
       1050       1060       1070       1080       1090       1100       1110

           630          640                650            660           670
inputs C--CGTCT-CCAGGGTGTG--C-----CCCATGTG----GGGGCAAACGTGACC---CTGAGCTGCCAGT
       :  :  :: ::..:: ..:  :       : :. ..:      ::.: :..:..:.::    : :.: .:::..:
       CTGCTGCTGCCGAGGGAAGGACGACAACACTGAAGACAAGGAGGATGCAAGGCCGAACCGGGAAGCCTAT
       1120       1130       1140       1150       1160       1170       1180

             680          690        700                              710
inputs -------CTCCAAGG-AG-TAAGCCCGCTGTCCAA---------------------TAC---CAGTGGG
              :.:::..: :: ::::    .:: ::::.                       :::    ::. ..:
       GAGGAGCCACCAGAGCAGCTAAGAGAACTTTCCAGAGAGAGGGAGGAGGAGGATGACTACAGGCAAGAAG
       1190       1200       1210       1220       1230       1240       1250

               720            730            740           750         760
inputs ATCGG-----CA----GCTTCCATCC---TTCCAG-ACTTTCTTTG-CA--CCAGCATTAGATGTCATCC
       : :.:   .   ::     :: :  ::::       .:::   .: . :. :: ::   ::::::  ::: : :. :
       AGCAGAGGAGCACTGGGCGTGAATCCCCGGACCACCTCGACCAGTGACAGGCCAGCAGCAGAGGGCGGCG
       1260       1270       1280       1290       1300       1310       1320

       770                  780         790          800        810        820
inputs GTGGG------------TCTTTAAGCCTCA-CCAA----CCTTTCGTCTTCCATGGCTGGAGTCTA-TGT
       :.::.             ::.:: . :: :. ::..     :: :::  ::: :...::    . :::  :::
       GAGGAAGGGTTAGGGGTTCATTCTCCCGCTTCCTGGCCTCCCTTCTCCTTTCTAAGCCCTGTTCTCCTGT
       1330       1340       1350       1360       1370       1380       1390

               830          840          850          860              870
inputs CTGCAAGGCCCA--CAATGAGGTGGGCA---CTGCCC-AATGTAA--TGTG----AC---GCTGG-----
       :      . ::::  ::.::: : ::.::    :: ::: :.::: :   ::::     ::    :::::
       CCCTCCATCCCAGACATTGATGGGGACATTTCTTCCCCAGTGTCAGCTGTGGGGAACATGGCTGGCCTGG
       1400       1410       1420       1430       1440       1450       1460

                 880        890        900        910        920          930
inputs -AAGTGAG-CACAGGGCCTGGAGCTGCAGTGGTTGCTGAAGCTGTTGTGGGTACCCT---GGTTG-GACT
        ::: :.: : :.: :: ::.. ::::.:.  : .:::.  :::: ..: .. ::::    :: :: :::.
       TAAGGGGGTCCCTGTGC-TGATCCTGCTGACCTCACTGTC-CTGTGAAGTAACCCCTCCTGGCTGTGACA
       1470       1480        1490       1500        1510       1520       1530

          940        950                  960        970                980
inputs GGGGTTGCTGGCTGGGC--------TGGTCCT--CTTGTACCACCGC------CGG----GGCAAG-GC-
        : ::: :::  :::          ..:.::.  ::  ..::.::.:          ::      ::::.: ::
       CCTGGTGCGGGCCTGGCCCTCACTCAAGACCAGGCTGCAGCCTCCACTTCCCTCGTAGTTGGCAGGAGCT
          1540       1550       1560       1570       1580       1590       1600
```

FIG.23C

```
          990                     1000          1010       1020
inputs CCTGGAGG---AGC-CAG-------------CCAAT--GATATC---AAGGAGG--ATGCCAT------
       :::::::.:   ::: :.:             ::: :  ::. ::   :.:::::  ::::::
       CCTGGAAGCACAGCGCTGAGCATGGGGCGCTCCCACTCAGAACTCTCCAGGGAGGCGATGCCAGCCTTGG
        1610      1620      1630      1640      1650      1660      1670

                          1030          1040           1050
inputs ----------------TGCTCCCCGGA---CCCTGC-CCTGG-----C-CCAAGAG---------CTCAG
                       ::::: :: :.  :::.:: :::::     : :::.:.:         :.:.
       GGGGTGGGGGCTGTCCTGCTCACCTGTGTGCCCAGCACCTGGAGGGGCACCAGGTGGAGGGTTTGCACTC
        1680      1690      1700      1710      1720      1730      1740

        1060      1070                             1080              1090
inputs -ACACAATCTCCAAGAATG-----------------------GGACCCT---TT-------CCTCTGT
        :::::.  : :..:::::                        ::.::::    ::       :::: .
       CACACATCTTTCTTGAATGAATGAAAGAATAAGTGAGTATGCTTGGGCCCTGCATTGGCCTGGCCTCCAG
        1750      1760      1770      1780      1790      1800      1810

                        1100          1110                   1120
inputs CACC-------------TCCGCACGAGCC----CT-CCGG------CCA--CCC-C-----ATGGCC--C
       :.::             .:: ::: . ::    :: ::.:      :::  ::: :     :.::::  :
       CTCCCACTCCCTTTCCAACCTCACTTCCCGTAGCTGCCAGTATGTTCCAAACCCTCCTGGGAAGGCCACC
        1820      1830      1840      1850      1860      1870      1880

       1130      1140                    1150      1160       1170
inputs TCCCAGGCCTGGTGCATTGACCC-------------CCACGCCCAGTCTATC-CAGCCAGGC-------
       :::::  :::: :::: .:.:::              :::::.: :. :: ::: :.:::.: :
       TCCCACTCCTGCTGCACAGGCCCTGGGGAGCTTTTGCCCACACACTTTCCATCTCTGCCTGTCAATATCG
        1890      1900      1910      1920      1930      1940      1950

          1180      1190      1200      1210          1220      1230
inputs --CCTGCCCTCACCAAGACATGCCCACGACAGATGGGG--CCC--ACCCTCAACCAATATCCCCCATCCC
         :::: :: :.:::.: : . : :: ..:: :.::.   : :  ::::: . : :::.  :: ::: :
       TACCTGTCC-CTCCAGGCCCATCTCAAATCACAAGGATTTCTCTAACCCTATCCTAATTGTCCACATACG
        1960       1970      1980      1990      2000      2010      2020

    1240               1250      1260          1270            1280
inputs TGGTGG------GGTTT---TTTCCTTTGGCTT----TGAGCCGCATGG----GT--GCTGNGC------
       :::...       :::.   : ::: . : : .    ::.:::.::.::    ::   :::.::
       TGGAAACAATCCTGTTACTCTGTCCCACGTCCAATCATGGGCCACAAGGCACAGTCTTCTGAGCGAGTGC
         2030      2040      2050      2060      2070      2080      2090

            1290        1300      1310         1320        1330
inputs -----CTGTGATGGNGC--CTGC-CCA-GAGTCAAG--CTGGCTCTC-TGG--TATGATGACCC-----C
            ::::..:.:.::  :.:: ::. :.: ::.:  ::::  ::: :::  :.:: : .:::     :
       TCTCACTGTATTAGAGCGCCAGCTCCTTGGGGCAGGGCCTGGGCCTCATGGCTTTTGCTTTCCCTGAAGC
         2100      2110      2120      2130      2140      2150      2160
```

FIG.23D

```
                 1340            1350        1360      1370      1380
inputs AC---------CACTCAT-----TGG---CTAAAG--GATTTGGGGTCTCTCCTTCCTATAAGGGT---
       :          :.: :::     :::   ::.:::   :.:::::. .:: :::  ..:.. ::
       CCTAGTAGCTGGCGCCCATCCTAGTGGGCACTTAAGCTTAATTGGGGAAACTGCTTTGATTGGTTGTGCC
         2170      2180      2190      2200      2210      2220      2230

               1390            1400      1410      1420      1430
inputs --CAC--CTCTAG-CAC----AGA-GGCCTGAGTCATGGGAAAGAGTCACACTCCTGACCC-----TTAG
        : :   :::::.: :.:    ::: :. : ::.:: .::.:.:: :: ::: ::..::::     :: .
       TTCCCTTCTCTGGTCTCCTTGAGATGATCGTAGACACAGGGATGATTCCCAC-CCAAACCCACGTATTCA
         2240      2250      2260      2270      2280       2290      2300

       1440      1450      1460      1470       1480      1490      1500
inputs TACTCTGCCCCCACCTCTCTTTACTGTGGGAAAACCA-TCTCAGTAAGACCTAAGTGTCCAGGAGACAGA
       :.:. ::      : :.:  .::. : :......: :: .:.::. ....: :.  :: : .. .:.:.::
       TTCAGTGAGTTAAACACGAATTGATTTAAAGTGAACACACACAAGGGAGCTTGCTTG-CAGATGGTCTGA
          2310      2320      2330      2340      2350      2360       2370

           1510      1520               1530      1540      1550      1560
inputs AG----GAGAAGAGGAAGT--------GGATCTGGAATTGGGAGGAGCCTCCACCCACCCCTGACTCCTC
       .     :.:.  .::.:.:          .:. :.:.:... :. ..: ::::.:   :: :. .    ::
       GTTCTTGTGTCCTGGTAATTCCTCTCCAGGCCAGAATAATTGGCATGTCTCCTCAACCCACATGGGGTTC
          2380      2390      2400      2410      2420      2430      2440

          1570      1580      1590        1600            1610      1620
inputs CTTATGAAGCCAGCTGCTGAAATTAGCTACTCA--CCAAG---AG---TGAGGGGCA-GAGACTTC----
       :: .: .. ::.::. :   .:..   :..: :.  :: .:   ::    . . ::::.   .:. :::
       CTGGTTGTTCCTGCATCCCGATACCTCAGCCCTGGCCCTGCCCAGCCCATTTGGGCTCTGGTTTTCTGGT
          2450      2460      2470      2480      2490      2500      2510

                1630        1640                1650      1660      1670
inputs ----CAGTCACTGAGTC--TCCCA-GGCCCCCTT---------GATCTGTACCCCACCCCTATCTAACAC
           :.::: :::    :  ::::: .::: ::::         :: :. :.:  :. : ::.   :.:.:
       GGGGCTGTC-CTGCTGCCCTCCCACAGCCTCCTTCTGTTTGTCGAGCATTTCTTCTACTCTTGAGAGCTC
          2520       2530      2540      2550      2560      2570      2580

           1680            1690      1700      1710      1720        1730
inputs ---CACCCTT--GGCTCCCA----CTCCAGCTCCCTGTATTGATATAACCTGTCAG--GCTGGCTTGGTT
          :: : ::  :::: : .    ::: .: .::     . ::.: : ::: ..:.:   : : .::.
       AGGCAGCGTTAGGGCTGCTTAGGTCTCATGGACCAGTGGCTGGTCTCACCCAACTGCAGTTTACTATTGC
          2590      2600      2610      2620      2630      2640      2650

         1740      1750      1760            1770      1780      1790
inputs AGGTTTTACTGGG-GCAGAGGATAGGGAATC------TCTTATTAAAACTAAC-ATGAAATATGTGTTGT
       ..  :::.::::. : . ::.:.:. .:.::       :::..: . .:::..: :: ...::.....:::
       TATCTTTTCTGGATGATCAGAAAAATAATTCCATAAATCTATTGTCTACTTGCGATTTTTTAAAAAATGT
          2660      2670      2680      2690      2700      2710      2720
```

FIG.23E

```
         1800      1810          1820      1830      1840      1850      1860
inputs TTTCATTTGCAAATTTAAATAAAG---ATACATAATGTTTGTATGAGATAAGAAAAAAAAAAAAAAAAGGG
       .:. .::::. :.::.:...::::    .:.:.: :: :  ..:::  .: ::.::.::.::::....:::
       ATATTTTTATATATATTGTTAAATCCTTTGCTTCAT-TCCAAATGCTTTCAGTAATAATAAAATTGTGGG
            2730      2740      2750        2760      2770      2780      2790

inputs CGGCCGC
        ::
       TGG----
```

FIG.23F

```
ALIGN calculates a global alignment of two sequences
 version 2.0uPlease cite: Myers and Miller, CABIOS (1989)
> mT258 a.a.                                   394 aa vs.
> SwissProt Q99795 - (untitled)                319 aa
scoring matrix: pam120.mat, gap penalties: -12/-4
23.0% identity;         Global alignment score: -149

               10        20        30        40        50        60        70
inputs MILQAGTPETSLLRVLFLGLSTLAAFSRAQMELHVPPGLNKLEAVEGEEVVLPAWYTMAREESWSHPREV
       :.        . ::     :: :   .  .. :    . : : .:  :.:: :  :  .     .  .
       MV-------GKMWPVLW----TLCAVRVTVDAISVETPQDVLRASQGKSVTLPCTYHTSTSSREGLIQWD
                  10           20        30        40        50

               80        90       100       110       120       130       140
inputs PILIWFLEQEGKEPNQVLSYINGVMTNKPGTALVHSISSRNVSLRLGALQEGDSGTYRCSVNVQNDEGKS
        .:.   :.    :    .::.: . ..  ... ..    ..:. .. :  .:.::: ::::.. .:
       KLLLTHTERVVIWPFSNKNYIHGELYKNR-VSISNNAEQSDASITIDQLTMADNGTYECSVSLMSDLE--
       60        70        80         90       100       110       120

              150       160       170       180       190       200       210
inputs IGHSIKSIELKVLVPPAPPSCSLQGVPYVGTNVTLNCKSPRSKPTAQYQWERLAPSSQVFFGPALDAVRG
        :..    . : :::::. : :...:    .:.:. :.:.:  . ::.:: : : .  .:    :  ... :
       -GNTKSRVRLLVLVPPSKPECGIEGETIIGNNIQLTCQSKEGSPTPQYSWKRYNILNQE--QPLAQPASG
         130       140       150       160       170       180         190

               220       230       240         250       260       270
inputs -SLKLTNLSIAMSGVYYVCKAQNRVGFAKCNVTLDVMTGS-KAAVVAGAVVGTFVGLVLIAGLVLLYQRRS
        .. : :.:.. :: :.: . :  :    ::.:..: . : ..:. .: .::. ..:..:.  ...:
       QPVSLKNISTDTSGYYICTSSNEEGTQFCNITVAVRSPSMNVALYVGIAVGVVAALIIIG--IIIYCCCC
           200       210       220       230       240       250         260

       280       290       300       310       320       330       340
inputs KTLEELANDIKEDAIAPRTLPWTKGSDTISKNGTLSSVTSARALRPPKAAPPRPGTFTPTPSVSSQALSS
       .  .. ..: ::::                          :. : . ..:: .              ..::
       RGKDDNTED-KEDA-------------------------RPNREAYEEPPEQ---------LRELSR
           270                                   280                   290

       350       360       370       380       390
inputs PRLPRVDEPPPQAVSLTPGGVSSSALSRMGAVPVMVPAQSQAGSLV
        :      ..    :.    . :  :.. :..
       EREE--EDDYRQEEQRSTGRESPDHLDQ------------------
           300       310
```

FIG.24

```
ALIGN calculates a global alignment of two sequences
 version 2.0uPlease cite: Myers and Miller, CABIOS (1989)
> mT258 n.a.                                     1846 aa vs.
> GenBank U79725 - Human A33 antigen precursor mR  2793 aa
scoring matrix: pam120.mat, gap penalties: -12/-4
40.0% identity;      Global alignment score: 908

                  10                  20                            30
inputs GTCGACCC------ACGC-GTC-----CG--GTGCAC--ATT-------------C--GGGTTGCCGCC
         : ::::       . :: :::     :   ::.:::  .::             :  :::. :  ::
       --CTACCCCTTTGTGAGCAGTCTAGGACTTTGTACACCTGTTAAGTAGGGAGAAGGCAGGGGAGGTGGCT
               10        20        30        40        50        60

                40                             50        60               70
inputs G------------CT-----------------CACC-CACAACACCTGTAGAC------AC-CGTGTGT
       :            ::                 :.:: :. .. :::: :.::       :: :.::.:
       GGTTTAAGGGGAACTTGAGGGAAGTAGGGAAGACTCCTCTTGGGACCTTTGGAGTAGGTGACACATGAGC
       70        80        90        100       110       120       130

                  80                    90                  100        110
inputs CCAAC------TCTCC-----------CTGAGTA-CTC------CGGGCCA----AGG-AGGGCCATGAT
       :::.:      ::.::           ::::: : :::      :.. :::    ::: .:::: ..:.:
       CCAGCCCCAGCTCACCTGCCAATCCAGCTGAGGAGCTCACCTGCCAATCCAGCTGAGGCTGGGCAGAGGT
      140       150       160       170       180       190       200
```

FIG.25A

```
                         120       130              140       150       160
inputs TCTTCAG------------GCTGGAACCCCCGA---GACCAG-C---TTGCTGCGGGTT-TTGTTCCTG
          : ::            ::.::.::: ::..   :.:::: :   ..::::: :  .  :: ..::.:
       GGGTGAGAAGAGGGAAAATTGCAGGGACCTCCAGTTGGGCCAGGCCAGAAGCTGCTGTAGCTTTAACCAG
       210       220       230       240       250       260       270

                170       180       190       200                 210
inputs G-GACTGAGTACCCTTGCTGCCTTCTCCCGAGCTCAGATGGAGTT----GCA---------CGTGCCC--
       . ..:: ::.  :::  :::    :: :::..  .:::.: ..:::    :::         :..: ::
       ACAGCTCAGA--CCTGTCTGGAGGCTGCCAGTGACAGGTTAGGTTTAGGGCAGAGAAGAAGCAAGACCAT
       280         290       300       310       320       330       340

                                220        230       240       250
inputs ---------------CC--------GGGC-CTCAA--CAAATTGGAAG-CGGTAGAGGGAGAAGAAGTG
                      ::        ::.: :::..  :::.. .:::..: : :: :: :  ..   .:::
       GGTGGGGAAGATGTGGCCTGTGTTGTGGACACTCTGTGCAGTCAGGGTGACCGTCGATGCCATCTCTGTG
        350       360       370       380       390       400       410

        260       270            280       290                 300
inputs GTGCTCCCCGCCTG--GTACA-CGA---TGGCACGGGAGGAGT---------CGTGGTCC---------
       :..  .: ::::  :  ::.:. ::.   : ::: ::.:.::::          : :: .::
       GAA-ACTCCGCAGGACGTTCTTCGGGCTTCGCAGGGAAAGAGTGTCACCCTGCCCTGCACCTACCACACT
         420       430       440       450       460       470       480

                   310       320            330                340       350
inputs --CACC-CC---CGGGAGGTGCCCATCCT----GATCTGGTTCT------TGGAACAAGAAGGGAAGGAA
         :::: ::   ::.:::: .:  :: :.    ::: .: : ::      : ..::..:::::..:  :
       TCCACCTCCAGTCGAGAGGGACTTATTCAATGGGATAAGCTCCTCCTCACTCATACGGAAAGGGTGGTCA
         490       500       510       520       530       540       550
```

FIG.25B

```
        360       370                                 380       390       400
inputs CCAAACCAGGTGTTGTCTTA-----------------CATTAATGGAGTCATGACAAATAAACCTG---
        :...::.  :  ...:..:                 :.:::...::.::. :.::. ..:.:::..
       TCTGGCCGTTTTCAAACAAAAACTACATCCATGGTGAGCTTTATAAGAATCGCGTCAGCATATCCAACAA
        560       570       580       590       600       610       620

            410       420                        430       440       450
inputs ----GAACAGCCCTGGTCCAC--TCT------ATCT------CTTCACGGAATGTGTC-CCTGCG-----
           ::.::: :: .  ::.:  ::.      :::.      :.: .: :: .. : : :::.::
       TGCTGAGCAGTCCGATGCCTCCATCACCATTGATCAGCTGACCATGGCTGACAACGGCACCTACGAGTGT
        630       640       650       660       670       680       690

                  460       470       480           490       500
inputs -C-------CTGGGGGCACTCCAGGAGGGAGACTCTGGGAC---TTACCGCTGTTCTGTCAATGTGC---
        :        :::. : :: .::.::::: .::.: ..:.:   : .:::   :  ::: . ::::
       TCTGTCTCGCTGATGTCAGACCTGGAGGGCAACACCAAGTCACGTGTCCGCCTGTTGGTCCTCGTGCCAC
        700       710       720       730       740       750       760

             510       520          530            540       550
inputs ------AGAATGATGAAGGCAA--AAGTATAGGCCACA----GCATCAAAAGCATA--GAGCT--CAA--
             :.  .::. . ::::.  :.: : ::.::: :    : :.::: : : ..  :: ::  :::
       CCTCCAAACCAGAATGCGGCATCGAGGGAGAGACCATAATTGGGAACAACATCCAGCTGACCTGCCAATC
        770       780       790       800       810       820       830

       560       570       580       590       600          610            620
inputs AGTGCTGGTTCCTCCAGCTCCTCCATCCTGTAGTTTACAGGGTGTAC--CCTATGTCGGGA----CCAAT
       :..: .::   :.:::.: :::: .: :.: .: ... ::: . .::  :::...::.:::     ::  :
       AAAGGAGGGCTCACCAACCCCTCAGTACAGCTGGAAG-AGGTACAACATCCTGAATCAGGAGCAGCCCCT
        840       850       860       870       880       890       900
```

FIG.25C

```
                630       640       650                            660
inputs GT---GACC-----CTGAACTGCAAGTCCCCAAGGAGTAAA---CC---------------TACTGC-TC
       :    ..::     :.:..:.:: .::: :: .:.::.:.:    ::               ::::.: ::
       GGCCCAGCCAGCCTCAGGTCAGCCTGTCTCCCTGAAGAATATCTCCACAGACACATCGGGTTACTACATC
           910       920       930       940       950       960       970

        670              680             690              700         710
inputs AGTACCA--------GTGGGAGAG--GCTG----GCCCCATC-CT----CC--CAGGTCT---TCTTTGG
       .:::::.         :.::..:.:  ::.:     ::  :::: :      ::  :::.:::   :: .::.
       TGTACCTCCAGCAATGAGGAGGGGACGCAGTTCTGCAACATCACGGTGGCCGTCAGATCTCCCTCCATGA
           980       990      1000      1010      1020      1030      1040

            720           730       740             750             760
inputs AC-CAGCCTTAGATG----CTGTTCGTGGATCTTTAAAGC-----TCACTAACCTT----TC--CAT---
       ::  .::: :. :::      :.    ::    :.  : : ...::   ::: ::.: ::     ::  :::
       ACGTGGCCCTGTATGTGGGCATCGCGGTGGGCGTGGTTGCAGCCCTCATTATCATTGGCATCATCATCTA
          1050      1060      1070      1080      1090      1100      1110

                                    770       780         790       800
inputs ----------TGCCATG-------------TCTGGAGTCTATGT--CTGCAAGGCTCAAAACAGAGTGG
                 :::::..:              .:::.::.:.: :.   :::::::: :.:: :.: :..:
       CTGCTGCTGCTGCCGAGGGAAGGACGACAACACTGAAGACAAGGAGGATGCAAGGC-CGAACCGG-GAAG
          1120      1130      1140      1150      1160      1170        1180

        810             820           830                    840
inputs GCTTTG-----CCA--AGTGCAAC---GTGACCTT-----------GGACGTGATG-------ACAGG--
        ::.::      :::  ::.:::.:    :.:: :::           ::: :.:..:        :::::
       CCTATGAGGAGCCACCAGAGCAGCTAAGAGAACTTTCCAGAGAGAGGGAGGAGGAGGATGACTACAGGCA
            1190      1200      1210      1220      1230      1240      1250
```

FIG.25D

```
              850       860                                    870         880
inputs ----GTCCAAGGCTGCAGTGGTCG----------------------------CTGG--AGCAGTTGTGGG
           :. ::..: .::: ::: ::                            :.::  ::::: .:.:::
       AGAAGAGCAGAGGAGCACTGGGCGTGAATCCCCGGACCACCTCGACCAGTGACAGGCCAGCAGCAGAGGG
           1260      1270      1280      1290      1300      1310      1320

               890       900                 910                       920
inputs CA-CTTTTGTTGGGTTGGTG----------CTGATAGCTGGGCT---------------GGTCCTGTT--
       :. :   . :..:::::.: :          : : :. :::: ::              .: ::::::
       CGGCGGAGGAAGGGTTAGGGGTTCATTCTCCCGCTTCCTGGCCTCCCTTCTCCTTTCTAAGCCCTGTTCT
           1330      1340      1350      1360      1370      1380      1390

                         930                                         940
inputs -----------GTACCAG---------------------CGCC--------------GGAGCAAGAC---
                 .: ::::                       : ::              :::.::.:.:
       CCTGTCCCTCCATCCCAGACATTGATGGGGACATTTCTTCCCCAGTGTCAGCTGTGGGGAACATGGCTGG
           1400      1410      1420      1430      1440      1450      1460

         950                  960              970        980
inputs CTTGGAA-----------GAGCTGG-CCAA-TGA------TATCAAG-GAAGATGCC----------ATT
       : :::.:           :.::::. ::.. :::      :.:: .: ::::...::          .:
       CCTGGTAAGGGGGTCCCTGTGCTGATCCTGCTGACCTCACTGTCCTGTGAAGTAACCCCTCCTGGCTGTG
           1470      1480      1490      1500      1510      1520      1530

         990      1000            1010                          1020
inputs GCTCCC----CGGACCTTGCCTT------GGACCAA-----AGGCTC---------------AGACACAA
       .:.::     :::.::: ::: :      .::::.     :: :::                .:.:: .:
       ACACCTGGTGCGGGCCTGGCCCTCACTCAAGACCAGGCTGCAGCCTCCACTTCCCTCGTAGTTGGCAGGA
           1540      1550      1560      1570      1580      1590      1600
```

FIG.25E

```
        1030      1040      1050      1060      1070                1080
inputs TCTCCAAGAATGG-GACACTTT-CTTCGGTCACCTCAGCAC-GAGCTCT--------GCG--GCCACCCA
        ::::..:::  . ..:.:: . :.: :: :.:  :  .:.: ::.::::        :::  :::: ::.
       GCTCCTGGAAGCACAGCGCTGAGCATGGGGCGCTCCCACTCAGAACTCTCCAGGGAGGCGATGCCAGCCT
           1610      1620      1630      1640      1650      1660      1670

                      1090          1100                     1110
inputs AGG--------------CTGCTC--CT------CCAAGACCTGG-----CAC---------ATTTACT
       .::               ::::::  ::      :::. ::::::     :::         .:::.:.
       TGGGGGGTGGGGGCTGTCCTGCTCACCTGTGTGCCCAGCACCTGGAGGGGCACCAGGTGGAGGGTTTGCA
           1680      1690      1700      1710      1720      1730      1740

         1120                                  1130      1140         1150
inputs C-CCACAC--C---C-----------------AGTGT-----CTCTAGCCAGGCCCTGTCCT---CAC
       : ::::::  :   :                 ::::.     ::  .:::  ::  :: :::   :.:
       CTCCACACATCTTTCTTGAATGAATGAAAGAATAAGTGAGTATGCTTGGGCCCTGCATTGGCCTGGCCTC
           1750      1760      1770      1780      1790      1800      1810

                1160      1170      1180      1190        1200        1210
inputs CAAGACT---GCCCAGGGTAGATGAACC-CCCACCTCAGGCAGT--GTCCCTGACCC--CAGGTGGGGTT
       ::. .:     ::::.    :.    :: :::.    :.: ::::  :: ::..::::  :.:: ..::
       CAGCTCCCACTCCCTTTCCAACCTCACTTCCCGTAGCTGCCAGTATGTTCCAAACCCTCCTGGGAAGGCC
           1820      1830      1840      1850      1860      1870      1880

                  1220      1230                        1240      1250
inputs TCTTC-------TTCTGCTCTGAGCC------GCATGGG-------------TGCTGTGCCTGT-GATG
       .: ::        : ::::.:.:. ::      ::.:  :             . :: ::::::: .::.
       ACCTCCCACTCCTGCTGCACAGGCCCTGGGGAGCTTTTGCCCACACACTTTCCATCTCTGCCTGTCAATA
           1890      1900      1910      1920      1930      1940      1950
```

FIG.25F

```
          1260       1270      1280      1290        1300      1310
inputs --GTGCCTG---CACAGAGTCAGGCT-GGGTCTCTTGTGTGA---TAGCCCAGGCACTCATTAGCTACAT
         ::.::::   :.: ..: : . :: ...::.:..: .: .   ::.:::.. : :: :::. : ::::
       TCGTACCTGTCCCTCCAGGCCCATCTCAAATCACAAGGATTTCTCTAACCCTATC-CTAATTGTCCACAT
           1960      1970      1980      1990      2000      2010      2020

        1320      1330      1340       1350      1360      1370
inputs -C-TGGTATCTGACCT--TTCTGTAAAGGTC-TCCTT--GTGGCACAGAGGACTCAATCTT--GGGAGGA
        : :::.:.:...:::  :.:: :..   .: :::..  .:::  :: :.:.:.::.::::  :.: :..
       ACGTGGAAACAATCCTGTTACTCTGTCCCACGTCCAATCATGGGCCACAAGGCACAGTCTTCTGAGCGAG
            2030      2040      2050      2060      2070      2080      2090

      1380      1390      1400       1410              1420
inputs TGCCCACA---TTCTAGACCTCCAG-TCCTTTG--CT---CCTA--CCTC----CTT---CTAT---TGT
       ::: :.::    :. :::: : :::: ::::: :  :.    :::.  ::::    :::   ::.:   ::.
       TGCTCTCACTGTATTAGAGCGCCAGCTCCTTGGGGCAGGGCCTGGGCCTCATGGCTTTTGCTTTCCCTGA
            2100      2110      2120      2130      2140      2150      2160

          1430      1440      1450
inputs TG----GAATACTGG-GCC--TC--AGTAAG-ACTAAA-------------ATCTG-------------
       .:    .....:::: :::  ::  :::..: :::.::             :.:::
       AGCCCTAGTAGCTGGCGCCCATCCTAGTGGGCACTTAAGCTTAATTGGGGAAACTGCTTTGATTGGTTGT
            2170      2180      2190      2200      2210      2220      2230

                 1460                1470      1480
inputs --------------GGTCA-------------AAGGACAAAAGGAGGAAAT------GGACC--------
                     ::::.             ...:::: :.::: ::..      ..:::
       GCCTTCCCTTCTCTGGTCTCCTTGAGATGATCGTAGACACAGGGATGATTCCCACCCAAACCCACGTATT
            2240      2250      2260      2270      2280      2290      2300
```

FIG.25G

```
             1490             1500         1510          1520               1530
inputs -------TGAGGTAGG---GGGTTGGGAGTGAGGAGGCT-TCACTT-----CCTCCCTGCT-----TCT-
                :::: :::..   :..:::. . ..:: ...:. .:::..      : : : :::.     :::
       CATTCAGTGAGTTAAACACGAATTGATTTAAAGTGAACACACACAAGGGAGCTTGCTTGCAGATGGTCTG
             2310        2320        2330        2340        2350        2360        2370

          1540         1550                   1560         1570                     1580
inputs ---CCCTGAAGCCAGATGAATGCT------GC--GGAAGATCGGCT----------ACCCTCCAAGGGCT
          : ::.. ::.:.:.:.: ::       ::  :.:..:: :::.             ::::.: ..::: :
       AGTTCTTGTGTCCTGGTAATTCCTCTCCAGGCCAGAATAATTGGCATGTCTCCTCAACCCACATGGGGTT
             2380        2390        2400        2410        2420        2430        2440

        1590        1600         1610           1620             1630        1640
inputs C-TGGAGGAGACTGCCAGTCAGTGATGC--CCCTGGCTCTG---TGATCTGTACAACACCC-TTATCTAA
       : :::. :.  :::: .   :..:.    :  ::::::: :::    .:   :. :. ..:.:   ::.:::..
       CCTGGTTGTTCCTGCATCCCGATACCTCAGCCCTGGCCCTGCCCAGCCCATTTGGGCTCTGGTTTTCTGG
             2450        2460        2470        2480        2490        2500        2510

    1650          1660         1670          1680                1690
inputs TG---CTGTCCTT-TGCCGTTCGCTCCATCTCC--CTGT---------ATTAATATAAC-----------
       ::    :::::::  ::::  :: :.: . :::: ::::          :::. :. .::
       TGGGGCTGTCCTGCTGCC-CTCCCACAGCCTCCTTCTGTTTGTCGAGCATTTCTTCTACTCTTGAGAGCT
             2520         2530        2540        2550        2560        2570        2580

                      1700                        1710                              1720
inputs CTGTC----------CTGCT---GGCT----------TGGCTGG---------------GTTT--TGTTG
       :.: :             :::::  : ::         :::::::                ::::  :.:::
       CAGGCAGCGTTAGGGCTGCTTAGGTCTCATGGACCAGTGGCTGGTCTCACCCAACTGCAGTTTACTATTG
              2590        2600        2610        2620        2630        2640        2650
```

FIG.25H

```
                  1730      1740        1750            1760      1770
inputs ------TAGCAGGGGGATAGGAAAGACATTT--TAAAATCTG------ACTTGAAATTGATGTTTTTGTT
             :. :.::. ::: .::::.: :.::  ..::::::.      ::::: .::: .: .......:
       CTATCTTTTCTGGATGATCAGAAAAATAATTCCATAAATCTATTGTCTACTTGCGATTTTTTAAAAAATG
             2660      2670      2680      2690      2700      2710      2720

    1780      1790      1800          1810         1820      1830      1840
inputs TTTATTTTGCAAATTTCAATAAAGA----TACATCG---CATTTGCATGGAAAAAAAAAAAAAAAAGGGCG
       :.:::::  .:..:. ..:.::..    :.:.::.  ::..:::.: :..::.::.::::..: : :
       TATATTTTTATATATATTGTTAAATCCTTTGCTTCATTCCAAATGCTTTCAGTAATAATAAAATTGTGGG
             2730      2740      2750      2760      2770      2780      2790

inputs GCCGC
          :
       T--GG
```

FIG.25I

```
ALIGN calculates a global alignment of two sequences
 version 2.0uPlease cite: Myers and Miller, CABIOS (1989)
> hT258 n.a.                                   1869 aa vs.
> pecam n.a.                                   2557 aa
scoring matrix: pam120.mat, gap penalties: -12/-4
40.5% identity:        Global alignment score: 1546

                                                    10         20
inputs G---TC----------GACC-----------------CAC---GCGTNCNTC-CAGCGTN---------
       :   ::          ::::                 :::   ::: . .:: ::.:: .
       GAATTCCGGGAGAAGTGACCAGAGCAATTTCTGCTTTTCACAGGGCGGGTTTCTCAACGGTGACTTGTGG
               10        20        30        40        50        60        70

          30          40          50        60           70           80
inputs -CGGAGCCGCC--CTGGG--TGTCAGCGGCTCGGCTCCCGCGCACGCT---CCGGC---CGTCGC-----
        :.:.:::  :  :::.:  .::::  ::: ::.   : : .:. .::   :: ::   : ::.:
       GCAGTGCCTTCTGCTGAGCGAGTCAT-GGCCCGAAGGCAGAACTAACTGTGCCTGCAGTCTTCACTCTCA
               80        90        100       110       120       130

                 90         100          110            120        130
inputs ----GCAGCCTCGGCA--CCTGCAGGTCCG---TGCGTCCCG-----CGGCTGGCGCCCCTGACTCCGTC
           ::::::  :: .  :: . .:: ::.   :: : :  :     : ::::.: :  ::: ::: ::
       GGATGCAGCCGAGGTGGGCCCAAGGGGCCACGATGTGGCTTGGAGTCCTGCTGACCCTTCTG-CTCTGTT
     140       150       160       170       180       190       200

        140        150        160           170              180
inputs CCGGCCAGGGAGGGCCATGATTTCCCT--CCCGG--GGCC-------CCTGGTGA-CCAAC--------T
       : .:::. : :::: ::.::...: ::  : :..  ..:       : ::..:: ::..:        .
       CAAGCCTTG-AGGGTCAAGAAAACTCTTTCACAATCAACAGTGTTGACATGAAGAGCCTGCCGGACTGGA
        210       220       230       240       250       260       270

        190          200        210                220         230
inputs TGNTGCGGTTT---TTGTTCCTGGGGCTG-AGTGC--C-C-----TC-GCGCCCCC-CTCGCG---GGCC
        :.:::....:   ..:..::::.  ::: :::::  : :     :: ::.:: :: :::.::   .:::
       CGGTGCAAAATGGGAAGAACCTGACCCTGCAGTGCTTCGCGGATGTCAGCACCACCTCTCACGTCAAGCC
       280       290       300       310       320       330       340

      240        250                                   260        270        280
inputs -CAGCTGCAACTGC---------------ACTTGC-------C-----CGCCAACCGGTTGCAGGCGGTG
        ::::. ::. :::                :: :::       :     : ::. :  :..: . .:.:.:
       TCAGCACCAGATGCTGTTCTATAAGGATGACGTGCTGTTTTACAACATCTCCTCCATGAAGAGCACAGAG
       350       360       370       380       390       400       410

           290              300        310          320        330        340
inputs GAGGAGGGGGA-----AAGT--GGTGCTTCAGCA-TGGTACACCT---TGCACAGGGAGGTGTCTTCATC
       ..  :     ..     ::::  ::. ::. ..:. .:: :::  :   :: ::.: ::  ::: ..::.:
       AGTTATTTTATTCCTGAAGTCCGGATCTATGACTCAGGGACATATAAATGTACTGTGAT-TGTGAACAAC
       420       430       440       450       460       470       480
```

FIG.26A

```
                    350          360           370         380         390
inputs CCAG------CCA-TGGGAGGTGCC--CTTT--GTGATGTGGTTCTTCAAACAGAAAGAAAAGGAGGATC
        ::       ::: :: ...::.::   :: :  :::... :. :    ::..:  :..:..: . .:::
       AAAGAGAAAACCACTGCAGAGTACCAGCTGTTGGTGGAAGGAGTGCCCAGTCCCAGGGTGACACTGGACA
        490       500       510       520       530       540       550

   400        410       420               430        440              450
inputs AGGTGTTGTCCTACATCAATGGGGTCA-------CAACAAG-CAAACCTGGAGTAT------CCTTGG-T
       ::... .: ::..: . ..::::.::.        :::::..  :...:: .::: :.       ::.. . .
       AGAAAGAGGCCATCCAAGGTGGGATCGTGAGGGTCAACTGTTCTGTCCCAGAGGAAAAGGCCCCAATACA
        560       570       580       590       600       610       620

         460                 470         480        490              500
inputs CTACTC----------CATGCCCTCCCGGAACC--TGTCCCTGC-GGGTGGAGGG------TCTC-----
       ::.:.:          :.::  ::     :::    ::  : .:: :....:::.:        ::::
       CTTCACAATTGAAAAACTTGAACTAAATGAAAAAATGGTCAAGCTGAAAAGAGAGAAGAATTCTCGAGAC
        630       640       650       660       670       680       690

             510              520          530       540              550
inputs CAGGAGAAAG--ACTCTGG----CCCCTAC----AGCTGCTCCGTGAATGTGC------AAGACAAACAA
       :::.:  ...:  : .::::     :::: .     :.:.: .::: :..: . :        :.:.:::.:.:
       CAGAATTTTGTGATACTGGAATTCCCCGTTGAGGAACAGGACCGCGTTTTATCCTTCCGATGTCAAGCTA
        700       710       720       730       740       750       760

           560       570            580                590
inputs GG--CAAATCTAGGGGCCA----CAG-CATCAAAA----CCTTA--------GAACTCAATG--------
       ::   ::..:::.::. :::     ::: : :::.::     ::...          :..:.: .::
       GGATCATTTCTGGGATCCATATGCAGACCTCAGAATCTACCAAGAGTGAACTGGTCACCGTGACGGAATC
        770       780       790       800       810       820       830

        600               610              620                630
inputs -TACT---------GGTTCCTC--CAGCTCCTCC------ATCCTG-------C-CGTCTCCA--GGGTG
        :.::          .:::::.:  :::: ::.::       ::: ::         : :. ::::      ..:
       CTTCTCTACACCCAAGTTCCACATCAGCCCCACCGGAATGATCATGGAAGGAGCTCAGCTCCACATTAAG
        840       850       860       870       880       890       900

   640         650       660        670              680              690
inputs TGCCCCATG-TGGGGGCAAACGTGACCCTG-AGCTGCCAG---TC-----TC-------CAAGGAGTAAG
       ::: ::::   ..: :.:. :: ::.:::.: :: : ::::    ::      ::        ::::: :...:
       TGCACCATTCAAGTGACTCACCTGGCCCAGGAGTTTCCAGAAATCATAATTCAGAAGGACAAGGCGATTG
        910       920       930       940       950       960       970

                                   700            710              720
inputs ---CCC-------------------GCTGT---C-----CAATACCAGTG-GGATC-----GGCAGCTT
          :::                   :::::   :      ::. .::: : ::: :       ::::.::.
       TGGCCCACAACAGACATGGCAACAAGGCTGTGTACTCAGTCATGGCCATGGTGGAGCACAGTGGCAACTA
        980       990      1000      1010      1020      1030      1040
```

FIG.26B

```
          730                 740        750       760       770
inputs C-CATCCT--------TCCAGAC---TTTCTTTG--CACCAGCATTAGATGTCATCCGTG--GGTCTTTA
       : :.: :.        ::::: :   :.:: ..:  :: ::::::  :. ::::.:  ..   :..::.:.
       CACGTGCAAAGTGGAGTCCAGCCGCATATCCAAGGTCAGCAGCATC-GTGGTCAACATAACAGAACTATT
       1050      1060      1070      1080      1090       1100      1110

    780        790       800            810            820        830
inputs AGCCTCACC-AACCTTTCGTCTTCCAT-----GGCTGGA-----GTCTATGTCTG--CAAGGCC--CACA
       . ::. .:: .: ::   .:::::::.:      . :::::      :: .:.:.:::  : .: ::  :.:
       TTCCAAGCCCGAACTGGAATCTTCCTTCACACATCTGGACCAAGGTGAAAGACTGAACCTGTCCTGCTCC
        1120      1130      1140      1150      1160      1170      1180

         840                850                      860       870
inputs ATG--AGGTG-------GGC--ACTGC-CCA-----ATGTAA--------TGTGACGCTGG---AAGTGA
       ::   ::::.:        .::  ::: : :::     :.: ::        ::::.:.:.:.   :::. .
       ATCCCAGGAGCACCTCCAGCCAACTTCACCATCCAGAAGGAAGATACGATTGTGTCACAGACTCAAGATT
        1190      1200      1210      1220      1230      1240      1250

        880            890         900       910         920         930
inputs GCAC----AGGGCCT-GGAG-CTG-CAGTGGTTGCTGAAGCTGT--TGTGGGTACC--CTGGTTGGACTG
        :::     : .:::: ..:: : : :::::: .   :..: :::   :: .::::    :... :::.:..
       TCACCAAGATAGCCTCAAAGTCGGACAGTGGGACGTATATCTGCACTGCAGGTATTGACAAAGTGGTCAA
        1260      1270      1280      1290      1300      1310      1320

         940       950       960                970          980
inputs GGGTTGCTG-GCTGGGCTGGTCCTCTTGTA-------C-CACC--GCCGGGG----CAAG----GCCCTG
       :.....::.. .:.:  :.:.:  :: :.:.        : :.:: ::: .::     :...    ::::.:
       GAAAAGCAACACAGTCCAGATAGTCGTATGTGAAATGCTCTCCCAGCCCAGGATTTCTTATGATGCCCAG
        1330      1340      1350      1360      1370      1380      1390

        990      1000      1010        1020      1030                  1040
inputs GAGGAGCCAGCCAATGATATCAAG--GAGGATG-CCATTGCTCCCCGGACC------CT--GCC-----C
        . :::  . : .:..: ..::.. .. ::.: ::.::::      ::..:         ::  :::      :
       TTTGAG--GTCATAAAAGGACAGACCATCGAAGTCCGTTGCGAATCGATCAGTGGAACTTTGCCTATTTC
        1400        1410      1420      1430      1440      1450      1460

                1050      1060      1070      1080      1090
inputs TGGCC--CAA--GAGCTCAGACACAATCTCCAAGAATGGGACCCTTTCCTCTGTCA--CCTCCG-----C
       : .::  :..  .:. .::.. : :.: :  .:::::.: ::: . . :::... .  ::: ::      :
       TTACCAACTTTTAAAAACAAGTAAAGTTTTGGAGAATAGTACCAAGAACTCAAATGATCCTGCGGTATTC
          1470      1480      1490      1500      1510      1520      1530

   1100          1110           1120                     1130
inputs A----CGAGCCCTCCG--GCCACC-----CCA-----TGGC---------CC--TCCCAGGCCT------
       :     :.: :::.: :  : :. :      :::     : ::         ::  ::::: :::.
       AAAGACAACCCCACTGAAGACGTCGAATACCAGTGTGTTGCAGATAATTGCCATTCCCATGCCAAAATGT
          1540      1550      1560      1570      1580      1590      1600
```

FIG.26C

```
              1140                  1150                1160      1170
inputs -------GGTGCATTG------------ACCCCC--------ACGCCCAG---TCTATCCAGCCAGG---
              ::: :. .:            : ::::         : : ::::   :::::::.: ::.:
       TAAGTGAGGTTCTGAGGGTGAAGGTGATAGCCCCGGTGGATGAGGTCCAGATTTCTATCCTGTCAAGTAA
           1610      1620      1630      1640      1650      1660      1670

                                                                 1180
inputs -----------C---------C------CTGC------------------------CC--TCACCAAG
                  :         :      ::::                        ::  :::::.:
       GGTGGTGGAGTCTGGAGAGGACATTGTGCTGCAATGTGCTGTGAATGAAGGATCTGGTCCCATCACCTAT
           1680      1690      1700      1710      1720      1730      1740

    1190        1200      1210       1220       1230          1240
inputs ACATGC--CCACGACAGATGGGGCCCACCCT-CAACCAA-TATCCCC-----CATCCCTGG---TGGGGT
       : .:    : . :: :.: .::::  ::::: :.: ::: :..:: :     : .:::.::   :  ::.
       AAGTTTTACAGAGAAAAAGAGGGCAAACCCTTCTATCAAATGACCTCAAATGCCACCCAGGCATTTTGGA
           1750      1760      1770      1780      1790      1800      1810

      1250      1260         1270             1280         1290      1300
inputs TTTTTCCTTTGGCTT---TGAGCCGCATGGGTG-------CTG---NGCCTGTGATGGNGCCTGCC----
         .. :  ..::::.   .:.. :. ..::::.:       :::   .::::  .: .:.:::..::
       CCAAGCAGAAGGCTAGCAAGGAACAGGAGGGAGAGTATTACTGCACAGCCTTCAACAGAGCCAACCACGC
           1820      1830      1840      1850      1860      1870      1880

                               1310      1320        1330      1340      1350
inputs ---CAGAGTC------------AAGCTGGCTCTCTG-GT-ATGATGACCCCACCACTCATTGG-CTAAAG
          :::.:::            :..:::.:. ::.: :: ::  : .:::::  . . :..:: ::.:.
       CTCCAGTGTCCCCAGAAGCAAAATACTGACAGTCAGAGTCATTCTTGCCCCATGGAAGAAAGGACTTATT
           1890      1900      1910      1920      1930      1940      1950

           1360               1370      1380            1390
inputs GATTTGGG-GTC-TC-------TCCTTCCTATAAGGGTCA------CCTCTAGCA-----CAGAGG----
       : . :::  .:: ::       :: :: :: : . :.:::      ::. ..: .      :.:::
       GCAGTGGTTATCATCGGAGTGATCATTGCTCTCTTGATCATTGCGGCCAAATGTTATTTTCTGAGGAAAG
           1960      1970      1980      1990      2000      2010      2020

     1400       1410        1420      1430          1440        1450
inputs CCTGAGTCATG-GGAA---AGAGTCACACTCCTGACCCTTAGTAC----TCTG--CCCCCACCTC-----
       ::...: ::.: .::.    ::.:  : . :::.:.::   :::::    ::::  : :: :: .:
       CCAAGGCCAAGCAGATGCCAGTGGAAATGTCCAGGCCAGCAGTACCACTTCTGAACTCCAACAACGAGAA
           2030      2040      2050      2060      2070      2080      2090

              1460        1470       1480      1490      1500      1510
inputs ----TCTTTAC--TGTGGGAAAACCATC--TCAGTAAGACCTAAGTGTCCAGGAGACAGAAGGAGAA-GA
          ::. ..:  ..:. :.::.: :.:  ::: :: :. :. :.::.:  :..:.::::.  ... .:
       AATGTCAGATCCCAATATGGAAGCTAACAGTCATTACGGTCACAATGAC--GATGTCAGAAACCATGCAA
           2100      2110      2120      2130      2140        2150      2160
```

FIG.26D

```
         1520      1530      1540      1550         1560          1570
inputs GGAAGTGGATCTGGAATTGGGAGGAGCCTCCACCCACC-CCTGAC--TCCTCC----TTATGAAGCCAGC
        :::.  .:: .. .::.. .:.:::::: .  :.:   :  .:  : :.:     :: ....: :  :
       TGAAACCAATAAATGATAATAAAGAGCCTCTGAACTCAGACGTGCAGTACACGGAAGTTCAAGTGTCCTC
            2170      2180      2190      2200      2210      2220      2230

      1580      1590      1600      1610      1620      1630         1640
inputs TGCTGAAATTAGCTACTCACCAAGAGTGAGGGGCAGAGACTTCCAGTCACTGAGTCTCCCAG---GCC--
       .::::::.. : .:.:    .: :.::..::.::.:: :::  .: .   ::.:.:.   ::.:   ::
       AGCTGAGTCTCACAAAGATCTAGGAAAGAAGGACACAGA-GACAGTGTACAGTGAAGTCCGGAAAGCTGT
            2240      2250      2260      2270      2280      2290      2300

           1650      1660              1670      1680        1690       1700
inputs CCCTTGATCTGTACCCCAC-----CCCTA--TCTAACACCACCCTTG--GCTCCCACTCCAGCTC--CCT
       :::: .. : ::.    .:     : :::  .: .: . :.:::::  : . : .   ::::.   ::.
       CCCTGATGCCGTGGAAAGCAGATACTCTAGAACGGAAGGCTCCCTTGATGGAACTTAGACAGCAAGGCCA
             2310      2320      2330      2340      2350      2360      2370

             1710      1720      1730      1740         1750      1760
inputs GTATTGATATAACCTGTCAGG-CTGGCTTGGTTAG-GTTTTACTGGGG----CAGAGGATAGGGA-----
       :.  :: . .. ::::  ::: :.  :.:: :  : :.. .::.:. .    :.:.. .: ..::
       GA--TGCACATCCCTGGAAGGACATCCATGTTCCGAGAAGAACAGATAATCCCTGTATTTCAAGACCTCT
                2380      2390      2400      2410      2420      2430

                1770        1780      1790      1800        1810      1820
inputs -ATCTCTTATTAAAA---CTAACATGAAATATGTGTTGTTTTCATTT--GCAAATTTAAATAAAGATACA
        . :.:::::::.:..    ::. : :: .    . .:.. . . ::.::   ::.. :.:. :.  :.:.:.
       GTGCACTTATTTATGAACCTGCCCTGCTCCCACAGAACACAGCAATTCCTCAGGCTAAGCTGCCGGTTCT
      2440      2450      2460      2470      2480      2490      2500

             1830      1840      1850      1860
inputs TAAT---GTTTGTATGAGATAAGAAAAAAAAAAAAAAAAGGGCGGCCGC-
       :::.   .:     :.::.::: ......:.:::.:.. .:.:  :
       TAAATCCATCCTGCTAAGTTAATGTTGGGTAGAAAGAGATACAGAGGGG
      2510      2520      2530      2540      2550
```

FIG.26E

TANGO 281

Input file AthPb81d10.seq; Output File AthPb81d10.pat
Sequence length 1812

```
                                                                  M   R   L       3
GTCGACCCACGCGTCCGGCGGAGGTTGTGGCTGCACCGTGGTCCTGGGCTTGGTCCTGGGCTTG ATG CGT CTG      73

 F   V   R   P   S   V   R   P   A   M   A   A   P   A   P   S   P   W   T   L    23
TTT GTC CGT CCG TCC GTC CGT CCC GCC ATG GCT GCG CCG GCG CCC TCT CCG TGG ACC CTT  133

 S   L   L   L   L   L   L   L   P   S   P   G   A   H   G   E   L   C   R   P    43
TCG CTG CTG CTG TTG TTG CTA CTG CCG TCT CCG GGT GCC CAT GGC GAG CTG TGC AGG CCC  193

 F   G   E   D   N   S   I   P   E   S   C   P   D   F   C   C   G   S   C   S    63
TTC GGT GAA GAC AAT TCG ATC CCA GAG TCC TGT CCT GAC TTC TGT TGT GGC TCC TGT TCC  253

 S   Q   Y   C   C   S   D   V   L   K   K   I   Q   W   N   E   E   M   C   P    83
AGC CAA TAC TGC TGC TCT GAC GTG CTG AAG AAA ATC CAG TGG AAT GAG GAA ATG TGC CCT  313

 E   P   E   S   S   R   F   S   A   H   P   E   T   P   E   Q   L   G   S   A   103
GAG CCA GAG TCC AGC AGA TTT TCC GCC CAC CCG GAG ACA CCA GAA CAG CTG GGT TCA GCG  373

 L   K   Y   Q   S   S   L   D   S   D   N   M   P   G   F   G   A   T   V   A   123
CTG AAG TAT CAG TCC AGT CTT GAC AGT GAC AAC ATG CCA GGG TTC GGA GCG ACC GTG GCC  433
```

FIG.27A

```
 I   G   L   T   V   F   V   V   F   I   A   T   I   I   V   C   F   T   C   S  143
ATC GGC CTG ACC GTC TTC GTG GTG TTT ATC GCT ACC ATC ATT GTG TGC TTT ACC TGC TCC 493

 C   C   C   L   Y   K   M   C   C   R   P   R   P   V   V   S   N   T   T   T  163
TGC TGC TGT CTA TAT AAG ATG TGC TGC CGC CCA CGA CCT GTC GTG TCC AAC ACC ACA ACT 553

 T   T   V   V   H   T   A   Y   P   Q   P   Q   P   V   A   P   S   Y   P   G  183
ACT ACC GTG GTT CAC ACC GCT TAC CCT CAG CCT CAA CCT GTG GCC CCC AGC TAT CCT GGA 613

 P   T   Y   Q   G   Y   H   P   M   P   P   Q   P   G   M   P   A   A   P   Y  203
CCA ACA TAC CAG GGC TAC CAT CCC ATG CCC CCC CAG CCA GGA ATG CCA GCA GCA CCC TAC 673

 P   T   Q   Y   P   P   P   Y   L   A   Q   P   T   G   P   P   A   Y   H   E  223
CCA ACG CAG TAC CCT CCA CCC TAC CTG GCC CAG CCC ACA GGG CCA CCA GCC TAT CAT GAG 733

 T   L   A   G   A   S   Q   P   P   Y   N   P   A   Y   M   D   P   P   K   A  243
ACG TTG GCT GGA GCC AGC CAG CCT CCA TAC AAC CCG GCC TAC ATG GAT CCC CCA AAG GCA 793

 V   P   *  246
GTT CCC TGA 802
```

FIG.27B

GCCTGCCCCCAGCCTCTTTGGCTAACATTTGATTATGTCATGTGTGTGTGAGTGCTATGCAGAGTTCTTTACTGCTGTC 881

TGTGGTGCGTGTGCCTTGTCTAGACATGTGGCTTCCTCTGCTGATGACCAGGTAGGCACAAATCTTACCAGTGCTGGTT 960

GGGACCAATCTGTTTTCTTCCTCACTTGAAATTGTAATTTCTGAAATTTCAAGTAAATTAAAAACAATAGGGTAGGAGG 1039

TATTTCCCGCTTCACCCCAAGGTGACCAGCCATAGCCTGCCACACATAGGAGAGCAAGCTTTTTGTGGGTCCATGTCCT 1118

GCTTTGGGGAGTAGCCAGCTAGCTGCTGCTATGGGTTTATTCCCAGGGCTTGGCTGCATTTAGCTGGACAGAGAACAAG 1197

GGGCCTCAGTGGCAGTGGGTCAGTGACTGATGTCAGAGCACACTAGGCAGAGAGCCCCGTCCGTCTCCATCAGCTGTCT 1276

GTCTGGACGGTCCCACTGTCTTTCCTGGGACTATGTAGAGGGCCACATGTATTCACTATTCAGGCTCCAGTGGCTTCCA 1355

GGCCAGGGGCCTCTGTCTACTACACACTCTGGTTTCTCCCTACAGTGTCTTTTTACGATTAGCCAAACATATTGCCTGT 1434

TTTTTGTATCCAGATGTGTGATAATTGGTGAGGTTGAAATCCTTGGTTCCTGGAGAACAGGAAACCTGACCTCTGACAG 1513

TCCGTTTCCCTTGACACCAGCTTCATAGAATACCTGACTCCTGTACTACAGTCCAGTTTGTTCCAGTAGCAGGGACACC 1592

AGGGCCAGGGGTTATCTGGACCAAGGGTGGGGGTGGAGAGCCTGGATGGTAGCTCTGGACCAGATGTGAATGCCTCCAT 1671

ATTCCCTGTTGGTTCCTGTTTCACTGGCTGTTTTAGTTTTGTGTTAATTGGTGTTTCTGAGCATTCAAACTCCGCACCC 1750

TCGTTTATAATAAATGAATATTTGGAAAAAAAAAAAAAAAAAAAAAAAAAAAAAAAAAAAA 1812

FIG.27C

>hT281
MRLFVRPSVRPAMAAPAPSPWTLSLLLLLLLPSPGAHGELCRPFGEDNSIPESCPDFCCG
SCSSQYCCSDVLKKIQWNEEMCPEPESSRFSAHPETPEQLGSALKYQSSLDSDNMPGFGA
TVAIGLTVFVVFIATIIVCFTCSCCCLYKMCCRPRPVVSNTTTTTVVHTAYPQPQPVAPS
YPGPTYQGYHPMPPQPGMPAAPYPTQYPPPYLAQPTGPPAYHETLAGASQPPYNPAYMDP
PKAVP

```
Alignments of top-scoring domains:
PSBH: domain 1 of 1, from 97 to 146: score 6.4, E = 8.5
                   *->ktalgelLkPlnseyGKvaPgWGttplmgvfmalfavFLliileiYn
                        +lg+ Lk   s     +Pg+G t+ +g  +++f+vF+  i+  +
       hT281    97    PEQLGSALKYQSSLDSDNMPGFGATVAIG--LTVFVVFIATIIVCFT 141

                   ssvll<-*
                    s
       hT281   142 CSCCC    146
```

FIG.29

```
Input file T281Atmea49d3; Output File T281Atmea49d3.pat
Sequence length 1858

GTCGACCCACGCGTCCGCGCGGAGGTTGCGGCGGCACCGTGGTCTTGGGCTTGGTCCGTCTGTTCGTCCGTCCGTTGGT  79

           M   A   A   P   A   P   S   L   W   T   L   L   L   L   L   L   L    17
CTGTCCCGCC ATG GCT GCG CCG GCG CCC TCT CTG TGG ACC CTA TTG CTG CTG CTG TTG CTG  140

 L   P   P   P   P   G   A   H   G   E   L   C   R   P   F   G   E   D   N   S    37
CTG CCG CCG CCT CCG GGT GCC CAT GGT GAG CTG TGC AGG CCC TTT GGT GAA GAC AAT TCG  200

 I   P   V   F   C   P   D   F   C   C   G   S   C   S   N   Q   Y   C   C   S    57
ATC CCA GTG TTC TGT CCT GAT TTC TGT TGT GGT TCC TGT TCC AAC CAA TAC TGC TGC TCG  260

 D   V   L   R   K   I   Q   W   N   E   E   M   C   P   E   P   E   S   S   R    77
GAC GTG CTG AGG AAA ATC CAG TGG AAT GAG GAA ATG TGT CCT GAG CCA GAG TCC AGC AGA  320

 F   S   T   P   A   E   E   T   P   E   H   L   G   S   A   L   K   F   R   S    97
TTT TCC ACC CCC GCG GAG GAG ACA CCC GAA CAT CTG GGT TCA GCG CTG AAA TTT CGA TCC  380

 S   F   D   S   D   P   M   S   G   F   G   A   T   V   A   I   G   V   T   I   117
AGT TTT GAC AGT GAC CCT ATG TCA GGG TTC GGA GCG ACC GTC GCC ATT GGC GTG ACC ATC  440

 F   V   V   F   I   A   T   I   I   I   C   F   T   C   S   C   C   C   L   Y   137
TTT GTG GTG TTT ATT GCC ACT ATC ATC ATC TGC TTC ACC TGC TCC TGC TGC TGT CTG TAT  500

 K   M   C   C   P   Q   R   P   V   V   T   N   T   T   T   T   T   V   V   H   157
AAG ATG TGC TGC CCC CAA CGC CCT GTC GTG ACC AAC ACC ACA ACT ACT ACC GTG GTT CAT  560

 A   P   Y   P   Q   P   Q   P   Q   P   V   A   P   S   Y   P   G   P   T   Y   177
GCC CCT TAC CCT CAG CCT CAA CCT CAA CCT GTG GCC CCC AGC TAT CCT GGA CCA ACA TAC  620

 Q   G   Y   H   P   M   P   P   P   A   R   N   A   S   S   T   L   P   N   A   197
CAG GGC TAC CAT CCC ATG CCC CCC CCA GCC AGG AAT GCC AGC AGC ACC CTA CCC AAC GCA  680
```

FIG.30A

```
 V   P   T   T   L   P   G   P   A   H   R   A   A   T   L   P   *       214
GTA CCC ACC ACC CTA CCT GGC CCA GCC CAC AGG GCC GCC ACC CTA CCA TGA      731

GTCCTTGGCTGGAGCCAGCCAGCCTCCATACAACCCGACCTACATGGATTCCCTAAAGACAATTCCCTGAACCTGCCCC  810

CAGCCTCTTTGGCTGCCATTTATGTCGTGTGTGAGTGAGTGATACGCAGAGTTCTTTACTGCTGTCTGTGGTGTGTGTG  889

CCTTGTCTAGACATGTGGCTTCCTCTGCTGTTGACCAGGTAGGCGCAAGTCTTACCAGTGTGGGTCGGGACCAACCTGT  968

TTTCTTCCTCACTTGAAATTGTACTTTCTGAAATTTCAAGCAAATTAAAAACAATAAGGTAGGAGGTATTTCCCACGTC  1047

ACCCCAAGGTGACCAGCCATGGCCTGTCATACTTAGGAGAGCAAGCTTTTTGCGGGTACAGAGCAGGCTTTGGGGGGTA  1126

ACCAGCTAGCTGCTGCTAGGCCTTTATTCCCAGGGTTTGGCTGCATTGGCAGTGAGGCAGGTGGCTGGGGGTGACACCA  1205

GGTGACAAGGGGACTCAGTGGCAGGGGGTCACACCAGGCAGAACACCATACACTCTCCATCAGCTGTCTGTCTGGATGT  1284

CACTGTCCTTCCCGGGGCTGTATAGAGGGCCACATGTGTTCACTATTCAGGCTCCACTGGGGGAATTTTCCTACCTTTG  1363

CTGGCTTGGCTCCTGCTCCCAGGCCAGGGACCTCGGTCTGTCTACTACACACTCTGGTTTCTCCCTGCACTGTCTTTTT  1442

ACTGTTAGCCAAACATTTTGCCTGTTTTCTGTCTCCAGATGTGTGATAATTGGTGTGAGGTTGAAATCCCTGGTTCCTG  1521

GAGGACAGACAACCTGACCTCCGACTGTCAGTTTCCCTTGACACCATCTTCATAGAAATACCTGACTCCTGTACCACAG  1600

TCCAGTTTGTCCCAGTAGCAGGGACACCAAGGCCAATGGGTTATCTGGACCAAAGGTGGGGTGGAGGGCCTAGATGGTA  1679

TCTCCGGCCCAGATGTGAATACCTCCATATTCCCTGTTGGTTCCTGTTTCACTGGCTGTTTTAGCTTTGTGTTGATTGG  1758

TGTTTCTGAGCATTCAGACTCCGCACCCTCATTTCTAATAAATGCAACATTGGAAAAAAAAAAAAAAAAAAAAAAAAAA  1837

AAAAAAAAAAAGGGCGGCCGC                                                            1858
```

FIG.30B

>mT281
MAAPAPSLWTLLLLLLLLPPPPGAHGELCRPFGEDNSIPVFCPDFCCGSCSNQYCCSDVL
RKIQWNEEMCPEPESSRFSTPAEETPEHLGSALKFRSSFDSDPMSGFGATVAIGVTIFVV
FIATIIICFTCSCCCLYKMCCPQRPVVTNTTTTTVVHAPYPQPQPQPVAPSYPGPTYQGY
HPMPPPARNASSTLPNAVPTTLPGPAHRAATLP

```
ALIGN calculates a global alignment of two sequences
 version 2.0uPlease cite: Myers and Miller, CABIOS (1989)
> hT281 a.a.                                      245 aa vs.
> mT281 a.a.                                      213 aa
scoring matrix: pam120.mat, gap penalties: -12/-4
66.5% identity;         Global alignment score: 739

               10        20        30        40        50        60        70
inputs MRLFVRPSVRPAMAAPAPSPWTLSLLLLLLLPSPGAHGELCRPFGEDNSIPESCPDFCCGSCSSQYCCSD
       :            :::::: ::: :::::: :.::::::::::::::::::  :::::::::::.:::::
       M------------AAPAPSLWTLLLLLLLLPPPPGAHGELCRPFGEDNSIPVFCPDFCCGSCSNQYCCSD
                             10        20        30        40        50

               80        90        100       110       120       130
inputs VLKKIQWNEEMCPEPESSRFSAHPE-TPEQLGSALKYQSSLDSDNMPGFGATVAIGLTVFVVFIATIIVC
       ::.::::::::::::::::::. .: :::.::::::..::.::: :.:::::::::.:.:::::::::.:
       VLRKIQWNEEMCPEPESSRFSTPAEETPEHLGSALKFRSSFDSDPMSGFGATVAIGVTIFVVFIATIIIC
        60        70        80        90       100       110       120

     140       150       160       170         180       190       200
inputs FTCSCCCLYKMCCRPRPVVSNTTTTTVVHTAYPQPQP--VAPSYPGPTYQGYHPMPPQPGMPAAPYPTQY
       ::::::::::::: .::::.:::::::::..::::::  ::::::::::::::::::         :..
       FTCSCCCLYKMCCPQRPVVTNTTTTTVVHAPYPQPQPQPVAPSYPGPTYQGYHPMPP---------PARN
      130       140       150       160       170       180

         210       220       230       240
inputs PPPYLAQPTGPPAYHETLAGASQPPYNPAYMDPPKAVP
       ... :  :.. :.   ::.:... .          ..:
       ASSTL--PNAVPT---TLPGPAHRA---------ATLP
     190         200                   210
```

FIG.32

SECRETED PROTEINS AND USES THEREOF

BACKGROUND OF THE INVENTION

Many secreted proteins, for example, cytokines and cytokine receptors, play a vital role in the regulation of cell growth, cell differentiation, and a variety of specific cellular responses. A number of medically useful proteins, including erythropoietin, granulocyte-macrophage colony stimulating factor, human growth hormone, and various interleukins, are secreted proteins. Thus, an important goal in the design and development of new therapies is the identification and characterization of secreted and transmembrane proteins and the genes which encode them.

Many secreted proteins are receptors which bind a ligand and transduce an intracellular signal, leading to a variety of cellular responses. The identification and characterization of such a receptor enables one to identify both the ligands which bind to the receptor and the intracellular molecules and signal transduction pathways associated with the receptor, permitting one to identify or design modulators of receptor activity, e.g., receptor agonists or antagonists and modulators of signal transduction.

SUMMARY OF THE INVENTION

The present invention is based, at least in part, on the discovery of cDNA molecules which encode the TANGO 253, 257 and 281 proteins and the INTERCEPT 258 protein, all of which are either wholly secreted or transmembrane proteins.

The TANGO 253 proteins are C1q domain-containing polypeptides that exhibit homologue to a human adipocyte complement-related protein precursor.

The TANGO 257 proteins are homologous to the human extracellular molecule olfactomedin, a molecule important in the maintenance, growth and differentiation of chemosensory cilia of olfactory neurons.

The INTERCEPT 258 proteins are Ig domain-containing polypeptides that exhibit homology to an antigen (A33) expressed in colonic and small bowel epithelium, a protein that may represent a cancer cell marker.

The TANGO 281 proteins represent proteins downregulated in megakaryocytes that fail to express the gata-1 transcription factor (a factor critical for blood cell formation) and can, therefore, represent direct or indirect gata-1 targets.

The TANGO 253, TANGO 257, INTERCEPT 258 and TANGO 281 proteins, fragments, derivatives, and variants thereof are collectively referred to herein as "polypeptides of the invention" or "proteins of the invention." Nucleic acid molecules encoding the polypeptides or proteins of the invention are collectively referred to as "nucleic acids of the invention."

The nucleic acids and polypeptides of the present invention are useful as modulating agents in regulating a variety of cellular processes. Accordingly, in one aspect, this invention provides isolated nucleic acid molecules encoding a polypeptide of the invention or a biologically active portion thereof The present invention also provides nucleic acid molecules which are suitable for use as primers or hybridization probes for the detection of nucleic acids encoding a polypeptide of the invention.

The invention features nucleic acid molecules which are at least 30%, 35%, 40%, 45%, 50%, 55%, 65%, 75%, 85%, 95%, or 98% identical to the nucleotide sequence of SEQ ID NO:1, SEQ ID NO:2, the nucleotide sequence of the cDNA insert of an EpT253 clone deposited with ATCC as Accession Number 207222, or a complement thereof.

The invention features nucleic acid molecules which are at least 30%, 35%, 40%, 45%, 50%, 55%, 65%, 75%, 85%, 95%, or 98% identical to the nucleotide sequence of SEQ ID NO:8, SEQ ID NO:9, the nucleotide sequence of the cDNA insert of an EpTm253 clone deposited with ATCC as Accession Number 207215, or a complement thereof.

The invention features nucleic acid molecules which are at least 95% or 98% identical to the nucleotide sequence of SEQ ID NO:15, the nucleotide sequence of the cDNA insert of an EpT257 clone deposited with ATCC as Accession Number 207222, or a complement thereof.

The invention features nucleic acid molecules which are at least 95% or 98% identical to the nucleotide sequence of SEQ ID NO:21, the nucleotide sequence of the cDNA insert of an EpTm257 clone deposited with ATCC as Accession Number 207217, or a complement thereof.

The invention features nucleic acid molecules which are at least 45%, 50%, 55%, 65%, 75%, 85%, 95%, or 98% identical to the nucleotide sequence of SEQ ID NO:26, SEQ ID NO:27, the nucleotide sequence of the cDNA insert of an EpT258 clone deposited with ATCC as Accession Number 207222, or a complement thereof.

The invention features nucleic acid molecules which are at least 45%, 50%, 55%, 65%, 75%, 85%, 95%, or 98% identical to the nucleotide sequence of SEQ ID NO:37, SEQ ID NO:38, the nucleotide sequence of the cDNA insert of an EpTm258 clone deposited with ATCC as Accession Number 207221, or a complement thereof.

The invention features nucleic acid molecules which are at least 30%, 35%, 40%, 35 45%, 50%, 55%, 60%, 65%, 75%, 85%, 95%, or 98% identical to the nucleotide sequence of SEQ ID NO:46, the nucleotide sequence of the cDNA insert of an EpT281 clone deposited with ATCC as Accession Number 207222, or a complement thereof.

The invention features nucleic acid molecules which are at least 35%, 40%, 45%, 50%, 55%, 65%, 75%, 85%, 95%, or 98% identical to the nucleotide sequence of SEQ ID NO:56, the nucleotide sequence of the cDNA insert of an EpmT281 clone deposited with ATCC as patent deposit Number PTA-224, or a complement thereof.

The invention features nucleic acid molecules of at least 450, 500, 550, 600, 650, 700, 750, 800, 850, 900, 1000, 1100, 1200 or 1300 nucleotides of the nucleotide sequence of SEQ ID NO:1, the nucleotide sequence of an EpT253 cDNA of ATCC Accession Number 207222, or a complement thereof.

The invention features nucleic acid molecules which include a fragment of at least 50, 100, 150, 200, 250, 300, 350, 400, 450, 500, 550, 600, 650, 700 or 720 nucleotides of the nucleotide sequence of SEQ ID NO:2, or a complement thereof.

The invention features nucleic acid molecules which include a fragment of at least 540, 600, 650, 700, 750, 800, 850, 900, 950, 1000, 1100, 1200 or 1250 nucleotides of the nucleotide sequence of SEQ ID NO:8 the nucleotide sequence of an EpTm253 cDNa of ATCC Accession Number 207215, or a complement thereof.

The invention features nucleic acid molecules of at least 310, 350, 400, 450, 500, 550, 600, 650 or 700 nucleotides of the nucleotide sequence of SEQ ID NO:9, or a complement thereof.

The invention features nucleic acid molecules which include a fragment of at least 1800 nucleotides of the nucleotide sequence of SEQ ID NO:15 or its complement.

The invention features nucleic acid molecules which include a fragment of at least 1150 or 1200 nucleotides of the nucleotide sequence of SEQ ID NO:16, or its complement.

The invention features nucleic acid molecules which include a fragment of at least 1100, 1200, 1300, 1400, 1500, 1600 or 1700 nucleotides of the nucleotide sequence of SEQ ID NO:21 the nucleotide sequence of an EpTm257 cDNA of ATCC Accession Number 207217, or a complement thereof.

The invention features nucleic acid molecules which include a fragment of at least 1150 or 1200 nucleotides of the nucleotide sequence of SEQ ID NO:22, or its complement.

The invention features nucleic acid molecules which include a fragment of at least 420, 450, 500, 600, 700, 800, 900, 1000, 1100, 1200, 1300, 1400, 1500, 1600, 1700, or 1800 nucleotides of the nucleotide sequence of SEQ ID NO:26 the nucleotide sequence of an EpT258 cDNA of ATCC Accession Number 207222, or a complement thereof.

The invention features nucleic acid molecules which include a fragment of at least 50, 100, 200, 300, 400, 500, 600, 700, 800, 900, 1000, 1100, 1200, 1300, 1400, 1500, 1600, 1700 or 1800 nucleotides of the nucleotide sequence of SEQ ID NO:27, or a complement thereof.

The invention features nucleic acid molecules which include a fragment of at least 675, 700, 800, 900, 1000, 1100, 1200, 1300, 1400, 1500, 1600, 1700 or 1800 nucleotides of the nucleotide sequence of SEQ ID NO:37 the nucleotide sequence of an EpTm258 cDNA of ATCC Accession Number 207221, or a complement thereof.

The invention features nucleic acid molecules which include a fragment of at least 500, 600, 700, 800, 900, 1000, 1100, 1200, 1300, 1400, 1500, 1600, 1700 or 1800 nucleotides of the nucleotide sequence of SEQ ID NO:38, or a complement thereof.

The invention features nucleic acid molecules which include a fragment of at least 50, 100, 200, 300, 400, 500, 600, 700, 800, 900, 1000, 1100, 1200, 1300, 1400, 1500, 1600, 1700 or 1800 nucleotides of the nucleotide sequence of SEQ ID NO:46 the nucleotide sequence of an EpT281 cDNA of ATCC Accession Number 207222, or a complement thereof.

The invention features nucleic acid molecules which include a fragment of at least 50, 100, 200, 300, 400, 500, 600, 700 or 750 nucleotides of the nucleotide sequence of SEQ ID NO:47, or a complement thereof.

The invention features nucleic acid molecules which include a fragment of at least 550, 600, 700, 800, 900, 1000, 1100, 1200, 1300, 1400, 1500, 1600, 1700, 1800 or 1850 nucleotides of the nucleotide sequence of SEQ ID NO:56 the nucleotide sequence of an EpTm281 cDNA of ATCC patent deposit Number PTA-224, or a complement thereof.

The invention features nucleic acid molecules which include a fragment of at least 50, 100, 200, 300, 400, 500, 600 or 700 nucleotides of the nucleotide sequence of SEQ ID NO:57, or a complement thereof.

The invention also features nucleic acid molecules which include a nucleotide sequence encoding a protein having an amino acid sequence that is at least 40%, 45%, 50%, 55%, 60%, 65%, 75%, 85%, 95%, or 98% identical to the amino acid sequence of SEQ ID NO:3, the amino acid sequence encoded by an EpT253 cDNA of ATCC Accession Number 207222, or a complement thereof.

The invention also features nucleic acid molecules which include a nucleotide sequence encoding a protein having an amino acid sequence that is at least 95%, or 98% identical to the amino acid sequence of SEQ ID NO:10, the amino acid sequence encoded by an EpTm253 cDNA of ATCC Accession Number 207115, or a complement thereof.

The invention also features nucleic acid molecules which include a nucleotide sequence encoding a protein having an amino acid sequence that is at least 88%, 90%, 95% or 98% identical to the amino acid sequence of SEQ ID NO:17, the amino acid sequence encoded by an EpT257 cDNA of ATCC Accession Number 207222, or a complement thereof.

The invention also features nucleic acid molecules which include a nucleotide sequence encoding a protein having an amino acid sequence that is at least 88%, 90%, 95%, or 98% identical to the amino acid sequence of SEQ ID NO:23, the amino acid sequence encoded by an EpTm257 cDNA of ATCC Accession Number 207117, or a complement thereof.

The invention also features nucleic acid molecules which include a nucleotide sequence encoding a protein having an amino acid sequence that is at least 45%, 50%, 55%, 60%, 65%, 75%, 85%, 95%, or 98% identical to the amino acid sequence of SEQ ID NO:28, the amino acid sequence encoded by an EpT258 cDNA of ATCC Accession Number 207222, or a complement thereof.

The invention also features nucleic acid molecules which include a nucleotide sequence encoding a protein having an amino acid sequence that is at least 45%, 50%, 55%, 60%, 65%, 75%, 85%, 95%, or 98% identical to the amino acid sequence of SEQ ID NO:39, the amino acid sequence encoded by an EpTm258 cDNA of ATCC Accession Number 207221, or a complement thereof.

The invention also features nucleic acid molecules which include a nucleotide sequence encoding a protein having an amino acid sequence that is at least 30%, 35%, 40%, 45%, 50%, 55%, 60%, 65%, 75%, 85%, 95%, or 98% identical to the amino acid sequence of SEQ ID NO:48, the amino acid sequence encoded by an EpT281 cDNA of ATCC Accession Number 207222, or a complement thereof.

The invention also features nucleic acid molecules which include a nucleotide sequence encoding a protein having an amino acid sequence that is at least 30%, 35%, 40%, 45%, 50%, 55%, 60%, 65%, 75%, 85%, 95%, or 98% identical to the amino acid sequence of SEQ ID NO:58, the amino acid sequence encoded by an EpTm281 of ATCC patent deposit Number PTA-224, or a complement thereof.

The invention also features nucleic acid molecules which include a nucleotide sequence encoding a protein having an amino acid sequence that is at least 30%, 35%, 40%, 45%, 50%, 55%, 60%, 65%, 75%, 85%, 95%, or 98% identical to the amino acid sequence of SEQ ID NO:3, 10, 17, 23, 28, 39, 48, or 58, the amino acid sequence encoded by EpT253, EpTm253, EpT257, EpTm257, EpT258, EpTm258, EpT281, EpTm281 of ATCC Accession Number 207222, Accession Number 207215, Accession Number 207217, or Accession Number 207221, patent deposit Number PTA-224, or a complement thereof, wherein the protein encoded by the nucleotide sequence also exhibits at least one structural and/or functional feature of a polypeptide of the invention.

In preferred embodiments, the nucleic acid molecules have the nucleotide sequence of SEQ ID NO:1, 2, 8, 9, 15, 16, 21, 22, 26, 27, 37, 38, 46, 47, 56, 57, or the nucleotide sequence of the cDNA clones of ATCC Accession Number 207222, 207215, 207217, 207221 or 207222.

Also within the invention are nucleic acid molecules which encode a fragment of a polypeptide having the amino acid sequence of SEQ ID NO:3, or a fragment including at least 10, 15, 20, 25, 30, 50, 75, 100, 125, 150, 175, 200 or 225 contiguous amino acids of SEQ ID NO:3, or the amino acid sequence encoded by an EpT253 cDNA of ATCC Accession Number 207222.

Also within the invention are nucleic acid molecules which encode a fragment of a polypeptide having the amino acid sequence of SEQ ID NO:17, or a fragment including at least 10, 15, 20, 25, 30, 50, 75, 100, 125, 150, 175, 200 or 225 contiguous amino acids of SEQ ID NO:10, or the amino acid sequence encoded by an EpTm253 cDNA of ATCC Accession Number 207215.

Also within the invention are nucleic acid molecules which encode a fragment of a polypeptide having the amino acid sequence of SEQ ID NO:10, or a fragment including at least 360, 370, 380, 390 or 400 contiguous amino acids of SEQ ID NO:17, or the amino acid sequence encoded by an EpT257 cDNA of ATCC Accession Number 207222.

Also within the invention are nucleic acid molecules which encode a fragment of a polypeptide having the amino acid sequence of SEQ ID NO:23, or a fragment including at least 360, 370, 380, 390 or 400 contiguous amino acids of SEQ ID NO:23, or the amino acid sequence encoded by an EpTm257 cDNA of ATCC Accession Number 207217.

Also within the invention are nucleic acid molecules which encode a fragment of a polypeptide having the amino acid sequence of SEQ ID NO:3, or a fragment including at least 15, 25, 30, 50, 75, 100, 125, 150, 175, 200, 225, 250, 275, 300, or 350 contiguous amino acids of SEQ ID NO:28, or the amino acid sequence encoded by an EpT258 cDNA of ATCC Accession Number 207222.

Also within the invention are nucleic acid molecules which encode a fragment of a polypeptide having the amino acid sequence of SEQ ID NO:39, or a fragment including at least 160, 175, 200, 225, 250, 275, 300, 350 or 375 contiguous amino acids of SEQ ID NO:39, or the amino acid sequence encoded by an EpT258 cDNA of ATCC Accession Number 207221.

Also within the invention are nucleic acid molecules which encode a fragment of a polypeptide having the amino acid sequence of SEQ ID NO:48, or a fragment including at least 15, 25, 30, 50, 75, 100, 125, 150, 175, 200, 225, 235 or 240 contiguous amino acids of SEQ ID NO:48, or the amino acid sequence encoded by an EpT281 cDNA of ATCC Accession Number 207222.

Also within the invention are nucleic acid molecules which encode a fragment of a polypeptide having the amino acid sequence of SEQ ID NO:58, or a fragment including at least 15, 25, 30, 50, 75, 100, 125, 150, 175 or 200 contiguous amino acids of SEQ ID NO:58, or the amino acid sequence encoded by an EpTm281 cDNA of ATCC patent deposit Number PTA-224.

The invention also features nucleic acid molecules which encode a polypeptide fragment of at least 15, 25, 30, 50, 75, 100, 125, 150, 175, 200 or more contiguous amino acids of SEQ ID NO:3, 10, 17, 23, 28, 39, 48 or 58, or the amino acid sequence encoded by EpT253, EpTm253, EpT257, EpTm257, EpT258, EpTm258, EpT281 or EpTm281 of ATCC Accession Number 207222, Accession Number 207215, Accession Number 207217, Accession Number 207221 or patent deposit Number PTA-224, wherein the fragment also exhibits at least one structural and/or functional feature of a polypeptide of the invention.

The invention includes nucleic acid molecules which encode a naturally occurring allelic variant of a polypeptide comprising the amino acid sequence of SEQ ID NO:3, 10, 17, 23, 28, 39, 48, 58 or the amino acid sequence encoded by a cDNA of ATCC Accession Numbers 207222, 207215, 207217 or 207221, wherein the nucleic acid molecule hybridizes to a nucleic acid molecule consisting of a nucleic acid sequence encoding SEQ ID NO:3, 10, 28, 39, 48, 58, or the amino acid sequence encoded by a cDNA of ATCC Accession Number 207222, 207215, 207217, 207221 or patent deposit Number PTA-224, a complement thereof under stringent conditions.

Also within the invention are isolated polypeptides or proteins having an amino acid sequence that is at least about 40%, preferably 45%, 55%, 65%, 75%, 85%, 95%, or 98% identical to the amino acid sequence of SEQ ID NO:3, or the amino acid sequence encoded by an EpT253 cDNA of ATCC Accession Number 207222.

Also within the invention are isolated polypeptides or proteins having an amino acid sequence that is at least about 40%, preferably 45%, 50%, 55%, 65%, 75%, 85%, 95%, or 98% identical to the amino acid sequence of SEQ ID NO:10, or the amino acid sequence encoded by an EpTm253 cDNA of ATCC Accession Number 207215.

Also within the invention are isolated polypeptides or proteins having an amino acid sequence that is at least 88%, 90%, 95%, or 98% identical to the amino acid sequence of SEQ ID NO:17, or the amino acid sequence encoded by an EpT257 cDNA of ATCC Accession Number 207222.

Also within the invention are isolated polypeptides or proteins having an amino acid sequence that is at least 88%; 90%, 95%, or 98% identical to the amino acid sequence of SEQ ID NO:23, or the amino acid sequence encoded by an EpTm257 cDNA of ATCC Accession Number 207217.

Also within the invention are isolated polypeptides or proteins having an amino acid sequence that is at least about 30%, preferably 35%, 45%, 55%, 65%, 75%, 85%, 95%, or 98% identical to the amino acid sequence of SEQ ID NO:28, or the amino acid sequence encoded by an EpT258 cDNA of ATCC Accession Number 207222.

Also within the invention are isolated polypeptides or proteins having an amino acid sequence that is at least about 30%, preferably 35%, 40%, 45%, 50%, 55%, 65%, 75%, 85%, 95%, or 98% identical to the amino acid sequence of SEQ ID NO:39, or the amino acid sequence encoded by an EpTm258 cDNA of ATCC Accession Number 207221.

Also within the invention are isolated polypeptides or proteins having an amino acid sequence that is at least about 30%, preferably 35%, 45%, 55%, 65%, 75%, 85%, 95%, or 98% identical to the amino acid sequence of SEQ ID NO:48, or the amino acid sequence encoded by an EpT281 cDNA of ATCC Accession Number 207222.

Also within the invention are isolated polypeptides or proteins having an amino acid sequence that is at least about 30%, preferably 35%, 40%, 45%, 50%, 55%, 65%, 75%, 85%, 95%, or 98% identical to the amino acid sequence of SEQ ID NO:58, or the amino acid sequence encoded by an EpTm28 1 cDNA of ATCC patent deposit Number PTA-224.

The invention also features isolated polypeptides or proteins having an amino acid sequence that is at least about 30%, preferably 35%, 40%, 45%, 50%, 55%, 65%, 75%, 85%, 95% or 98% identical to the amino acid sequence of SEQ ID NO:3, 10, 17, 23, 28, 39, 48 or 58, or the amino acid sequence encoded by EpT253, EpTm253, EpT257, EpTm257, EpT258, EpTm258, EpT281 or EpTm281 of ATCC Accession Number 207222, Accession Number 207215, Accession Number 207217, Accession Number 207221, patent deposit Number PTA-224, wherein the protein or polypeptides also exhibit at least one structural and/or functional feature of a polypeptide of the invention.

Also within the invention are isolated polypeptides or proteins which are encoded by a nucleic acid molecule having a nucleotide sequence that is at least about 30%, preferably 35%, 40%, 45%, 50%, 55%, 60%, 65%, 75%, 85%, 95% or 98% identical the nucleic acid sequence encoding SEQ ID NO:3, and isolated polypeptides or proteins which are encoded by a nucleic acid molecule having a nucleotide sequence which hybridizes under stringent hybridization conditions to a nucleic acid molecule having the nucleotide sequence of SEQ ID NO:1 or 2, a complement thereof, or the non-coding strand of an EpT253 cDNA of ATCC Accession Number 207222.

Also within the invention are isolated polypeptides or proteins which are encoded by a nucleic acid molecule having a nucleotide sequence that is at least about 30%, preferably 35%, 40%, 45%, 50%, 55%, 60%, 65%, 75%, 85%, 95% or 98% identical the nucleic acid sequence encoding SEQ ID NO:10, and isolated polypeptides or proteins which are encoded by a nucleic acid molecule having a nucleotide sequence which hybridizes under stringent hybridization conditions to a nucleic acid molecule having the nucleotide sequence of SEQ ID NO:8 or 9, a complement thereof, or the non-coding strand of an EpTm253 cDNA of ATCC Accession Number 207215.

Also within the invention are isolated polypeptides or proteins which are encoded by a nucleic acid molecule having a nucleotide sequence that is at least about 45%, 50%, 55%, 60%, 65%, 75%, 85%, or 95% identical to the nucleic acid sequence encoding SEQ ID NO:28, and isolated polypeptides or proteins which are encoded by a nucleic acid molecule having a nucleotide sequence which hybridizes under stringent hybridization conditions to a nucleic acid molecule having the nucleotide sequence of SEQ ID NO:26 or 27, a complement thereof, or the non-coding strand of an EpT258 cDNA of ATCC Accession Number 207222.

Also within the invention are isolated polypeptides or proteins which are encoded by a nucleic acid molecule having a nucleotide sequence that is at least about 45%, 50%, 55%, 60%, 65%, 75%, 85%, or 95% identical to the nucleic acid sequence encoding SEQ ID NO:39, and isolated polypeptides or proteins which are encoded by a nucleic acid molecule having a nucleotide sequence which hybridizes under stringent hybridization conditions to a nucleic acid molecule having the nucleotide sequence of SEQ ID NO:37 or 38, a complement thereof, or the non-coding strand of an EpTm258 cDNA of ATCC Accession Number 207221.

Also within the invention are isolated polypeptides or proteins which are encoded by a nucleic acid molecule having a nucleotide sequence that is at least about 30%, preferably 35%, 40%, 45%, 50%, 55%, 60%, 65%, 75%, 85%, or 95% identical to the nucleic acid sequence encoding SEQ ID NO:48, and isolated polypeptides or proteins which are encoded by a nucleic acid molecule having a nucleotide sequence which hybridizes under stringent hybridization conditions to a nucleic acid molecule having the nucleotide sequence of SEQ ID NO:46 or 47, a complement thereof, or the non-coding strand of an EpT281 cDNA of ATCC Accession Number 207222.

Also within the invention are isolated polypeptides or proteins which are encoded by a nucleic acid molecule having a nucleotide sequence that is at least about 30%, preferably 35%, 40%, 45%, 50%, 55%, 60%, 65%, 75%, 85%, or 95% identical to the nucleic acid sequence encoding SEQ ID NO:58, and isolated polypeptides or proteins which are encoded by a nucleic acid molecule having a nucleotide sequence which hybridizes under stringent hybridization conditions to a nucleic acid molecule having the nucleotide sequence of SEQ ID NO:56 or 57, a complement thereof, or the non-coding strand of an EpTm281 cDNA of ATCC patent deposit Number PTA-224.

The invention also features isolated polypeptides or proteins which are encoded by a nucleic acid molecule having a nucleotide sequence that is at least about 30%, preferably 35%, 40%, 45%, 50%, 55%, 60%, 65%, 75%, 85%, 95% or 98% identical to a nucleic acid sequence encoding SEQ ID NO:3, 10, 17, 23, 28, 39, 48 or 58, isolated polypeptides or proteins which are encoded by a nucleic acid molecule having a nucleotide sequence which hybridizes under stringent hybridization conditions to a nucleic acid molecule having the nucleotide sequence of SEQ ID NO:1, 2, 8, 9, 15, 16, 21, 22, 26, 27, 37, 38, 46, 47, 56 or 57, a complement thereof, or the non-coding strand of EpT253, EpTm253, EpT257, EpTm257, EpT258, EpTm258, EpT281, EpTm281 of ATCC Accession Number 207222, Accession Number 207215, Accession Number 207217, Accession Number 207221, patent deposit Number PTA-224, wherein polypeptides or proteins also exhibit at least one structural and/or functional feature of a polypeptide of the invention.

Also within the invention are polypeptides which are naturally occurring allelic variants of a polypeptide that includes the amino acid sequence of SEQ ID NO:3, 10, 17, 23, 28, 39, 48, 58 or the amino acid sequence encoded by a cDNA of ATCC Accession Number 207222, Accession Number 207215, Accession Number 207217 Accession Number 207221, or patent deposit Number PTA-224 wherein the polypeptide is encoded by a nucleic acid molecule which hybridizes to a nucleic acid molecule having the sequence of SEQ ID NO:1, 2, 8, 9, 15, 16, 21, 22, 26, 27, 37, 38, 46, 47, 56, 57 or a complement thereof under stringent conditions.

The invention also features nucleic acid molecules that hybridize under stringent conditions to a nucleic acid molecule having the nucleotide sequence of SEQ ID NO:1 or 2, or an EpT253 cDNA of ATCC Accession Number 207222, or a complement thereof. In other embodiments, the nucleic acid molecules are at least 450, 500, 550, 600, 650, 700, 750, 800, 1000, 1100, 1200 or 1300 nucleotides in length and hybridize under stringent conditions to a nucleic acid molecule comprising the nucleotide sequence of SEQ ID NO:1 or 2, an EpT253 cDNA of ATCC Accession Number 207222, or a complement thereof.

The invention also features nucleic acid molecules that hybridize under stringent conditions to a nucleic acid molecule having the nucleotide sequence of SEQ ID NO:8 or SEQ ID NO:9, an EpTm253 cDNA of ATCC Accession Number 207215, or a complement thereof. In other embodiments, the nucleic acid molecules are at least 540, 550, 600, 650, 700, 750, 800, 850, 900, 950, 1000, 1050, 1100, 1159, 1200, or 1250 nucleotides in length and hybridize under stringent conditions to a nucleic acid molecule comprising the nucleotide sequence of SEQ ID NO:8 or SEQ ID NO:9, an EpTm253 cDNA of ATCC Accession Number 207215, or a complement thereof.

The invention also features nucleic acid molecules that hybridize under stringent conditions to a nucleic acid molecule having the nucleotide sequence of SEQ ID NO:15 or SEQ ID NO:16, an EpT257 cDNA of ATCC Accession Number 207222, or a complement thereof and encode a polypeptide comprising the amino acid sequence of SEQ ID NO:17, or encode a polypeptide comprising at least 360, 370, 380, 390 or 400 contiguous amino acids or SEQ ID NO:17.

The invention also features nucleic acid molecules that hybridize under stringent conditions to a nucleic acid molecule having the nucleotide sequence of SEQ ID NO:21 or SEQ ID NO:22, an EpTm257 cDNA of ATCC Accession Number 207217, or a complement thereof, and encode a polypeptide comprising the amino acid sequence of SEQ ID NO:23, or a polypeptide comprising at least 360, 370, 380, 390, or 400 contiguous amino acids of SEQ ID NO:23.

The invention also features nucleic acid molecules that hybridize under stringent conditions to a nucleic acid molecule having the nucleotide sequence of SEQ ID NO:26 or SEQ ID NO:27, an EpT258 cDNA of ATCC Accession Number 207222, or a complement thereof. In other embodiments, the nucleic acid molecules are at least 550, 600, 700, 800, 900, 1000, 1100, 1200, 1300, 1400, 1500, 1600, 1700 or 1800 nucleotides in length and hybridize under stringent conditions to a nucleic acid molecule comprising the nucleotide sequence of SEQ ID NO:26 or SEQ ID NO:27, an EpT258 cDNA of ATCC Accession Number 207222, or a complement thereof.

The invention also features nucleic acid molecules that hybridize under stringent conditions to a nucleic acid molecule having the nucleotide sequence of SEQ ID NO:37 or SEQ ID NO:38, an EpTm258 cDNA of ATCC Accession Number 207221, or a complement thereof. In other embodiments, the nucleic acid molecules are at least 650, 700, 800, 900, 1000, 1100, 1200, 1300, 1400, 1500, 1600, 1700 or 1800, nucleotides in length and hybridize under stringent conditions to a nucleic acid molecule comprising the nucleotide sequence of SEQ ID NO:37 or SEQ ID NO:38, an EpTm258 cDNA of ATCC Accession Number 207221, or a complement thereof.

The invention also features nucleic acid molecules that hybridize under stringent conditions to a nucleic acid molecule having the nucleotide sequence of SEQ ID NO:46 or 47, an EpTm281 cDNA of ATCC Accession Number 207222, or a complement thereof. In other embodiments, the nucleic acid molecules are at least 710, 750, 800, 900, 1000, 1100, 1200, 1300, 1400, 1500, 1600, 1700 or 1800 nucleotides in length and hybridize under stringent conditions to a nucleic acid molecule comprising the nucleotide sequence of SEQ ID NO:46 or SEQ ID NO:47, an EpT281 cDNA of ATCC Accession Number 207222, or a complement thereof.

The invention also features nucleic acid molecules that hybridize under stringent conditions to a nucleic acid molecule having the nucleotide sequence of SEQ ID NO:56 or 57, an EpTm281 cDNA of ATCC patent deposit Number PTA-244, or a complement thereof In other embodiments, the nucleic acid molecules are at least 580, 600, 700, 800, 900, 1000, 1100, 1200, 1300, 1400, 1500, 1600, 1700, 1800 or 1850 nucleotides in length and hybridize under stringent conditions to a nucleic acid molecule comprising the nucleotide sequence of SEQ ID NO:56 or SEQ ID NO:57, an EpTm281 cDNA of ATCC patent deposit Number PTA-224, or a complement thereof.

The invention also features nucleic acid molecules that hybridize under stringent conditions to a nucleic acid molecule having the nucleotide sequence of SEQ ID NO:1, 2, 8, 9, 15, 16, 21, 22, 26, 27, 37, 38, 46, 47, 56 or 57, or a nucleotide sequence of EpT253, EpTm253, EpT257, EpTm257, EpT258, EpTm258, EpT281 or EpTm281 of ATCC Accession Number 207222, Accession Number 207215, Accession Number 207217, Accession Number 207221, patent deposit Number PTA-224, or complement thereof, wherein such nucleic acid molecules encode polypeptides or proteins that exhibit at least one structural and/or functional feature of a polypeptide of the invention.

The invention also features nucleic acid molecules at least 15, preferably 50, 75, 100, 150, 200, 250, 300, 350, 400, 500, 600, 700, 800, 1000, 1100 or 1200 nucleotides in length and hybridize under stringent conditions to a nucleic acid molecule comprising the nucleotide sequence of SEQ ID NO:1, 2, 8, 9, 15, 16, 21, 22, 26, 27, 37, 38, 46, 47, 56 or 57, or a nucleotide sequence of EpT253, EpTm253, EpT257, EpTm257, EpT258, EpTm258, EpT281 or EpTm281 of ATCC Accession Number 207222, Accession Number 207215, Accession Number 207217, Accession Number 207221, patent deposit Number PTA-224, or a complement thereof, wherein such nucleic acid molecules encode polypeptides or proteins that exhibit at least one structural and/or functional feature of a polypeptide of the invention.

In one embodiment, the invention provides an isolated nucleic acid molecule which is antisense to the coding strand of a nucleic acid of the invention.

Another aspect of the invention provides vectors, e.g., recombinant expression vectors, comprising a nucleic acid molecule of the invention. In another embodiment, the invention provides host cells containing such a vector or engineered to contain and/or express a nucleic acid molecule of the invention. The invention also provides methods for producing a polypeptide of the invention by culturing, in a suitable medium, a host cell of the invention such that a polypeptide of the invention is produced.

Another aspect of this invention features isolated or recombinant proteins and polypeptides of the invention. Preferred proteins and polypeptides possess at least one biological activity possessed by the corresponding naturally-occurring human polypeptide. An activity, a biological activity, or a functional activity of a polypeptide or nucleic acid of the invention refers to an activity exerted by a protein, polypeptide or nucleic acid molecule of the invention on a responsive cell as determined in vivo or in vitro, according to standard techniques. Such activities can be a direct activity, such as an association with or an enzymatic activity on a second protein, or an indirect activity, such as a cellular signaling activity mediated by interaction of the protein with a second protein.

For TANGO 253, biological activities include, e.g., (1) the ability to modulate (this term, as used herein, includes, but is not limited to, "stabilize", promote, inhibit or disrupt, protein-protein interactions (e.g., homophilic and/or heterophilic), and protein-ligand interactions, e.g., in receptor-ligand recognition; (2) ability to modulate cell-cell interactions and/or cell-extracellular matrix interactions; (3) the ability to modulate the host immune response, e.g., by modulating one or more elements in the serum complement cascade; (4) the ability to modulate the proliferation, differentiation and/or activity of cells that form blood vessels and coronary tissue (e.g., coronary smooth muscle cells and/or blood vessel endothelial cells); (5) the ability to modulate intracellular signaling cascades (e.g., signal transduction cascades); and (6) the ability to modulate adipocyte function.

For TANGO 257, biological activities include, e.g., (1) ability to modulate development, differentiation, proliferation and/or activity of neuronal cells, e.g., olfactory neurons (2) ability to modulate development, differentiation, proliferation and/or activity of pulmonary system cells, e.g., lung cell types; (3) ability to modulate cell-cell interactions and/or cell-extracellular matrix interactions, e.g., neuronal cell-extracellular matrix interactions; (4) ability to modulate cell proliferation, e.g., abnormal cell proliferation; and (5) the ability to modulate the development, differentiation, proliferation and/or activity of cells that form blood vessels and coronary tissue, e.g., coronary smooth muscle cells and/or blood vessel endothelial cells.

For INTERCEPT 258, biological activities include, e.g., (1) the ability to modulate protein-protein interactions (e.g., homophilic and/or heterophilic), and protein-ligand interactions, e.g., in receptor-ligand recognition; (2) ability to modulate cell-cell interactions; (3) the ability to modulate the host immune response; (4) the ability to modulate cell proliferation, e.g., gastrointestinal tract epithelial cell proliferation; (5) the ability to modulate intracellular signaling cascades (eg., signal transduction cascades); (6) the ability to modulate pulmonary cell development, differentiation and/or function; and (7) the ability to modulate thrombosis and/or vascularization.

For TANGO 281, biological activities include, e.g., (1) the ability to modulate, e.g., stabilize, promote, inhibit or disrupt protein-protein interactions (e.g., homophilic and/or heterophilic), and protein-ligand interactions, e.g., in receptor-ligand recognition; (2) ability to modulate cell-cell interactions; (3) the ability to modulate the host immune response; (4) the ability to modulate the proliferation, differentiation and/or activity of hematopoeitic cells (e.g. megakaryocytes); (5) the ability to modulate intracellular signaling cascades (e.g., signal transduction cascades) and (6) the ability to modulate platelet function.

In one embodiment, a polypeptide of the invention has an amino acid sequence sufficiently identical to an identified domain of a polypeptide of the invention. As used herein, the term "sufficiently identical" refers to a first amino acid or nucleotide sequence which contains a sufficient or minimum number of identical or equivalent (e.g., with a similar side chain) amino acid residues or nucleotides to a second amino acid or nucleotide sequence such that the first and second amino acid or nucleotide sequences have or encode a common structural domain and/or common functional activity. For example, amino acid or nucleotide sequences which contain or encode a common structural domain having about 60% identity, preferably 65% identity, more preferably 75%, 85%, 95%, 98% or more identity are defined herein as sufficiently identical.

In one embodiment, a TANGO 253 protein includes at least one or more of the following domains: a signal sequence, a collagen domain and a C1q domain.

In one embodiment, a TANGO 257 protein includes at least a signal peptide.

In one embodiment, an INTERCEPT 258 includes at least one or more of the following domains: a signal sequence, an extracellular domain, an immunoglobulin (Ig) domain, a transmembrane domain, and an intracellular or cytoplasmic domain.

In one embodiment, a TANGO 281 protein includes at least one or more of the following domains: a signal sequence, an extracellular domain, a photosystem II 10 kD phosphoprotein domain, a transmembrane domain, and an intracellular or cytoplasmic domain.

The polypeptides of the present invention, or biologically active portions thereof, can be operably linked to a heterologous amino acid sequence to form fusion proteins. The invention further features antibodies, such as monoclonal or polyclonal antibodies, that specifically bind a polypeptide of the invention. In addition, the polypeptides of the invention or biologically active portions thereof can be incorporated into pharmaceutical compositions, which optionally include pharmaceutically acceptable carriers.

In another aspect, the present invention provides methods for detecting the presence, activity or expression of a polypeptide of the invention in a biological sample by contacting the biological sample with an agent capable of detecting an indicator of the presence, activity or expression such that the presence activity or expression of a polypeptide of the invention is detected in the biological sample.

In another aspect, the invention provides methods for modulating activity of a polypeptide of the invention comprising contacting a cell with an agent that modulates (inhibits or stimulates) the activity or expression of a polypeptide of the invention such that activity or expression in the cell is modulated. In one embodiment, the agent is an antibody that specifically binds to a polypeptide of the invention.

In another embodiment, the agent modulates expression of a polypeptide of the invention by modulating transcription, splicing, or translation of an mRNA encoding a polypeptide of the invention. In yet another embodiment, the agent is a nucleic acid molecule having a nucleotide sequence that is antisense to the coding strand of an mRNA encoding a polypeptide of the invention.

The present invention also provides methods to treat a subject having a disorder characterized by aberrant activity of a polypeptide of the invention or aberrant expression of a nucleic acid of the invention by administering an agent which is a modulator of the activity of a polypeptide of the invention or a modulator of the expression of a nucleic acid of the invention to the subject. In one embodiment, the modulator is a protein of the invention. In another embodiment, the modulator is a nucleic acid of the invention. In other embodiments, the modulator is a peptide, peptidomimetic, or other small molecule.

The present invention also provides diagnostic assays for identifying the presence or absence of a genetic lesion or mutation characterized by at least one of: (i) aberrant modification or mutation of a gene encoding a polypeptide of the invention, (ii) mis-regulation of a gene encoding a polypeptide of the invention, and (iii) aberrant post-translational modification of the invention wherein a wild-type form of the gene encodes a protein having the activity of the polypeptide of the invention.

In another aspect, the invention provides a method for identifying a compound that binds to or modulates the activity of a polypeptide of the invention. In general, such methods entail measuring a biological activity of the polypeptide in the presence and absence of a test compound and identifying those compounds which alter the activity of the polypeptide.

The invention also features methods for identifying a compound which modulates the expression of a polypeptide or nucleic acid of the invention by measuring the expression of the polypeptide or nucleic acid in the presence and absence of the compound.

Other features and advantages of the invention will be apparent from the following detailed description and claims.

BRIEF DESCRIPTIONS OF THE DRAWINGS

FIGS. 1A–1B depict the cDNA sequence of human TANGO 253 (SEQ ID NO:1) and the predicted amino acid sequence of human TANGO 253 (SEQ ID NO:3). The open reading frame of SEQ ID NO:1 extends from nucleotide 188 to nucleotide 916 of SEQ ID NO:1 (SEQ ID NO:2).

FIG. 2 depicts a hydropathy plot of human TANGO 253. Relatively hydrophobic regions of the protein are above the dashed horizontal line, and relatively hydrophilic regions of the protein are below the dashed horizontal line. The cysteine residues (cys) are indicated by short vertical lines just below the hydropathy trace. The dashed vertical line separates the signal sequence (amino acids 1 to 15 of SEQ ID NO:3; SEQ ID NO:5) on the left from the mature protein (amino acids 16 to 243 of SEQ ID NO:3; SEQ ID NO:4) on the right. Below the hydropathy plot, the amino acid sequence of human TANGO 253 is depicted.

FIGS. 3A–3B depict a cDNA sequence of mouse TANGO 253 (SEQ ID NO:8) and the predicted amino acid sequences of mouse TANGO 253 (SEQ ID NO:10). The open reading frame of SEQ ID NO:10 extends from nucleotide 135 to 863 of SEQ ID NO:10 (SEQ ID NO:9).

Figure 4:
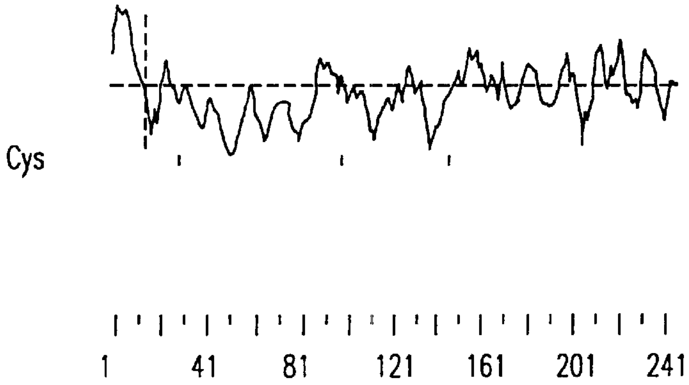

FIG. 4 depicts a hydropathy plot of mouse TANGO 253. Relatively hydrophobic regions of the protein are shown above the dashed horizontal line, and relatively hydrophilic regions of the protein are below the dashed horizontal line. The cysteine residues (cys) are indicated by short vertical lines just below the hydropathy trace. The dashed vertical line separates the signal sequence (amino acids 1 to 15 of SEQ ID NO:10; SEQ ID NO:12) on the left from the mature protein (amino acids 16 to 243 of SEQ ID NO:10; SEQ ID NO:11) on the right. Below the hydropathy plot, the amino acid sequence of mouse TANGO 253 is depicted.

FIG. 5 depicts an alignment of the amino acid sequence of human TANGO 253 (SEQ ID NO:3) and the amino acid sequence of mouse TANGO 253 (SEQ ID NO:10). The alignment demonstrates that the amino acid sequences of human and mouse TANGO 253 are 93.8% identical. This alignment was performed using the ALIGN program with a PAM120 scoring matrix, a gap length penalty of 12 and a gap penalty of 4.

FIGS. 6A–6B depict alignments of the amino acid sequence of human adipocyte complement-mediated protein precursor (SEQ ID NO:20; Swiss Prot Accession Number Q15848) and the amino acid sequence of human TANGO 253 (SEQ ID NO:3; 6A) or mouse TANGO 253 (SEQ ID NO:10; 6B). 6A shows the amino acid sequences of human adipocyte complement-mediated protein precursor and human TANGO 253 are 38.7% identical. 6B shows the amino acid sequences of human adipocyte complement-mediated precursor procursor protein and mouse TANGO 253 are 38.3% identical. These alignments were performed using the ALIGN alignment program with a PAM120 scoring matrix, a gap length penalty of 12, and a gap penalty of 4.

FIGS. 7A, 7A-1, 7A-2, 7A-3, 7B, 7B-1, 7B-2 and 7B-3 depict alignments of the nucleotide sequence of human adipocyte complement-mediated protein precursor (SEQ ID NO:32; GenBank Accession Number A1417523) and the nucleotide sequence of human TANGO 253 (SEQ ID NO:1; FIGS. 7A, 7A-1, 7A-2, and 7A-3) or mouse TANGO 253 (SEQ ID NO:8; FIGS. 7B, 7B-1, 7B-2, and 7B-3). The nucleotide sequences of human adipocyte complement-mediated protein precursor and human TANGO 253 are 29.1% identical. The nucleotide sequences of human adipocyte complement-mediated protein precursor and mouse TANGO 253 are 30.4% identical. These alignments were performed using the ALIGN alignment program with a PAM120 scoring matrix, a gap length penalty of 12, and a gap penalty of 4.

FIGS. 8A–8C depict the cDNA sequence of human TANGO 257 (SEQ ID NO:15) and the predicted amino acid sequence of human TANGO 257 (SEQ ID NO:17). The open reading frame of SEQ ID NO:16 extends from nucleotide 88 to nucleotide 1305 of SEQ ID NO:15 (SEQ ID NO:16).

FIG. 9 depicts a hydropathy plot of human TANGO 257. Relatively hydrophobic regions of the protein are shown above the dashed horizontal line, and relatively hydrophilic regions of the protein are below the dashed horizontal line. The cysteine residues (cys) and potential N-glycosylation sites (Ngly) are indicated by short vertical lines just below the hydropathy trace. The dashed vertical line separates the signal sequence (amino acids 1 to 21 of SEQ ID NO:16; SEQ ID NO:19) on the left from the mature protein (amino acids 22 to 406 of SEQ ID NO:16; SEQ ID NO:18) on the right. Below the hydropathy plot, the amino acid sequence of human TANGO 257 is depicted.

FIGS. 10A–10C depict a cDNA sequence of mouse TANGO 257 (SEQ ID NO:21) and the predicted amino acid sequence of mouse TANGO 257 (SEQ ID NO:23). The open reading frame of SEQ ID NO:21 extends from nucleotide 31 to 1248 of SEQ ID NO:21 (SEQ ID NO:22).

FIG. 11 depicts a hydropathy plot of mouse TANGO 257. Relatively hydrophobic regions of the protein are shown above the dashed horizontal line, and relatively hydrophilic regions of the protein are below the dashed horizontal line. The cysteine residues (cys) and potential N-glycosylation sites (Ngly) are indicated by short vertical lines just below the hydropathy trace. The dashed vertical line separates the signal sequence (amino acids 1 to 21 of SEQ ID NO:23; SEQ ID NO:25) on the left from the mature protein (amino acids 22 to 406 of SEQ ID NO:23; SEQ ID NO:24) on the right. Below the hydropathy plot, the amino acid sequence of mouse TANGO 257 is depicted.

FIG. 12 depicts an alignment of the amino acid sequence of human TANGO 257 (SEQ ID NO:17) and the amino acid sequence of mouse TANGO 257 (SEQ ID NO:23). This alignment demonstrates that the amino acid sequences of human and mouse TANGO 257 are 94.1% identical. This alignment was performed using the ALIGN program with a PAM120 scoring matrix, a gap length penalty of 12 and a gap penalty of 4.

FIG. 13 depicts an alignment of the amino acid sequence (SEQ ID NO:43) encoded by a nucleotide sequence referred to in PCT publication WO 98/39446 as “gene 64”, and the amino acid sequence of human TANGO 257 (SEQ ID NO:17). Gene 64 encodes a 353 amino acid residue protein that exhibits homology with the human extracellular molecule olfactomedin, which is though to be involved in maintenance, growth and/or differentiation of chemosensory cilia on the apical dendrites of olfactory neurons. The polypeptide encoded by gene 64 also exhibits homology to human TANGO 257, which contains 406 amino acids (i.e., an additional 53 amino acids carboxy to residue 353). The amino acid sequences of amino acid residues 1–353 of the gene 64-encoded polypeptide and human TANGO 257 are identical. As such, the overall amino acid sequence identity between the full length polypeptide encoded by gene 64, and the full-length human TANGO 257 polypeptide is approximately 87%. This alignment was performed using the ALIGN alignment program with a PAM120 scoring matrix, a gap length penalty of 12, and a gap penalty of 4.

FIGS. 14A–14D depict an alignment of the nucleotide sequence of gene 64 (SEQ ID NO:66; PCT Publication WO 98/39446) and the nucleotide sequence of human TANGO 257 (SEQ ID NO:15). The nucleotide sequences of gene 64 and human TANGO 257 are 93.5% identical. It is noted, however, that among the differences between the two sequences is a cytosine nucleotide at human TANGO 257 (SEQ ID NO:15) position 1146 that results in a human TANGO 257 amino acid sequence (SEQ ID NO:17) of 406 amino acids as opposed to the gene 64 amino acid sequence of only 353 amino acids (SEQ ID NO:43). Alignment of the nucleotide sequence of the gene 64 open reading frame and that of human TANGO 257 (SEQ ID NO:16) show that the two nucleotide sequences are 87.2% identical. These alignments were performed using the ALIGN program with a PAM220 scoring matrix, a gap length penalty of 12 and a gap penalty of 4.

FIG. 15 depicts an alignment of the acid sequence of the gene 64-encoded polypeptide (SEQ ID NO:43) and the amino acid sequence of mouse TANGO 257 (SEQ ID NO:23). The sequences exhibit an overall amino acid sequence identity of approximately 81.8%. This alignment was performed using an ALIGN program with a PAM120 scoring matrix, a gap length penalty of 12 and a gap penalty of 4.

FIGS. 16A–16F depict an alignment of the nucleotide sequence of gene 64 (SEQ ID NO:66) and the nucleotide sequence of mouse TANGO 257 (SEQ ID NO:21). The two sequences are approximately 76.2% identical. Alignment of the nucleotide sequence of the gene 64 open reading frame and that of mouse TANGO 257 (SEQ ID NO:22) show that the two nucleotide sequences are 77.8% identical. These alignments were performed using the ALIGN program with a PAM220 scoring matrix, a gap length penalty of 12 and a gap penalty of 4.

FIGS. 17A–17C depict the cDNA sequence of human INTERCEPT 258 (SEQ ID NO:26) and the predicted amino acid sequence of INTERCEPT 258 (SEQ ID NO:28). The open reading frame of SEQ ID NO:26 extends from nucleotide 153 to nucleotide 1262 of SEQ ID NO:26 (SEQ ID NO:27).

FIG. 18 depicts a hydropathy plot of human INTERCEPT 258. Relatively hydrophobic regions of the protein are above the dashed horizontal line, and relatively hydrophilic regions of the protein are below the dashed horizontal line. The cysteine residues (Cys) and potential N-glycosylation sites (Ngly) are indicated by short vertical lines just below the hydropathy trace. Below the hydropathy plot, the amino acid sequence of human INTERCEPT 258 is depicted.

FIGS. 19A–19C depict a cDNA sequence of mouse INTERCEPT 258 (SEQ ID NO:37) and the predicted amino acid sequence of mouse INTERCEPT 258 (SEQ ID NO:39). The open reading frame of SEQ ID NO:37 extends from nucleotide 107 TO 1288 of SEQ ID NO:60 (SEQ ID NO:38).

FIG. 20 depicts a hydropathy plot of mouse INTERCEPT 258. Relatively hydrophobic regions of the protein are shown above the dashed horizontal line, and relatively hydrophilic regions of the protein are below the dashed horizontal line. The cysteine residues (cys) and potential N-glycosylation sites (Ngly) are indicated by short vertical lines just below the hydropathy trace. The dashed vertical line separates the signal sequence (amino acids 1 to 29 of SEQ ID NO:39; SEQ ID NO:41) on the left from the mature protein (amino acids 30 to 394 of SEQ ID NO:39; SEQ ID NO:40) on the right. Below the hydropathy plot, the amino acid sequence of mouse INTERCEPT 258 is depicted.

FIG. 21 depicts an alignment of the amino acid sequence of human INTERCEPT 258 (SEQ ID NO:28) and the amino acid sequence of mouse INTERCEPT 258 (SEQ ID NO:39). The alignment demonstrates that the amino acid sequences of human and mouse INTERCEPT 258 are 62.8% identical. This alignment was performed using the ALIGN program with a PAM120 scoring matrix, a gap length penalty of 12 and a gap penalty of 4.

FIG. 22 depicts an alignment of the amino acid sequence of human A33 antigen (SEQ ID NO:67; Swiss Prot Accession Number Q99795) and the amino acid sequence of human INTERCEPT 258 (SEQ ID NO:28). The A33 antigen is a transmembrane glycoprotein and member of the Ig superfamily that may be a cancer cell marker. The amino acid sequences of A33 antigen and human INTERCEPT 258 are 23% identical. This alignment was performed using the ALIGN alignment program with a PAM120 scoring matrix, a gap length penalty of 12, and a gap penalty of 4.

FIGS. 23A–23F depict an alignment of the nucleotide sequence of human A33 antigen (SEQ ID NO:68; Gen Bank Accession Number U79725) and the nucleotide sequence of human INTERCEPT 258 (SEQ ID NO:26). These two nucleotide sequences are 40.6% identical. The nucleotide sequence of the open reading frame of human A33 antigen and that of human INTERCEPT 258 are 44% identical. These alignments were performed using the ALIGN alignment program with a PAM120 scoring matrix, a gap length penalty of 12, and a gap penalty of 4.

FIG. 24 depicts an alignment of the amino acid sequence of human A33 antigen (SEQ ID NO:67; Swiss Prot Accession Number Q99795) and the amino acid sequence of mouse INTERCEPT 258 (SEQ ID NO:39). These two amino acid sequences have an overall amino acid identity of 23%. This alignment was performed using the ALIGN alignment program with a PAM120 scoring matrix, a gap length penalty of 12, and a gap penalty of 4.

FIGS. 25A–25I depict an alignment of the nucleotide sequence of human A33 antigen (SEQ ID NO:68; GenBank Accession Number U79725) and the nucleotide sequence of mouse INTERCEPT 258 (SEQ ID NO:37). These two nucleotide sequences are 40% identical. The nucleotide sequence of the open reading frame of human A33 antigen and that of mouse INTERCEPT 258 are 43.2% identical. These alignments were performed using the ALIGN alignment program with a PAM120 scoring matrix, a gap length penalty of 12, and a gap penalty of 4.

FIGS. 26A–26E depict an alignment of the nucleotide sequence of human PECAM-1, an integrin expressed on endothelial cells (SEQ ID NO:72) and the nucleotide sequence of human INTERCEPT 258 (SEQ ID NO:26). These two nucleotide sequences are 40.5% identical. This alignment was performed using ALIGN alignment program with a PAM120 scoring matrix, a gap length of 12, and a gap penalty of 4.

FIGS. 27A–27C depict the cDNA sequence of human TANGO 281 (SEQ ID NO:46) and the predicted amino acid sequence of human TANGO 281 (SEQ ID NO:48). The open reading frame of SEQ ID NO:46 extends from nucleotide 65 to nucleotide 799 of SEQ ID NO:46 (SEQ ID NO:47).

Figure 28:
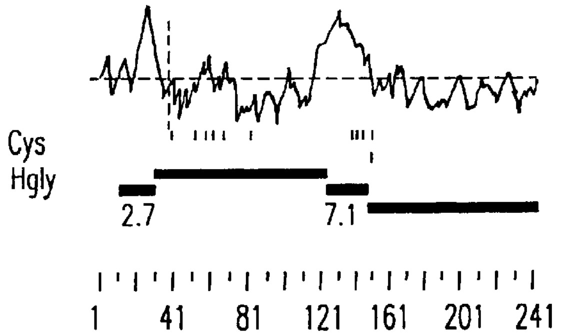

FIG. 28 depicts a hydropathy plot of human TANGO 281. Relatively hydrophobic regions of the protein are above the dashed horizontal line, and relatively hydrophilic regions of the protein are below the dashed horizontal line. The cysteine residues (cys) are indicated by short vertical lines just below the hydropathy trace. The dashed vertical line separates the signal sequence (amino acids 1 to 38 of SEQ ID NO:48; SEQ ID NO:49) on the left from the mature protein (amino acids 39 to 245 of SEQ ID NO:48; SEQ ID NO:50) on the right. Below the hydropathy plot, the amino acid sequence of human TANGO 281 is depicted.

FIG. 29 depicts an alignment of the amino acid sequence of photosystem II 10 kD phosphoprotein domain (SEQ ID NO:69; GenBank Accession Number PF00737) and the amino acid sequence 97 to 146 of human TANGO 281 (SEQ ID NO:48). This alignment was performed using the ALIGN alignment program with a PAM120 scoring matrix, a gap length penalty of 12, and a gap penalty of 4.

FIGS. 30A–30B depict the cDNA sequence of mouse TANGO 281 (SEQ ID NO:56) and the predicted amino acid sequence of mouse TANGO 281 (SEQ ID NO:58). The open reading frame of SEQ ID NO:56 extends from nucleotide 90 to nucleotide 728 of SEQ ID NO:56 (SEQ ID NO:57).

Figure 31:
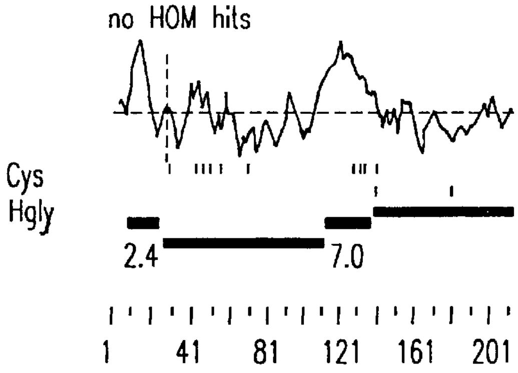

FIG. 31 depicts a hydropathy plot of mouse TANGO 281. Relatively hydrophobic regions of the protein are above the dashed horizontal line, and relatively hydrophilic regions of the protein are below the dashed horizontal line. The cysteine residues (cys) are indicated by short vertical lines just below the hydropathy trace. The dashed vertical line separates the signal sequence (amino acids 1 to 26 of SEQ ID NO:58; SEQ ID NO:59) on the left from the mature protein (amino acids 27 to 213 of SEQ ID NO:58; SEQ ID NO:60) on the right. Below the hydropathy plot, the amino acid sequence of mouse TANGO 281 is depicted.

FIG. 32 depicts an alignment of the amino acid sequence of human TANGO 281 (SEQ ID NO:48) and the amino acid sequence of mouse TANGO 281 (SEQ ID NO:58). The alignment demonstrates that the amino acid sequences of human and mouse TANGO 281 are 66.5% identical. This alignment was performed using the ALIGN program with a PAM120 scoring matrix, a gap length penalty of 12 and a gap penalty of 4.

DETAILED DESCRIPTION OF THE INVENTION

The TANGO 253, TANGO 257, INTERCEPT 258 and TANGO 281 proteins and nucleic acid molecules comprise families of molecules having certain conserved structural and functional features. As used herein, the terms "family" or "families" are intended to mean two or more proteins or nucleic acid molecules having a common structural domain and having sufficient amino acid or nucleotide sequence identity as defined herein. Family members can be from either the same or different species. For example, a family can comprises two or more proteins of human origin, or can comprise one or more proteins of human origin and one or more of non-human origin. Members of the same family may also have common structural domains.

For example, TANGO 253 proteins, TANGO 257 proteins, INTERCEPT 258 proteins and TANGO 281 proteins of the invention have signal sequences. As used herein, a "signal sequence" includes a peptide of at least about 15 or 20 amino acid residues in length which occurs at the N-terminus of secretory and membrane-bound proteins and which contains at least about 70% hydrophobic amino acid residues such as alanine, leucine, isoleucine, phenylalanine, proline, tyrosine, tryptophan, or valine. In a preferred embodiment, a signal sequence contains at least about 10 to 40 amino acid residues, preferably about 19–34 amino acid residues, and has at least about 60–80%, more preferably 65–75%, and more preferably at least about 70% hydrophobic residues. A signal sequence serves to direct a protein containing such a sequence to a lipid bilayer. Thus, in one embodiment, a TANGO 253 protein contains a signal sequence of about amino acids 1 to 15 of SEQ ID NO:3 (SEQ ID NO:5) or about amino acids 1 to 15 of SEQ ID NO:10 (SEQ ID NO:12). In another embodiment, a TANGO 257 protein contains a signal sequence of about amino acids 1 to 21 of SEQ ID NO:17 (SEQ ID NO:19) or about amino acids 1 to 21 of SEQ ID NO:23 (SEQ ID NO:25). In another embodiment, an INTERCEPT 258 protein contains a signal sequence at about amino acids 1 to 29 of SEQ ID NO:28 (SEQ ID NO:30) or about amino acids 1 to 29 of SEQ ID NO:39 (SEQ ID NO:41). In yet another embodiment, a TANGO 281 protein contains a signal sequence of about amino acids 1 to 38 of SEQ ID NO:48 (SEQ ID NO:49) or about amino acids 1 to 26 of SEQ ID NO:58 (SEQ ID NO:59). The signal sequence is cleaved during processing of the mature protein.

In one embodiment, TANGO 253 includes at least one RGD cell attachment site. An RGD domain contains a contiguous arginine-glycine-aspartic acid amino acid sequence and is involved in cell-cell, cell-extracellular matrix and cell adhesion interactions. In a preferred embodiment, a TANGO 253 family member has the amino acid sequence of SEQ ID NO:3 and, preferably, a RGD cell attachment site is located at about amino acid positions 77 to 79.

TANGO 253 family members can also include a collagen domain. As used herein, the term "collagen domain" refers to a protein domain containing a G-X-Y amino acid repeat motif, wherein the first amino acid residue is glycine and the second and third amino acid residues can be any residue but are preferably proline or hydroxyproline. Typically, a collagen domain contains at least about 3 to 5 G-X-Y repeats, and can contain about 3, 5, 8, 10, 12, 15, 20 or more continuous G-X-Y repeats. In one embodiment, a collagen domain can fold to form a triple helical structure.

In one embodiment, a TANGO 253 family member includes at least one collagen domain having an amino acid sequence that is at least about 40%, 50%, 60%, 70%, 80%, 90%, 95% or 98% identical to amino acids 36 to 95 of SEQ ID NO:3, which is the collagen domain of human TANGO 253 (SEQ ID NO:6), or amino acids 36 to 95 of SEQ ID NO:10, which is the collagen domain of mouse TANGO 253 (SEQ ID NO:13), while maintaining a glycine residue at the first position of G-X-Y repeats within the domain to maintain at least 3, 5, 8, 10, 12, 15 or 20 contiguous G-X-Y repeats, or while most preferably maintaining a glycine repeat at the first position of each G-X-Y repeat within the domain.

TANGO 253 family members can also include a C1q domain or at least one of the conserved amino acid motifs found therein. As used herein, the term "C1q domain" refers to a protein domain that bears homology to a C1q domain present within a member of the C1 enzyme complex. A C1q domain typically includes about 130–140 amino acid residues. C1q domains are utilized in processes involving, e.g., correct protein folding and alignment and protein-protein interactions.

In one embodiment, a TANGO 253 family member includes one or more C1q domains having an amino acid sequence that is at least 45%, preferably about 50%, 55%, 60%, 70%, 75%, 80%, 90%, 95% and most preferably at least about 98% identical to amino acids 105 to 232 of SEQ ID NO:3, which is the human TANGO 253 C1q domain (SEQ ID NO:7) or amino acids 105 to 232 of SEQ ID NO:10, which is the mouse TANGO 253 C1q domain (SEQ ID NO:14).

Embodiments of TANGO 253 family members include, but are not limited to, human, mouse and rat TANGO 253 nucleic acids and proteins. The features of the human and mouse TANGO 253 are described below. A cDNA encoding a rat TANGO 253 nucleotide sequence (SEQ ID NO:74), identified in clone jtrxa001e10t1, is 75.4% identical to human TANGO 253 (SEQ ID NO:1) in a 536 bp overlap. Further, the isolated rat TANGO 253 nucleotide sequence (SEQ ID NO:74) is 86% identical to mouse TANGO 253 (SEQ ID NO:9) in a 472 bp overlap.

Embodiments of TANGO 257 family members include, but are not limited to, human, mouse and rat TANGO 257 nucleic acids and proteins. The features of the human and mouse TANGO 257 are described below. A cDNA encoding a rat TANGO 257 nucleotide sequence (SEQ ID NO:75), identified within clone jtrxa001e10t1, is 83.8% identical to human TANGO 257 (SEQ ID NO:15) in a 734 bp overlap. Further, the isolated rat TANGO 257 nucleotide sequence (SEQ ID NO:75) is 88.4% identical to mouse TANGO 257 (SEQ ID NO:21) in a 731 bp overlap.

In another example, an INTERCEPT 258 family member includes one or more of the following domains: (1) an extracellular domain; (2) a transmembrane domain; and (3) a cytoplasmic domain. Thus, in one embodiment, an INTERCEPT 258 protein contains an extracellular domain of about amino acids 1 to 246 of SEQ ID NO:28 (SEQ ID NO:31), or a mature extracellular domain of about amino acids 30 to 246 of SEQ ID NO:28. In another embodiment, an INTERCEPT 258 protein contains a transmembrane domain of about amino acids 247 to 271 of SEQ ID NO:28 (SEQ ID NO:33). In another embodiment, an INTERCEPT 258 protein contains a cytoplasmic domain of about amino acids 272 to 370 of SEQ ID NO:28 (SEQ ID NO:34). In yet another embodiment, an INTERCEPT 258 protein is a mature protein containing an extracellular, transmembrane and cytoplasmic domain of about amino acids 30 to 370 of SEQ ID NO:28 (SEQ ID NO:29). In still another embodiment, an INTERCEPT 258 protein contains an extracellular domain of about amino acids 1 to 249 of SEQ ID NO:39 (SEQ ID NO:42), or a mature extracellular domain of about amino acids 30 to 249 of SEQ ID NO:39. In another embodiment, an INTERCEPT 258 protein contains a transmembrane domain of about amino acids 250 to 274 of SEQ ID NO:39 (SEQ ID NO:44). In another embodiment, an INTERCEPT 258 protein contains a cytoplasmic domain of about amino acids 275 to 394 of SEQ ID NO:39 (SEQ ID NO:45). In yet another embodiment, an INTERCEPT 258 protein is a mature protein containing an extracellular, transmembrane and cytoplasmic domain of about 30 to 394 of SEQ ID NO:39 (SEQ ID NO:40).

INTERCEPT 258 family members can also include an immunoglobulin (Ig) domain contained within the extracellular domain. As used herein, the term "Ig domain" refers to a protein domain bearing homology to immunoglobulin superfamily members. An Ig domain includes about 30–90 amino acid residues, preferably about 40–80 amino acid residues, more preferably about 50–70 amino acid residues, still more preferably about 55–65 amino acid residues, and most preferably about 57 to 59 amino acid residues. In certain embodiments, an Ig domain contains a conserved cysteine residue within about to 15 amino acid residues, preferably about 7 to 12 amino acid residues, and most preferably about 8 amino acid residues from its N-terminal end, and another conserved cysteine residue within about 1 to 5 amino acid residues, preferably about 2 to 4 amino acid residues, and most preferably about 3 amino acid residues from its C-terminal end.

An Ig domain typically has the following consensus sequence, beginning about 1 to 15 amino acid residues, more preferably about 3 to 10 amino acid residues, and most preferably about 5 amino acid residues from the C terminal end of the domain: (FY)-Xaa-C-Xaa-(VA)-COO—, wherein (FY) is either a phenylalanine or a tyrosine residue (preferably tyrosine), where "Xaa" is any amino acid, C is a cysteine residue, (VA) is either a valine or an alanine residue (preferably alanine), and COO— is the protein C terminus.

In one embodiment, an INTERCEPT 258 family member includes one or more Ig domains having an amino acid sequence that is at least about 55%, preferably at least about 65%, more preferably at least 75%, yet more preferably at least about 85%, and most preferably at least about 95% identical to amino acids 49 to 128 and/or amino acids 167 to 226 of SEQ ID NO:28, which are the Ig domains of human INTERCEPT 258 (these Ig domains are also represented as SEQ ID NO:35 and 36, respectively).

In another embodiment, an INTERCEPT 258 family member includes one or more Ig domains having an amino acid sequence that is at least about 55%, preferably at least about 65%, more preferably at least about 75%, yet more preferably at least about 85%, and most preferably at least about 95% identical to amino acids 167 to 226 of SEQ ID NO:28 (SEQ ID NO:36), includes a conserved cysteine residue about 8 residues downstream from the N-terminus of the Ig domain, and has one or more Ig domain consensus sequences described herein. In another embodiment, an INTERCEPT 258 family member includes one or more Ig domains having an amino acid sequence that is at least 55%, preferably at least about 65%, more preferably at least about 75%, yet more preferably at least about 85%, and most preferably at least about 95% identical to amino acids 167 to 226 of SEQ ID NO:28 (SEQ ID NO:36), includes a conserved cysteine residue 8 residues downstream from the N-terminus of the Ig domain, has one or more Ig domain consensus sequences described herein, and has a conserved cysteine within the consensus sequence that forms a disulfide both with said first conserved cysteine. In yet another embodiment, an INTERCEPT 258 family member includes one or more Ig domains having an amino acid sequence that is at least 55%, preferably at least about 65%, more preferably at least about 75%, yet more preferably at least about 85%, and most preferably at least about 95% identical to amino acids 167 to 226 of SEQ ID NO:28 (SEQ ID NO:36), includes a conserved cysteine residue 8 residues downstream from the N-terminus of the Ig domain, has one or more Ig domain consensus sequences described herein, has a conserved cysteine within the consensus sequence that forms a disulfide both with said first conserved cysteine, and has at least one INTERCEPT 258 biological activity as described herein.

In a preferred embodiment, an INTERCEPT 258 family member has the amino acid sequence of SEQ ID NO:28 wherein the aforementioned Ig conserved residues are located as follows: the N-terminal conserved cysteine residue is located at about amino acid position 174 (within the Ig domain SEQ ID NO:36) and the C-terminal conserved cysteine is located at about amino acid position 224 (within the Ig domain SEQ ID NO:36).

In another embodiment, an INTERCEPT 258 family member includes one or more Ig domains having an amino acid sequence that is at least about 55%, preferably at least about 65%, more preferably at least about 75%, yet more preferably at least about 85%, and most preferably at least about 95% identical to amino acids 170 to 229 of SEQ ID NO:39, which is the Ig domain of mouse INTERCEPT 258 (SEQ ID NO:71). In another embodiment, an INTERCEPT 258 family member includes one or more Ig domains having an amino acid sequence that is at least about 55%, preferably at least about 65%, more preferably at least about 75%, yet more preferably at least about 85%, and most preferably at least about 95% identical to amino acids 170 to 229 of SEQ ID NO:39 (SEQ ID NO:71), includes a conserved cysteine residue about 8 residues downstream from the N-terminus of the Ig domain, and has one or more Ig domain consensus sequences described herein, has a conserved cysteine within the consensus sequence that forms a disulfide both with said first conserved cysteine, and has at least one INTERCEPT 258 biological activity as described herein.

In a preferred embodiment, an INTERCEPT 258 family member has the amino acid sequence of SEQ ID NO:39 wherein the aforementioned Ig domain conserved residues are located as follows: the N-terminal conserved cysteine residue is located at about amino acid residue position 177 (within the Ig domain SEQ ID NO:71) and the C-terminal conserved cysteine residue is located at about amino acid position 227 (within the Ig domain SEQ ID NO:71).

In another example, a TANGO 281 family member consists of one or more of the following domains: (1) an extracellular domain; (2) a transmembrane domain; and (3) a cytoplasmic domain. In one embodiment, a TANGO 281 protein contains an extracellular domain at amino acids 1 to about 123 of SEQ ID NO:48 or a mature extracellular domain at about amino acid residues 39 to 123 of SEQ ID NO:48 (SEQ ID NO:51), a transmembrane domain at about amino acid residues 124 to 148 of SEQ ID NO:48 (SEQ ID NO:52), and a cytoplasmic domain at about amino acid residues 149 to 245 of SEQ ID NO:48 (SEQ ID NO:53). In another embodiment, a TANGO 281 family contains an extracellular domain at amino acids 1 to about 112 of SEQ ID NO:58 or a mature extracellular domain at about amino acid residues 27 to 112 of SEQ ID NO:58 (SEQ ID NO:61), a transmembrane domain at about amino acid residues 113 to 137 of SEQ ID NO:78 (SEQ ID NO:62), and a cytoplasmic domain at about amino acid residues 138 to 213 of SEQ ID NO:78 (SEQ ID NO:63).

In one embodiment, a TANGO 281 family member includes a signal sequence. In a preferred embodiment, a TANGO 281 family member has the amino acid sequence of SEQ ID NO:48, and the signal sequence is located at about amino acids 1 to 38. In an another preferred embodiment, a TANGO 281 family member has the amino acid sequence of SEQ ID NO:58, and the signal sequence is located at about amino acids 1 to 26.

A photosystem II 10 kd phosphoprotein (PSBH) domain has been identified in the TANGO 281 proteins. The domain is also present in the chloroplast gene PSBH that encodes a 9–10 kDa thylakoid membrane protein (PSII-H) which is associated with photosystem II. In one embodiment, a TANGO 281 family member includes one or more PSBH domains having an amino acid sequence that is at least about 55%, preferably at least about 65%, more preferably at least 75%, yet more preferably at least about 85%, and most preferably at least about 95% identical to amino acids 41 to 90 and/or amino acids 127 to 182 of SEQ ID NO:48, which are the PSBH domains of human TANGO 281 (these PSBH domains are also represented as SEQ ID NO:54 and 55, respectively). In another embodiment, a TANGO 281 family member includes one or more PSBH domains having an amino acid sequence that is at least about 55%, preferably at least about 65%, more preferably at least about 75%, yet more preferably at least about 85%, and most preferably at least about 95% identical to amino acids 41 to 90 and/or amino acids 127 to 182 of SEQ ID NO:48, which are the PSBH domains of human TANGO 281 (these PSBH domains are also represented as SEQ ID NO:54 and 55, respectively), includes one or more PSBH domain consensus sequences described herein, and has at least one TANGO 281 biological activity as described herein.

In another embodiment, a TANGO 281 family member includes one or more PSBH domains having an amino acid sequence that is at least about 55%, preferably at least about 65%, more preferably at least 75%, yet more preferably at least about 85%, and most preferably at least about 95% to 98% identical to amino acids 42 to 91 and/or amino acids 128 to 183 of SEQ ID NO:58, which are the PSBH domains of mouse TANGO 281 (these PSBH domains are also represented as SEQ ID NO:64 and 65, respectively). In another embodiment, a TANGO 281 family member includes one or more PSBH domains having an amino acid sequence that is at least about 55%, preferably at least about 65%, more preferably at least about 75%, yet more preferably at least about 85%, and most preferably at least about 95% identical to amino acids 42 to 91 and/or amino acids 128 to 183 of SEQ ID NO:58, which are the PSBH domains of mouse TANGO 281 (these PSBH domains are also represented as SEQ ID NO:64 and 65, respectively), includes one or more PSBH domain consensus sequences described herein, and has at least one TANGO 281 biological activity as described herein.

Various features of human and mouse TANGO 253, TANGO 257, INTERCEPT 258 and TANGO 281 are summarized below.

Human TANGO 253

A cDNA encoding human TANGO 253 was identified by analyzing the sequences of clones present in a coronary artery smooth muscle library for sequences that encode secreted proteins. The primary cells utilized in construction of the library had been stimulated with agents that included phorbol 12-myristate 13-acetate (PMA), tumor neurosis factor (TNF), ionomycin, and cyclohexamide (CHX). This analysis led to the identification of a clone, EpT253, encoding full-length human TANGO 253. The human TANGO 253 cDNA of this clone is 1339 nucleotides long (FIGS. 1A–1B; SEQ ID NO:1). The open reading frame of this cDNA, nucleotides 188 to 916 of SEQ ID NO:1 (SEQ ID NO:2), encodes a 243 amino acid secreted protein (FIGS. 1A–1B; SEQ ID NO:3).

FIG. 2 depicts a hydropathy plot of human TANGO 253. Relatively hydrophobic regions of the protein are shown above the horizontal line, and relatively hydrophilic regions of the protein are below the horizontal line. The cysteine residues (cys) are indicated by short vertical lines just below the hydropathy trace. The dashed vertical line separates the signal sequence (amino acids 1 to 15 of SEQ ID NO:3; SEQ ID NO:5) on the left from the mature protein (amino acids 15 to 243 of SEQ ID NO:3; SEQ ID NO:4) on the right.

The signal peptide prediction program SIGNALP (Nielsen et al., 1997, *Protein Engineering* 10:1–6) predicted that human TANGO 253 includes a 15 amino acid signal peptide (amino acid 1 to amino acid 15 of SEQ ID NO:3; SEQ ID NO:5) preceding the mature human TANGO 253 protein (corresponding to amino acid 16 to amino acid 243 of SEQ ID NO:3; SEQ ID NO:4). The molecular weight of TANGO 253 protein without post-translational modifications is 25.3 kDa prior to the cleavage of the signal peptide, 23.8 kDa after cleavage of the signal peptide.

Human TANGO 253 includes a collagen domain (at about amino acids 36 to 95 of SEQ ID NO:3; SEQ ID NO:6) and a C1q domain (at about amino acids 105 to 232 of SEQ ID NO:3; SEQ ID NO:7) containing 23 G-X-Y repeats. An RGD cell attachment site is found at amino acids 77 to 79 of SEQ ID NO:3.

Three protein kinase C phosphorylation sites are present in human TANGO 253. The first has the sequence SAK (at amino acids 107 to 109 of SEQ ID NO:3), the second has the sequence TGK (at amino acids 140 to 142 of SEQ ID NO:3), and the third has the sequence SIK (at amino acids 220 to 222 of SEQ ID NO:3). Human TANGO 253 has three N-myristylation sites. The first has the sequence GLAAGS (at amino acids 11 to 16 of SEQ ID NO:3), the second has the sequence GGRPGL (at amino acids 68 to 73 of SEQ ID NO:3) and the third has the sequence GIYASI (at amino acids 216 to 221 of SEQ ID NO:3).

Northern analysis of human TANGO 253 expression demonstrates strong expression in heart, lung, liver, kidney and pancreas, and moderate expression in brain, placenta and skeletal muscle. Liver expression reveals two human TANGO mRNA bands, one of approximately 1.3 kb (which is the size observed in the other tissues) as well as a band at approximately 1 kb, which may be the result of an alternative splicing event.

Secretion assays reveal a human TANGO 253 protein of approximately 30 kDa. The secretion assays were performed as follows: $8\times10^5$ 293T cells were plated per well in a 6-well plate and the cells were incubated in growth medium (DMEM, 10% fetal bovine serum, penicillin/strepomycin) at 37° C., 5% $CO_2$ overnight. 293T cells were transfected with 2 $\mu$g of full-length TANGO 253 inserted in the pMET7 vector/well and 10 $\mu$g LipofectAMINE (GIBCO/BRL Cat. # 18324-012)/well according to the protocol for GIBCO/BRL LipofectAMINE. The transfectant was removed 5 hours later and fresh growth medium was added to allow the cells to recover overnight. The medium was removed and each well was gently washed twice with DMEM without methionine and cysteine (ICN Cat. # 16-424-54). 1 ml DMEM without methionine and cysteine with 50 $\mu$Ci Trans-$^{35}$S (ICN Cat. # 51006) was added to each well and the cells were incubated at 37° C., 5% $CO_2$ for the appropriate time period. A 150 $\mu$l aliquot of conditioned medium was obtained and 150 $\mu$l of 2×SDS sample buffer was added to the aliquot. The sample was heat-inactivated and loaded on a 4–20% SDS-PAGE gel. The gel was fixed and the presence of secreted protein was detected by autoradiography.

TANGO 253 is exhibits homology to an adipocyte complement-mediated protein precursor and so may be involved in adipocyte function, e.g., may act as a signaling molecule for adipocyte tissue. FIG. 6A shows an alignment of the human TANGO 253 amino acid sequence (SEQ ID NO:3) with the human adipocyte complement-mediated protein precursor amino acid sequence (SEQ ID NO:20). The alignment shows that there is a 38.7% overall amino acid sequence identity between human TANGO 253 and human adipocyte complement-mediated protein precursor.

FIGS. 7A, 7A-1, 7A-2, and 7A-3 show an alignment of the nucleotide sequence of human adipocyte complement-mediated protein precursor nucleotide sequence (SEQ ID NO:32); GenBank Accession Number A1417523) and the nucleotide sequence of human TANGO 253 (SEQ ID NO:1). The alignment shows a 29.1% overall sequence identity between the two nucleotide sequences.

Mapping of the human TANGO 253 nucleotide sequence demonstrates that the TANGO 253 gene lies on human chromosome 11, between makers D11S1356 and D11S924.

Clone EpT253, which encodes human TANGO 253, was deposited with the American Type Culture Collection (10801 University Boulevard, Manassas, Va. 20110-2209) on Apr. 21, 1999 and assigned Accession Number 207222. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Mouse TANGO 253

A cDNA encoding mouse TANGO 253 was identified by analyzing the sequences of clones present in a mouse microglia library using a rat TANGO 253 probe from sciatic nerve. This analysis led to the identification of a clone, EpTm253 encoding full-length mouse TANGO 253. The mouse TANGO 253 cDNA of this clone is 1263 nucleotides long (FIGS. 3A–3B; SEQ ID NO:8). The open reading frame of this cDNA, nucleotides 135 to 863 of SEQ ID NO:8 (SEQ ID NO:9), encodes a 243 amino acid secreted protein (FIGS. 3A–3B; SEQ ID NO:10).

FIG. 4 depicts a hydropathy plot of mouse TANGO 253. Relatively hydrophobic regions of the protein are shown above the horizontal line, and relatively hydrophilic regions of the protein are below the horizontal line. The cysteine residues (cys) are indicated by short vertical lines just below the hydropathy trace. The dashed vertical line separates the signal sequence (amino acid 1 to amino acid 15 of SEQ ID NO:10; SEQ ID NO:12) on the left from the mature protein (amino acid 16 to amino acid 243 of SEQ ID NO:10; SEQ ID NO:11) on the right.

The signal peptide prediction program SIGNALP (Nielsen et al., 1997, Protein Engineering 10:1–6) predicted that mouse TANGO 253 includes a 15 amino acid signal peptide (amino acid 1 to amino acid 15 of SEQ ID NO:10; SEQ ID NO:12) preceding the mature mouse TANGO 253 protein (corresponding to amino acid 16 to amino acid 243 of SEQ ID NO:10; SEQ ID NO:11). The molecular weight of mouse TANGO 253 protein without post-translational modifications is 25.4 kDa prior to the cleavage of the signal peptide, 23.9 kDa after cleavage of the signal peptide.

Mouse TANGO 253 includes a collagen domain (at amino acids 36 to 95 of SEQ ID NO:10; SEQ ID NO:13) and a C1q domain (at amino acids 105–232 of SEQ ID NO:10; SEQ ID NO:14).

Three protein kinase C phosphorylation sites are present in mouse TANGO 253. The first has the sequence SAK (at amino acids 107 to 109 of SEQ ID NO:10), the second has the sequence TGK (at amino acids 140 to 142 of SEQ ID NO:10), and the third has the sequence SIK (at amino acids 220 to 222 of SEQ ID NO:10). Mouse TANGO 253 has four N-myristylation sites. The first has the sequence GLVSGS (at amino acids 11 to 16 of SEQ ID NO:10), the second has the sequence GGRPGL (at amino acids 68 to 73 of SEQ ID NO:10), the third has the sequence GQSIAS (at amino acids 172 to 177 of SEQ ID NO:10), and the fourth has the sequence GIYASI (at amino acids 216 to 221 of SEQ ID NO:10).

As shown in FIG. 5, human TANGO 253 protein and mouse TANGO 253 protein are 93.8% identical. FIG. 6B shows an alignment of the mouse TANGO 253 amino acid sequence (SEQ ID NO:10) with the human adipocyte complement-mediated protein precursor amino acid sequence (SEQ ID NO:20). The alignment shows that there is a 38.3% overall amino acid sequence identity between mouse TANGO 253 and human adipocyte complement-mediated protein precursor.

FIGS. 7B, 7B-1, 7B-2, 7B-3 show an alignment of the nucleotide sequence of human adipocyte complement-mediated protein precursor nucleotide sequence (SEQ ID NO:32); GenBank Accession Number A1417523) and the nucleotide sequence of mouse TANGO 253 (SEQ ID NO:8). The alignment shows a 30.4% overall sequence identity between the two nucleotide sequences.

Clone EpTm253, which encodes mouse TANGO 253, was deposited with the American Type Culture Collection (10801 University Boulevard, Manassas, Va. 20110-2209) on Apr. 21, 1999 and assigned Accession Number 207215. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Uses of TANGO 253 Nucleic Acids, Polypeptides and Modulators Thereof

As TANGO 253 was originally found in the coronary artery smooth muscle library described above, TANGO 253 nucleic acids, proteins, and modulators thereof can be used to modulate the proliferation, development, differentiation, and/or function of organs, e.g., tissues and cells that form blood vessels and coronary tissue, e.g., cells of the coronary connective tissue, e.g., abnormal coronary smooth muscle cells and/or endothelial cells of blood vessels. TANGO 253 nucleic acids, proteins, and modulators thereof can also be used to modulate symptoms associated with abnormal coronary function, e.g., heart diseases and disorders such as atherosclerosis., coronary artery disease and plaque formation.

In light of the collagen domain, TANGO 253 nucleic acids, proteins and modulators thereof can be utilized to modulate (e.g., stabilize, promote, inhibit or disrupt) cell/extracellular matrix (ECM) interactions, cell/cell interactions and, for example, signal transduction events associated with such interactions. For example, such TANGO 253 compositions and modulators thereof can be used to modulate binding of such ECM-associated factors as integrin and can function to modulate ligand binding to cell surface receptors. In addition, TANGO 253 nucleic acids, proteins and modulators thereof can be utilized to modulate connective tissue formation, maintenance and function, as well as to modulate symptoms associated with connective tissue-related disorders, to promote wound healing, and to reduce, slow or inhibit ameliorate connective tissue-related signs of aging, such as wrinkle formation.

In light of the C1 q domain exhibited by TANGO 253 proteins and their similarity to the collectin family, TANGO 253 nucleic acids, proteins and modulators thereof can be utilized to modulate immune-related processes such as the ability to modulate host immune response by, e.g., modulating one or more elements in the serum complement cascade, including, for example activation of the cascade, formation of and/or binding to immune complexes, detection and defense against surface antigens and bacteria, and immune surveillance for rapid removal or pathogens. Such TANGO 253 compositions and modulators thereof can be utilized, e.g., to ameliorate incidence of any symptoms associated with disorders that involve such immune-related processes, including, but not limited to infection and autoimmune disorders.

In addition, such compositions and modulators thereof can be utilized to modulate folding and alignment of the collagen domain (e.g., into a triple helix), disorders associated with collagen defects, including but not limited to bone disorders, e.g., bone resorption disorders, or hearing, e.g., inner ear, disorders, to modulate protein-protein interactions and recognition events (either homotypic or heterotypic) and cellular response events (e.g., signal transduction events) associated with such interactions and recognitions, and to ameliorate symptoms associated with abnormal signaling, protein-protein interaction and/or cellular response events including, but not limited to cell proliferation disorders such as cancer, abnormal neuronal interactions, such as disorders involving abnormal synaptic activity, e.g., abnormal Purkinje cell activities.

Human TANGO 253 protein contains an RGD domain. As such, TANGO 253 nucleic acids, proteins and modulators thereof can be utilized to modulate processes involved in, e.g., bone development, sepsis, tumor progression, metastasis, cell migration, fertilization, and cellular interactions with the extracellular matrix required for growth, differentiation, and apoptosis, as well as cellular processes involving cell adhesion, such as cell migration.

TANGO 253 proteins exhibit similarity to adipocyte complement-related protein precursor and can act as signaling molecules for adipocyte tissue. In light of this, TANGO 253 nucleic acids, proteins and modulators thereof can be utilized to modulate adipocyte function and adipocyte-related processes and disorders such as, e.g., obesity.

TANGO 253 nucleic acids, proteins and modulators thereof can, in addition to the above, be utilized to regulate or modulate development and/or differentiation of processes involved in microglial, lung, liver, kidney, pancreas, brain, placental and skeletal muscle formation and activity, as well as in ameliorating any symptom associated with a disorder of such cell types, tissues and organs.

Human TANGO 257

A cDNA encoding human TANGO 257 was identified by analyzing the sequences of clones present in a coronary smooth muscle library for sequences that encode secreted proteins. This analysis led to the identification of a clone, EpT257, encoding full-length human TANGO 257. The human TANGO 257 cDNA of this clone is 1832 nucleotides long (FIGS. 8A–8C; SEQ ID NO:15). The open reading frame of this cDNA, nucleotides 88 to 1305 of SEQ ID NO:15 (SEQ ID NO:16), encodes a 406 amino acid secreted protein (FIGS. 8A–8C; SEQ ID NO:17).

FIG. 9 depicts a hydropathy plot of human TANGO 257. Relatively hydrophobic regions of the protein are above the horizontal line, and relatively hydrophilic regions of the protein are below the horizontal line. The cysteine residues (cys) and N-glycosylation sites are (Ngly) are indicated by short vertical lines just below the hydropathy trace. The dashed vertical line separates the signal sequence from the mature protein described below.

The signal peptide prediction program SIGNALP (Nielsen et al., 1997, *Protein Engineering* 10:1–6) predicted that human TANGO 257 includes a 21 amino acid signal peptide (amino acid 1 to amino acid 21 of SEQ ID NO:17; SEQ ID NO:19) preceding the mature human TANGO 257 protein (corresponding to amino acid 22 to amino acid 406 of SEQ ID NO:17; SEQ ID NO:18). The molecular weight of human TANGO 257 protein without post-translational modifications is 46.0 kDa prior to the cleavage of the signal peptide, 43.8 kDa after cleavage of the signal peptide.

Two N-glycosylation sites are present in human TANGO 257. The first has the sequence NDTA and is found at amino acids 177 to 180 of SEQ ID NO:17, and the second has the sequence NRTV and is found at amino acids 248 to 251 of SEQ ID NO:17. A cAMP and cGMP dependent protein kinase phosphorylation site having the sequence RKAS is found in human TANGO 257 at amino acids 196 to 199 of SEQ ID NO:17. Five protein kinase C phosphorylation sites are present in human TANGO 257. The first has the sequence SSR (at amino acids 48 to 50 of SEQ ID NO:17), the second has the sequence SGR (at amino acids 84 to 86 of SEQ ID NO:17), the third has the sequence SMK (at amino acids 144 to 146 of SEQ ID NO:17), the fourth has the sequence TEK (at amino acids 166 to 168 of SEQ ID NO:17) and the fifth has the sequence SLR (at amino acids 374 to 376 of SEQ ID NO:17). Five casein kinase II phosphorylation sites are present in human TANGO 257. The first has the sequence TEAD (at amino acids 78 to 81 of SEQ ID NO:17), the second has the sequence TQND (at amino acids 175 to 178 of SEQ ID NO:17), the third has the sequence TVVD (at amino acids 250 to 253 of SEQ ID NO:17), the fourth has the sequence TYID (at amino acids 272 to 275 of SEQ ID NO:17), and the fifth has the sequence TRED (at amino acids 289 to 292 of SEQ ID NO:17). Human TANGO 257 has a tyrosine kinase phosphorylation site having the sequence RLEREVDY at amino acids 89 to 96 of SEQ ID NO:17). Human TANGO 257 has three N-myristylation sites. The first has the sequence GGPGTK (at amino acids 115 to 120 of SEQ ID NO:17), the second has the sequence GGPAGL (at amino acids 152 to 157 of SEQ ID NO:17) and the third has the sequence GAHASL (at amino acids 370 to 375 of SEQ ID NO:17). Human TANGO 257 has an amidation site having the sequence KGRR at amino acids 122 to 125 of SEQ ID NO:17.

Northern analysis of human TANGO 257 expression demonstrates moderate expression in heart, liver and pancreas, and low expression in kidney, lung and skeletal muscle.

Secretion assays reveal a human TANGO 257 protein of approximately 50kDa. The secretion assays were performed as described in the human TANGO 253 section above.

Human TANGO 257 mapping indicates that the human TANGO 257 gene maps to human chromosome 1 between markers D1S418 to D1S252.

TANGO 257 is homologous to a protein encoded by a nucleic acid sequence referred to in PCT Publication WO 98/39446 as "gene 64". FIG. 13 shows an alignment of the human TANGO 257 amino acid sequence (SEQ ID NO:17) with the gene 64-encoded amino acid sequence (SEQ ID NO:43). As shown in the figure, the 353 amino acid gene 64 polypeptide is identical to amino acid residues 1–353 of human TANGO 257 (SEQ ID NO:17). Human TANGO 257 contains 406 amino acids, i.e., contains an additional 53 amino acid residues carboxy to residue 353. The overall amino acid sequence identity between full-length human TANGO 257 polypeptide and the gene 64-encoded polypeptide is approximately 87%.

FIGS. 14A–14D show an alignment of the nucleotide sequence of gene 64 (SEQ ID NO:66; PCT Publication WO 98/39446) and the nucleotide sequence of human TANGO 257 (SEQ ID NO:15). The nucleotide sequences of gene 64 and human TANGO 257 are 93.5% identical. Among the differences between the sequences is a cytosine nucleotide at human TANGO 257 (SEQ ID NO:15) position 1587 that represents an insertion relative to the corresponding gene 64 position when the gene 64 and TANGO 257 sequences are aligned. This additional cytosine results in the TANGO 257 open reading frame being 1218 base pairs encoding a polypeptide of 406 amino acid residues. In contrast, the gene 64 nucleic acid sequence encodes a polypeptide of only 353 amino acid residues, as discussed above.

Clone EpT257, which encodes human TANGO 257, was deposited with the American Type Culture Collection (10801 University Boulevard, Manassas, Va. 20110-2209) on Apr. 21, 1999 and assigned Accession Number 207222. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Mouse TANGO 257

A cDNA encoding mouse TANGO 257 was identified by analyzing the sequences of clones present in a mouse microglia library using a rat TANGO 257 probe. This analysis led to the identification of a clone, EpTm257 encoding full-length mouse TANGO 257. The mouse TANGO 257 cDNA of this clone is 1721 nucleotides long (FIGS. 10A–10C; SEQ ID NO:21). The open reading frame of this cDNA, nucleotides 31 to 1248 of SEQ ID NO:21 (SEQ ID NO:22), encodes a 406 amino acid secreted protein (FIGS. 10A–10C; SEQ ID NO:23).

FIG. 11 depicts a hydropathy plot of mouse TANGO 257. Relatively hydrophobic regions of the protein are above the horizontal line, relatively hydrophilic regions of the protein are below the horizontal line. The cysteine residues (cys) and N-glycosylation sites are (Ngly) are indicated by short vertical lines just below the hydropathy trace. The dashed vertical line separates the signal sequence from the mature protein described below.

The signal peptide prediction program SIGNALP (Nielsen et al., 1997, Protein Engineering 10:1–6) predicted that mouse TANGO 257 includes a 21 amino acid signal peptide (amino acid 1 to amino acid 21 of SEQ ID NO:23; SEQ ID NO:25) preceding the mature TANGO 257 protein (corresponding to amino acid 22 to amino acid 406 of SEQ ID NO:23; (SEQ ID NO:24). The molecular weight of mouse TANGO 257 protein without post-translational modifications is 45.8 kDa prior to the cleavage of the signal peptide, 43.6 kDa after cleavage of the signal peptide.

Two N-glycosylation sites are present in mouse TANGO 257. The first has the sequence NDTA and is found at amino acids 177 to 180 of SEQ ID NO:23, and the second has the sequence NRTV and is found at amino acids 248 to 251 of SEQ ID NO:23. A cAMP and cGMP-dependent protein kinase phosphorylation site having the sequence RKAS is found in mouse TANGO 257 at amino acids 196 to 199 of SEQ ID NO:23. Five protein kinase C phosphorylation sites are present in mouse TANGO 257. The first has the sequence SSR (at amino acids 48 to 50 of SEQ ID NO:23), the second has the sequence TLR (at amino acids 75 to 77 of SEQ ID NO:23), the third has the sequence SGR (at amino acids 84 to 86 of SEQ ID NO:23), the fourth has the sequence SMK (at amino acids 144 to 146 of SEQ ID NO:23) and the fifth has the sequence SLR (at amino acids 374 to 376 of SEQ ID NO:23). Five casein kinase II phosphorylation sites are present in mouse TANGO 257. The first has the sequence TEAD (at amino acids 78 to 81 of SEQ ID NO:23), the second has the sequence TQND (at amino acids 175 to 178 of SEQ ID NO:23), the third has the sequence TVVD (at amino acids 250 to 253 of SEQ ID NO:23), the fourth has the sequence TYID (at amino acids 272 to 275 of SEQ ID NO:23), and the fifth has the sequence TRRD (at amino acids 289 to 292 of SEQ ID NO:23). Mouse TANGO 257 has a tyrosine kinase phosphorylation site having the sequence RLEREVDY at amino acids 89 to 96 of SEQ ID NO:23. Mouse TANGO 257 has four N-myristylation sites. The first has the sequence GGPGAK (at amino acids 115 to 120 of SEQ ID NO:23), the second has the sequence GGSVGL (at amino acids 151 to 157 of SEQ ID NO:23), the third has the sequence GGPGGG (at amino acids 227 to 232 of SEQ ID NO:23), and the fourth has the sequence GAHASL (at amino acids 370 to 375 of SEQ ID NO:23). Mouse TANGO 257 has an amidation site having the sequence KGRR at amino acids 122 to 125 of SEQ ID NO:23.

As shown in FIG. 12, human TANGO 257 protein and mouse TANGO 257 protein are 94.1% identical.

FIG. 15 shows an alignment of mouse TANGO 257 amino acid sequence (SEQ ID NO:23) with the amino acid sequence encoded by gene 64 (SEQ ID NO:43). As shown in the figure, the 253 amino acid gene 64 polypeptide and the 406 amino acid mouse TANGO 257 polypeptide and the 406 amino acid mouse TANGO 257 polypeptide are approximately 82% identical. FIGS. 16A–16F show an alignment of the nucleotide sequence of gene 64 (SEQ ID NO:66; PCT publication no. 98/39446) and the nucleotide sequence of mouse TANGO 257 (SEQ ID NO:21). As shown in the figure, the two nucleotide sequences are approximately 76% identical.

Clone EpTm257, which encodes mouse TANGO 257, was deposited with the American Type Culture Collection (10801 University Boulevard, Manassas, Va. 20110-2209) on Apr. 21, 1999 and assigned Accession Number 207117. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Uses of TANGO 257 Nucleic Acids, Polypeptides, and Modulators Thereof

As TANGO 257 was originally found in a coronary artery smooth muscle library, TANGO 257 nucleic acids, proteins, and modulators thereof can be used to modulate the proliferation, development, differentiation, and/or function of organs, e.g., heart, tissues and cells that form blood vessels and coronary tissue, e.g., cells of the coronary connective tissue, e.g., coronary smooth muscle cells and/or endothelial cells of blood vessels. TANGO 257 nucleic acids, proteins, and modulators thereof can also be used to modulate symptoms associated with abnormal coronary function, e.g., heart diseases and disorders such as atherosclerosis, coronary artery disease and plaque formation.

In light of TANGO 257's homology to the extracellular molecule olfactomedin, TANGO 257 nucleic acids, proteins and modulators thereof can be utilized to modulate development, differentiation, proliferation and/or activity of neuronal cells, e.g., olfactory neurons and to modulate neuronal activities involving maintenance, growth and/or differentiation of chemosensory cilia, modulate cell-cell interactions and cell-ECM interactions, e.g., neuronal (such as olfactory) cell-ECM interactions. TANGO 257 nucleic acids, proteins and modulations thereof can also be used to modulate symptoms associated with abnormal processes involving such cells and/or activities, for example neuronal function, e.g., neurological disorders, neurodegenerative disorders, neuromuscular disorders, cognitive disorders, personality disorders, and motor disorders, and chemosensory disorders, such as olfactory-related disorders.

TANGO 257 exhibits homology to a gene referred to as "gene 64" (PCT Publication No. WO 98/39446), which is expressed primarily in fetal lung tissue. In light of this, TANGO 257 nucleic acids, proteins and modulators thereof can also be used to modulate development, differentiation, proliferation and/or activity of pulmonary system cells, e.g., lung cell types, and to modulate a symptom associated with disorders of pulmonary development, differentiation and/or activity, e.g., cystic fibrosis. TANGO 257 nucleic acids, proteins and modulators thereof can also be used to modulate symptoms associated with abnormal pulmonary development or function, such as lung diseases or disorders associated with abnormal pulmonary development or function, e.g., cystic fibrosis.

TANGO 257 nucleic acids, proteins and modulators thereof can also be used to modulate cell proliferation, e.g., abnormal cell proliferation. Such modulation may, for example, be via modulation of one or more elements involved in signal transduction cascades.

TANGO 257 nucleic acids, proteins and modulators thereof can, in addition to the above, be utilized to regulate or modulate development and/or differentiation of processes involved in microglial, liver, kidney, and skeletal muscle formation and activity, as well as in ameliorating a symptom associated with a disorder of such cell types, tissues and organs.

Human INTERCEPT 258

A cDNA encoding human INTERCEPT 258 was identified by analyzing the sequences of clones present in a human mixed lymphocyte reaction library for sequences that encode secreted proteins. This analysis led to the identification of a clone, EpT258, encoding full-length human INTERCEPT 258. The human INTERCEPT 258 cDNA of this clone is 1869 nucleotides long (FIGS. 17A–17C; SEQ ID NO:26). The open reading frame of this cDNA, nucleotides 153 to 1262 of SEQ ID NO:26 (SEQ ID NO:27), encodes a 370 amino acid transmembrane protein (FIG. 17; SEQ ID NO:28).

FIG. 18 depicts a hydropathy plot of human INTERCEPT 258. Relatively hydrophobic regions of the protein are shown above the horizontal line, and relatively hydrophilic regions of the protein are below the horizontal line. The cysteine residues (cys) are indicated by short vertical lines just below the hydropathy trace. The dashed vertical line separates the signal sequence (amino acids 1 to 29 of SEQ ID NO:28; SEQ ID NO:30) on the left from the mature protein (amino acids 30 to 370 of SEQ ID NO:28; SEQ ID NO:29) on the right.

The signal peptide prediction program SIGNALP (Nielsen et al., 1997, *Protein Engineering* 10:1–6) predicted that human INTERCEPT 258 includes a 29 amino acid signal peptide (amino acid 1 to amino acid 29 of SEQ ID NO:26; SEQ ID NO:30) preceding the mature INTERCEPT 258 protein (corresponding to amino acid 30 to amino acid 370 of SEQ ID NO:26; SEQ ID NO:29). The molecular weight of human INTERCEPT 258 protein without post-translational modifications is 40.0 kDa prior to the cleavage of the signal peptide, 37.0 kDa after cleavage of the signal peptide.

Human INTERCEPT 258 contains a hydrophobic transmembrane domain at amino acids 247 to 271 of SEQ ID NO:28 (SEQ ID NO:33). Human INTERCEPT 258 also contains two Ig domains, one at amino acids 49 to 128 of SEQ ID NO:28 (SEQ ID NO:35) and a second at amino acids 167 to 226 of SEQ ID NO:28 (SEQ ID NO:36).

Five N-glycosylation sites are present in human INTERCEPT 258. The first has sequence NLSL and is found at amino acids 108 to 111 of SEQ ID NO:28, the second has the sequence NUTL and is found at amino acids 169 to 172 of SEQ ID NO:28; the third is has the sequence NLSS and is found at amino acids 213 to 216 of SEQ ID NO:28, the fourth has the sequence NUTL and is found at amino acids, 236 to 239 of SEQ ID NO:28, and the fifth has the sequence NGTL and is found at amino acids 307 to 310 of SEQ ID NO:28. Seven protein kinase C phosphorylation sites are present in human INTERCEPT 258. The first has the sequence TSK and is found at amino acids 93 to 95 of SEQ ID NO:28, the second has the sequence SLR and is found at amino acids 110 to 112 of SEQ ID NO:28, the third has the sequences SIK and is found at amino acids 141 to 143 or SEQ ID NO:28, the fourth has the sequence SCR and is found at amino acids 157 to 159, the fifth has the sequence SPR and is found at amino acids 176 to 179 of SEQ ID NO:28, the sixth has the sequence SAR and is found at amino acids 315 to 317 of SEQ ID NO:28, and the seventh has the sequence SPR and is found at amino acids 344 to 346 of SEQ ID NO:28. The human INTERCEPT 258 protein has seven N-myristoylation sites. The first has the sequence GUTTSK and is found at amino acids 90 to 95 of SEQ ID NO:28, the second has the sequence GANVTL and is found at amino acids 167 to 172 of SEQ ID NO:28, the third has the sequence GVYVCK and is found at amino acids 220 to 225, the fourth has the sequence GTAQCN and is found at amino acids 231 to 236 of SEQ ID NO:28, the fifth has the sequence GTLVGL and is found at amino acids 256 to 261, the sixth has the sequence GLLAGL and is found at amino acids 262 to 267 of SEQ ID NO:28, and the seventh has the sequence GTLSSU and is found at acids 308 to 313 of SEQ ID NO:28.

Human multi-tissue dot blot analysis of human INTERCEPT 258 expression demonstrates strongest expression in lung, fetal lung, placenta, thyroid gland and mammary gland. Moderate expression is observed in heart, aorta, kidney, small intestine, fetal heart, fetal kidney, fetal spleen, uterus, and stomach. Weak expression is observed in whole brain, amygdala, caudate nucleus, cerebellum, cerebral cortex frontal lobe, hippocampus, medulla oblongata, occipital lobe, putamen, substantia nigra, temporal lobe, thalamus, acumens, spinal cord, skeletal muscle, colon, bladder, prostate, ovary, pancreas, pituitary gland, adrenal gland, salivary gland, liver, spleen, thymus, lymph node, bone marrow, appendix, trachea, fetal brain, fetal liver, and fetal thymus.

A human cancer cell line Northern blot analysis showed a roughly 2.0 kb INTERCEPT 258 band only in the lane containing cell line Chronic Myelogenous Leukemia (K-562). The cancerous cell lines in which INTERCEPT 258 was not expressed include promyeocytic leukemia, Hela, lymphoblastic leukemia, Burkitt's lymphoma Raji, colorectal adenocarcinoma, lung carcinoma and melanoma.

INTERCEPT 258 exhibits homology to a human A33 antigen. A33 antigen is a transmembrane glycoprotein and a member of the immunoglobulin superfamily that may represent a cancer cell marker (Heath et al., 1997, Proc. Natl. Acad. Sci. USA 94:469–474). FIG. 22 shows an alignment of the human INTERCEPT 258 amino acid sequence (SEQ ID NO:28) with the human A33 amino acid sequence (SEQ ID NO:67). The alignment shows that there is a 23.0% overall amino acid sequence identity between human INTERCEPT 258 and A33. FIGS. 23A–23F show an alignment of the human INTERCEPT 258 nucleotide sequence (SEQ ID NO:26) with that of human A33 nucleotide sequence (SEQ ID NO:68). The alignment shows that there is a 40.6% identity between the two sequences.

Human INTERCEPT 258 nucleotide sequence (SEQ ID NO:26) exhibits homology to human PECAM-1 nucleotide sequence (SEQ ID NO:72). FIGS. 26A–26E show that there is an overall 40.5% identity between the two nucleotide sequences. Human INTERCEPT 258 amino acid sequence (SEQ ID NO:28) and human PECAM-1 amino acid sequence (SEQ ID NO:73) share less than 18% identity. PECAM-1 (platelet endothelial cell adhesion molecule-1) is an integrin expressed on endothelial cells.

Clone EpT258, which encodes human INTERCEPT 258, was deposited with the American Type Culture Collection (10801 University Boulevard, Manassas, Va. 20110-2209) on Apr. 21, 1999 and assigned Accession Number 207222. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. § 112.

Mouse INTERCEPT 258

A cDNA encoding mouse INTERCEPT 258 was identified by analyzing the sequences of clones present in a mouse megakaryocyte library for sequences that encode secreted proteins. This analysis led to the identification of a clone, EpTm258, encoding full-length mouse INTERCEPT 258. The mouse INTERCEPT 258 cDNA of this clone is 1846 nucleotides long (FIGS. 19A–19C; SEQ ID NO:37). The open reading frame of this cDNA, nucleotides 107 to 1288 of SEQ ID NO:37 (SEQ ID NO:38), encodes a 394 amino acid transmembrane protein (FIGS. 19A–19C, SEQ ID NO:39).

FIG. 20 depicts a hydropathy plot for mouse INTERCEPT 258. Relatively hydrophobic regions of the protein are above the horizontal line, relatively hydrophilic regions of the protein are below the horizontal line. The cysteine residues (cys) and N-glycosylation sites are (Ngly) are indicated by short vertical lines just below the hydropathy trace. The dashed vertical line separates the signal sequence from the mature protein described below.

The signal peptide prediction program SIGNALP (Nielsen et al., 1997, *Protein Engineering* 10:1–6) predicted that mouse INTERCEPT 258 includes a 29 amino acid signal peptide (amino acid 1 to amino acid 29 of SEQ ID NO:39; SEQ ID NO:41) preceding the mature INTERCEPT 258 protein (corresponding to amino acid 30 to amino acid 394 of SEQ ID NO:39; SEQ ID NO:40). The molecular weight INTERCEPT 258 without post-translational modifications is 41.8 kDa prior to the cleavage of the signal peptide, 38.90 kDa after cleavage of the signal peptide.

Mouse INTERCEPT 258 contains a hydrophobic transmembrane domain at amino acids 250 to 274 SEQ ID NO:39 (SEQ ID NO:44). Mouse INTERCEPT 258 also contains an Ig domain at amino acids 170 to 229 of SEQ ID NO:39 (SEQ ID NO:71).

Five N-glycosylation sites are present in mouse INTERCEPT 258. The first has sequence NVSL and is found at amino acids 111 to 114 of SEQ ID NO:39, the second has the sequence NVTL and is found at amino acids 172 to 175 of SEQ ID NO:39, the third has the sequence NLSI and is found at amino acids 216 to 219 of SEQ ID NO:39, the fourth has the sequence NVTL and is found at amino acids, 239 to 242 of SEQ ID NO:39, and the fifth has the sequence NGTL and is found at amino acids 310 to 313 of SEQ ID NO:39. Nine protein kinase C phosphorylation sites are present in mouse INTERCEPT 258. the first has the sequence TNK and is found at amino acids 96 to 98 of SEQ ID NO:39, the second has the sequence SSR and is found at amino acids 108 to 110 of SEQ ID NO:39, the third has the sequence SLR and is found at amino acids 113 to 115 of SEQ ID NO:39, the fourth has the sequence TYR and is found at amino acids 126 to 128, the fifth has the sequence SIK and is found at amino acids 144 to 146 of SEQ ID NO:39, the sixth has the sequence SPR and is found at amino acids 179 to 181 of SEQ ID NO:39, the seventh has the sequence SLK and is found at amino acids 211 and 213, the eighth has the sequence SAR and is found at amino acids 318 to 320 of SEQ ID NO:39, and the ninth has the sequence SPR and is found at amino acids 348 to 350 of SEQ ID NO:39. The mouse INTERCEPT 258 contains a casein kinase II phosphorylation site having the sequence TLEE, found at amino acids 280 to 283 of SEQ ID NO:39. The mouse INTERCEPT 258 protein has nine N-myristoylation sites. The first has the sequence GTPETS and is found at amino acids 6 to 11 of SEQ ID NO:39, the second has the sequence GVMTNK and is found at amino acids 125 to 130 of SEQ ID NO:39, the third has the sequence GTYRCS and is found at amino acids 125 to 130, the fourth has the sequence GTNVTL and is found at amino acids 170 to 175 of SEQ ID NO:39, the fifth has the sequence GVYVCK and is found at amino acids 223 to 228, the sixth has the sequence GSKAAV and is found at amino acids 247 to 252, the seventh has the sequence GAVVGT and is found at amino acids 255 to 260 of SEQ ID NO:39, the eighth has sequence GTLSSV and is found at amino acids 311 to 316 of SEQ ID NO:39, and the ninth has the sequence GGVSSS and is found at amino acids 367 to 372 of SEQ ID NO:39.

An in situ expression analysis of INTERCEPT 258 was performed as summarized herein. Mouse INTERCEPT 258 expression during embryogenesis (E73.5 to P1.5 were examined) was observed throughout the animal in a punctate pattern. This pattern is very similar to that seen with the molecule PECAM-1, but at a lower intensity. PECAM-1 is an integrin expressed on endothelial cells. In addition, lung and brown fat exhibited a much higher signal in a more ubiquitous pattern in all embryonic stages examined. Heart and kidney also have a higher expression, but to a lesser degree. Adult mouse INTERCEPT 258 expression was seen in many tissues, often in a multifocal, punctate pattern suggestive of vessels. Expression was also predominant in many highly vascularized tissues such as ovary (especially the septol region), kidney and adrenal cortex.

In general, both embryonic and adult expression patterns were suggestive of endothelial cells being a component in the expression patters observed. In summary, tissues in which INTERCEPT 258 expression was observed were as follows: brain, eye, harderian gland, submanibular gland, bladder, brown fat, stomach, heart, kidney, adrenal gland, colon, liver, thymus, lymph node, spleen, spinal cord, ovary, testes and placenta. No INTERCEPT 258 expression was observed in small intestine, lung, pancreas, white fat or skeletal muscle.

As shown in FIG. 21, human INTERCEPT 258 protein and mouse INTERCEPT 258 protein are 62.8% identical.

Mouse INTERCEPT 258 exhibits homology to a human A33 antigen. FIG. 24 shows an alignment of mouse INTERCEPT 258 amino acid sequence (SEQ ID NO:39) with the human A33 amino acid sequence (SEQ ID NO:96). The alignment shows that there is a 23% overall amino acid sequence identity between the two sequences. FIGS. 25A–25I show an alignment of the mouse INTERCEPT 258 nucleotide sequence (SEQ ID NO:37) with that of the human A33 nucleotide sequence (SEQ ID NO:97). The alignment shows that there is a 40% identity between these two nucleotide sequences.

Clone EpTm258, which encodes mouse INTERCEPT 258, was deposited with the American Type Culture Collection (10801 University Boulevard, Manassas, Va. 20110-2209) on Apr. 21, 1999 and assigned Accession Number 207221. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Uses of INTERCEPT 258 Nucleic Acids, Polypeptides, and Modulators Thereof

INTERCEPT 258 was identified as being expressed in a mixed lymphocyte library. In light of this, INTERCEPT 258 nucleic acids, proteins and modulators thereof can be utilized to modulate processes involved in lymphocyte development, differentiation and activity, including, but not limited to development, differentiation and activation of T cells, including T helper, T cytotoxic and non-specific T killer cell types and subtypes, and B cells, immune functions associated with such cells, and amelioration of one or more symptoms associated with abnormal function of such cell types. Such disorders can include, but are not limited to, autoimmune disorders, such as organ specific autoimmune disorders, e.g., autoimmune thyroiditis, Type I diabetes mellitus, insulin-resistant diabetes, autoimmune anemia, multiple sclerosis, and/or systemic autoimmune disorders, e.g., rheumatoid arthritis, lupus or sclerodoma, allergy, including allergic rhinitis and food allergies, asthma, psoriasis, graft rejection, transplantation rejection, graft versus host disease, pathogenic susceptibilities, e.g., susceptibility to certain bacterial or viral pathogens, wound healing and inflammatory reactions.

INTERCEPT 258 includes one or more Ig domains. INTERCEPT 258 nucleic acids, proteins, and modulators thereof can, therefore, be used to modulate immune function, e.g., by the modulation of immunoglobulins and the formation of antibodies. For the same reason, INTERCEPT 258 nucleic acids, proteins, and modulators thereof can be used to modulate immune response, leukocyte trafficking, cancer, Type I immunologic disorders, e.g., anaphylaxis and/or rhinitis, by modulating the interaction between antigens and cell receptors, e.g., high affinity IgE receptors.

INTERCEPT 258 exhibits homology to PECAM-1, a cell adhesion integrin molecule that has been shown to mediate cell-cell interactions, play an important role in bidirectional signal transduction, and may be involved in thrombotic, inflammatory and immunological disorders. As such, INTERCEPT 258 nucleic acids, proteins, and modulators thereof can be utilized to modulate cell/cell interactions and, for example, signal transduction events associated with such interactions. For example, such INTERCEPT 258 compositions and modulators thereof can be used to modulate binding of cellular factors or ECM-associated factors such as integrin and can function to modulate ligand binding to cell surface receptors. Further, such INTERCEPT 258 compositions and modulators thereof can be utilized to ameliorate at least one symptom associated with thrombotic disorders, e.g., stroke, inflammatory processes or disorders, and immune disorders.

In light of INTERCEPT 258 expression, INTERCEPT 258 nucleic acids, proteins and modulators thereof can be utilized modulate development, differentiation, proliferation and/or activity of pulmonary system cells, e.g., lung cell types, and to modulate a symptom associated with disorders of pulmonary development, differentiation and/or activity, such as lung diseases or disorders associated with abnormal pulmonary development or function, e.g., cystic fibrosis. INTERCEPT 258 nucleic acids, proteins and modulators thereof can also be utilized modulate development, differentiation, proliferation and/or activity of thyroid cells, megakaryocytes or mammary gland cells, and can further be utilized to ameliorate at least one symptom of disorders associated with, abnormal thyroid function, e.g., thyroiditis or Grave's disease, abnormal megakaryocyte differentiation or function, e.g., anemias or leukemias, hematological diseases such as thrombocytopenia, platelet disorders and bleeding disorders, such as hemophilia or abnormal mammary development or function.

INTERCEPT 258 nucleic acids, proteins, and modulators thereof can still further be utilized to modulate development, differentiation proliferation and/or activity of cells involved in kidney or heart formation and function. In addition, such compositions and modulators thereof can be utilized to ameliorate at least one symptom of disorders associated with abnormal kidney or heart formation or function, including, but not limited to nephritis, coronary disease, atherosclerosis and plaque formation.

INTERCEPT 258 expression indicates that INTERCEPT 258 is involved, in addition to the above, in such processes as thermogenesis, adipocyte function, and vascularization. As such, INTERCEPT 258 nucleic acids, proteins, and modulators thereof can be utilized to modulate such processes as well as for ameliorating at least one symptom associated with such processes. Such disorders include, but are not limited to obesity, regulation of body temperature, and disorders involving abnormal vascularization, e.g., vascularization of solid tumors.

In further light of INTERCEPT 258 expression, as well as in light of its homology to A33 antigen, INTERCEPT 258 nucleic acids, proteins and modulators thereof can be utilized to modulate cell proliferation, including, for example, epithelial, e.g., gastrointestinal tract epithelial cell proliferation, and to ameliorate at least one symptom of cell proliferative disorders such as cancer, and, in particular, chronic myelogenous leukemia, colon cancers, small bowel epithelium cancers and other gastrointestinal tract cancers.

Human TANGO 281

A cDNA encoding human TANGO 281 was identified by analyzing the sequences of clones present in a human megakarocyte cDNA library. This analysis led to the identification of a clone, AThPb81d10, encoding full-length human TANGO 281. The human TANGO 281 cDNA of this clone is 1812 nucleotides long (FIGS. 27A–27C; SEQ ID NO:46). The open reading frame of this cDNA, nucleotides 65 to 799 of SEQ ID NO:46 (SEQ ID NO:47), encodes a 245 amino acid transmembrane protein (FIGS. 27A–27C; SEQ ID NO:48).

The signal peptide prediction program SIGNALP (Nielsen, et al. (1997) *Protein Engineering* 10:1–6) predicted that human TANGO 281 includes an 38 amino acid signal peptide (amino acid 1 to amino acid 38 of SEQ ID NO:48; SEQ ID NO:49) preceding the mature TANGO 281 protein (corresponding to amino acid 39 to amino acid 245 of SEQ ID NO:48; SEQ ID NO:50). The molecular weight of TANGO 281 without post-translational modifications is 26.5 kDa prior to the cleavage of the signal peptide, 20.2 kDa after cleavage of the signal peptide.

Human TANGO 281 is a transmembrane protein which contains one or more of the following domains: (1) an extracellular domain; (2) a transmembrane domain; and (3) a cytoplasmic domain. The human TANGO 281 protein contains an extracellular domain at amino acids 1 to 123 of SEQ ID NO:48 or a mature extracellular domain at about amino acid residues 39 to 123 of SEQ ID NO:48 (SEQ ID NO:51), a transmembrane domain at amino acid residues 124 to 148 of SEQ ID NO:48 (SEQ ID NO:52), and a cytoplasmic domain at amino acid residues 149 to 245 of SEQ ID NO:48 (SEQ ID NO:573).

FIG. 28 depicts a hydropathy plot of human TANGO 281. Relatively hydrophobic regions of the protein are shown above the horizontal line, and relatively hydrophilic regions of the protein are below the horizontal line. The cysteine residues (cys) and potential N-glycosylation sites (Ngly) are indicated by short vertical lines just below the hydropathy trace. The dashed vertical line separates the signal sequence (amino acids 1 to 38 of SEQ ID NO:48; SEQ ID NO:49) on the left from the mature protein (amino acids 38 to 245 of SEQ ID NO:48; SEQ ID NO:50) on the right.

Human TANGO 281 comprises photosystem II 10 kD phosphoprotein (PSBH) domain sequences, which have been shown to be phosphorylated in a light-dependent reaction, from amino acids 41 to 90 and 127 to 182 of SEQ ID NO:48 (SEQ ID NO:54 and SEQ ID NO:55, respectively). FIG. 29 depicts an alignment between the PSBH domain (SEQ ID NO:69;

Accession No. PF00737) and human TANGO 281 from amino acids 97 to 146 of SEQ ID NO:48. An N-glycosylation site having the sequence NTTT is present in TANGO 281 at about amino acids 160 to 163 of SEQ ID NO:48. Two protein kinase C phosphorylation sites are present in human TANGO 281. The first has the sequence SVR (at amino acids 8 to 10 of SEQ ID NO:48), and the second has the sequence SSR (at amino acids 87 to 89 of SEQ ID NO :48). Three casein kinase II phosphorylation sites are present in human TANGO 281. The first has the sequence SIPE (at amino acids 49 to 52 of SEQ ID NO:48), the second has the sequence SCPD (at amino acids 53 to 56 of SEQ ID NO:48), and the third has the sequence SSLD (at amino acids 108 to 111 of SEQ ID NO:48). Human TANGO 281 has two N-myristylation sites. The first has the sequence GSCSSQ (at amino acids 60 to 65 of SEQ ID NO:48), and the second has the sequence GATVAI (at amino acids 119 to 124 of SEQ ID NO:48).

Nucleic acid base pairs 413 to 746 of human TANGO 281 (SEQ ID NO:46) have 81% identity to the nucleic acid sequence identified as N.U.C Patent database Accession Number V34245. Nucleic acid base pairs 438 to 746 of human TANGO 281 (SEQ ID NO:46) have 80% identity to a nucleic acid sequence referred to as "gene 31" described in PCT Publication No. WO 98/39446 (SEQ ID NO:70). "Gene 31" is characterized as being expressed primarily in brain and thymus, and to a lesser extent in such organs as liver, skin, bone and bone marrow.

Clone EpT281 was deposited with the American Type Culture Collection (10801 University Boulevard, Manassas, Va. 20110-2209) on Apr. 21, 1999 and assigned Accession Number 207222. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Mouse TANGO 281

A cDNA encoding mouse TANGO 281 was identified in a normal mouse megakaryocyte library by performing expression profiling on megakarocytes obtained from mice with a the deletion of the element of the gata-1 gene responsible for megakaryocyte-specific expression. This analysis led to the identification of a clone, Atmea49d3, encoding full-length mouse TANGO 281. The mouse TANGO 281 cDNA of this clone is 1858 nucleotides long (FIGS. 30A–30B; SEQ ID NO:56). The open reading frame of this cDNA, nucleotides 90 to 728 of SEQ ID NO:56 (SEQ ID NO:57), encodes a 213 amino acid transmembrane protein (FIGS. 30A–30B; SEQ ID NO:58).

The signal peptide prediction program SIGNALP (Nielsen, et al. (1997) *Protein Engineering* 10:1–6) predicted that mouse TANGO 281 includes an 26 amino acid signal peptide (amino acid 1 to amino acid 26 of SEQ ID NO:58; SEQ ID NO:59) preceding the mature TANGO 281 protein (corresponding to amino acid 27 to amino acid 213 of SEQ ID NO:58; SEQ ID NO:60). The molecular weight of mouse TANGO 281 without post-translational modifications is 22.9 kDa prior to the cleavage of the signal peptide, 20.2 kDa after cleavage of the signal peptide.

Mouse TANGO 281 is a transmembrane protein which contains one or more of the following domains: (1) an extracellular domain; (2) a transmembrane domain; and (3)

a cytoplasmic domain. The mouse TANGO 281 protein contains an extracellular domain at amino acid residues 27 to 112 of SEQ ID NO:58 (SEQ ID NO:61), a transmembrane domain at amino acid residues 113 to 137 of SEQ ID NO:58 (SEQ ID NO:62), and a cytoplasmic domain at amino acid residues 138 to 213 of SEQ ID NO:58 (SEQ ID NO:63).

FIG. 31 depicts a hydropathy plot of mouse TANGO 281. Relatively hydrophobic regions of the protein are shown above the horizontal line, and relatively hydrophilic regions of the protein are below the horizontal line. The cysteine residues (cys) and potential N-glycosylation sites (Ngly) are indicated by short vertical lines just below the hydropathy trace. The dashed vertical line separates the signal sequence (amino acids 1 to 26 of SEQ ID NO:58; SEQ ID NO:59) on the left from the mature protein (amino acids 27 to 213 of SEQ ID NO:58; SEQ ID NO:60) on the right.

Mouse TANGO 281 comprises photosystem II 10 kDa phosphoprotein(PSBH) domain sequences, which have been shown to be phosphorylated in a light-dependent reaction, from amino acids 42 to 91 and 128 to 183 of SEQ ID NO:58 (SEQ ID NO:64 and SEQ ID NO:65, respectively). Two N-glycosylation sites having the sequences NTTT (at amino acids 149 to 152 of SEQ ID NO:58) and NASS (at about amino 189 to 192 of SEQ ID NO:58) are present in TANGO 281. A glycosaminoglycan attachment site having the sequence SGFG is present in mouse TANGO 281, and protein kinase C phosphorylation site having the sequence SSR is present in mouse TANGO 281. Two casein kinase II phosphorylation sites are present in human TANGO 281. The first has the sequence TPAE (at amino acids 80 to 83 of SEQ ID NO:58), and the second has the sequence SSFD (at amino acids 97 to 100 of SEQ ID NO:58). Mouse TANGO 281 has two N-myristylation sites. The first has the sequence GSCSNQ (at amino acids 48 to 53 of SEQ ID NO:58), and the second has the sequence GATVAI (at amino acids 108 to 113 of SEQ ID NO:58).

Northern blot analysis of mouse TANGO 281 expression revealed two mRNA bands, one of approximately 1.8 kb and another approximately 1.4 kb. Expression of the 1.8 kb band was detected in the heart, spleen, lung and kidney, with the greatest abundance detected in the heart and lung, followed by the kidney and trace amounts in the spleen. Expression of the 1.4 kb band was detected in the brain, spleen, and lung. Expression of the 1.4 kb and 1.8 kb species of mouse TANGO 281 was detected in 7 day old normal mouse embryos. Neither the 1.4 kb or the 1.8 kb species of mouse TANGO 281 were detected in 11 day old normal mouse embryos. The 1.8 kb species of mouse TANGO 281 was detected in 15 day old normal mouse embryos at 20% the level detected in 7 day old normal mouse embryos. Expression of the 1.8 kb species detected in 17 day old normal mouse embryos was comparable to the level of expression detected in 7 day old normal mouse embryos. Expression of mouse TANGO 281 expression was greatly reduced in megakaryocytes obtained from gata-1 knockout mice.

FIG. 32 shows that there is an overall 66.5% identity between the precursor human TANGO 281 amino acid sequence and the precursor mouse TANGO 281 amino acid sequence.

Clone EpTm281 was deposited with the American Type Culture Collection (10801 University Boulevard, Manassas, Va. 20110-2209) on Jun. 15, 1999 and assigned patent deposit Number PTA-224. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Uses of TANGO 281 Nucleic Acids, Polypeptides and Modulators Thereof

As TANGO 281 was originally found in a megakaryocyte library, TANGO 281 nucleic acids, proteins, and modulators thereof can be used to modulate the proliferation, differentiation, and/or function of megakaryocytes and platelets. TANGO 281 nucleic acids, proteins, and modulators thereof can be used to treat associated hematological diseases such as thrombocytopenia, platelet disorders and bleeding disorders (e.g., hemophilia). TANGO 281 nucleic acids, proteins, and modulators thereof can be used to modulate platelet aggregation and degranulation. Further, as TANGO 281 expression varies in mouse embryos during development, TANGO 281 nucleic acids, proteins, and modulators thereof can be used to modulate the development of cells, tissues or organs in embryos.

As TANGO 281 expression is greatly reduced in megakaryocytes obtained from gata-1 knockout mice compared normal mice, TANGO 281 is either a direct or indirect target of gata-1 and has profound biological implications. Gata-1 is a transcription factor involved in the development of hemapoietic cell lineages—gata-1 expression is required for proper development of erythocytes and megakaryocytes. Although deletion of the gata-1 gene is lethal at the embryonic stage due to a failure to form red blood cells, deletion of only the element of the gata-1 gene responsible for megakaryocyte-specific expression (a 10 kb region of genomic DNA containing a megakaryocyte specific DNase I hypersensitive) is not lethal and results in a reduction in gata-1 expression in the megakaryocyte without affecting gata-1 expression in red blood cells. The megakaryocytes of mice with this element of the gata-1 gene knocked out fail to develop into mature platelets, and the mice experience abnormal bleeding due to their profound thrombocytopenia. TANGO 281 nucleic acids, proteins, and modulators thereof can be used to treat disease and/or disorders associated with gata-1 dysfunction.

As TANGO 281 is expressed in the heart, brain, spleen, lung, kidney, embryo and megakaryocytes, TANGO 281 nucleic acids, proteins, and modulators thereof can be used to treat disorders of these cells, tissues, or organs, e.g., ischemic heart disease or atherosclerosis, head trauma, brain cancer, splenic lymphoma, splenomegaly, lung cancer, cystic fibrosis, rheumatoid lung disease, glomerulonephritis, end stage renal disease, uremia, DiGeorge syndrome, thymoma, autoimmune disorders, atresia, Crohns's disease, and various embryonic disorders. TANGO 281 nucleic acids, proteins, and modulators thereof can be used to modulate the bleeding associated with uremia. Further, TANGO 281 nucleic acids, proteins, and modulators thereof can be used to treat hypercoagulation associated with a damaged endothelium, e.g., pre-eclampsia, malignant hypertension, disseminated intravascular coagulopathy, renal transplant rejection, cyclosporin toxicity, microangiopathic hemolytic anemia, and thrombotic thrombocytopenic purpura.

TANGO 281 exhibits homology to a gene referred to as "gene 31" (PCT Publication No. W098/39446), which is expressed primarily in the brain and thymus. In light of this, TANGO 281 nucleic acids, proteins and modulators thereof can be utilized to ameliorate at least one symptom associated with central nervous (CNS) disorders, hematopoietic disorder, and disorders of the endocrine system.

Tables 1–4 below provide a summary of the sequence information for TANGO 253, TANGO 257, INTERCEPT 258 and TANGO 281.

TABLE 1

Summary of Human TANGO 253, TANGO 257, INTERCEPT 258, and TANGO 281 Sequence Information

| Gene | cDNA | ORF | Figure | Accession Number |
|---|---|---|---|---|
| TANGO 253 | SEQ ID NO:1 | SEQ ID NO:2 | FIG. 1 | 207222 |
| TANGO 257 | SEQ ID NO:15 | SEQ ID NO:16 | FIG. 8 | 207222 |
| INTERCEPT 258 | SEQ ID NO:26 | SEQ ID NO:27 | FIG. 17 | 207222 |
| TANGO 281 | SEQ ID NO:46 | SEQ ID NO:47 | FIG. 27 | 207222 |

TABLE 2

Summary of Domains of Human TANGO 253, TANGO 257, INTERCEPT 258 and TANGO 281 Proteins

| Protein | Signal Sequence | Mature Protein | Extracellular | PSBH | Ig | CIq | Collagen | Trans-membrane | Cytoplasmic |
|---|---|---|---|---|---|---|---|---|---|
| TANGO 253 | aa 1–15 of SEQ ID NO: 3 (SEQ ID NO: 5) | aa 16–243 of SEQ ID NO: 3 (SEQ ID NO: 4) | | | | aa 102–232 of SEQ ID NO: 3 (SEQ ID NO: 7) | aa 36–45 of SEQ ID NO: 3 (SEQ ID NO: 6) | | |
| TANGO 257 | aa 1–21 of SEQ ID NO: 17 (SEQ ID NO: 19) | aa 22–406 of SEQ ID NO: 17 (SEQ ID NO: 18) | | | | | | | |
| INTERCEPT 258 | aa 1–29 of SEQ ID NO: 28 (SEQ ID NO: 30) | aa 30–370 of SEQ ID NO: 28 (SEQ ID NO: 29) | aa 1–246 of SEQ ID NO: 28 (SEQ ID NO: 31) | | aa 49–128; 167–226 of SEQ ID NO: 28 (SEQ ID NO: 35; SEQ ID NO: 36) | | | aa 247–271 of SEQ ID NO: 28 (SEQ ID NO: 33) | aa 272–370 of SEQ ID NO: 28 (SEQ ID NO: 34) |
| TANGO 281 | aa 1–38 of SEQ ID NO: 48 (SEQ ID NO: 49) | aa 39–245 of SEQ ID NO: 48 (SEQ ID NO: 50) | aa 39–123 of SEQ ID NO: 48 (SEQ ID NO: 51) | aa 41–90; 12–187 of SEQ ID NO: 48 (SEQ ID NO: 54; SEQ ID NO: 55) | | | | aa 124–148 of SEQ ID NO: 48 (SEQ ID NO: 52) | aa 149–245 of SEQ ID NO: 48 (SEQ ID NO: 53) |

TABLE 3

Summary of Mouse TANGO 253, TANGO 257, INTERCEPT 258 and TANGO 281 Sequence Information

| Gene | cDNA | ORF | Figure | Accession Number |
|---|---|---|---|---|
| TANGO 253 | SEQ ID NO:8 | SEQ ID NO:9 | FIG. 3 | 207215 |
| TANGO 257 | SEQ ID NO:21 | SEQ ID NO:22 | FIG. 10 | 207217 |
| INTERCEPT 258 | SEQ ID NO:37 | SEQ ID NO:38 | FIG. 19 | 207221 |
| TANGO 281 | SEQ ID NO:56 | SEQ ID NO:57 | FIG. 30 | PTA-224 |

TABLE 4

Summary of Domains of Mouse TANGO 253, TANGO 257, INTERCEPT 258 and TANGO 281 Proteins

| Protein | Signal Sequence | Mature Protein | Extracellular | PSBH | Ig | CIq | Collagen | Trans-membrane | Cytoplasmic |
|---|---|---|---|---|---|---|---|---|---|
| TANGO 253 | aa 1–15 of SEQ ID NO:10 (SEQ ID NO:12) | aa 16–243 of SEQ ID NO:10 (SEQ ID NO:11) | | | | aa 105–232 of SEQ ID NO:10 (SEQ ID NO:13) | aa 36–95 of SEQ ID NO:10 (SEQ ID NO:14) | | |
| TANGO 257 | aa 1–21 of SEQ ID NO:23 (SEQ ID NO:25) | aa 22–406 of SEQ ID NO:23 (SEQ ID NO:24) | | | | | | | |
| INTERCEPT 258 | aa 1–29 of SEQ ID NO:39 (SEQ ID NO:41) | aa 30–394 of SEQ ID NO:39 (SEQ ID NO:40) | | | aa 170–229 of SEQ ID NO:39 (SEQ ID NO:46) | | | | |
| TANGO 281 | aa 1–26 of SEQ ID NO:58 (SEQ ID NO:59) | aa 27–213 of SEQ ID NO:58 (SEQ ID NO:60) | aa 27–112 of SEQ ID NO:58 (SEQ ID NO:61) | aa 42–91; 128–183 of SEQ ID NO:58 (SEQ ID NO:64; SEQ ID NO:65) | | | | aa 113–137 of SEQ ID NO:58 (SEQ ID NO:62) | aa 138–213 of SEQ ID NO:58 (SEQ ID NO:63 |

Various aspects of the invention are described in further detail in the following subsections:

I. Isolated Nucleic Acid Molecules

One aspect of the invention pertains to isolated nucleic acid molecules that encode a polypeptide of the invention or a biologically active portion thereof, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules. As used herein, the term “nucleic acid molecule” is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An “isolated” nucleic acid molecule is one which is separated from other nucleic acid molecules which are present in the natural source of the nucleic acid molecule. Preferably, an “isolated” nucleic acid molecule is free of sequences (preferably protein encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an “isolated” nucleic acid molecule, such as a cDNA molecule, can be substantially free of other cellular material, or culture medium when produced by recombinant techniques, or substantially free of chemical precursors or other chemicals when chemically synthesized. As used herein, the term “isolated” when referring to a nucleic acid molecule does not include an isolated chromosome.

A nucleic acid molecule of the present invention, e.g., a nucleic acid molecule having the nucleotide sequence of SEQ ID NO:1, 2, 8, 9, 15, 16, 21, 22, 26, 27, 37, 38, 46, 47, 56 or 57 or a complement thereof, can be isolated using standard molecular biology techniques and the sequence information provided herein. Using all or a portion of the nucleic acid sequences of SEQ ID NO:1, 2, 8, 9, 15, 16, 21, 22, 26, 27, 37, 38, 46, 47, 56 or 57, as a hybridization probe, nucleic acid molecules of the invention can be isolated using standard hybridization and cloning techniques (e.g., as described in Sambrook et al., eds., *Molecular Cloning: A Laboratory Manual, 2nd ed., Cold Spring Harbor Laboratory,* Cold Spring Harbor Laboratory Press, Cold Spring Harbor, N.Y., 1989).

A nucleic acid molecule of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which is a complement of the nucleotide sequence of SEQ ID NO:1, 2, 8, 9, 15, 16, 21, 22, 26, 27, 37, 38, 46, 47, 56 or 57 or a portion thereof. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence encoding a full length polypeptide of the invention for example, a fragment which can be used as a probe or primer or a fragment encoding a biologically active portion of a polypeptide of the invention. The nucleotide sequence determined from the cloning one gene allows for the generation of probes and primers designed for use in identifying and/or cloning homologues in other cell types, e.g., from other tissues, as well as homologues from other mammals. The probe/primer typically comprises substantially purified oligonucleotide. In one embodiment, the oligonucleotide comprises a region of nucleotide sequence that hybridizes under stringent conditions to at least about 12, preferably 25, more preferably about 50, 75, 100, 125, 150, 175, 200, 250, 300, 350 or 400 consecutive oligonucleotides of the sense or anti-sense sequence of SEQ ID NO:1, 2, 8, 9, 15, 16, 21, 22, 26, 27, 37, 38, 46, 47, 56 or 57 or of a naturally occurring mutant of SEQ ID NO:1, 2, 8, 9, 15, 16, 21, 22, 26, 27, 37, 38, 46, 47, 56 or 57.

In a preferred embodiment, the oligonucleotide typically comprises a region of nucleotide sequence that hybridizes under stringent conditions to at least about 450, preferably about 500, 550, 600, 650, 700, 750, 800, 850, 900, 1000, 1100 or 1300 consecutive nucleotides of the sense or anti-sense sequence of SEQ ID NO:1 or of a naturally occurring mutant of SEQ ID NO:1. In another preferred embodiment, the oligonucleotide typically comprises a region of nucleotide sequence that hybridizes under stringent conditions to at least about 12, preferably 25, 50, 100, 150, 200, 250, 300, 350, 400, 450, 500, 550, 600, 650, 700 or 720 consecutive nucleotides of the sense or anti-sense sequence of SEQ ID NO:2 or of a naturally occurring mutant of SEQ ID NO:2. In another preferred embodiment, the oligonucleotide typically comprises a region of nucleotide sequence that hybridizes under stringent conditions to at least about 540, preferably about 600, 650, 700, 750, 800, 850, 900, 950, 1000, 1100, 1200 or 1250 consecutive nucleotides of the sense or anti-sense sequence of SEQ ID NO:8 or of a naturally occurring mutant of SEQ ID NO:8. In another preferred embodiment, the oligonucleotide typically comprises a region of nucleotide sequence that hybridizes under stringent conditions to at least about 310, preferably about 350, 400, 450, 500, 550, 600, 650 or 700 consecutive nucleotides of the sense or anti-sense sequence of SEQ ID NO:9 or of a naturally occurring mutant of SEQ ID NO:9. In another preferred embodiment, the oligonucleotide typically comprises a region of nucleotide sequence that hybridizes under stringent conditions to at least about 1800 consecutive nucleotides of the sense or anti-sense sequence of SEQ ID NO:15 or of a naturally occurring mutant of SEQ ID NO:15. In another preferred embodiment, the oligonucleotide typically comprises a region of nucleotide sequence that hybridizes under stringent conditions to at least about 1150 consecutive nucleotides of the sense or anti-sense sequence of SEQ ID NO:16 or of a naturally occurring mutant of SEQ ID NO:16. In another preferred embodiment, the oligonucleotide typically comprises a region of nucleotide sequence that hybridizes under stringent conditions to at least about 1100, preferably about 1200, 1300, 1400, 1500, 16500 or 1700 consecutive nucleotides of the sense or anti-sense sequence of SEQ ID NO:21 or of a naturally occurring mutant of SEQ ID NO:21. In another preferred embodiment, the oligonucleotide typically comprises a region of nucleotide sequence that hybridizes under stringent conditions to at least about 1150 consecutive nucleotides of the sense or anti-sense sequence of SEQ ID NO:22 or of a naturally occurring mutant of SEQ ID NO:22. In another preferred embodiment, the oligonucleotide typically comprises a region of nucleotide sequence that hybridizes under stringent conditions to at least about 420, preferably about 450, 500, 600, 700, 800, 900, 1000, 1100, 1200, 1300, 1400, 1500, 1600, 1700 or 1800 consecutive nucleotides of the sense or anti-sense sequence of SEQ ID NO:26 or of a naturally occurring mutant of SEQ ID NO:26. In another preferred embodiment, the oligonucleotide typically comprises a region of nucleotide sequence that hybridizes under stringent conditions to at least about 12, preferably about 25, more preferably about 50, 100, 200, 300, 400, 500, 600, 700, 800, 900, 1000, 1100, 1200, 1300, 1400, 1500, 1600, 1700 or 1800 consecutive nucleotides of the sense or anti-sense sequence of SEQ ID NO:27 or of a naturally occurring mutant of SEQ ID NO:27. In another preferred embodiment, the oligonucleotide typically comprises a region of nucleotide sequence that hybridizes under stringent conditions to at least about 675, preferably about 700, 800, 900, 1000, 1200, 1300, 1400, 1500, 1600, 1700 or 1800 consecutive nucleotides of the sense or anti-sense sequence of SEQ ID NO:37 or of a naturally occurring mutant of SEQ ID NO:37. In another preferred embodiment, the oligonucleotide typically comprises a region of nucleotide sequence that hybridizes under stringent conditions to at least about 500, preferably about 600, 700, 800, 900, 1000, 1100, 1200, 1300, 1400, 1500, 1600, 1700 or 1800 consecutive nucleotides of the sense or anti-sense sequence of SEQ ID NO:38 or of a naturally occurring mutant of SEQ ID NO:38. In another preferred embodiment, the oligonucleotide typically comprises a region of nucleotide sequence that hybridizes under stringent conditions to at least about 12, preferably about 25, more preferably about 50, 100, 200, 300, 400, 500, 600, 700, 800, 900, 1000, 1100, 1200, 1300, 1400, 1500, 1600, 1700 or 1800 consecutive nucleotides of the sense or anti-sense sequence of SEQ ID NO:46 or of a naturally occurring mutant of SEQ ID NO:46. In another preferred embodiment, the oligonucleotide typically comprises a region of nucleotide sequence that hybridizes under stringent conditions to at least about 12, preferably about 25, more preferably about 50, 100, 200, 300, 400, 500, 600, 700, 800, 900, 1000, 1100, 1200, 1300, 1400, 1500, 1600, 1700 or 1800 consecutive nucleotides of the sense or anti-sense sequence of SEQ ID NO:47 or of a naturally occurring mutant of SEQ ID NO:47. In another preferred embodiment, the oligonucleotide typically comprises a region of nucleotide sequence that hybridizes under stringent conditions to at least about 550, preferably about 600, 700, 800, 900, 1000, 1100, 1200, 1300, 1400, 1500, 1600, 1700,1800 or 1850 consecutive nucleotides of the sense or anti-sense sequence of SEQ ID NO:56 or of a naturally occurring mutant of SEQ ID NO:56. In another preferred embodiment, the oligonucleotide typically comprises a region of nucleotide sequence that hybridizes under stringent conditions to at least about 12, preferably about 25, more preferably about 50, 100, 200, 300, 400, 500, 600 or 700 consecutive nucleotides of the sense or anti-sense sequence of SEQ ID NO:57 or of a naturally occurring mutant of SEQ ID NO:57.

Probes based on the sequence of a nucleic acid molecule of the invention can be used to detect transcripts or genomic sequences encoding the same protein molecule encoded by a selected nucleic acid molecule. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

A nucleic acid fragment encoding a biologically active portion of a polypeptide of the invention can be prepared by isolating a portion of any of SEQ ID NO:3, 10, 17, 23, 28, 39, 48 or 58 expressing the encoded portion of the polypeptide protein (e.g., by recombinant expression in vitro) and assessing the activity of the encoded portion of the polypeptide.

The invention further encompasses nucleic acid molecules that differ from the nucleotide sequence of SEQ ID NO:1, 2, 8, 9, 15, 16, 21, 22, 26, 27, 37, 38, 46, 47, 56 or 57 due to degeneracy of the genetic code and thus encode the same protein as that encoded by the nucleotide sequence of SEQ ID NO:3, 10, 17, 28, 39, 48, or 58.

In addition to the nucleotide sequences of SEQ ID NO:3, 10, 17, 23, 28, 39, or 58, it will be appreciated by those skilled in the art that DNA sequence polymorphisms that lead to changes in the amino acid sequence may exist within a population (e.g., the human population). Such genetic polymorphisms may exist among individuals within a population due to natural allelic variation. An allele is one of a group of genes which occur alternatively at a given genetic locus. As used herein, the phrase "allelic variant" refers to a nucleotide sequence which occurs at a given locus or to a polypeptide encoded by the nucleotide sequence. As used herein, the terms "gene" and "recombinant gene" refer to nucleic acid molecules comprising an open reading frame encoding a polypeptide of the invention. Such natural allelic variations can typically result in 1–5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

Moreover, nucleic acid molecules encoding proteins of the invention from other species (homologues), which have a nucleotide sequence which differs from that of the human or mouse protein described herein are intended to be within the scope of the invention. Nucleic acid molecules corresponding to natural allelic variants and homologues of a cDNA of the invention can be isolated based on their identity to the human nucleic acid molecule disclosed herein using the human cDNAs, or a portion thereof, as a hybridization probe according to standard hybridization techniques under stringent hybridization conditions. For example, a cDNA encoding a soluble form of a membrane-bound protein of the invention isolated based on its hybridization to a nucleic acid molecule encoding all or part of the membrane-bound form. Likewise, a cDNA encoding a membrane-bound form can be isolated based on its hybridization to a nucleic acid molecule encoding all or part of the soluble form.

Accordingly, in another embodiment, an isolated nucleic acid molecule of the invention is at least 450, 500, 550, 600, 650, 700, 750, 800, 850, 900, 1000, 1100, 1200 or 1300 nucleotides in length and hybridizes under stringent conditions to the nucleic acid molecule comprising the nucleotide sequence, preferably the coding sequence, of SEQ ID NO:1, or a complement thereof.

Accordingly, in another embodiment, an isolated nucleic acid molecule of the invention is at least 50, 100, 150, 200, 250, 300, 350, 400, 450, 500, 550, 600, 650, 700 or 720 nucleotides in length and hybridizes under stringent conditions to the nucleic acid molecule comprising the nucleotide sequence, preferably the coding sequence, of SEQ ID NO:2, or a complement thereof.

Accordingly, in another embodiment, an isolated nucleic acid molecule of the invention is at least 540, 600, 650, 700, 750, 800, 850, 900, 950, 1000, 1100, 1200 or 1250 nucleotides in length and hybridizes under stringent conditions to the nucleic acid molecule comprising the nucleotide sequence, preferably the coding sequence, of SEQ ID NO:8, or a complement thereof.

Accordingly, in another embodiment, an isolated nucleic acid molecule of the invention is at least 310, 350, 400, 450, 500, 550, 600, 650 or 700 nucleotides in length and hybridizes under stringent conditions to the nucleic acid molecule comprising the nucleotide sequence, preferably the coding sequence, of SEQ ID NO:9, or a complement thereof.

Accordingly, in another embodiment, an isolated nucleic acid molecule of the invention is at least 1800 nucleotides in length and hybridizes under stringent conditions to the nucleic acid molecule comprising the nucleotide sequence, preferably the coding sequence, of SEQ ID NO:15, or a complement thereof.

Accordingly, in another embodiment, an isolated nucleic acid molecule of the invention is at least 1150 or 1200 nucleotides in length and hybridizes under stringent conditions to the nucleic acid molecule comprising the nucleotide sequence, preferably the coding sequence, of SEQ ID NO:16, or a complement thereof.

Accordingly, in another embodiment, an isolated nucleic acid molecule of the invention is at least 1100, 1200, 1300, 1400, 1500, 1600 or 1700 nucleotides in length and hybridizes under stringent conditions to the nucleic acid molecule comprising the nucleotide sequence, preferably the coding sequence, of SEQ ID NO:21, or a complement thereof.

Accordingly, in another embodiment, an isolated nucleic acid molecule of the invention is at least 1150 or 1200 nucleotides in length and hybridizes under stringent conditions to the nucleic acid molecule comprising the nucleotide sequence, preferably the coding sequence, of SEQ ID NO:22, or a complement thereof.

Accordingly, in another embodiment, an isolated nucleic acid molecule of the invention is at least 420, 450, 500, 600, 700, 800, 900, 1000, 1100, 1200, 1300, 1400, 1500, 1600, 1700, or 1800 nucleotides in length and hybridizes under stringent conditions to the nucleic acid molecule comprising the nucleotide sequence, preferably the coding sequence, of SEQ ID No:26, or a complement thereof.

Accordingly, in another embodiment, an isolated nucleic acid molecule of the invention is at least 50, 100, 200, 300, 400, 500, 600, 700, 800, 900, 1000, 1100, 1200, 1300, 1400, 1500, 1600, 1700 or 1800 nucleotides in length and hybridizes under stringent conditions to the nucleic acid molecule comprising the nucleotide sequence, preferably the coding sequence, of SEQ ID NO:27, or a complement thereof.

Accordingly, in another embodiment, an isolated nucleic acid molecule of the invention is at least 675, 700, 800, 900, 1000, 1100, 1200, 1300, 1400, 1500, 1600, 1700 or 1800 nucleotides in length and hybridizes under stringent conditions to the nucleic acid molecule comprising the nucleotide sequence, preferably the coding sequence, of SEQ ID NO:37, or a complement thereof.

Accordingly, in another embodiment, an isolated nucleic acid molecule of the invention is at least 500, 600, 700, 800, 900, 1000, 1100, 1200, 1300, 1400, 1500, 1600, 1700 or 1800 nucleotides in length and hybridizes under stringent conditions to the nucleic acid molecule comprising the nucleotide sequence, preferably the coding sequence, of SEQ ID NO:38, or a complement thereof.

Accordingly, in another embodiment, an isolated nucleic acid molecule of the invention is at least 50, 100, 200, 300, 400, 500, 600, 700, 800, 900, 1000, 1100, 1200, 1300, 1400, 1500, 1600, 1700 or 1800 nucleotides in length and hybridizes under stringent conditions to the nucleic acid molecule comprising the nucleotide sequence, preferably the coding sequence, of SEQ ID NO:46, or a complement thereof.

Accordingly, in another embodiment, an isolated nucleic acid molecule of the invention is at least 50, 100, 200, 300, 400, 500, 600, 700 or 750 nucleotides in length and hybridizes under stringent conditions to the nucleic acid molecule comprising the nucleotide sequence, preferably the coding sequence, of SEQ ID NO:47, or a complement thereof.

Accordingly, in another embodiment, an isolated nucleic acid molecule of the invention is at least 550, 600, 700, 800, 900, 1000, 1100, 1200, 1300, 1400, 1500, 1600, 1700, 1800 or 1850 nucleotides in length and hybridizes under stringent conditions to the nucleic acid molecule comprising the nucleotide sequence, preferably the coding sequence, of SEQ ID NO:56, or a complement thereof.

Accordingly, in another embodiment, an isolated nucleic acid molecule of the invention is at least 50, 100, 200, 300, 400, 500, 600 or 700 nucleotides in length and hybridizes under stringent conditions to the nucleic acid molecule comprising the nucleotide sequence, preferably the coding sequence, of SEQ ID NO:57, or a complement thereof.

As used herein, the term "hybridizes under stringent conditions" is intended to describe conditions for hybridization and washing under which nucleotide sequences at least 60%, 65%, 70%, preferably 75%, identical to each other typically remain hybridized to each other. Such stringent conditions are known to those skilled in the art and can be found in *Current Protocols in Molecular Biology,* John Wiley & Sons, N.Y. (1989), 6.3.1–6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1, 2, 8, 9, 15, 16, 21, 22, 26, 27, 37, 38, 46, 47, 56 or 57, or a complement thereof, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of a nucleic acid molecule of the invention sequence that may exist in the population, the skilled artisan will further appreciate that changes can be introduced by mutation thereby leading to changes in the amino acid sequence of the encoded protein, without altering the biological activity of the protein. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologues of various species may be non-essential for activity and thus would be likely targets for alteration. Alternatively, amino acid residues that are conserved among the homologues of various species (e.g., mouse and human) may be essential for activity and thus would not be likely targets for alteration.

Accordingly, another aspect of the invention pertains to nucleic acid molecules encoding a polypeptide of the invention that contain changes in amino acid residues that are not essential for activity. Such polypeptides differ in amino acid sequence from SEQ ID NO:3, yet retain biological activity. In one embodiment, the isolated nucleic acid molecule includes a nucleotide sequence encoding a protein that includes an amino acid sequence that is at least about 40%, 45%, 50%, 55%, 60%, 65%, 75%, 85%, 95%, or 98% identical to the amino acid sequence of SEQ ID NO:3.

Accordingly, another aspect of the invention pertains to nucleic acid molecules encoding a polypeptide of the invention that contain changes in amino acid residues that are not essential for activity. Such polypeptides differ in amino acid sequence from SEQ ID NO:10, yet retain biological activity. In one embodiment, the isolated nucleic acid molecule includes a nucleotide sequence encoding a protein that includes an amino acid sequence that is at least about 95%, or 98% identical to the amino acid sequence of SEQ ID NO:10.

Accordingly, another aspect of the invention pertains to nucleic acid molecules encoding a polypeptide of the invention that contain changes in amino acid residues that are not essential for activity. Such polypeptides differ in amino acid sequence from SEQ ID NO:17, yet retain biological activity. In one embodiment, the isolated nucleic acid molecule includes a nucleotide sequence encoding a protein that includes an amino acid sequence that is at least about 88%, 90%, 95% or 98% identical to the amino acid sequence of SEQ ID NO:17.

Accordingly, another aspect of the invention pertains to nucleic acid molecules encoding a polypeptide of the invention that contain changes in amino acid residues that are not essential for activity. Such polypeptides differ in amino acid sequence from SEQ ID NO:23, yet retain biological activity. In one embodiment, the isolated nucleic acid molecule includes a nucleotide sequence encoding a protein that includes an amino acid sequence that is at least about 88%, 90%, 95%, or 98% identical to the amino acid sequence of SEQ ID NO:23.

Accordingly, another aspect of the invention pertains to nucleic acid molecules encoding a polypeptide of the invention that contain changes in amino acid residues that are not essential for activity. Such polypeptides differ in amino acid sequence from SEQ ID NO:28, yet retain biological activity. In one embodiment, the isolated nucleic acid molecule includes a nucleotide sequence encoding a protein that includes an amino acid sequence that is at least about 45%, 50%, 55%, 60%, 65%, 75%, 85%, 95%, or 98% identical to the amino acid sequence of SEQ ID NO:28.

Accordingly, another aspect of the invention pertains to nucleic acid molecules encoding a polypeptide of the invention that contain changes in amino acid residues that are not essential for activity. Such polypeptides differ in amino acid sequence from SEQ ID NO:39, yet retain biological activity. In one embodiment, the isolated nucleic acid molecule includes a nucleotide sequence encoding a protein that includes an amino acid sequence that is at least about 45%, 50%, 55%, 60%, 65%, 75%, 85%, 95%, or 98% identical to the amino acid sequence of SEQ ID NO:39.

Accordingly, another aspect of the invention pertains to nucleic acid molecules encoding a polypeptide of the invention that contain changes in amino acid residues that are not essential for activity. Such polypeptides differ in amino acid sequence from SEQ ID NO:48, yet retain biological activity. In one embodiment, the isolated nucleic acid molecule includes a nucleotide sequence encoding a protein that includes an amino acid sequence that is at least about 30%, 35%, 40%, 45%, 50%, 55%, 60%, 65%, 75%, 85%, 95%, or 98% identical to the amino acid sequence of SEQ ID NO:48.

Accordingly, another aspect of the invention pertains to nucleic acid molecules encoding a polypeptide of the invention that contain changes in amino acid residues that are not essential for activity. Such polypeptides differ in amino acid sequence from SEQ ID NO:58, yet retain biological activity. In one embodiment, the isolated nucleic acid molecule includes a nucleotide sequence encoding a protein that includes an amino acid sequence that is at least about 30%, 35%, 40%, 45%, 50%, 55%, 60%, 65%, 75%, 85%, 95%, or 98% identical to the amino acid sequence of SEQ ID NO:58.

An isolated nucleic acid molecule encoding a variant protein can be created by introducing one or more nucleotide substitutions, additions or deletions into the nucleotide sequence of SEQ ID NO:1, 2, 8, 9, 15, 16, 21, 22, 26, 27, 37, 38, 46, 47, 56 or 57 such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In a preferred embodiment, a mutant polypeptide that is a variant of a polypeptide of the invention can be assayed for: (1) the ability to form protein: protein interactions with proteins in a signaling pathway of the polypeptide of the invention; (2) the ability to bind a ligand of the polypeptide of the invention; or (3) the ability to bind to an intracellular target protein of the polypeptide of the invention. In yet another preferred embodiment, the mutant polypeptide can be assayed for the ability to modulate cellular proliferation, cellular migration or chemotaxis, or cellular differentiation.

The present invention encompasses antisense nucleic acid molecules, i.e., molecules which are complementary to a sense nucleic acid encoding a polypeptide of the invention, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45 or 50 nucleotides or more in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a selected polypeptide of the invention to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an -anomeric (alpha) nucleic acid molecule. An -anomeric nucleic acid molecule forms specific double-stranded hybrids with complementary RNA in which, contrary to the usual 62-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave mRNA transcripts to thereby inhibit translation of the protein encoded by the mRNA. A ribozyme having specificity for a nucleic acid molecule encoding a polypeptide of the invention can be designed based upon the nucleotide sequence of a cDNA disclosed herein. For example, a derivative of a Tetrahymena L-19 IVS RNA can be constructed in which the nucleotide sequence of the active site is complementary to the nucleotide sequence to be cleaved in a Cech et al. U.S. Pat. No. 4,987,071; and Cech et al. U.S. Pat. No. 5,116,742. Alternatively, an mRNA encoding a polypeptide of the invention can be used to select a catalytic RNA having a specific ribonuclease activity from a pool of RNA molecules. See, e.g., Bartel and Szostak (1993) *Science* 261:1411–1418.

The invention also encompasses nucleic acid molecules which form triple helical structures. For example, expression of a polypeptide of the invention can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569–84; Helene (1992) *Ann. N.Y. Acad. Sci.* 660:27–36; and Maher (1992) *Bioassays* 14(12):807–15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4(1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93: 14670–675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1 996), supra; or as probes or primers for DNA sequence and hybridization (Hyrup (1996), supra; Perry-O'Keefe et al. (1996) *Proc. Natl. Acad. Sci. USA* 93: 14670–675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996), supra). The synthesis of PNA-DNA chimeras can be performed as described in Hyrup (1996), supra, and Finn et al. (1996) *Nucleic Acids Res.* 24(17):3357–63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al. (1989) *Nucleic Acids Res.* 17:5973–88). PNA monomers are then coupled in a stepwise manner to produce a chimeric molecule with a 5' PNA segment and a 3' DNA segment (Finn et al. (1996) *Nucleic Acids Res.* 24(17):3357–63). Alternatively, chimeric molecules can be synthesized with a 5' DNA segment and a 3' PNA segment (Peterser et al. (1975) *Bioorganic Med. Chem. Lett.* 5:1119–11124).

In other embodiments, the oligonucleotide may include other appended groups such as peptides (e.g., for targeting host cell receptors in vivo ), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) *Bio/Techniques* 6:958–976) or intercalating agents (see, e.g., Zon (1988) *Pharm. Res.* 5:539–549). To this end, the oligonucleotide may be conjugated to another molecule, e.g., a peptide, hybridization triggered cross-linking agent, transport agent, hybridization-triggered cleavage agent, etc.

II. Isolated Proteins and Antibodies

One aspect of the invention pertains to isolated proteins, and biologically active portions thereof, as well as polypeptide fragments suitable for use as immunogens to raise antibodies directed against a polypeptide of the invention. In one embodiment, the native polypeptide can be isolated from cells or tissue sources by an appropriate purification scheme using standard protein purification techniques. In another embodiment, polypeptides of the invention are produced by recombinant DNA techniques. Alternative to recombinant expression, a polypeptide of the invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a polypeptide of the invention include polypeptides comprising amino acid sequences sufficiently identical to or derived from the amino acid sequence of the protein (e.g., the amino acid sequence shown in any of SEQ ID NO:6, 7, 13, 14, 33, 34, 35, 36, 42, 44, 45, 51, 52, 53, 54, 55, 61, 62, 63, 64, 65 or 71, which include fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have the amino acid sequence of SEQ ID NO:6, 7, 13, 14, 33, 34, 35, 36, 42, 44, 45, 51, 52, 53, 54, 55, 61, 62, 63, 64, 65 or 71. Other useful proteins are substantially identical (e.g., at least about 45%, preferably 55%, 65%, 75%, 85%, 95%, or 99%) to any of SEQ ID NO:6, 7, 13, 14, 33, 34, 35, 36, 42, 44, 45, 51, 52, 53, 54, 55, 61, 62, 63, 64, 65 or 71, and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment, the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264–2268, modified as in Karlin and Altschul (1993) *Proc. Natl. Acad. Sci. USA* 90:5873–5877. Such an algorithm is incorporated into the NBLAST and XBLAST programs of Altschul, et al. (1990) *J. Mol. Biol.* 215:403–410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389–3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. See http://www.ncbi.nlm.nih.gov.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (1994) *Comput. Appl. Biosci.,* 10:3–5; and FASTA described in Pearson and Lipman (1988) *Proc. Natl. Acad. Sci.* 85:2444–8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. For a further description of FASTA parameters, see http://bioweb.pasteur.fr/docs/man/man/fasta.1.html#sect2, the contents of which are incorporated herein by reference.

The percent identity between two sequences can be determined using techniques similar to those described above, with or without allowing gaps. In calculating percent identity, only exact matches are counted.

The invention also provides chimeric or fusion proteins. As used herein, a "chimeric protein" or "fusion protein" comprises all or part (preferably biologically active) of a polypeptide of the invention operably linked to a heterologous polypeptide (i.e., a polypeptide other than the same polypeptide of the invention). Within the fusion protein, the term "operably linked" is intended to indicate that the polypeptide of the invention and the heterologous polypeptide are fused in-frame to each other. The heterologous polypeptide can be fused to the N-terminus or C-terminus of the polypeptide of the invention.

One useful fusion protein is a GST fusion protein in which the polypeptide of the invention is fused to the C-terminus of GST sequences. Such fusion proteins can facilitate the purification of a recombinant polypeptide of the invention.

In another embodiment, the fusion protein contains a heterologous signal sequence at its N-terminus. For example, the native signal sequence of a polypeptide of the invention can be removed and replaced with a signal sequence from another protein. For example, the gp67 secretory sequence of the baculovirus envelope protein can be used as a heterologous signal sequence (*Current Protocols in Molecular Biology,* Ausubel et al., eds., John Wiley & Sons, 1992). Other examples of eukaryotic heterologous signal sequences include the secretory sequences of melittin and human placental alkaline phosphatase (Stratagene; La Jolla, Calif.). in yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a polypeptide of the invention is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a polypeptide of the invention. Inhibition of ligand/receptor interaction may be useful therapeutically, both for treating proliferative and differentiative disorders and for modulating (e.g., promoting or inhibiting) cell survival. Moreover, the immunoglobulin fusion proteins of the invention can be used as immunogens to produce antibodies directed against a polypeptide of the invention in a subject, to purify ligands and in screening assays to identify molecules which inhibit the interaction of receptors with ligands.

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence of a polypeptide of the invention (SEQ ID NO:5, 12, 19, 25, 30, 41, 49 or 59) can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to the signal sequence itself and to the polypeptide in the absence of the signal sequence (i.e., the cleavage products). In one embodiment, a nucleic acid sequence encoding a signal sequence of the invention can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

In another embodiment, the signal sequences of the present invention can be used to identify regulatory sequences, e.g., promoters, enhancers, repressors. Since signal sequences are the most amino-terminal sequences of a peptide, it is expected that the nucleic acids which flank the signal sequence on its amino-terminal side will be regulatory sequences which affect transcription. Thus, a nucleotide sequence which encodes all or a portion of a signal sequence can be used as a probe to identify and isolate signal sequences and their flanking regions, and these flanking regions can be studied to identify regulatory elements therein.

The present invention also pertains to variants of the polypeptides of the invention. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein of the invention which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of the coding sequence of a polypeptide of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) *Proc. Natl. Acad. Sci. USA* 89:7811–7815; Delgrave et al. (1993) *Protein Engineering* 6(3):327–331).

An isolated polypeptide of the invention, or a fragment thereof, can be used as an immunogen to generate antibodies using standard techniques for polyclonal and monoclonal antibody preparation. The full-length polypeptide or protein can be used or, alternatively, the invention provides antigenic peptide fragments for use as immunogens. The antigenic peptide of a protein of the invention comprises at least 8 (preferably 10, 15, 20, or 30) amino acid residues of the amino acid sequence of SEQ ID NO:3, 10, 17, 23, 28, 39, 48 or 58, and encompasses an epitope of the protein such that an antibody raised against the peptide forms a specific immune complex with the protein.

Preferred epitopes encompassed by the antigenic peptide are regions that are located on the surface of the protein, e.g., hydrophilic regions. FIGS. 2, 4, 9, 11, 18, 20, 28 and 31, are hydropathy plots of the proteins of the invention. These plots or similar analyses can be used to identify hydrophilic regions.

An immunogen typically is used to prepare antibodies by immunizing a suitable subject, (e.g., rabbit, goat, mouse or other mammal). An appropriate immunogenic preparation can contain, for example, recombinantly expressed or chemically synthesized polypeptide. The preparation can further include an adjuvant, such as Freund's complete or incomplete adjuvant, or similar immunostimulatory agent.

Accordingly, another aspect of the invention pertains to antibodies directed against a polypeptide of the invention. The term "antibody" as used herein refers to immunoglobulin molecules and immunologically active portions of immunoglobulin molecules, i.e., molecules that contain an antigen binding site which specifically binds an antigen, such as a polypeptide of the invention. A molecule which specifically binds to a given polypeptide of the invention is a molecule which binds the polypeptide, but does not substantially bind other molecules in a sample, e.g., a biological sample, which naturally contains the polypeptide. Examples of immunologically active portions of immunoglobulin molecules include F(ab) and $F(ab')_2$ fragments which can be generated by treating the antibody with an enzyme such as pepsin. The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope.

Polyclonal antibodies can be prepared as described above by immunizing a suitable subject with a polypeptide of the invention as an immunogen. The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985), *Monoclonal Antibodies and Cancer Therapy,* Alan R. Liss, Inc., pp. 77–96) or trioma techniques. The technology for producing hybridomas is well known (see generally *Current Protocols in Immunology* (1994) Coligan et al. (eds.) John Wiley & Sons, Inc., New York, N.Y.). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System,* Catalog No. 27-9400-01; and the Stratagene SurfZAP™ *Phage Display Kit,* Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816397, which are incorporated herein by reference in their entirety.) Humanized antibodies are antibody molecules from non-human species having one or more complementarily determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison (1985) *Science* 229:1202–1207; Oi et al. (1986) *Bio/Techniques* 4:214; U.S. Pat. 5,225,539; Jones et al. (1986) *Nature* 321:552–525; Verhoeyan et al. (1988) *Sci-*

*ence* 239:1534; and Beidler et al. (1988) *J. Immunol.* 141:4053–4060.

Completely human antibodies are particularly desirable for therapeutic treatment of human patients. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, *Int. Rev. Immunol.* 13:65–93). For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al. (1994) *Bio/technology* 12:899–903).

An antibody directed against a polypeptide of the invention (e.g., monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythin; an example of a luminescent material includes luminol; examples of bioluminescent materials include luciferase, luciferin, and aequorin, and examples of suitable radioactive material include $^{125}I$, $^{131}i$, $^{35}S$ or $^{3}H$.

III. Recombinant Expression Vectors and Host Cells

Another aspect of the invention pertains to vectors, preferably expression vectors, containing a nucleic acid encoding a polypeptide of the invention (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g. non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide of the invention in prokaryotic (e.g., *E. coli*) or eukaryotic cells (e.g., insect cells (using baculovirus expression vectors), yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

In another embodiment, the expression vector is a yeast expression vector. Examples of vectors for expression in yeast *S. cerivisae* include pYepSec1 (Baldari et al. (1987) *EMBO J.* 6:229–234), pMFa (Kurjan and Herskowitz, (1982) *Cell* 30:933–943), pJRY88 (Schultz et al. (1987) *Gene* 54:113–123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the mouse hox promoters (Kessel and Gruss (1990) *Science* 249:374–379) and the beta-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (*Reviews—Trends in Genetics,* Vol. 1(1) 1986).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

In another embodiment, the expression characteristics of an endogenous (e.g., TANGO 253, TANGO 257, INTERCEPT 258 and TANGO 281 genes) within a cell, cell line or microorganism may be modified by inserting a DNA regulatory element heterologous to the endogenous gene of interest into the genome of a cell, stable cell line or cloned microorganism such that the inserted regulatory element is operatively linked with the endogenous gene (e.g., TANGO 253, TANGO 257, INTERCEPT 258 and TANGO 281 genes) and controls, modulates or activates. For example, endogenous TANGO 253, TANGO 257, INTERCEPT 258 and TANGO 281 genes which are normally "transcriptionally silent", i.e., a TANGO 253, TANGO 257, INTERCEPT 258 and TANGO 281 genes which is normally not expressed, or are expressed only at very low levels in a cell line or microorganism, may be activated by inserting a regulatory element which is capable of promoting the expression of a normally expressed gene product in that cell line or microorganism. Alternatively, transcriptionally silent, endogenous TANGO 253, TANGO 257, INTERCEPT 258 and TANGO 281 genes may be activated by insertion of a promiscuous regulatory element that works across cell types.

A heterologous regulatory element may be inserted into a stable cell line or cloned microorganism, such that it is operatively linked with endogenous TANGO 253, TANGO 257, INTERCEPT 258 and TANGO 281 genes, using techniques, such as targeted homologous recombination, which are well known to those of skill in the art, and described e.g., in Chappel, U.S. Pat. No. 5,272,071; PCT publication No. WO 91/06667, published May 16, 1991.

A host cell of the invention, such as a prokaryotic or eukaryotic host cell in culture, can be used to produce a polypeptide of the invention. Accordingly, the invention further provides methods for producing a polypeptide of the invention using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

The host cells of the invention can also be used to produce nonhuman transgenic animals. For example, in one embodiment, a host cell of the invention is a fertilized oocyte or an embryonic stem cell into which a sequence encoding a polypeptide of the invention has been introduced. Such host cells can then be used to create non-human transgenic animals in which exogenous sequences encoding a polypeptide of the invention have been introduced into their genome or homologous recombinant animals in which endogenous encoding a polypeptide of the invention sequences have been altered. Such animals are useful for studying the function and/or activity of the polypeptide and for identifying and/or evaluating modulators of polypeptide activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing nucleic acid encoding a polypeptide of the invention (or a homologue thereof) into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, 4,873,191 and in Hogan, *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create an homologous recombinant animal, a vector is prepared which contains at least a portion of a gene encoding a polypeptide of the invention into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation) and cells in which the introduced gene has homologously recombined with the endogenous gene are selected (see, e.g., Li et al. (1992) *Cell* 69:915). The selected cells are then injected into a blastocyst of an animal (e.g., a mouse) to form aggregation chimeras (see, e.g., Bradley in *Teratocarcinomas and Embryonic Stem Cells: A Practical Approach,* Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813 and PCT Publication NOS. WO 97/07668 and WO 97/07669.

IV. Pharmaceutical Compositions

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid of the invention and one or more additional active compounds.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology); c) predictive medicine (e.g., diagnostic assays, prognostic assays, monitoring clinical trials, and pharmacogenomics); and d) methods of treatment (e.g., therapeutic and prophylactic). The isolated nucleic acid molecules of the invention can be used to express proteins (e.g., via a recombinant expression vector in a host cell in gene therapy applications), to detect mRNA (e.g., in a biological sample) or a genetic lesion, and to modulate activity of a polypeptide of the invention. In addition, the polypeptides of the invention can be used to screen drugs or compounds which modulate activity or expression of a polypeptide of the invention as well as to treat disorders characterized by insufficient or excessive production of a protein of the invention or production of a form of a protein of the invention which has decreased or aberrant activity compared to the wild type protein. In addition, the antibodies of the invention can be used to detect and isolate a protein of the and modulate activity of a protein of the invention.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to polypeptide of the invention or have a stimulatory or inhibitory effect on, for example, expression or activity of a polypeptide of the invention.

In one embodiment, the invention provides assays for screening candidate or test compounds which bind to or modulate the activity of the membrane-bound form of a polypeptide of the invention or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermam et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865–1869) or phage (Scott and Smith (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

In one embodiment, an assay is a cell-based assay in which a cell which expresses a membrane-bound form of a polypeptide of the invention, or a biologically active portion thereof, on the cell surface is contacted with a test compound and the ability of the test compound to bind to the polypeptide determined. The cell, for example, can be a yeast cell or a cell of mammalian origin. Determining the ability of the test compound to bind to the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a membrane-bound form of a polypeptide of the invention, or a biologically active portion thereof, on the cell surface with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or a biologically active portion thereof as compared to the known compound.

In another embodiment, an assay is a cell-based assay comprising contacting a cell expressing a membrane-bound form of a polypeptide of the invention, or a biologically active portion thereof, on the cell surface with a test compound and determining the ability of the test compound to modulate (e.g., stimulate or inhibit) the activity of the polypeptide or biologically active portion thereof. Determining the ability of the test compound to modulate the activity of the polypeptide or a biologically active portion thereof can be accomplished, for example, by determining the ability of the polypeptide protein to bind to or interact with a target molecule.

Determining the ability of a polypeptide of the invention to bind to or interact with a target molecule can be accomplished by one of the methods described above for determining direct binding. As used herein, a "target molecule" is a molecule with which a selected polypeptide (e.g., a polypeptide of the invention) binds or interacts with in nature, for example, a molecule on the surface of a cell which expresses the selected protein, a molecule on the surface of a second cell, a molecule in the extracellular milieu, a molecule associated with the internal surface of a cell membrane or a cytoplasmic molecule. A target molecule can be a polypeptide of the invention or some other polypeptide or protein. For example, a target molecule can be a component of a signal transduction pathway which facilitates transduction of an extracellular signal (e.g., a signal generated by binding of a compound to a polypeptide of the invention) through the cell membrane and into the cell or a second intercellular protein which has catalytic activity or a protein which facilitates the association of downstream signaling molecules with a polypeptide of the invention. Determining the ability of a polypeptide of the invention to bind to or interact with a target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a regulatory element that is responsive to a polypeptide of the invention operably linked to a nucleic acid encoding a detectable marker, e.g., luciferase), or detecting a cellular response, for example, cellular differentiation, or cell proliferation.

In yet another embodiment, an assay of the present invention is a cell-free assay comprising contacting a polypeptide of the invention or biologically active portion thereof with a test compound and determining the ability of the test compound to bind to the polypeptide or biologically active portion thereof. Binding of the test compound to the polypeptide can be determined either directly or indirectly as described above. In a preferred embodiment, the assay includes contacting the polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or biologically active portion thereof as compared to the known compound.

In another embodiment, an assay is a cell-free assay comprising contacting a polypeptide of the invention or biologically active portion thereof with a test compound and determining the ability of the test compound to modulate (e.g., stimulate or inhibit) the activity of the polypeptide or biologically active portion thereof. Determining the ability of the test compound to modulate the activity of the polypeptide can be accomplished, for example, by determining the ability of the polypeptide to bind to a target molecule by one of the methods described above for determining direct binding. In an alternative embodiment, determining the ability of the test compound to modulate the activity of the polypeptide can be accomplished by determining the ability of the polypeptide of the invention to further modulate the target molecule. For example, the catalytic/enzymatic activity of the target molecule on an appropriate substrate can be determined as previously described.

In yet another embodiment, the cell-free assay comprises contacting a polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the polypeptide to preferentially bind to or modulate the activity of a target molecule.

The cell-free assays of the present invention are amenable to use of both a soluble form or the membrane-bound form of a polypeptide of the invention. In the case of cell-free assays comprising the membrane-bound form of the polypeptide, it may be desirable to utilize a solubilizing agent such that the membrane-bound form of the polypeptide is maintained in solution. Examples of such solubilizing agents include non-ionic detergents such as n-octylglucoside, n-dodecylglucoside, n-octylmaltoside, octanoyl-N-methylglucamide, decanoyl-N-methylglucamide, Triton X-100, Triton X-114, Thesit, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N, N-dimethyl-3-ammonio-1-propane sulfonate.

In more than one embodiment of the above assay methods of the present invention, it may be desirable to immobilize either the polypeptide of the invention or its target molecule to facilitate separation of complexed from uncomplexed forms of one or both of the proteins, as well as to accommodate automation of the assay. Binding of a test compound to the polypeptide, or interaction of the polypeptide with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase fusion proteins or glutathione-S-transferase fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or A polypeptide of the invention, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of binding or activity of the polypeptide of the invention can be determined using standard techniques.

Other techniques for immobilizing proteins on matrices can also be used in the screening assays of the invention. For example, either the polypeptide of the invention or its target molecule can be immobilized utilizing conjugation of biotin and streptavidin. Biotinylated polypeptide of the invention or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with the polypeptide of the invention or target molecules but which do not interfere with binding of the polypeptide of the invention to its target molecule can be derivatized to the wells of the plate, and unbound target or polypeptide of the invention trapped in the wells by antibody conjugation. Methods for detecting such complexes, in addition to those described above for the GST-immobilized complexes, include immunodetection of complexes using antibodies reactive with the polypeptide of the invention or target molecule, as well as enzyme-linked assays which rely on detecting an enzymatic activity associated with the polypeptide of the invention or target molecule.

In another embodiment, modulators of expression of a polypeptide of the invention are identified in a method in which a cell is contacted with a candidate compound and the expression of the selected mRNA or protein (i.e., the mRNA or protein corresponding to a polypeptide or nucleic acid of the invention) in the cell is determined. The level of expression of the selected mRNA or protein in the presence of the candidate compound is compared to the level of expression of the selected mRNA or protein in the absence of the candidate compound. The candidate compound can then be identified as a modulator of expression of the polypeptide of the invention based on this comparison. For example, when expression of the selected mRNA or protein is greater (statistically significantly greater) in the presence of the candidate compound than in its absence, the candidate compound is identified as a stimulator of the selected mRNA or protein expression. Alternatively, when expression of the selected mRNA or protein is less (statistically significantly less) in the presence of the candidate compound than in its absence, the candidate compound is identified as an inhibitor of the selected mRNA or protein expression. The level of the selected mRNA or protein expression in the cells can be determined by methods described herein.

In yet another aspect of the invention, a polypeptide of the inventions can be used as "bait proteins" in a two-hybrid assay or three hybrid assay (see, e.g., U.S. Pat. No. 5,283, 317; Zervos et al. (1993) *Cell* 72:223–232; Madura et al. (1993) *J. Biol Chem.* 268:12046–12054; Bartel et al. (1993) *Bio/Techniques* 14:920–924; Iwabuchi et al. (1993) *Oncogene* 8:1693–1696; and PCT Publication No. WO 94/10300), to identify other proteins, which bind to or interact with the polypeptide of the invention and modulate activity of the polypeptide of the invention. Such binding proteins are also likely to be involved in the propagation of signals by the polypeptide of the inventions as, for example, upstream or downstream elements of a signaling pathway involving the polypeptide of the invention.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, nucleic acid molecules described herein or fragments thereof, can be used to map the location of the corresponding genes on a chromosome. The mapping of the sequences to chromosomes is an important first step in correlating these sequences with genes associated with disease.

Briefly, genes can be mapped to chromosomes by preparing PCR primers preferably 15–25 bp in length) from the sequence of a gene of the invention. Computer analysis of the sequence of a gene of the invention can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the gene sequences will yield an amplified fragment. For a review of this technique, see D'Eustachio et al. ((1983) *Science* 220:919–924).

PCR mapping of somatic cell hybrids is a rapid procedure for assigning a particular sequence to a particular chromosome. Three or more sequences can be assigned per day using a single thermal cycler. Using the nucleic acid sequences of the invention to design oligonucleotide primers, sublocalization can be achieved with panels of fragments from specific chromosomes. Other mapping strategies which can similarly be used to map a gene to its chromosome include in situ hybridization (described in Fan et al. (1990) *Proc. Natl. Acad. Sci. USA* 87:6223–27), pre-screening with labeled flow-sorted chromosomes (CITE), and pre-selection by hybridization to chromosome specific cDNA libraries. Fluorescence in situ hybridization (FISH) of a DNA sequence to a metaphase chromosomal spread can further be used to provide a precise chromosomal location in one step. For a review of this technique, see Verma et al., (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783–787.

Moreover, differences in the DNA sequences between individuals affected and unaffected with a disease associated with a gene of the invention can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The nucleic acid sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the nucleic acid sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The nucleic acid sequences of the invention uniquely represent portions of the human genome. Allelic variation occurs to some degree in the coding regions of these sequences, and to a greater degree in the noncoding regions. It is estimated that allelic variation between individual humans occurs with a frequency at about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, 8, 15, 21, 26, 37, 46 or 56, can comfortably provide positive individual identification with a panel of perhaps 10 to 1,000 primers which each yield a noncoding amplified sequence of 100 bases. If predicted coding sequences, such as those in SEQ ID NO:2, 9, 16, 22, 27, 38, 47 or 57 are used, a more appropriate number of primers for positive individual identification would be 500–2,000.

If a panel of reagents from the nucleic acid sequences described herein is used to generate a unique identification database for an individual, those same reagents can later be used to identify tissue from that individual. Using the unique identification database, positive identification of the individual, living or dead, can be made from extremely small tissue samples.

3. Use of Partial Gene Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions are particularly appropriate for this use as greater numbers of polymorphisms occur in the noncoding regions, making it easier to differentiate individuals using this technique. Examples of polynucleotide reagents include the nucleic acid sequences of the invention or portions thereof, e.g. fragments derived from noncoding regions having a length of at least 20 or 30 bases.

The nucleic acid sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such probes can be used to identify tissue by species and/or by organ type.

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining expression of a polypeptide or nucleic acid of the invention and/or activity of a polypeptide of the invention, in the context of a biological sample (e.g., blood, serum, cells, tissue) to thereby determine whether an individual is afflicted with a disease or disorder, or is at risk of developing a disorder, associated with aberrant expression or activity of a polypeptide of the invention. The invention also provides for prognostic (or predictive) assays for determining whether an individual is at risk of developing a disorder associated with aberrant expression or activity of a polypeptide of the invention. For example, mutations in a gene of the invention can be assayed in a biological sample. Such assays can be used for prognostic or predictive purpose to thereby prophylactically treat an individual prior to the onset of a disorder characterized by or associated with aberrant expression or activity of a polypeptide of the invention.

Another aspect of the invention provides methods for expression of a nucleic acid or polypeptide of the invention or activity of a polypeptide of the invention in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent).

Yet another aspect of the invention pertains to monitoring the influence of agents (e.g., drugs or other compounds) on the expression or activity of a polypeptide of the invention in clinical trials. These and other agents are described in further detail in the following sections.

1. Diagnostic Assays

An exemplary method for detecting the presence or absence of a polypeptide or nucleic acid of the invention in a biological sample involves obtaining a biological sample from a test subject and contacting the biological sample with a compound or an agent capable of detecting a polypeptide or nucleic acid (e.g., mRNA, genomic DNA) of the invention such that the presence of a polypeptide or nucleic acid of the invention is detected in the biological sample. A preferred agent for detecting mRNA or genomic DNA encoding a polypeptide of the invention is a labeled nucleic acid probe capable of hybridizing to mRNA or genomic DNA encoding a polypeptide of the invention. The nucleic acid probe can be, for example, a full-length cDNA, such as the nucleic acid of SEQ ID NO:1, 2, 8, 9, 15, 16, 21, 22, 26, 27, 37, 38, 46, 47, 56 or 57, or a portion thereof, such as an oligonucleotide of at least 15, 30, 50, 100, 250 or 500 nucleotides in length and sufficient to specifically hybridize under stringent conditions to a mRNA or genomic DNA encoding a polypeptide of the invention. Other suitable probes for use in the diagnostic assays of the invention are described herein.

A preferred agent for detecting a polypeptide of the invention is an antibody capable of binding to a polypeptide of the invention, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect mRNA, protein, or genomic DNA in a biological sample in vitro as well as in vivo. For example, in vitro techniques for detection of mRNA include Northern hybridizations and in situ hybridizations. In vitro techniques for detection of a polypeptide of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide of the invention include introducing into a subject a labeled antibody directed against the polypeptide. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting a polypeptide of the invention or mRNA or genomic DNA encoding a polypeptide of the invention, such that the presence of the polypeptide or mRNA or genomic DNA encoding the polypeptide is detected in the biological sample, and comparing the presence of the polypeptide or mRNA or genomic DNA encoding the polypeptide in the control sample with the presence of the polypeptide or mRNA or genomic DNA encoding the polypeptide in the test sample.

The invention also encompasses kits for detecting the presence of a polypeptide or nucleic acid of the invention in a biological sample (a test sample). Such kits can be used to determine if a subject is suffering from or is at increased risk of developing a disorder associated with aberrant expression of a polypeptide of the invention, as discussed, for example, in sections above relating to uses of the sequences of the invention.

For example, kits can be used to determine if a subject is suffering from or is at increased risk of disorders such as coronary disorders (e.g., heart diseases and disorders such as atherosclerosis., coronary artery disease and plaque formation), and adipocyte-related disorders (e.g., obesity), which are associated with aberrant TANGO 253 expression. In another example, kits can be used to determine if a subject is suffering from or is at increased risk of disorders such as coronary disorders (e.g., heart diseases and disorders such as atherosclerosis, coronary artery disease and plague formation), olfactory disorders, neurological disorders (e.g., neurodegenerative disorders, neuromuscular disorders, cognitive disorders, personality disorders, and motor disorder) and pulmonary disorders, (e.g., cystic fibrosis), which are associated with aberrant TANGO 257 expression. In another example, kits can be used to determine if a subject is suffering from or is at increased risk of disorders such as Type I immunologic disorders, (e.g., anaphylaxis and rhinitis), which are associated with aberrant INTERCEPT 258 expression. In another example, kits can be used to determine if a subject is suffering from or is at increased risk of disorders such as immunological disorders, (e.g. thrombocytopenia and platelet disorders), developmental disorders, coronary disorders, e.g., ischemic heart disease or atherosclerosis, neurological disorders, (e.g., head trauma and brain cancer), pulmonary disorders, (e.g., lung cancer, cystic fibrosis and rheumatoid lung disease), kidney disorders, (e.g., glomerulonephritis and end stage renal disease), autoimmune disorders, (e.g., Crohn's disease) and embryonic disorders, which are associated with aberrant TANGO 281 expression. The kit, for example, can comprise a labeled compound or agent capable of detecting the polypeptide or mRNA encoding the polypeptide in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for observing that the tested subject is suffering from or is at risk of developing a disorder associated with aberrant expression of the polypeptide if the amount of the polypeptide or mRNA encoding the polypeptide is above or below a normal level.

For antibody-based kits, the kit can comprise, for example: (1) a first antibody (e.g., attached to a solid support) which binds to a polypeptide of the invention; and, optionally, (2) a second, different antibody which binds to either the polypeptide or the first antibody and is conjugated to a detectable agent.

For oligonucleotide-based kits, the kit can comprise, for example: (1) an oligonucleotide, e.g., a detectably labeled oligonucleotide, which hybridizes to a nucleic acid sequence encoding a polypeptide of the invention or (2) a pair of primers useful for amplifying a nucleic acid molecule encoding a polypeptide of the invention. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the polypeptide.

2. Prognostic Assays

The methods described herein can furthermore be utilized as diagnostic or prognostic assays to identify subjects having or at risk of developing a disease or disorder associated with aberrant expression or activity of a polypeptide of the invention. For example, the assays described herein, such as the preceding diagnostic assays or the following assays, can be utilized to identify a subject having or at risk of developing a disorder associated with aberrant expression or activity of a polypeptide of the invention, e.g., coronary disorders, pulmonary disorders, kidney disorders or embryonic disorders. Alternatively, the prognostic assays can be utilized to identify a subject having or at risk for developing such a disease or disorder. Thus, the present invention provides a method in which a test sample is obtained from a subject and a polypeptide or nucleic acid (e.g., mRNA, genomic DNA) of the invention is detected, wherein the presence of the polypeptide or nucleic acid is diagnostic for a subject having or at risk of developing a disease or disorder associated with aberrant expression or activity of the polypeptide. As used herein, a "test sample" refers to a biological sample obtained from a subject of interest. For example, a test sample can be a biological fluid (e.g., serum), cell sample, or tissue.

The prognostic assays described herein, for example, can be used to identify a subject having or at risk of developing disorders such as disorders discussed, for example, in Sections above relating to uses of the sequences of the invention.

For example, such disorders can include coronary disorders (e.g., heart diseases and disorders such as atherosclerosis, coronary artery disease and plague formation) and adipocyte disorders (e.g., obesity), which are associated with aberrant TANGO 253 expression. In another example, prognostic assays described herein, can be used to identify a subject having or at risk of developing disorders such as coronary disorders (e.g., heart diseases and disorders such as atherosclerosis, coronary artery disease and plague formation), olfactory disorders, neurological disorders (e.g., neurodegenerate disorders, neuromuscular disorders, cognitive disorders, personality disorders, and motor disorders), and pulmonary disorders, (e.g., cystic fibrosis), which are associated with aberrant TANGO 257 expression. In another example, prognostic assays described herein, can be used to identify a subject having or at risk of developing disorders such as Type I immunologic disorders, (e.g., anaphylaxis and rhinitis), which are associated with aberrant INTERCEPT 258 expression. In another example, prognostic assays described herein, for example, can be used to identify a subject having or at risk of developing disorders such as immunological disorders, (e.g. thrombocytopenia and platelet disorders), developmental disorders, coronary disorders, (e.g., ischemic heart disease and atherosclerosis), neurological disorders, (e.g., head trauma and brain cancer), pulmonary disorders, (e.g., lung cancer, cystic fibrosis and rheumatoid lung disease), kidney disorders, (e.g., glomerulonephritis and end stage renal disease), autoimmune disorders, (e.g., Crohn's disease) and embryonic disorders, which are associated with aberrant TANGO 281 expression.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant expression or activity of a polypeptide of the invention. For example, such methods can be used to determine whether a subject can be effectively treated with a specific agent or class of agents (e.g., agents of a type which decrease activity of the polypeptide). Thus, the present invention provides methods for determining whether a subject can be effectively treated with an agent for a disorder associated with aberrant expression or activity of a polypeptide of the invention in which a test sample is obtained and the polypeptide or nucleic acid encoding the polypeptide is detected (e.g., wherein the presence of the polypeptide or nucleic acid is diagnostic for a subject that can be administered the agent to treat a disorder associated with aberrant expression or activity of the polypeptide).

The methods of the invention can also be used to detect genetic lesions or mutations in a gene of the invention, thereby determining if a subject with the lesioned gene is at risk for a disorder characterized aberrant expression or activity of a polypeptide of the invention. In preferred embodiments, the methods include detecting, in a sample of cells from the subject, the presence or absence of a genetic lesion or mutation characterized by at least one of an alteration affecting the integrity of a gene encoding the polypeptide of the invention, or the mis-expression of the gene encoding the polypeptide of the invention. For example, such genetic lesions or mutations can be detected by ascertaining the existence of at least one of: 1) a deletion of one or more nucleotides from the gene; 2) an addition of one or more nucleotides to the gene; 3) a substitution of one or more nucleotides of the gene; 4) a chromosomal rearrangement of the gene; 5) an alteration in the level of a messenger RNA transcript of the gene; 6) an aberrant modification of the gene, such as of the methylation pattern of the genomic DNA; 7) the presence of a non-wild type splicing pattern of a messenger RNA transcript of the gene; 8) a non-wild type level of a the protein encoded by the gene; 9) an allelic loss of the gene; and 10) an inappropriate post-translational modification of the protein encoded by the gene. As described herein, there are a large number of assay techniques known in the art which can be used for detecting lesions in a gene.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in a gene (see, e.g., Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to the selected gene under conditions such that hybridization and amplification of the gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874–1878), transcriptional amplification system (Kwoh, et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a selected gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). For example, genetic mutations can be identified in two-dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the selected gene and detect mutations by comparing the sequence of the sample nucleic acids with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in a selected gene include methods in which protection from cleavage agents is used to detect mismatched bases in RNA/RNA or RNA/DNA heteroduplexes (Myers et al. (1985) *Science* 230:1242). In general, the technique of mismatch cleavage entails providing heteroduplexes formed by hybridizing (labeled) RNA or DNA containing the wild-type sequence with potentially mutant RNA or DNA obtained from a tissue sample. The double-stranded duplexes are treated with an agent which cleaves single-stranded regions of the duplex such as which will exist due to basepair mismatches between the control and sample strands. RNA/DNA duplexes can be treated with RNase to digest mismatched regions, and DNA/DNA hybrids can be treated with S1 nuclease to digest mismatched regions.

In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al. (1988) *Proc. Natl. Acad. Sci. USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a selected sequence, e.g., a wild-type sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in genes. For example, single strand conformation polymorphism (SSCP) may be used to detect differences in electrophoretic mobility between mutant and wild type nucleic acids (Orita et al. (1989) *Proc. Natl. Acad. Sci. USA* 86:2766; see also Cotton (1993) *Mutat. Res.* 285:125–144; Hayashi (1992) *Genet. Anal. Tech. Appl.* 9:73–79). Single-stranded DNA fragments of sample and control nucleic acids will be denatured and allowed to renature. The secondary structure of single-stranded nucleic acids varies according to sequence, and the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a 'GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a gene encoding a polypeptide of the invention. Furthermore, any cell type or tissue, e.g., chondrocytes, in which the polypeptide of the invention is expressed may be utilized in the prognostic assays described herein.

3. Pharmacogenomics

Agents, or modulators which have a stimulatory or inhibitory effect on activity or expression of a polypeptide of the invention as identified by a screening assay described herein can be administered to individuals to treat (prophylactically or therapeutically) disorders associated with aberrant activity of the polypeptide. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of a polypeptide of the invention, expression of a nucleic acid of the invention, or mutation content of a gene of the invention in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of a polypeptide of the invention, expression of a nucleic acid encoding the polypeptide, or mutation content of a gene encoding the polypeptide in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of activity or expression of the polypeptide, such as a modulator identified by one of the exemplary screening assays described herein.

4. Monitoring of Effects During Clinical Trials

Monitoring the influence of agents (e.g., drugs, compounds) on the expression or activity of a polypeptide of the invention (e.g., the ability to modulate aberrant cell proliferation chemotaxis, and/or differentiation) can be applied not only in basic drug screening, but also in clinical trials. For example, the effectiveness of an agent, as determined by a screening assay as described herein, to increase gene expression, protein levels or protein activity, can be monitored in clinical trials of subjects exhibiting decreased gene expression, protein levels, or protein activity. Alternatively, the effectiveness of an agent, as determined by a screening assay, to decrease gene expression, protein levels or protein activity, can be monitored in clinical trials of subjects exhibiting increased gene expression, protein levels, or protein activity. In such clinical trials, expression or activity of a polypeptide of the invention and preferably, that of other polypeptide that have been implicated in for example, a cellular proliferation disorder, can be used as a marker of the immune responsiveness of a particular cell.

For example, and not by way of limitation, genes, including those of the invention, that are modulated in cells by treatment with an agent (e.g., compound, drug or small molecule) which modulates activity or expression of a polypeptide of the invention (e.g., as identified in a screening assay described herein) can be identified. Thus, to study the effect of agents on cellular proliferation disorders, for example, in a clinical trial, cells can be isolated and RNA prepared and analyzed for the levels of expression of a gene of the invention and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of a gene of the invention or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of the polypeptide or nucleic acid of the invention in the preadministration sample; (iii) obtaining one or more post-administration samples from the subject; (iv) detecting the level the of the polypeptide or nucleic acid of the invention in the post-administration samples; (v) comparing the level of the polypeptide or nucleic acid of the invention in the pre-administration sample with the level of the polypeptide or nucleic acid of the invention in the post-administration sample or samples; and (vi) altering the administration of the agent to the subject accordingly. For example, increased administration of the agent may be desirable to increase the expression or activity of the polypeptide to higher levels than detected, i.e., to increase the effectiveness of the agent. Alternatively, decreased administration of the agent may be desirable to decrease expression or activity of the polypeptide to lower levels than detected, i.e., to decrease the effectiveness of the agent.

C. Methods of Treatment

The present invention provides for both prophylactic and therapeutic methods of treating a subject at risk of (or susceptible to) a disorder or having a disorder associated with aberrant expression or activity of a polypeptide of the invention, as discussed, for example, in sections above relating to uses of the sequences of the invention.

For example, disorders characterized by aberrant expression or activity of the polypeptides of the invention include immunologic disorders, coronary disorders, pulmonary disorders, neurological disorders, kidney disorders, and autoimmune disorders. The nucleic acids, polypeptides, and modulators thereof of the invention can be used to treat immunologic diseases and disorders, including but not limited to, allergic disorders (e.g., anaphylaxis and allergic asthma) autoimmune and inflammatory disorders (e.g., atopic dermatitis). Polypeptides of the invention can be used to treat diseases associated with bacterial infection (e.g., tuberculosis, e.g., pulmonary tuberculosis), inflammatory arthropathy, and bone and cartilage degenerative diseases and disorders (e.g., arthritis, e.g., rheumatoid arthritis). Polypeptides of the invention can be used to treat pulmonary disorders such as lung cancer, cystic fibrosis and rheumatoid lung diseases. Polypeptides of the invention can be used to treat coronary disorders, such as ischemic heart disease, atherosclerosis and plague formation. Polypeptides of the invention can also be used to treat neurological disorders such as neurodegenerate disorders, neuromuscular disorders and cognitive disorders. Polypeptides of the invention can also be used to treat kidney disorders such as glomerulonephritis and end stage renal disease. Further, polypeptides of the invention can be used to treat autoimmune disorders such as Crohns disease, and other disorders described herein.

1. Prophylactic Methods

In one aspect, the invention provides a method for preventing in a subject, a disease or condition associated with an aberrant expression or activity of a polypeptide of the invention, by administering to the subject an agent which modulates expression or at least one activity of the polypeptide. Subjects at risk for a disease which is caused or contributed to by aberrant expression or activity of a polypeptide of the invention can be identified by, for example, any or a combination of diagnostic or prognostic assays as described herein. Administration of a prophylactic agent can occur prior to the manifestation of symptoms characteristic of the aberrancy, such that a disease or disorder is prevented or, alternatively, delayed in its progression. Depending on the type of aberrancy, for example, an agonist or antagonist agent can be used for treating the subject. For example, an antagonist of a TANGO 253, tango 257, intercept 258 OR tango 281 proteins may be used to treat an arthropathic disorder, e.g., rheumatoid arthritis. The appropriate agent can be determined based on screening assays described herein.

2. Therapeutic Methods

Another aspect of the invention pertains to methods of modulating expression or activity of a polypeptide of the invention for therapeutic purposes. The modulatory method of the invention involves contacting a cell with an agent that modulates one or more of the activities of the polypeptide. An agent that modulates activity can be an agent as described herein, such as a nucleic acid or a protein, a naturally-occurring cognate ligand of the polypeptide, a peptide, a peptidomimetic, or other small molecule. In one embodiment, the agent stimulates one or more of the biological activities of the polypeptide. Examples of such stimulatory agents include the active polypeptide of the invention and a nucleic acid molecule encoding the polypeptide of the invention that has been introduced into the cell. In another embodiment, the agent inhibits one or more of the biological activities of the polypeptide of the invention. Examples of such inhibitory agents include antisense nucleic acid molecules and antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a polypeptide of the invention. In one embodiment, the method involves administering an agent (e.g., an agent identified by a screening assay described herein), or combination of agents that modulates (e.g., upregulates or downregulates) expression or activity. In another embodiment, the method involves administering a polypeptide of the invention or a nucleic acid molecule of the invention as therapy to compensate for reduced or aberrant expression or activity of the polypeptide.

Stimulation of activity is desirable in situations in which activity or expression is abnormally low or downregulated and/or in which increased activity is likely to have a beneficial effect. Conversely, inhibition of activity is desirable in situations in which activity or expression is abnormally high or upregulated and/or in which decreased activity is likely to have a beneficial effect.

This invention is further illustrated by the following examples which should not be construed as limiting. The contents of all references, patents and published patent applications cited throughout this application are hereby incorporated by reference.

Deposit of Clones

Clones containing cDNA molecules encoding human TANGO 253, (clone EpT253) human TANGO 257 (EpT257), human INTERCEPT 258 (clone EpT258) and human TANGO 281 (clone EpT 281) were deposited with the American Type Culture Collection, 10801 University Boulevard, Manassas, Va., 20110-2209, on Apr. 21, 1999 as Accession Number 207222, as part of a composite deposit representing a mixture of strains, each carrying one recombinant plasmid harboring a particular cDNA clone.

For this composite deposit, to distinguish the strains and isolate a strain harboring a particular cDNA clone, an aliquot of the mixture can be streaked out to single colonies on nutrient medium (e.g., LB plates) supplemented with 100 g/ml ampicillin, single colonies grown, and then plasmid DNA extracted using a standard minipreparation procedure. Next, a sample of the DNA minipreparation can be digested with a combination of the restriction enzymes SalI, NotI, XbaI and EcorV and the resultant products resolved on a 0.8% agarose gel using standard DNA electrophoresis conditions. The digest liberates fragments as follows:

Human TANGO 253 (clone EpT253): 1.3 kb

Human TANGO 257 (clone EpT257): 1.8 kb

Human INTERCEPT 258 (clone EpT258): 1.0 kb and 0.85 kb (human INTERCEPT 258 has a EcorV cut site at about bp 1004).

Human TANGO 281 (clone EpT281): 0.9 kb and 0.9kb (human TANGO 281 Has an XbaI cut site at about bp 900).

The identity of the strains can be inferred from the fragments liberated.

Clones containing cDNA molecules encoding mouse INTERCEPT 258 were deposited with the American Type Culture Collection (Manassas, Va.) on Apr. 21, 1999 as Accession Number 207221, as part of a composite deposit representing a mixture of five strains, each carrying one recombinant plasmid harboring a particular cDNA clone.

To distinguish the strains and isolate a strain harboring a particular cDNA clone, an aliquot of the mixture can be streaked out to single colonies on nutrient medium (e.g., LB plates) supplemented with 100 μg/ml ampicillin, single colonies grown, and then plasmid DNA extracted using a standard minipreparation procedure. Next, a sample of the DNA minipreparation can be digested with a combination of the restriction enzymes SalI, and NotI, and the resultant products resolved on a 0.8% agarose gel using standard DNA electrophoresis conditions. The digest liberates fragments as follows:

Mouse INTERCEPT 258 (clone EpT258): 1.8 kb

The identity of the strains can be inferred from the fragments liberated.

A clone containing a cDNA molecule encoding mouse TANGO 253 (Clone EpTm 253) was deposited with American Type Culture Collection, 10801 University Boulevard, Manassas, Va. 20110-2209, on Apr. 21, 1999 as Accession Number 207215.

A clone containing a cDNA molecule encoding mouse TANGO 257 (Clone EpTm 257) was deposited with American Type Culture Collection, 10801 University Boulevard, Manassas, Va. 20110-2209, on Apr. 21, 1999 as Accession Number 207217.

A clone containing a cDNA molecule encoding mouse TANGO 281 (Clone EpTm 281) was deposited with American Type Culture Collection, 10801 University Boulevard, Manassas, Va. 20110-2209, on Jun. 15, 1999 as patent deposit Number PTA-224.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule comprising:
   (a) the nucleotide sequence of SEQ ID NO:46;
   (b) the nucleotide sequence of SEQ ID NO:47;
   (c) the nucleotide sequence of SEQ ID NO:56;
   (d) the nucleotide sequence of SEQ ID NO:57;
   (e) the nucleotide sequence of the cDNA insert of the plasmid deposited with the ATCC as Accession Number 207222; or
   (f) the nucleotide sequence of the cDNA insert of the plasmid deposited with the ATCC as patent deposit Number PTA-224.

2. An isolated nucleic acid molecule comprising a nucleotide sequence which encodes a polypeptide comprising the amino acid sequence of SEQ ID NO:48.

3. An isolated nucleic acid molecule comprising a nucleotide sequence which encodes a polypeptide comprising the amino acid sequence of SEQ ID NO:58.

4. An isolated nucleic acid molecule which is at least 800 nucleotides in length and hybridizes over its full length to the complement of the nucleic acid molecule of SEQ ID NO:46 under conditions of incubation at 45° C. in 6.0×SSC followed by washing in 0.2×SSC, 0.1% SDS at 50° C., wherein said isolated nucleic acid molecule is expressed in megakaryocytes, and wherein expression of said isolated nucleic acid molecule is a marker for gata-1 activity.

5. An isolated nucleic acid molecule which is at least 200 nucleotides in length and hybridizes over its full length to the complement of the nucleic acid molecule of SEQ ID NO:47 under conditions of incubation at 45° C. in 6.0×SSC followed by washing in 0.2×SSC, 0.1% SDS at 50° C., wherein said isolated nucleic acid molecule is expressed in megakaryocytes, and wherein expression of said isolated nucleic acid molecule is a marker for gata-1 activity.

6. An isolated nucleic acid molecule which is at least 800 nucleotides in length and hybridizes over its full length to the complement of the nucleic acid molecule of SEQ ID NO:46 under conditions of incubation at 45° C. in 6.0×SSC followed by washing in 0.2×SSC, 0.1% SDS at 65° C., wherein said isolated nucleic acid molecule is expressed in megakaryocytes, and wherein expression of said isolated nucleic acid molecule is a marker for gata-1 activity.

7. An isolated nucleic acid molecule which is at least 200 nucleotides in length and hybridizes over its full length to the complement of the nucleic acid molecule of SEQ ID NO:47 under conditions of incubation at 45° C. in 6.0×SSC followed by washing in 0.2×SSC, 0.1% SDS at 65° C., wherein said isolated nucleic acid molecule is expressed in megakaryocytes, and wherein expression of said isolated nucleic acid molecule is a marker for gata-1 activity.

8. An isolated nucleic acid molecule which is at least 600 nucleotides in length and hybridizes over its full length to the complement of the nucleic acid molecule of SEQ ID NO:56 under conditions of incubation at 45° C. in 6.0×SSC followed by washing in 0.2×SSC, 0.1% SDS at 50° C., wherein said isolated nucleic acid molecule is expressed in megakaryocytes, and wherein expression of said isolated nucleic acid molecule is a marker for gata-1 activity.

9. An isolated nucleic acid molecule which is at least 300 nucleotides in length and hybridizes over its full length to the complement of the nucleic acid molecule of SEQ ID NO:57 under conditions of incubation at 45° C. in 6.0×SSC followed by washing in 0.2×SSC, 0.1% SDS at 50° C., wherein said isolated nucleic acid molecule is expressed in megakaryocytes, and wherein expression of said isolated nucleic acid molecule is a marker for gata-1 activity.

10. An isolated nucleic acid molecule which is at least 600 nucleotides in length and hybridizes over its full length to the complement of the nucleic acid molecule of SEQ ID NO:56 under conditions of incubation at 45° C. in 6.0×SSC followed by washing in 0.2×SSC, 0.1% SDS at 65° C., wherein said isolated nucleic acid molecule is expressed in megakaryocytes, and wherein expression of said isolated nucleic acid molecule is a marker for gata-1 activity.

11. An isolated nucleic acid molecule which is at least 300 nucleotides in length and hybridizes over its full length to the complement of the nucleic acid molecule of SEQ ID NO:57 under conditions of incubation at 45° C. in 6.0×SSC followed by washing in 0.2×SSC, 0.1% SDS at 65° C., wherein said isolated nucleic acid molecule is expressed in megakaryocytes, and wherein expression of said isolated nucleic acid molecule is a marker for gata-1 activity.

12. An isolated nucleic acid molecule comprising:

(a) at least 800 contiguous nucleotides of SEQ ID NO:46 or a complement thereof;

(b) at least 200 contiguous nucleotides of SEQ ID NO:47 or a complement thereof;

(c) at least 600 contiguous nucleotides of SEQ ID NO:56 or a complement thereof; or (d) at least 300 contiguous nucleotides of SEQ ID NO:57 or a complement thereof, wherein said nucleic acid molecule is expressed in megakaryocytes, and wherein expression of said nucleic acid molecule is a marker for gata-1 activity.

13. A nucleic acid molecule comprising a nucleotide sequence which encodes a fusion polypeptide comprising, first, a polypeptide consisting of at least one of the following polypeptide domains encoded by the nucleic acid of SEQ ID NO:48: a signal sequence, extracellular domain, PSBH domain, transmembrane domain or cytoplasmic domain, and second, a heterologous polypeptide.

14. The nucleic acid molecule of claim 13, wherein the fusion polypeptide comprises the extracellular domain of the polypeptide of SEQ ID NO:48 and a heterologous polypeptide.

15. A nucleic acid molecule comprising a nucleotide sequence which encodes a fusion polypeptide comprising, first, a polypeptide consisting of at least one of the following polypeptide domains encoded by the nucleic acid of SEQ ID NO:58: a signal sequence, extracellular domain, PSBH domain, transmembrane domain or cytoplasmic domain, and second, a heterologous polypeptide.

16. The nucleic acid molecule of claim 15, wherein the fusion polypeptide comprises the extracellular domain of the polypeptide of SEQ ID NO:58 and a heterologous polypeptide.

17. The nucleic acid molecule of claim 13, 15, 1, 2, 3, 6, 7, 10, 11, or 12, further comprising vector nucleic acid sequences.

18. A host cell comprising the nucleic acid molecule of claim 17.

19. The host cell of claim 18 which is a mammalian host cell.

20. The nucleic acid molecule of claim 13, 15, 1, 2, 3, 6, 7, 10, 11, or 12 further comprising nucleic acid sequences encoding a heterologous polypeptide.

21. A host cell engineered to contain the nucleic acid molecule of claim 13, 15, 1, 2, 3, 6, 7, 10, 11, or 12.

22. The host cell of claim 21 which is a mammalian host cell.

23. A non-human mammalian host cell engineered to contain the nucleic acid molecule of claim 13, 15, 1, 2, 3, 6, 7, 10, 11, or 12.

24. A host cell engineered to express the nucleic acid molecule of claim 13, 15, 1, 2, 3, 6, 7, 10, 11, or 12.

25. The host cell of claim 24 which is a mammalian host cell.

26. A non-human mammalian host cell engineered to express the nucleic acid molecule of claim 13, 15, 1, 2, 3, 6, 7, 10, 11, or 12.

* * * * *

SEQUENCE LISTING

```
<160> NUMBER OF SEQ ID NOS: 75

<210> SEQ ID NO 1
<211> LENGTH: 1338
<212> TYPE: DNA
<213> ORGANISM: Homo sapiens
```

-continued

<400> SEQUENCE: 1
gtcgacccac gcgtccggga ctggggtgac ggcagggcag ggggcgcctg g ccggggaga 60 agcgcggggg ctggagcacc accaactgga gggtccggag tagcgagcgc c ccgaaggag 120 gccatcgggg agccgggagg ggggactgcg agaggacccc ggcgtccggg c tcccggtgc 180 cagcgctatg aggccactcc tcgtcctgct gctcctgggc ctggcggccg g ctcgccccc 240 actggacgac aacaagatcc ccagcctctg cccggggcac cccggccttc c aggcacgcc 300 gggccaccat ggcagccagg gcttgccggg ccgcgatggc cgcgacggcc g cgacggcgc 360 gcccggggct ccgggagaga aaggcgaggg cgggaggcgg gactgccggg a cctcgaggg 420 gaccccgggc cgcgaggaga ggcgggaccc gcggggccca ccgggcctgc c ggggagtgc 480 tcggtgcctc cgcgatccgc cttcagcgcc aagcgctccg agagccgggt g cctccgccg 540 tctgacgcac ccttgccctt cgaccgcgtg ctggtgaacg agcagggaca t tacgacgcc 600 gtcaccggca agttcacctg ccaggtgcct ggggtctact acttcgccgt c catgccacc 660 gtctaccggg ccagcctgca gtttgatctg gtgaagaatg gcgaatccat t gcctctttc 720 ttccagtttt tcggggggtg gcccaagcca gcctcgctct cgggggggc c atggtgagg 780 ctggagcctg aggaccaagt gtgggtgcag gtgggtgtgg gtgactacat t ggcatctat 840 gccagcatca agacagacag caccttctcc ggatttctgg tgtactccga c tggcacagc 900 tccccagtct ttgcttagtg cccactgcaa agtgagctca tgctctcact c ctagaagga 960 gggtgtgagg ctgacaacct ggtcatccag gagggctggc ccccctggaa t attgtgaat 1020 gactagggag gtggggtaga gcactctccg tcctgctgct ggcaaggaat g ggaacagtg 1080 gctgtctgcg atcaggtctg gcagcatggg gcagtggctg gatttctgcc c aagaccaga 1140 ggagtgtgct gtgctggcaa gtgtaagtcc cccagttgct ctggtccagg a gcccacggt 1200 ggggtgctct cttcctggtc ctctgcttct ctggatcctc cccacccct c ctgctcctg 1260 gggccggccc ttttctcaga gatcactcaa taaacctaag aaccctccaa a aaaaaaaaa 1320 aaaaaaaagg gcggccgc 1338

<210> SEQ ID NO 2
<211> LENGTH: 728
<212> TYPE: DNA
<213> ORGANISM: Homo sapiens

<400> SEQUENCE: 2
atgaggccac tcctcgtcct gctgctcctg ggcctggcgg ccggctcgcc c ccactggac 60 gacaacaaga tccccagcct ctgcccgggg caccccggcc ttccaggcac g ccgggccac 120 catggcagcc agggcttgcc gggccgcgat ggccgcgacg gccgcgacgg c gcgcccggg 180 gctccgggag agaaaggcga gggcgggagg cgggactgcc gggacctcga g gggaccccg 240 ggccgcgagg agaggcggga cccgcggggc ccaccgggcc tgccggggag t gctcggtgc 300 ctccgcgatc cgccttcagc gccaagcgct ccgagagccg ggtgcctccg c cgtctgacg 360 cacccttgcc cttcgaccgc gtgctggtga acgagcaggg acattacgac g ccgtcaccg 420 gcaagttcac ctgccaggtg cctggggtct actacttcgc cgtccatgcc a ccgtctacc 480 gggccagcct gcagtttgat ctggtgaaga atggcgaatc cattgcctct t tcttccagt 540 ttttcggggg gtggcccaag ccagcctcgc tctcgggggg ggccatggtg a ggctggagc 600 ctgaggacca agtgtgggtg caggtgggtg tgggtgacta cattggcatc t atgccagca 660 tcaagacaga cagcaccttc tccggatttc tggtgtactc cgactggcac a gctccccag 720

-continued tctttgct 728

<210> SEQ ID NO 3
<211> LENGTH: 243
<212> TYPE: PRT
<213> ORGANISM: Homo sapiens

<400> SEQUENCE: 3

```
Met Arg Pro Leu Leu Val Leu Leu Leu Leu G ly Leu Ala Ala Gly Ser
  1               5                  10                  15

Pro Pro Leu Asp Asp Asn Lys Ile Pro Ser L eu Cys Pro Gly His Pro
             20                  25                  30

Gly Leu Pro Gly Thr Pro Gly His His Gly S er Gln Gly Leu Pro Gly
         35                  40                  45

Arg Asp Gly Arg Asp Gly Arg Asp Gly Ala P ro Gly Ala Pro Gly Glu
     50                  55                  60

Lys Gly Glu Gly Gly Arg Pro Gly Leu Pro G ly Pro Arg Gly Asp Pro
 65                  70                  75                  80

Gly Pro Arg Gly Glu Ala Gly Pro Ala Gly P ro Thr Gly Pro Ala Gly
                 85                  90                  95

Glu Cys Ser Val Pro Pro Arg Ser Ala Phe S er Ala Lys Arg Ser Glu
            100                 105                 110

Ser Arg Val Pro Pro Pro Ser Asp Ala Pro L eu Pro Phe Asp Arg Val
        115                 120                 125

Leu Val Asn Glu Gln Gly His Tyr Asp Ala V al Thr Gly Lys Phe Thr
    130                 135                 140

Cys Gln Val Pro Gly Val Tyr Tyr Phe Ala V al His Ala Thr Val Tyr
145                 150                 155                 160

Arg Ala Ser Leu Gln Phe Asp Leu Val Lys A sn Gly Glu Ser Ile Ala
                165                 170                 175

Ser Phe Phe Gln Phe Phe Gly Gly Trp Pro L ys Pro Ala Ser Leu Ser
            180                 185                 190

Gly Gly Ala Met Val Arg Leu Glu Pro Glu A sp Gln Val Trp Val Gln
        195                 200                 205

Val Gly Val Gly Asp Tyr Ile Gly Ile Tyr A la Ser Ile Lys Thr Asp
    210                 215                 220

Ser Thr Phe Ser Gly Phe Leu Val Tyr Ser A sp Trp His Ser Ser Pro
225                 230                 235                 240

Val Phe Ala
```

<210> SEQ ID NO 4
<211> LENGTH: 228
<212> TYPE: PRT
<213> ORGANISM: Homo sapiens

<400> SEQUENCE: 4

```
Ser Pro Pro Leu Asp Asp Asn Lys Ile Pro S er Leu Cys Pro Gly His
  1               5                  10                  15

Pro Gly Leu Pro Gly Thr Pro Gly His His G ly Ser Gln Gly Leu Pro
             20                  25                  30

Gly Arg Asp Gly Arg Asp Gly Arg Asp Gly A la Pro Gly Ala Pro Gly
         35                  40                  45

Glu Lys Gly Glu Gly Gly Arg Pro Gly Leu P ro Gly Pro Arg Gly Asp
     50                  55                  60

Pro Gly Pro Arg Gly Glu Ala Gly Pro Ala G ly Pro Thr Gly Pro Ala
```

-continued

```
65                  70                  75                  80

Gly Glu Cys Ser Val Pro Pro Arg Ser Ala Phe Ser Ala Lys Arg Ser
                85                  90                  95

Glu Ser Arg Val Pro Pro Pro Ser Asp Ala Pro Leu Pro Phe Asp Arg
            100                 105                 110

Val Leu Val Asn Glu Gln Gly His Tyr Asp Ala Val Thr Gly Lys Phe
        115                 120                 125

Thr Cys Gln Val Pro Gly Val Tyr Tyr Phe Ala Val His Ala Thr Val
    130                 135                 140

Tyr Arg Ala Ser Leu Gln Phe Asp Leu Val Lys Asn Gly Glu Ser Ile
145                 150                 155                 160

Ala Ser Phe Phe Gln Phe Phe Gly Gly Trp Pro Lys Pro Ala Ser Leu
                165                 170                 175

Ser Gly Gly Ala Met Val Arg Leu Glu Pro Glu Asp Gln Val Trp Val
            180                 185                 190

Gln Val Gly Val Gly Asp Tyr Ile Gly Ile Tyr Ala Ser Ile Lys Thr
        195                 200                 205

Asp Ser Thr Phe Ser Gly Phe Leu Val Tyr Ser Asp Trp His Ser Ser
    210                 215                 220

Pro Val Phe Ala
225


<210> SEQ ID NO 5
<211> LENGTH: 15
<212> TYPE: PRT
<213> ORGANISM: Homo sapiens

<400> SEQUENCE: 5

Met Arg Pro Leu Leu Val Leu Leu Leu Leu Gly Leu Ala Ala Gly
  1               5                  10                  15


<210> SEQ ID NO 6
<211> LENGTH: 60
<212> TYPE: PRT
<213> ORGANISM: Homo sapiens

<400> SEQUENCE: 6

Gly Thr Pro Gly His His Gly Ser Gln Gly Leu Pro Gly Arg Asp Gly
  1               5                  10                  15

Arg Asp Gly Arg Asp Gly Ala Pro Gly Ala Pro Gly Glu Lys Gly Glu
             20                  25                  30

Gly Gly Arg Pro Gly Leu Pro Gly Pro Arg Gly Asp Pro Gly Pro Arg
         35                  40                  45

Gly Glu Ala Gly Pro Ala Gly Pro Thr Gly Pro Ala
     50                  55                  60


<210> SEQ ID NO 7
<211> LENGTH: 128
<212> TYPE: PRT
<213> ORGANISM: Homo sapiens

<400> SEQUENCE: 7

Ala Phe Ser Ala Lys Arg Ser Glu Ser Arg Val Pro Pro Pro Ser Asp
  1               5                  10                  15

Ala Pro Leu Pro Phe Asp Arg Val Leu Val Asn Glu Gln Gly His Tyr
             20                  25                  30

Asp Ala Val Thr Gly Lys Phe Thr Cys Gln Val Pro Gly Val Tyr Tyr
         35                  40                  45
```

-continued

```
Phe Ala Val His Ala Thr Val Tyr Arg Ala S er Leu Gln Phe Asp Leu
     50                  55                  60

Val Lys Asn Gly Glu Ser Ile Ala Ser Phe P he Gln Phe Phe Gly Gly
 65                  70                  75                  80

Trp Pro Lys Pro Ala Ser Leu Ser Gly Gly A la Met Val Arg Leu Glu
                85                  90                  95

Pro Glu Asp Gln Val Trp Val Gln Val Gly V al Gly Asp Tyr Ile Gly
            100                 105                 110

Ile Tyr Ala Ser Ile Lys Thr Asp Ser Thr P he Ser Gly Phe Leu Val
        115                 120                 125


<210> SEQ ID NO 8
<211> LENGTH: 1263
<212> TYPE: DNA
<213> ORGANISM: Mus musculus

<400> SEQUENCE: 8

gtcgacccac gcgtccgcgc tgtgaagcca gcaaggagca accagaagct a ggagtcagt     60

cagcaaggac aggggctgcc tgcctacaga ctacaagaga ggttcctgga g tctgagcct    120

ccggggtcac caccatgagg ccacttcttg cccttctgct tctgggtctg g tgtcaggct    180

ctcctcctct ggacgacaac aagatcccca gcctgtgtcc cgggcagccc g gccttccag    240

gcacaccagg tcaccatggc agccaaggcc tgcctggccg tgacggccgt g atggccgcg    300

acggtgcacc cggagctccg ggagagaaag gcgagggcgg gagaccggga c tacctggcc    360

cacgtgggga gcccgggccg cgtggagagg cagggcccat gggggctatc g ggcctgcgg    420

gggagtgctc ggtaccccca cgatcagcct tcagtgccaa gcgatccgag a gccgggtac    480

ctccgccagc cgacacaccc ctacctttcg accgtgtgct gctaaatgag c agggccatt    540

acgaccccac tactggcaag ttcacctgcc aagtgcctgg cgtctactac t ttgctgtgc    600

acgccactgt ctaccgggcc agcttgcagt ttgatcttgt caaaaacggg c agtccatcg    660

cctctttctt ccagtatttt ggggggtggc ccaagccagc ctcgctctca g ggggtgcga    720

tggtaaggct agaacctgag gaccaggtgt gggtgcaggt gggcgtgggt g attacattg    780

gcatctatgc cagcatcaag acagacagta ccttctctgg atttctcgtc t attctgact    840

ggcacagctc cccagtcttc gcttaaaaca cagtgaaccc ggagctggca c ttgctcctc    900

agtggagggt gtgacactaa cccgcgcagc gcataccagg agggctggcc c cctggaata    960

ttgtgaatga cttaggaaga gagggagcca cttccagtcc cactgctggc a atgaatgga   1020

gacaggctgt ctgaggtcaa gacagcgtgg agcagtggct gggtttctgc c caggacttt   1080

agaatgcagt aggctggcag ctgtgggtcc tggcccagga ctccaaggtg g gatgctcca   1140

ttcctagtcc tgtgtcccct ctaggtccct gactccatct ctgctgctcc c agggcaggc   1200

ctttttctca gaggtcactt aataaaccta aaatcctcaa aaaaaaaaaa a aagggcggc   1260

cgc                                                                 1263


<210> SEQ ID NO 9
<211> LENGTH: 729
<212> TYPE: DNA
<213> ORGANISM: Mus musculus

<400> SEQUENCE: 9

atgaggccac ttcttgccct tctgcttctg ggtctggtgt caggctctcc t cctctggac     60

gacaacaaga tccccagcct gtgtcccggg cagcccggcc ttccaggcac a ccaggtcac    120
```

-continued

```
catggcagcc aaggcctgcc tggccgtgac ggccgtgatg gccgcgacgg t gcacccgga    180

gctccgggag agaaaggcga gggcgggaga ccgggactac ctggcccacg t ggggagccc    240

gggccgcgtg gagaggcagg gcccatgggg gctatcgggc ctgcggggga g tgctcggta    300

cccccacgat cagccttcag tgccaagcga tccgagagcc gggtacctcc g ccagccgac    360

acacccctac ctttcgaccg tgtgctgcta aatgagcagg gccattacga c cccactact    420

ggcaagttca cctgccaagt gcctggcgtc tactactttg ctgtgcacgc c actgtctac    480

cgggccagct tgcagtttga tcttgtcaaa aacgggcagt ccatcgcctc t ttcttccag    540

tattttgggg ggtggcccaa gccagcctcg ctctcagggg gtgcgatggt a aggctagaa    600

cctgaggacc aggtgtgggt gcaggtgggc gtgggtgatt acattggcat c tatgccagc    660

atcaagacag acagtacctt ctctggattt ctcgtctatt ctgactggca c agctcccca    720

gtcttcgct                                                        729
```

```
<210> SEQ ID NO 10
<211> LENGTH: 243
<212> TYPE: PRT
<213> ORGANISM: Mus musculus

<400> SEQUENCE: 10

Met Arg Pro Leu Leu Ala Leu Leu Leu Leu G ly Leu Val Ser Gly Ser
  1               5                  10                  15

Pro Pro Leu Asp Asp Asn Lys Ile Pro Ser L eu Cys Pro Gly Gln Pro
             20                  25                  30

Gly Leu Pro Gly Thr Pro Gly His His Gly S er Gln Gly Leu Pro Gly
        35                  40                  45

Arg Asp Gly Arg Asp Gly Arg Asp Gly Ala P ro Gly Ala Pro Gly Glu
     50                  55                  60

Lys Gly Glu Gly Gly Arg Pro Gly Leu Pro G ly Pro Arg Gly Glu Pro
 65                  70                  75                  80

Gly Pro Arg Gly Glu Ala Gly Pro Met Gly A la Ile Gly Pro Ala Gly
                 85                  90                  95

Glu Cys Ser Val Pro Pro Arg Ser Ala Phe S er Ala Lys Arg Ser Glu
            100                 105                 110

Ser Arg Val Pro Pro Pro Ala Asp Thr Pro L eu Pro Phe Asp Arg Val
        115                 120                 125

Leu Leu Asn Glu Gln Gly His Tyr Asp Pro T hr Thr Gly Lys Phe Thr
    130                 135                 140

Cys Gln Val Pro Gly Val Tyr Tyr Phe Ala V al His Ala Thr Val Tyr
145                 150                 155                 160

Arg Ala Ser Leu Gln Phe Asp Leu Val Lys A sn Gly Gln Ser Ile Ala
                165                 170                 175

Ser Phe Phe Gln Tyr Phe Gly Gly Trp Pro L ys Pro Ala Ser Leu Ser
            180                 185                 190

Gly Gly Ala Met Val Arg Leu Glu Pro Glu A sp Gln Val Trp Val Gln
        195                 200                 205

Val Gly Val Gly Asp Tyr Ile Gly Ile Tyr A la Ser Ile Lys Thr Asp
    210                 215                 220

Ser Thr Phe Ser Gly Phe Leu Val Tyr Ser A sp Trp His Ser Ser Pro
225                 230                 235                 240

Val Phe Ala
```

-continued

<210> SEQ ID NO 11
<211> LENGTH: 228
<212> TYPE: PRT
<213> ORGANISM: Mus musculus

<400> SEQUENCE: 11

```
Ser Pro Pro Leu Asp Asp Asn Lys Ile Pro S er Leu Cys Pro Gly Gln
  1               5                  10                  15

Pro Gly Leu Pro Gly Thr Pro Gly His His G ly Ser Gln Gly Leu Pro
            20                  25                  30

Gly Arg Asp Gly Arg Asp Gly Arg Asp Gly A la Pro Gly Ala Pro Gly
        35                  40                  45

Glu Lys Gly Glu Gly Gly Arg Pro Gly Leu P ro Gly Pro Arg Gly Glu
     50                  55                  60

Pro Gly Pro Arg Gly Glu Ala Gly Pro Met G ly Ala Ile Gly Pro Ala
 65                  70                  75                  80

Gly Glu Cys Ser Val Pro Pro Arg Ser Ala P he Ser Ala Lys Arg Ser
                 85                  90                  95

Glu Ser Arg Val Pro Pro Pro Ala Asp Thr P ro Leu Pro Phe Asp Arg
            100                 105                 110

Val Leu Leu Asn Glu Gln Gly His Tyr Asp P ro Thr Thr Gly Lys Phe
        115                 120                 125

Thr Cys Gln Val Pro Gly Val Tyr Tyr Phe A la Val His Ala Thr Val
    130                 135                 140

Tyr Arg Ala Ser Leu Gln Phe Asp Leu Val L ys Asn Gly Gln Ser Ile
145                 150                 155                 160

Ala Ser Phe Phe Gln Tyr Phe Gly Gly Trp P ro Lys Pro Ala Ser Leu
                165                 170                 175

Ser Gly Gly Ala Met Val Arg Leu Glu Pro G lu Asp Gln Val Trp Val
            180                 185                 190

Gln Val Gly Val Gly Asp Tyr Ile Gly Ile T yr Ala Ser Ile Lys Thr
        195                 200                 205

Asp Ser Thr Phe Ser Gly Phe Leu Val Tyr S er Asp Trp His Ser Ser
    210                 215                 220

Pro Val Phe Ala
225
```

<210> SEQ ID NO 12
<211> LENGTH: 15
<212> TYPE: PRT
<213> ORGANISM: Mus musculus

<400> SEQUENCE: 12

```
Met Arg Pro Leu Leu Ala Leu Leu Leu Leu G ly Leu Val Ser Gly
  1               5                  10                  15
```

<210> SEQ ID NO 13
<211> LENGTH: 60
<212> TYPE: PRT
<213> ORGANISM: Mus musculus

<400> SEQUENCE: 13

```
Gly Thr Pro Gly His His Gly Ser Gln Gly L eu Pro Gly Arg Asp Gly
  1               5                  10                  15

Arg Asp Gly Arg Asp Gly Ala Pro Gly Ala P ro Gly Glu Lys Gly Glu
            20                  25                  30

Gly Gly Arg Pro Gly Leu Pro Gly Pro Arg G ly Glu Pro Gly Pro Arg
        35                  40                  45
```

-continued

```
Gly Glu Ala Gly Pro Met Gly Ala Ile Gly P ro Ala
     50                  55                  60


<210> SEQ ID NO 14
<211> LENGTH: 128
<212> TYPE: PRT
<213> ORGANISM: Mus musculus

<400> SEQUENCE: 14

Ala Phe Ser Ala Lys Arg Ser Glu Ser Arg V al Pro Pro Pro Ala Asp
  1               5                  10                  15

Thr Pro Leu Pro Phe Asp Arg Val Leu Leu A sn Glu Gln Gly His Tyr
             20                  25                  30

Asp Pro Thr Thr Gly Lys Phe Thr Cys Gln V al Pro Gly Val Tyr Tyr
         35                  40                  45

Phe Ala Val His Ala Thr Val Tyr Arg Ala S er Leu Gln Phe Asp Leu
     50                  55                  60

Val Lys Asn Gly Gln Ser Ile Ala Ser Phe P he Gln Tyr Phe Gly Gly
 65                  70                  75                  80

Trp Pro Lys Pro Ala Ser Leu Ser Gly Gly A la Met Val Arg Leu Glu
                 85                  90                  95

Pro Glu Asp Gln Val Trp Val Gln Val Gly V al Gly Asp Tyr Ile Gly
            100                 105                 110

Ile Tyr Ala Ser Ile Lys Thr Asp Ser Thr P he Ser Gly Phe Leu Val
        115                 120                 125


<210> SEQ ID NO 15
<211> LENGTH: 1831
<212> TYPE: DNA
<213> ORGANISM: Homo sapiens

<400> SEQUENCE: 15

gtcgacccac gcgtccgcgg acgcgtgggt gaggggaaga ggctgactgt a cgttccttc      60

tactctggca ccactctcca ggctgccatg gggcccagca cccctctcct c atcttgttc     120

cttttgtcat ggtcgggacc cctccaagga cagcagcacc accttgtgga g tacatggaa     180

cgccgactag ctgctttaga ggaacggctg gcccagtgcc aggaccagag t agtcggcat     240

gctgctgagc tgcgggactt caagaacaag atgctgccac tgctggaggt g gcagagaag     300

gagcgggagg cactcagaac tgaggccgac accatctccg ggagagtgga t cgtctggag     360

cgggaggtag actatctgga gacccagaac ccagctctgc cctgtgtaga g tttgatgag     420

aaggtgactg gaggccctgg gaccaaaggc aagggaagaa ggaatgagaa g tacgatatg     480

gtgacagact gtggctacac aatctctcaa gtgagatcaa tgaagattct g aagcgattt     540

ggtggcccag ctggtctatg gaccaaggat ccactggggc aaacagagaa g atctacgtg     600

ttagatggga cacagaatga cacagccttt gtcttcccaa ggctgcgtga c ttcaccctt     660

gccatggctg cccggaaagc ttcccgagtc cgggtgccct tcccctgggt a ggcacaggg     720

cagctggtat atggtggctt tctttatttt gctcggaggc ctcctggaag a cctggtgga     780

ggtggtgaga tggagaacac tttgcagcta atcaaattcc acctggcaaa c cgaacagtg     840

gtggacagct cagtattccc agcagagggg ctgatccccc cctacggctt g acagcagac     900

acctacatcg acctggcagc tgatgaggaa ggtctttggg ctgtctatgc c acccgggag     960

gatgacaggc acttgtgtct ggccaagtta gatccacaga cactggacac a gagcagcag    1020

tgggacacac catgtcccag agagaatgct gaggctgcct ttgtcatctg t gggaccctc    1080
```

-continued

```
tatgtcgtct ataacacccg tcctgccagt cgggcccgca tccagtgctc c tttgatgcc   1140
agcggcaccc tgacccctga acgggcagca ctcccttatt ttccccgcag a tatggtgcc   1200
catgccagcc tccgctataa cccccgagaa cgccagctct atgcctggga t gatggctac   1260
cagattgtct ataagctgga gatgaggaag aaagaggagg aggtttgagg a gctagcctt   1320
gtttttgca tctttctcac tcccatacat ttatattata tccccactaa a tttcttgtt   1380
cctcattctt caaatgtggg ccagttgtgg ctcaaatcct ctatattttt a gccaatggc   1440
aatcaaattc tttcagctcc tttgtttcat acggaactcc agatcctgag t aatcctttt   1500
agagcccgaa gagtcaaaac cctcaatgtt ccctcctgct ctcctgcccc a tgtcaacaa   1560
atttcaggct aaggatgccc cagacccagg gctctaacct tgtatgcggg c aggcccagg   1620
gagcaggcag cagtgttctt cccctcagag tgacttgggg agggagaaat a ggaggagac   1680
gtccagctct gtcctctctt cctcactcct cccttcagtg tcctgaggaa c aggactttc   1740
tccacattgt tttgtattgc aacattttgc attaaaagga aaatccactg c taaaaaaaa   1800
aaaaaaaaaa aaaaaaaaaa agggcggccg c                               1831
```

<210> SEQ ID NO 16
<211> LENGTH: 1218
<212> TYPE: DNA
<213> ORGANISM: Homo sapiens

<400> SEQUENCE: 16

```
atggggccca gcacccctct cctcatcttg ttccttttgt catggtcggg a cccctccaa     60
ggacagcagc accaccttgt ggagtacatg gaacgccgac tagctgcttt a gaggaacgg    120
ctggcccagt gccaggacca gagtagtcgg catgctgctg agctgcggga c ttcaagaac    180
aagatgctgc cactgctgga ggtggcagag aaggagcggg aggcactcag a actgaggcc    240
gacaccatct ccgggagagt ggatcgtctg gagcgggagg tagactatct g gagacccag    300
aacccagctc tgccctgtgt agagtttgat gagaaggtga ctggaggccc t gggaccaaa    360
ggcaagggaa gaaggaatga gaagtacgat atggtgacag actgtggcta c acaatctct    420
caagtgagat caatgaagat tctgaagcga tttggtggcc cagctggtct a tggaccaag    480
gatccactgg ggcaaacaga gaagatctac gtgttagatg ggacacagaa t gacacagcc    540
tttgtcttcc caaggctgcg tgacttcacc cttgccatgg ctgcccggaa a gcttcccga    600
gtccgggtgc ccttcccctg ggtaggcaca gggcagctgg tatatggtgg c tttctttat    660
tttgctcgga ggcctcctgg aagacctggt ggaggtggtg agatggagaa c actttgcag    720
ctaatcaaat tccacctggc aaaccgaaca gtggtggaca gctcagtatt c ccagcagag    780
gggctgatcc ccccctacgg cttgacagca gacacctaca tcgacctggc a gctgatgag    840
gaaggtcttt gggctgtcta tgccacccgg gaggatgaca ggcacttgtg t ctggccaag    900
ttagatccac agacactgga cacagagcag cagtgggaca caccatgtcc c agagagaat    960
gctgaggctg cctttgtcat ctgtgggacc ctctatgtcg tctataacac c cgtcctgcc   1020
agtcgggccc gcatccagtg ctcctttgat gccagcggca ccctgacccc t gaacgggca   1080
gcactccctt attttccccg cagatatggt gcccatgcca gcctccgcta t aacccccga   1140
gaacgccagc tctatgcctg ggatgatggc taccagattg tctataagct g gagatgagg   1200
aagaaagagg aggaggtt                                               1218
```

<210> SEQ ID NO 17

-continued

<211> LENGTH: 406
<212> TYPE: PRT
<213> ORGANISM: Homo sapiens

<400> SEQUENCE: 17

Met Gly Pro Ser Thr Pro Leu Leu Ile Leu P he Leu Leu Ser Trp Ser
1 5 10 15

Gly Pro Leu Gln Gly Gln Gln His His Leu V al Glu Tyr Met Glu Arg
20 25 30

Arg Leu Ala Ala Leu Glu Glu Arg Leu Ala G ln Cys Gln Asp Gln Ser
35 40 45

Ser Arg His Ala Ala Glu Leu Arg Asp Phe L ys Asn Lys Met Leu Pro
50 55 60

Leu Leu Glu Val Ala Glu Lys Glu Arg Glu A la Leu Arg Thr Glu Ala
65 70 75 80

Asp Thr Ile Ser Gly Arg Val Asp Arg Leu G lu Arg Glu Val Asp Tyr
85 90 95

Leu Glu Thr Gln Asn Pro Ala Leu Pro Cys V al Glu Phe Asp Glu Lys
100 105 110

Val Thr Gly Gly Pro Gly Thr Lys Gly Lys G ly Arg Arg Asn Glu Lys
115 120 125

Tyr Asp Met Val Thr Asp Cys Gly Tyr Thr I le Ser Gln Val Arg Ser
130 135 140

Met Lys Ile Leu Lys Arg Phe Gly Gly Pro A la Gly Leu Trp Thr Lys
145 150 155 160

Asp Pro Leu Gly Gln Thr Glu Lys Ile Tyr V al Leu Asp Gly Thr Gln
165 170 175

Asn Asp Thr Ala Phe Val Phe Pro Arg Leu A rg Asp Phe Thr Leu Ala
180 185 190

Met Ala Ala Arg Lys Ala Ser Arg Val Arg V al Pro Phe Pro Trp Val
195 200 205

Gly Thr Gly Gln Leu Val Tyr Gly Gly Phe L eu Tyr Phe Ala Arg Arg
210 215 220

Pro Pro Gly Arg Pro Gly Gly Gly Gly Glu M et Glu Asn Thr Leu Gln
225 230 235 240

Leu Ile Lys Phe His Leu Ala Asn Arg Thr V al Val Asp Ser Ser Val
245 250 255

Phe Pro Ala Glu Gly Leu Ile Pro Pro Tyr G ly Leu Thr Ala Asp Thr
260 265 270

Tyr Ile Asp Leu Ala Ala Asp Glu Glu Gly L eu Trp Ala Val Tyr Ala
275 280 285

Thr Arg Glu Asp Asp Arg His Leu Cys Leu A la Lys Leu Asp Pro Gln
290 295 300

Thr Leu Asp Thr Glu Gln Gln Trp Asp Thr P ro Cys Pro Arg Glu Asn
305 310 315 320

Ala Glu Ala Ala Phe Val Ile Cys Gly Thr L eu Tyr Val Val Tyr Asn
325 330 335

Thr Arg Pro Ala Ser Arg Ala Arg Ile Gln C ys Ser Phe Asp Ala Ser
340 345 350

Gly Thr Leu Thr Pro Glu Arg Ala Ala Leu P ro Tyr Phe Pro Arg Arg
355 360 365

Tyr Gly Ala His Ala Ser Leu Arg Tyr Asn P ro Arg Glu Arg Gln Leu
370 375 380

Tyr Ala Trp Asp Asp Gly Tyr Gln Ile Val T yr Lys Leu Glu Met Arg

-continued 385 390 395 400

Lys Lys Glu Glu Glu Val
405

<210> SEQ ID NO 18
<211> LENGTH: 385
<212> TYPE: PRT
<213> ORGANISM: Homo sapiens

<400> SEQUENCE: 18

Gln Gln His His Leu Val Glu Tyr Met Glu A rg Arg Leu Ala Ala Leu
1 5 10 15

Glu Glu Arg Leu Ala Gln Cys Gln Asp Gln S er Ser Arg His Ala Ala
20 25 30

Glu Leu Arg Asp Phe Lys Asn Lys Met Leu P ro Leu Leu Glu Val Ala
35 40 45

Glu Lys Glu Arg Glu Ala Leu Arg Thr Glu A la Asp Thr Ile Ser Gly
50 55 60

Arg Val Asp Arg Leu Glu Arg Glu Val Asp T yr Leu Glu Thr Gln Asn
65 70 75 80

Pro Ala Leu Pro Cys Val Glu Phe Asp Glu L ys Val Thr Gly Gly Pro
85 90 95

Gly Thr Lys Gly Lys Gly Arg Arg Asn Glu L ys Tyr Asp Met Val Thr
100 105 110

Asp Cys Gly Tyr Thr Ile Ser Gln Val Arg S er Met Lys Ile Leu Lys
115 120 125

Arg Phe Gly Gly Pro Ala Gly Leu Trp Thr L ys Asp Pro Leu Gly Gln
130 135 140

Thr Glu Lys Ile Tyr Val Leu Asp Gly Thr G ln Asn Asp Thr Ala Phe
145 150 155 160

Val Phe Pro Arg Leu Arg Asp Phe Thr Leu A la Met Ala Ala Arg Lys
165 170 175

Ala Ser Arg Val Arg Val Pro Phe Pro Trp V al Gly Thr Gly Gln Leu
180 185 190

Val Tyr Gly Gly Phe Leu Tyr Phe Ala Arg A rg Pro Pro Gly Arg Pro
195 200 205

Gly Gly Gly Gly Glu Met Glu Asn Thr Leu G ln Leu Ile Lys Phe His
210 215 220

Leu Ala Asn Arg Thr Val Val Asp Ser Ser V al Phe Pro Ala Glu Gly
225 230 235 240

Leu Ile Pro Pro Tyr Gly Leu Thr Ala Asp T hr Tyr Ile Asp Leu Ala
245 250 255

Ala Asp Glu Glu Gly Leu Trp Ala Val Tyr A la Thr Arg Glu Asp Asp
260 265 270

Arg His Leu Cys Leu Ala Lys Leu Asp Pro G ln Thr Leu Asp Thr Glu
275 280 285

Gln Gln Trp Asp Thr Pro Cys Pro Arg Glu A sn Ala Glu Ala Ala Phe
290 295 300

Val Ile Cys Gly Thr Leu Tyr Val Val Tyr A sn Thr Arg Pro Ala Ser
305 310 315 320

Arg Ala Arg Ile Gln Cys Ser Phe Asp Ala S er Gly Thr Leu Thr Pro
325 330 335

Glu Arg Ala Ala Leu Pro Tyr Phe Pro Arg A rg Tyr Gly Ala His Ala
340 345 350

-continued

Ser Leu Arg Tyr Asn Pro Arg Glu Arg Gln L eu Tyr Ala Trp Asp Asp
355 360 365

Gly Tyr Gln Ile Val Tyr Lys Leu Glu Met A rg Lys Lys Glu Glu Glu
370 375 380

Val
385

<210> SEQ ID NO 19
<211> LENGTH: 21
<212> TYPE: PRT
<213> ORGANISM: Homo sapiens

<400> SEQUENCE: 19

Met Gly Pro Ser Thr Pro Leu Leu Ile Leu P he Leu Leu Ser Trp Ser
1 5 10 15

Gly Pro Leu Gln Gly
20

<210> SEQ ID NO 20
<211> LENGTH: 244
<212> TYPE: PRT
<213> ORGANISM: Homo sapiens

<400> SEQUENCE: 20

Met Leu Leu Leu Gly Ala Val Leu Leu Leu L eu Ala Leu Pro Gly His
1 5 10 15

Asp Gln Glu Thr Thr Thr Gln Gly Pro Gly V al Leu Leu Pro Leu Pro
20 25 30

Lys Gly Ala Cys Thr Gly Trp Met Ala Gly I le Pro Gly His Pro Gly
35 40 45

His Asn Gly Ala Pro Gly Arg Asp Gly Arg A sp Gly Thr Pro Gly Glu
50 55 60

Lys Gly Glu Lys Gly Asp Pro Gly Leu Ile G ly Pro Lys Gly Asp Ile
65 70 75 80

Gly Glu Thr Gly Val Pro Gly Ala Glu Gly P ro Arg Gly Phe Pro Gly
85 90 95

Ile Gln Gly Arg Lys Gly Glu Pro Gly Glu G ly Ala Tyr Val Tyr Arg
100 105 110

Ser Ala Phe Ser Val Gly Leu Glu Thr Tyr V al Thr Ile Pro Asn Met
115 120 125

Pro Ile Arg Phe Thr Lys Ile Phe Tyr Asn G ln Gln Asn His Tyr Asp
130 135 140

Gly Ser Thr Gly Lys Phe His Cys Asn Ile P ro Gly Leu Tyr Tyr Phe
145 150 155 160

Ala Tyr His Ile Thr Val Tyr Met Lys Asp V al Lys Val Ser Leu Phe
165 170 175

Lys Lys Asp Lys Ala Met Leu Phe Thr Tyr A sp Gln Tyr Gln Glu Asn
180 185 190

Asn Val Asp Gln Ala Ser Gly Ser Val Leu L eu His Leu Glu Val Gly
195 200 205

Asp Gln Val Trp Leu Gln Val Tyr Gly Glu G ly Glu Arg Asn Gly Leu
210 215 220

Tyr Ala Asp Asn Asp Asn Asp Ser Thr Phe T hr Gly Phe Leu Leu Tyr
225 230 235 240

His Asp Thr Asn

-continued

<210> SEQ ID NO 21
<211> LENGTH: 1721
<212> TYPE: DNA
<213> ORGANISM: Mus musculus

<400> SEQUENCE: 21

```
gtcgacccac gcgtccgact taaggctgcc atggggccca gtgctcctct g ctgctcctc     60
ttctttttgt catggacggg accccttcag ggacagcagc accaccttgt g gagtacatg    120
gaacgccgac tagctgcctt agaggaacgg ctggcccaat gccaggatca g agtagtcgg    180
catgctgccg agcttcggga cttcaaaaac aagatgttgc ctctcctgga g gtggcagag    240
aaggagcggg agaccctcag aactgaagca gactccatct caggaagagt g gaccgtctt    300
gaaagggagg tagactatct ggagacacag aacccagctt tgccctgtgt a gagctggat    360
gagaaggtga ctggaggtcc tggagccaaa ggcaagggcc gaagaaatga g aaatacgat    420
atggtgacgg actgtagcta cacagtcgct caggtgaggt caatgaagat c ctgaagcgg    480
tttggtggtt cagttggcct atggaccaag gatccgctgg ggccagcaga g aagatctac    540
gtgttagacg gcacccagaa cgacacggct tttgtcttcc caaggctgcg t gacttcacc    600
cttgccatgg ctgcccggaa agcttcccga attcgggtgc ccttcccctg g gtaggcacg    660
gggcagctgg tgtacggtgg cttcctttat tatgctcgaa ggcctcctgg a ggacctgga    720
gggggtggtg aattggagaa cactctgcag ctgatcaaat ttcacttggc a aaccgaaca    780
gtggtggata gctcagtgtt ccctgcagag agcctgatac ccccctacgg c ctgacagca    840
gatacatata tcgacctggc agctgatgag gagggcctgt gggctgtcta t gccactcga    900
gatgatgaca ggcatttgtg tctagccaag ttagacccac agacacttga c acagagcag    960
cagtgggaca caccatgtcc cagagagaac gcagaggctg cgtttgtcat c tgtgggacc   1020
ctgtacgttg tctataacac ccgccctgcc agtagggctc gtattcagtg t tccttcgat   1080
gccagtggta ctctcgcccc tgaaagggca gcactctcct attttccacg c cgatatggt   1140
gcccatgcca gccttcgcta taacccccgt gagcgccagc tgtatgcctg g gatgatggc   1200
taccagattg tctacaaatt ggagatgaag aagaaggagg aggaagttta a gcagctagc   1260
cttgtgctct tgattcttat gcccagacat ttatattcct gtgagctctc c tgcagttca   1320
tccttcaaaa cgaaggccag tggtggtagc tcatataccc taatttctaa a ggacaacca   1380
aattctcaag cccctctgtt ttatgcagaa ctccagatcc tgggtagcat t ttagaactg   1440
aacagcaaac aaacacccta aatcttcact cctgccttat gtccacaaag t ttagttcca   1500
aactcagagc cctgtccttt ggagagggtc aaccccagac agcaggcgac a gcattcttg   1560
ccctcagtat gaccgaaggg agagaactca gagacaaagc tgccctccct c ccttccccc   1620
tccagtgtag gggagaatgg ggctttcccc acatcacttt gtatggtaac a gtttgcatt   1680
aaaaggaaaa cccaccaaaa aaaaaaaaaa agggcggccg c                       1721
```

<210> SEQ ID NO 22
<211> LENGTH: 1218
<212> TYPE: DNA
<213> ORGANISM: Mus musculus

<400> SEQUENCE: 22

```
atggggccca gtgctcctct gctgctcctc ttctttttgt catggacggg a ccccttcag     60
ggacagcagc accaccttgt ggagtacatg gaacgccgac tagctgcctt a gaggaacgg    120
ctggcccaat gccaggatca gagtagtcgg catgctgccg agcttcggga c ttcaaaaac    180
```

-continued

```
aagatgttgc ctctcctgga ggtggcagag aaggagcggg agaccctcag a actgaagca    240

gactccatct caggaagagt ggaccgtctt gaaagggagg tagactatct g gagacacag    300

aacccagctt tgccctgtgt agagctggat gagaaggtga ctggaggtcc t ggagccaaa    360

ggcaagggcc gaagaaatga gaaatacgat atggtgacgg actgtagcta c acagtcgct    420

caggtgaggt caatgaagat cctgaagcgg tttggtggtt cagttggcct a tggaccaag    480

gatccgctgg ggccagcaga gaagatctac gtgttagacg gcacccagaa c gacacggct    540

tttgtcttcc caaggctgcg tgacttcacc cttgccatgg ctgcccggaa a gcttcccga    600

attcgggtgc ccttcccctg ggtaggcacg gggcagctgg tgtacggtgg c ttcctttat    660

tatgctcgaa ggcctcctgg aggacctgga gggggtggtg aattggagaa c actctgcag    720

ctgatcaaat ttcacttggc aaaccgaaca gtggtggata gctcagtgtt c cctgcagag    780

agcctgatac ccccctacgg cctgacagca gatacatata tcgacctggc a gctgatgag    840

gagggcctgt gggctgtcta tgccactcga gatgatgaca ggcatttgtg t ctagccaag    900

ttagacccac agacacttga cacagagcag cagtgggaca caccatgtcc c agagagaac    960

gcagaggctg cgtttgtcat ctgtgggacc ctgtacgttg tctataacac c cgccctgcc   1020

agtagggctc gtattcagtg ttccttcgat gccagtggta ctctcgcccc t gaaagggca   1080

gcactctcct attttccacg ccgatatggt gcccatgcca gccttcgcta t aacccccgt   1140

gagcgccagc tgtatgcctg ggatgatggc taccagattg tctacaaatt g gagatgaag   1200

aagaaggagg aggaagtt                                                 1218
```

<210> SEQ ID NO 23
<211> LENGTH: 406
<212> TYPE: PRT
<213> ORGANISM: Mus musculus

<400> SEQUENCE: 23

```
Met Gly Pro Ser Ala Pro Leu Leu Leu Leu P he Phe Leu Ser Trp Thr
  1               5                  10                  15

Gly Pro Leu Gln Gly Gln Gln His His Leu V al Glu Tyr Met Glu Arg
             20                  25                  30

Arg Leu Ala Ala Leu Glu Glu Arg Leu Ala G ln Cys Gln Asp Gln Ser
         35                  40                  45

Ser Arg His Ala Ala Glu Leu Arg Asp Phe L ys Asn Lys Met Leu Pro
     50                  55                  60

Leu Leu Glu Val Ala Glu Lys Glu Arg Glu T hr Leu Arg Thr Glu Ala
 65                  70                  75                  80

Asp Ser Ile Ser Gly Arg Val Asp Arg Leu G lu Arg Glu Val Asp Tyr
                 85                  90                  95

Leu Glu Thr Gln Asn Pro Ala Leu Pro Cys V al Glu Leu Asp Glu Lys
            100                 105                 110

Val Thr Gly Gly Pro Gly Ala Lys Gly Lys G ly Arg Arg Asn Glu Lys
        115                 120                 125

Tyr Asp Met Val Thr Asp Cys Ser Tyr Thr V al Ala Gln Val Arg Ser
    130                 135                 140

Met Lys Ile Leu Lys Arg Phe Gly Gly Ser V al Gly Leu Trp Thr Lys
145                 150                 155                 160

Asp Pro Leu Gly Pro Ala Glu Lys Ile Tyr V al Leu Asp Gly Thr Gln
                165                 170                 175

Asn Asp Thr Ala Phe Val Phe Pro Arg Leu A rg Asp Phe Thr Leu Ala
            180                 185                 190
```

-continued

Met Ala Ala Arg Lys Ala Ser Arg Ile Arg V al Pro Phe Pro Trp Val
195 200 205

Gly Thr Gly Gln Leu Val Tyr Gly Gly Phe L eu Tyr Tyr Ala Arg Arg
210 215 220

Pro Pro Gly Gly Pro Gly Gly Gly Gly Glu L eu Glu Asn Thr Leu Gln
225 230 235 240

Leu Ile Lys Phe His Leu Ala Asn Arg Thr V al Val Asp Ser Ser Val
245 250 255

Phe Pro Ala Glu Ser Leu Ile Pro Pro Tyr G ly Leu Thr Ala Asp Thr
260 265 270

Tyr Ile Asp Leu Ala Ala Asp Glu Glu Gly L eu Trp Ala Val Tyr Ala
275 280 285

Thr Arg Asp Asp Asp Arg His Leu Cys Leu A la Lys Leu Asp Pro Gln
290 295 300

Thr Leu Asp Thr Glu Gln Gln Trp Asp Thr P ro Cys Pro Arg Glu Asn
305 310 315 320

Ala Glu Ala Ala Phe Val Ile Cys Gly Thr L eu Tyr Val Val Tyr Asn
325 330 335

Thr Arg Pro Ala Ser Arg Ala Arg Ile Gln C ys Ser Phe Asp Ala Ser
340 345 350

Gly Thr Leu Ala Pro Glu Arg Ala Ala Leu S er Tyr Phe Pro Arg Arg
355 360 365

Tyr Gly Ala His Ala Ser Leu Arg Tyr Asn P ro Arg Glu Arg Gln Leu
370 375 380

Tyr Ala Trp Asp Asp Gly Tyr Gln Ile Val T yr Lys Leu Glu Met Lys
385 390 395 400

Lys Lys Glu Glu Glu Val
405

<210> SEQ ID NO 24
<211> LENGTH: 385
<212> TYPE: PRT
<213> ORGANISM: Mus musculus

<400> SEQUENCE: 24

Gln Gln His His Leu Val Glu Tyr Met Glu A rg Arg Leu Ala Ala Leu
1 5 10 15

Glu Glu Arg Leu Ala Gln Cys Gln Asp Gln S er Ser Arg His Ala Ala
20 25 30

Glu Leu Arg Asp Phe Lys Asn Lys Met Leu P ro Leu Leu Glu Val Ala
35 40 45

Glu Lys Glu Arg Glu Thr Leu Arg Thr Glu A la Asp Ser Ile Ser Gly
50 55 60

Arg Val Asp Arg Leu Glu Arg Glu Val Asp T yr Leu Glu Thr Gln Asn
65 70 75 80

Pro Ala Leu Pro Cys Val Glu Leu Asp Glu L ys Val Thr Gly Gly Pro
85 90 95

Gly Ala Lys Gly Lys Gly Arg Arg Asn Glu L ys Tyr Asp Met Val Thr
100 105 110

Asp Cys Ser Tyr Thr Val Ala Gln Val Arg S er Met Lys Ile Leu Lys
115 120 125

Arg Phe Gly Gly Ser Val Gly Leu Trp Thr L ys Asp Pro Leu Gly Pro
130 135 140

Ala Glu Lys Ile Tyr Val Leu Asp Gly Thr G ln Asn Asp Thr Ala Phe

-continued

```
145                 150                 155                 160

Val Phe Pro Arg Leu Arg Asp Phe Thr Leu A la Met Ala Ala Arg Lys
                165                 170                 175

Ala Ser Arg Ile Arg Val Pro Phe Pro Trp V al Gly Thr Gly Gln Leu
            180                 185                 190

Val Tyr Gly Gly Phe Leu Tyr Tyr Ala Arg A rg Pro Pro Gly Gly Pro
        195                 200                 205

Gly Gly Gly Gly Glu Leu Glu Asn Thr Leu G ln Leu Ile Lys Phe His
    210                 215                 220

Leu Ala Asn Arg Thr Val Val Asp Ser Ser V al Phe Pro Ala Glu Ser
225                 230                 235                 240

Leu Ile Pro Pro Tyr Gly Leu Thr Ala Asp T hr Tyr Ile Asp Leu Ala
                245                 250                 255

Ala Asp Glu Glu Gly Leu Trp Ala Val Tyr A la Thr Arg Asp Asp Asp
            260                 265                 270

Arg His Leu Cys Leu Ala Lys Leu Asp Pro G ln Thr Leu Asp Thr Glu
        275                 280                 285

Gln Gln Trp Asp Thr Pro Cys Pro Arg Glu A sn Ala Glu Ala Ala Phe
    290                 295                 300

Val Ile Cys Gly Thr Leu Tyr Val Val Tyr A sn Thr Arg Pro Ala Ser
305                 310                 315                 320

Arg Ala Arg Ile Gln Cys Ser Phe Asp Ala S er Gly Thr Leu Ala Pro
                325                 330                 335

Glu Arg Ala Ala Leu Ser Tyr Phe Pro Arg A rg Tyr Gly Ala His Ala
            340                 345                 350

Ser Leu Arg Tyr Asn Pro Arg Glu Arg Gln L eu Tyr Ala Trp Asp Asp
        355                 360                 365

Gly Tyr Gln Ile Val Tyr Lys Leu Glu Met L ys Lys Lys Glu Glu Glu
    370                 375                 380

Val
385
```

<210> SEQ ID NO 25
<211> LENGTH: 21
<212> TYPE: PRT
<213> ORGANISM: Mus musculus

<400> SEQUENCE: 25

```
Met Gly Pro Ser Ala Pro Leu Leu Leu Leu P he Phe Leu Ser Trp Thr
  1               5                  10                  15

Gly Pro Leu Gln Gly
            20
```

<210> SEQ ID NO 26
<211> LENGTH: 1869
<212> TYPE: DNA
<213> ORGANISM: Homo sapiens
<220> FEATURE:
<221> NAME/KEY: modified_base
<222> LOCATION: all "n" positions
<223> OTHER INFORMATION: n=a, c, g, or t

<400> SEQUENCE: 26

```
gtcgacccac gcgtncntcc agcgtncgga gccgccctgg gtgtcagcgg c tcggctccc     60

gcgcacgctc cggccgtcgc gcagcctcgg cacctgcagg tccgtgcgtc c cgcggctgg    120

cgcccctgac tccgtcccgg ccagggaggg ccatgatttc cctcccgggg c ccctggtga    180
```

-continued

```
ccaacttgnt gcggtttttg ttcctggggc tgagtgccct cgcgcccccc t cgcgggccc    240

agctgcaact gcacttgccc gccaaccggt tgcaggcggt ggaggagggg g aaagtggtg    300

cttcagcatg gtacaccttg cacagggagg tgtcttcatc ccagccatgg g aggtgccct    360

ttgtgatgtg gttcttcaaa cagaaagaaa aggaggatca ggtgttgtcc t acatcaatg    420

gggtcacaac aagcaaacct ggagtatcct tggtctactc catgccctcc c ggaacctgt    480

ccctgcgggt ggagggtctc caggagaaag actctggccc ctacagctgc t ccgtgaatg    540

tgcaagacaa acaaggcaaa tctaggggcc acagcatcaa aaccttagaa c tcaatgtac    600

tggttcctcc agctcctcca tcctgccgtc tccagggtgt gccccatgtg g gggcaaacg    660

tgaccctgag ctgccagtct ccaaggagta agcccgctgt ccaataccag t gggatcggc    720

agcttccatc cttccagact ttctttgcac cagcattaga tgtcatccgt g ggtctttaa    780

gcctcaccaa cctttcgtct tccatggctg gagtctatgt ctgcaaggcc c acaatgagg    840

tgggcactgc ccaatgtaat gtgacgctgg aagtgagcac agggcctgga g ctgcagtgg    900

ttgctgaagc tgttgtgggt accctggttg gactggggtt gctggctggg c tggtcctct    960

tgtaccaccg ccggggcaag gccctggagg agccagccaa tgatatcaag g aggatgcca   1020

ttgctccccg gaccctgccc tggcccaaga gctcagacac aatctccaag a atgggaccc   1080

tttcctctgt cacctccgca cgagccctcc ggccacccca tggccctccc a ggcctggtg   1140

cattgacccc cacgcccagt ctatccagcc aggccctgcc ctcaccaaga c atgcccacg   1200

acagatgggg cccacctcca accaatatcc cccatccctg gtggggtttt t tcctttggc   1260

tttgagccgc atgggtgctg ngcctgtgat ggngcctgcc cagagtcaag c tggctctct   1320

ggtatgatga ccccaccact cattggctaa aggatttggg gtctctcctt c ctataaggg   1380

tcacctctag cacagaggcc tgagtcatgg gaaagagtca cactcctgac c cttagtact   1440

ctgcccccac ctctctttac tgtgggaaaa ccatctcagt aagacctaag t gtccaggag   1500

acagaaggag aagaggaagt ggatctggaa ttgggaggag cctccaccca c ccctgactc   1560

ctccttatga agccagctgc tgaaattagc tactcaccaa gagtgagggg c agagacttc   1620

cagtcactga gtctcccagg ccccttgat ctgtacccca cccctatcta a caccaccct   1680

tggctcccac tccagctccc tgtattgata taacctgtca ggctggcttg g ttaggtttt   1740

actggggcag aggataggga atctcttatt aaaactaaca tgaaatatgt g ttgttttca   1800

tttgcaaatt taaataaaga tacataatgt ttgtatgaga taagaaaaaa a aaaaaaaag   1860

ggcggccgc                                                           1869
```

<210> SEQ ID NO 27
<211> LENGTH: 1110
<212> TYPE: DNA
<213> ORGANISM: Homo sapiens
<220> FEATURE:
<221> NAME/KEY: modified_base
<222> LOCATION: all “n” positions
<223> OTHER INFORMATION: n=a, c, g, or t

<400> SEQUENCE: 27

```
atgatttccc tcccggggcc cctggtgacc aacttgntgc ggtttttgtt c ctggggctg     60

agtgccctcg cgcccccctc gcgggcccag ctgcaactgc acttgcccgc c aaccggttg    120

caggcggtgg aggaggggga aagtggtgct tcagcatggt acaccttgca c agggaggtg    180

tcttcatccc agccatggga ggtgcccttt gtgatgtggt tcttcaaaca g aaagaaaag    240

gaggatcagg tgttgtccta catcaatggg gtcacaacaa gcaaacctgg a gtatccttg    300
```

-continued

```
gtctactcca tgccctcccg gaacctgtcc ctgcgggtgg agggtctcca g gagaaagac    360

tctggcccct acagctgctc cgtgaatgtg caagacaaac aaggcaaatc t aggggccac    420

agcatcaaaa ccttagaact caatgtactg gttcctccag ctcctccatc c tgccgtctc    480

cagggtgtgc cccatgtggg ggcaaacgtg accctgagct gccagtctcc a aggagtaag    540

cccgctgtcc aataccagtg ggatcggcag cttccatcct tccagacttt c tttgcacca    600

gcattagatg tcatccgtgg gtctttaagc ctcaccaacc tttcgtcttc c atggctgga    660

gtctatgtct gcaaggccca caatgaggtg ggcactgccc aatgtaatgt g acgctggaa    720

gtgagcacag ggcctggagc tgcagtggtt gctgaagctg ttgtgggtac c ctggttgga    780

ctggggttgc tggctgggct ggtcctcttg taccaccgcc ggggcaaggc c ctggaggag    840

ccagccaatg atatcaagga ggatgccatt gctccccgga ccctgccctg g cccaagagc    900

tcagacacaa tctccaagaa tgggaccctt tcctctgtca cctccgcacg a gccctccgg    960

ccaccccatg gccctcccag gcctggtgca ttgaccccca cgcccagtct a tccagccag   1020

gccctgccct caccaagaca tgcccacgac agatggggcc caccctcaac c aatatcccc   1080

catccctggt ggggtttttt cctttggctt                                   1110
```

<210> SEQ ID NO 28
<211> LENGTH: 370
<212> TYPE: PRT
<213> ORGANISM: Homo sapiens
<220> FEATURE:
<221> NAME/KEY: SITE
<222> LOCATION: (13)
<223> OTHER INFORMATION: Xaa=unknown amino acid

<400> SEQUENCE: 28

```
Met Ile Ser Leu Pro Gly Pro Leu Val Thr A sn Leu Xaa Arg Phe Leu
  1               5                  10                  15

Phe Leu Gly Leu Ser Ala Leu Ala Pro Pro S er Arg Ala Gln Leu Gln
             20                  25                  30

Leu His Leu Pro Ala Asn Arg Leu Gln Ala V al Glu Glu Gly Glu Ser
         35                  40                  45

Gly Ala Ser Ala Trp Tyr Thr Leu His Arg G lu Val Ser Ser Ser Gln
     50                  55                  60

Pro Trp Glu Val Pro Phe Val Met Trp Phe P he Lys Gln Lys Glu Lys
 65                  70                  75                  80

Glu Asp Gln Val Leu Ser Tyr Ile Asn Gly V al Thr Thr Ser Lys Pro
                 85                  90                  95

Gly Val Ser Leu Val Tyr Ser Met Pro Ser A rg Asn Leu Ser Leu Arg
            100                 105                 110

Val Glu Gly Leu Gln Glu Lys Asp Ser Gly P ro Tyr Ser Cys Ser Val
        115                 120                 125

Asn Val Gln Asp Lys Gln Gly Lys Ser Arg G ly His Ser Ile Lys Thr
    130                 135                 140

Leu Glu Leu Asn Val Leu Val Pro Pro Ala P ro Pro Ser Cys Arg Leu
145                 150                 155                 160

Gln Gly Val Pro His Val Gly Ala Asn Val T hr Leu Ser Cys Gln Ser
                165                 170                 175

Pro Arg Ser Lys Pro Ala Val Gln Tyr Gln T rp Asp Arg Gln Leu Pro
            180                 185                 190

Ser Phe Gln Thr Phe Phe Ala Pro Ala Leu A sp Val Ile Arg Gly Ser
        195                 200                 205
```

-continued

```
Leu Ser Leu Thr Asn Leu Ser Ser Ser Met A la Gly Val Tyr Val Cys
    210                 215                 220

Lys Ala His Asn Glu Val Gly Thr Ala Gln C ys Asn Val Thr Leu Glu
225                 230                 235                 240

Val Ser Thr Gly Pro Gly Ala Ala Val Val A la Glu Ala Val Val Gly
                245                 250                 255

Thr Leu Val Gly Leu Gly Leu Leu Ala Gly L eu Val Leu Leu Tyr His
            260                 265                 270

Arg Arg Gly Lys Ala Leu Glu Glu Pro Ala A sn Asp Ile Lys Glu Asp
        275                 280                 285

Ala Ile Ala Pro Arg Thr Leu Pro Trp Pro L ys Ser Ser Asp Thr Ile
    290                 295                 300

Ser Lys Asn Gly Thr Leu Ser Ser Val Thr S er Ala Arg Ala Leu Arg
305                 310                 315                 320

Pro Pro His Gly Pro Pro Arg Pro Gly Ala L eu Thr Pro Thr Pro Ser
                325                 330                 335

Leu Ser Ser Gln Ala Leu Pro Ser Pro Arg H is Ala His Asp Arg Trp
            340                 345                 350

Gly Pro Pro Ser Thr Asn Ile Pro His Pro T rp Trp Gly Phe Phe Leu
        355                 360                 365

Trp Leu
    370


<210> SEQ ID NO 29
<211> LENGTH: 341
<212> TYPE: PRT
<213> ORGANISM: Mus musculus

<400> SEQUENCE: 29

Gln Leu Gln Leu His Leu Pro Ala Asn Arg L eu Gln Ala Val Glu Glu
  1               5                  10                  15

Gly Glu Ser Gly Ala Ser Ala Trp Tyr Thr L eu His Arg Glu Val Ser
            20                  25                  30

Ser Ser Gln Pro Trp Glu Val Pro Phe Val M et Trp Phe Phe Lys Gln
        35                  40                  45

Lys Glu Lys Glu Asp Gln Val Leu Ser Tyr I le Asn Gly Val Thr Thr
     50                  55                  60

Ser Lys Pro Gly Val Ser Leu Val Tyr Ser M et Pro Ser Arg Asn Leu
 65                  70                  75                  80

Ser Leu Arg Val Glu Gly Leu Gln Glu Lys A sp Ser Gly Pro Tyr Ser
                 85                  90                  95

Cys Ser Val Asn Val Gln Asp Lys Gln Gly L ys Ser Arg Gly His Ser
            100                 105                 110

Ile Lys Thr Leu Glu Leu Asn Val Leu Val P ro Pro Ala Pro Pro Ser
        115                 120                 125

Cys Arg Leu Gln Gly Val Pro His Val Gly A la Asn Val Thr Leu Ser
    130                 135                 140

Cys Gln Ser Pro Arg Ser Lys Pro Ala Val G ln Tyr Gln Trp Asp Arg
145                 150                 155                 160

Gln Leu Pro Ser Phe Gln Thr Phe Phe Ala P ro Ala Leu Asp Val Ile
                165                 170                 175

Arg Gly Ser Leu Ser Leu Thr Asn Leu Ser S er Ser Met Ala Gly Val
            180                 185                 190

Tyr Val Cys Lys Ala His Asn Glu Val Gly T hr Ala Gln Cys Asn Val
```

-continued

```
        195                 200                 205

Thr Leu Glu Val Ser Thr Gly Pro Gly Ala A la Val Val Ala Glu Ala
    210                 215                 220

Val Val Gly Thr Leu Val Gly Leu Gly Leu L eu Ala Gly Leu Val Leu
225                 230                 235                 240

Leu Tyr His Arg Arg Gly Lys Ala Leu Glu G lu Pro Ala Asn Asp Ile
                245                 250                 255

Lys Glu Asp Ala Ile Ala Pro Arg Thr Leu P ro Trp Pro Lys Ser Ser
            260                 265                 270

Asp Thr Ile Ser Lys Asn Gly Thr Leu Ser S er Val Thr Ser Ala Arg
        275                 280                 285

Ala Leu Arg Pro Pro His Gly Pro Pro Arg P ro Gly Ala Leu Thr Pro
    290                 295                 300

Thr Pro Ser Leu Ser Ser Gln Ala Leu Pro S er Pro Arg His Ala His
305                 310                 315                 320

Asp Arg Trp Gly Pro Pro Ser Thr Asn Ile P ro His Pro Trp Trp Gly
                325                 330                 335

Phe Phe Leu Trp Leu
            340


<210> SEQ ID NO 30
<211> LENGTH: 29
<212> TYPE: PRT
<213> ORGANISM: Mus musculus
<220> FEATURE:
<221> NAME/KEY: SITE
<222> LOCATION: (13)
<223> OTHER INFORMATION: Xaa=unknown amino acid

<400> SEQUENCE: 30

Met Ile Ser Leu Pro Gly Pro Leu Val Thr A sn Leu Xaa Arg Phe Leu
  1               5                  10                  15

Phe Leu Gly Leu Ser Ala Leu Ala Pro Pro S er Arg Ala
             20                  25


<210> SEQ ID NO 31
<211> LENGTH: 246
<212> TYPE: PRT
<213> ORGANISM: Mus musculus
<220> FEATURE:
<221> NAME/KEY: SITE
<222> LOCATION: (13)
<223> OTHER INFORMATION: Xaa=unknown amino acid

<400> SEQUENCE: 31

Met Ile Ser Leu Pro Gly Pro Leu Val Thr A sn Leu Xaa Arg Phe Leu
  1               5                  10                  15

Phe Leu Gly Leu Ser Ala Leu Ala Pro Pro S er Arg Ala Gln Leu Gln
             20                  25                  30

Leu His Leu Pro Ala Asn Arg Leu Gln Ala V al Glu Glu Gly Glu Ser
         35                  40                  45

Gly Ala Ser Ala Trp Tyr Thr Leu His Arg G lu Val Ser Ser Ser Gln
     50                  55                  60

Pro Trp Glu Val Pro Phe Val Met Trp Phe P he Lys Gln Lys Glu Lys
 65                  70                  75                  80

Glu Asp Gln Val Leu Ser Tyr Ile Asn Gly V al Thr Thr Ser Lys Pro
                 85                  90                  95

Gly Val Ser Leu Val Tyr Ser Met Pro Ser A rg Asn Leu Ser Leu Arg
            100                 105                 110
```

-continued

```
Val Glu Gly Leu Gln Glu Lys Asp Ser Gly P ro Tyr Ser Cys Ser Val
        115                 120                 125

Asn Val Gln Asp Lys Gln Gly Lys Ser Arg G ly His Ser Ile Lys Thr
    130                 135                 140

Leu Glu Leu Asn Val Leu Val Pro Pro Ala P ro Pro Ser Cys Arg Leu
145                 150                 155                 160

Gln Gly Val Pro His Val Gly Ala Asn Val T hr Leu Ser Cys Gln Ser
                165                 170                 175

Pro Arg Ser Lys Pro Ala Val Gln Tyr Gln T rp Asp Arg Gln Leu Pro
            180                 185                 190

Ser Phe Gln Thr Phe Phe Ala Pro Ala Leu A sp Val Ile Arg Gly Ser
        195                 200                 205

Leu Ser Leu Thr Asn Leu Ser Ser Ser Met A la Gly Val Tyr Val Cys
    210                 215                 220

Lys Ala His Asn Glu Val Gly Thr Ala Gln C ys Asn Val Thr Leu Glu
225                 230                 235                 240

Val Ser Thr Gly Pro Gly
                245


<210> SEQ ID NO 32
<211> LENGTH: 653
<212> TYPE: DNA
<213> ORGANISM: Homo sapiens

<400> SEQUENCE: 32

tttttgcat gtaacttttt tattgaggca caacaaggca ttgtaacttg c ctggacttg     60

aggcagtcag tttagtaagc tgaacgttaa tacagttaag gattaagtgc a aacaatata    120

cattcacagc ttgactagcg aggctacatc acaatttata aagtgccaga t tagtgctaa    180

ttgtcattca gcttgatttt tcacctcagg aaggaaaaca aaaaagtaag g acctcctcc    240

ctctaggaac aaaaaacatt ttcctaaacc aatcagtcat gagggcaaag a ctacttttc    300

cttcaatccc actaattaga acaccatcct tttattgtca atactgtact g actttcaat    360

cttgataaag aagatagcct gaaaacgtag aatatttcca gctacttcca t aaattgctc    420

ccctgtgcag acgtaaccat atctggtctc cctggaagag ctgaagaatt g catgattgc    480

tagcagtttc atggtctgga gcaccatcat tggcataggc tgataccaag a cctcttcat    540

tcttcantga ggttgacata cagtggcaca ttcactgcca gcttttacat g tgaaaaatg    600

aaaaacgtag tgccattcac ttggcaatta aatctaccaa agctgagatc a aa           653


<210> SEQ ID NO 33
<211> LENGTH: 25
<212> TYPE: PRT
<213> ORGANISM: Mus musculus

<400> SEQUENCE: 33

Ala Ala Val Val Ala Glu Ala Val Val Gly T hr Leu Val Gly Leu Gly
  1               5                  10                  15

Leu Leu Ala Gly Leu Val Leu Leu Tyr
             20                  25


<210> SEQ ID NO 34
<211> LENGTH: 99
<212> TYPE: PRT
<213> ORGANISM: Mus musculus

<400> SEQUENCE: 34
```

-continued

```
His Arg Arg Gly Lys Ala Leu Glu Glu Pro A la Asn Asp Ile Lys Glu
  1               5                  10                  15

Asp Ala Ile Ala Pro Arg Thr Leu Pro Trp P ro Lys Ser Ser Asp Thr
             20                  25                  30

Ile Ser Lys Asn Gly Thr Leu Ser Ser Val T hr Ser Ala Arg Ala Leu
         35                  40                  45

Arg Pro Pro His Gly Pro Pro Arg Pro Gly A la Leu Thr Pro Thr Pro
     50                  55                  60

Ser Leu Ser Ser Gln Ala Leu Pro Ser Pro A rg His Ala His Asp Arg
 65                  70                  75                  80

Trp Gly Pro Pro Ser Thr Asn Ile Pro His P ro Trp Trp Gly Phe Phe
                 85                  90                  95

Leu Trp Leu
```

<210> SEQ ID NO 35
<211> LENGTH: 80
<212> TYPE: PRT
<213> ORGANISM: Mus musculus

<400> SEQUENCE: 35

```
Gly Ala Ser Ala Trp Tyr Thr Leu His Arg G lu Val Ser Ser Ser Gln
  1               5                  10                  15

Pro Trp Glu Val Pro Phe Val Met Trp Phe P he Lys Gln Lys Glu Lys
             20                  25                  30

Glu Asp Gln Val Leu Ser Tyr Ile Asn Gly V al Thr Thr Ser Lys Pro
         35                  40                  45

Gly Val Ser Leu Val Tyr Ser Met Pro Ser A rg Asn Leu Ser Leu Arg
     50                  55                  60

Val Glu Gly Leu Gln Glu Lys Asp Ser Gly P ro Tyr Ser Cys Ser Val
 65                  70                  75                  80
```

<210> SEQ ID NO 36
<211> LENGTH: 60
<212> TYPE: PRT
<213> ORGANISM: Mus musculus

<400> SEQUENCE: 36

```
Gly Ala Asn Val Thr Leu Ser Cys Gln Ser P ro Arg Ser Lys Pro Ala
  1               5                  10                  15

Val Gln Tyr Gln Trp Asp Arg Gln Leu Pro S er Phe Gln Thr Phe Phe
             20                  25                  30

Ala Pro Ala Leu Asp Val Ile Arg Gly Ser L eu Ser Leu Thr Asn Leu
         35                  40                  45

Ser Ser Ser Met Ala Gly Val Tyr Val Cys L ys Ala
     50                  55                  60
```

<210> SEQ ID NO 37
<211> LENGTH: 1846
<212> TYPE: DNA
<213> ORGANISM: Mus musculus

<400> SEQUENCE: 37

```
gtcgacccac gcgtccggtg cacattcggg ttgccgccgc tcacccacaa c acctgtaga     60

caccgtgtgt ccaactctcc ctgagtactc cgggccaagg agggccatga t tcttcaggc    120

tggaaccccc gagaccagct tgctgcgggt tttgttcctg ggactgagta c ccttgctgc    180

cttctcccga gctcagatgg agttgcacgt gcccccgggc ctcaacaaat t ggaagcggt    240
```

-continued

```
agagggagaa gaagtggtgc tccccgcctg gtacacgatg gcacgggagg a gtcgtggtc    300

ccacccccgg gaggtgccca tcctgatctg gttcttggaa caagaaggga a ggaaccaaa    360

ccaggtgttg tcttacatta atggagtcat gacaaataaa cctggaacag c cctggtcca    420

ctctatctct tcacggaatg tgtccctgcg cctgggggca ctccaggagg g agactctgg    480

gacttaccgc tgttctgtca atgtgcagaa tgatgaaggc aaaagtatag g ccacagcat    540

caaaagcata gagctcaaag tgctggttcc tccagctcct ccatcctgta g tttacaggg    600

tgtaccctat gtcgggacca atgtgaccct gaactgcaag tccccaagga g taaacctac    660

tgctcagtac cagtgggaga ggctggcccc atcctcccag gtcttctttg g accagcctt    720

agatgctgtt cgtggatctt taaagctcac taacctttcc attgccatgt c tggagtcta    780

tgtctgcaag gctcaaaaca gagtgggctt tgccaagtgc aacgtgacct t ggacgtgat    840

gacagggtcc aaggctgcag tggtcgctgg agcagttgtg ggcacttttg t tgggttggt    900

gctgatagct gggctggtcc tgttgtacca gcgccggagc aagaccttgg a agagctggc    960

caatgatatc aaggaagatg ccattgctcc ccggaccttg ccttggacca a aggctcaga   1020

cacaatctcc aagaatggga cactttcttc ggtcacctca gcacgagctc t gcggccacc   1080

caaggctgct cctccaagac ctggcacatt tactcccaca cccagtgtct c tagccaggc   1140

cctgtcctca ccaagactgc ccagggtaga tgaacccca cctcaggcag t gtccctgac    1200

cccaggtggg gtttcttctt ctgctctgag ccgcatgggt gctgtgcctg t gatggtgcc   1260

tgcacagagt caggctgggt ctcttgtgtg atagcccagg cactcattag c tacatctgg   1320

tatctgacct ttctgtaaag gtctccttgt ggcacagagg actcaatctt g ggaggatgc   1380

ccacattcta gacctccagt cctttgctcc tacctccttc tattgttgga a tactgggcc   1440

tcagtaagac taaaatctgg gtcaaaggac aaaaggagga aatggacctg a ggtaggggg   1500

ttgggagtga ggaggcttca cttcctccct gcttctccct gaagccagat g aatgctgcg   1560

gaagatcggc taccctccaa gggctctgga ggagactgcc agtcagtgat g cccctggct   1620

ctgtgatctg tacaacaccc ttatctaatg ctgtcctttg ccgttcgctc c atctccctg   1680

tattaatata acctgtcctg ctggcttggc tgggttttgt tgtagcaggg g gataggaaa   1740

gacattttaa aatctgactt gaaattgatg tttttgtttt tattttgcaa a tttcaataa   1800

agatacatcg catttgcatg gaaaaaaaaa aaaaaagggc ggccgc                  1846
```

<210> SEQ ID NO 38
<211> LENGTH: 1182
<212> TYPE: DNA
<213> ORGANISM: Mus musculus

<400> SEQUENCE: 38

```
atgattcttc aggctggaac ccccgagacc agcttgctgc gggttttgtt c ctgggactg     60

agtacccttg ctgccttctc ccgagctcag atggagttgc acgtgccccc g ggcctcaac    120

aaattggaag cggtagaggg agaagaagtg gtgctccccg cctggtacac g atggcacgg    180

gaggagtcgt ggtcccaccc ccgggaggtg cccatcctga tctggttctt g gaacaagaa    240

gggaaggaac caaaccaggt gttgtcttac attaatggag tcatgacaaa t aaacctgga    300

acagccctgg tccactctat ctcttcacgg aatgtgtccc tgcgcctggg g gcactccag    360

gagggagact ctgggactta ccgctgttct gtcaatgtgc agaatgatga a ggcaaaagt    420

ataggccaca gcatcaaaag catagagctc aaagtgctgg ttcctccagc t cctccatcc    480
```

-continued

```
tgtagtttac agggtgtacc ctatgtcggg accaatgtga ccctgaactg c aagtcccca    540

aggagtaaac ctactgctca gtaccagtgg gagaggctgg ccccatcctc c caggtcttc    600

tttggaccag ccttagatgc tgttcgtgga tctttaaagc tcactaacct t tccattgcc    660

atgtctggag tctatgtctg caaggctcaa aacagagtgg gctttgccaa g tgcaacgtg    720

accttggacg tgatgacagg gtccaaggct gcagtggtcg ctggagcagt t gtgggcact    780

tttgttgggt tggtgctgat agctgggctg gtcctgttgt accagcgccg g agcaagacc    840

ttggaagagc tggccaatga tatcaaggaa gatgccattg ctccccggac c ttgccttgg    900

accaaaggct cagacacaat ctccaagaat gggacacttt cttcggtcac c tcagcacga    960

gctctgcggc cacccaaggc tgctcctcca agacctggca catttactcc c acacccagt   1020

gtctctagcc aggccctgtc ctcaccaaga ctgcccaggg tagatgaacc c ccacctcag   1080

gcagtgtccc tgaccccagg tggggtttct tcttctgctc tgagccgcat g ggtgctgtg   1140

cctgtgatgg tgcctgcaca gagtcaggct gggtctcttg tg                      1182
```

<210> SEQ ID NO 39
<211> LENGTH: 394
<212> TYPE: PRT
<213> ORGANISM: Mus musculus

<400> SEQUENCE: 39

```
Met Ile Leu Gln Ala Gly Thr Pro Glu Thr S er Leu Leu Arg Val Leu
  1               5                  10                  15

Phe Leu Gly Leu Ser Thr Leu Ala Ala Phe S er Arg Ala Gln Met Glu
             20                  25                  30

Leu His Val Pro Pro Gly Leu Asn Lys Leu G lu Ala Val Glu Gly Glu
         35                  40                  45

Glu Val Val Leu Pro Ala Trp Tyr Thr Met A la Arg Glu Glu Ser Trp
     50                  55                  60

Ser His Pro Arg Glu Val Pro Ile Leu Ile T rp Phe Leu Glu Gln Glu
 65                  70                  75                  80

Gly Lys Glu Pro Asn Gln Val Leu Ser Tyr I le Asn Gly Val Met Thr
                 85                  90                  95

Asn Lys Pro Gly Thr Ala Leu Val His Ser I le Ser Ser Arg Asn Val
            100                 105                 110

Ser Leu Arg Leu Gly Ala Leu Gln Glu Gly A sp Ser Gly Thr Tyr Arg
        115                 120                 125

Cys Ser Val Asn Val Gln Asn Asp Glu Gly L ys Ser Ile Gly His Ser
    130                 135                 140

Ile Lys Ser Ile Glu Leu Lys Val Leu Val P ro Pro Ala Pro Pro Ser
145                 150                 155                 160

Cys Ser Leu Gln Gly Val Pro Tyr Val Gly T hr Asn Val Thr Leu Asn
                165                 170                 175

Cys Lys Ser Pro Arg Ser Lys Pro Thr Ala G ln Tyr Gln Trp Glu Arg
            180                 185                 190

Leu Ala Pro Ser Ser Gln Val Phe Phe Gly P ro Ala Leu Asp Ala Val
        195                 200                 205

Arg Gly Ser Leu Lys Leu Thr Asn Leu Ser I le Ala Met Ser Gly Val
    210                 215                 220

Tyr Val Cys Lys Ala Gln Asn Arg Val Gly P he Ala Lys Cys Asn Val
225                 230                 235                 240

Thr Leu Asp Val Met Thr Gly Ser Lys Ala A la Val Val Ala Gly Ala
                245                 250                 255
```

-continued

```
Val Val Gly Thr Phe Val Gly Leu Val Leu I le Ala Gly Leu Val Leu
            260                 265                 270

Leu Tyr Gln Arg Arg Ser Lys Thr Leu Glu G lu Leu Ala Asn Asp Ile
        275                 280                 285

Lys Glu Asp Ala Ile Ala Pro Arg Thr Leu P ro Trp Thr Lys Gly Ser
    290                 295                 300

Asp Thr Ile Ser Lys Asn Gly Thr Leu Ser S er Val Thr Ser Ala Arg
305                 310                 315                 320

Ala Leu Arg Pro Pro Lys Ala Ala Pro Pro A rg Pro Gly Thr Phe Thr
                325                 330                 335

Pro Thr Pro Ser Val Ser Ser Gln Ala Leu S er Ser Pro Arg Leu Pro
            340                 345                 350

Arg Val Asp Glu Pro Pro Pro Gln Ala Val S er Leu Thr Pro Gly Gly
        355                 360                 365

Val Ser Ser Ser Ala Leu Ser Arg Met Gly A la Val Pro Val Met Val
    370                 375                 380

Pro Ala Gln Ser Gln Ala Gly Ser Leu Val
385                 390


<210> SEQ ID NO 40
<211> LENGTH: 365
<212> TYPE: PRT
<213> ORGANISM: Mus musculus

<400> SEQUENCE: 40

Gln Met Glu Leu His Val Pro Pro Gly Leu A sn Lys Leu Glu Ala Val
  1               5                  10                  15

Glu Gly Glu Glu Val Val Leu Pro Ala Trp T yr Thr Met Ala Arg Glu
             20                  25                  30

Glu Ser Trp Ser His Pro Arg Glu Val Pro I le Leu Ile Trp Phe Leu
         35                  40                  45

Glu Gln Glu Gly Lys Glu Pro Asn Gln Val L eu Ser Tyr Ile Asn Gly
     50                  55                  60

Val Met Thr Asn Lys Pro Gly Thr Ala Leu V al His Ser Ile Ser Ser
 65                  70                  75                  80

Arg Asn Val Ser Leu Arg Leu Gly Ala Leu G ln Glu Gly Asp Ser Gly
                 85                  90                  95

Thr Tyr Arg Cys Ser Val Asn Val Gln Asn A sp Glu Gly Lys Ser Ile
            100                 105                 110

Gly His Ser Ile Lys Ser Ile Glu Leu Lys V al Leu Val Pro Pro Ala
        115                 120                 125

Pro Pro Ser Cys Ser Leu Gln Gly Val Pro T yr Val Gly Thr Asn Val
    130                 135                 140

Thr Leu Asn Cys Lys Ser Pro Arg Ser Lys P ro Thr Ala Gln Tyr Gln
145                 150                 155                 160

Trp Glu Arg Leu Ala Pro Ser Ser Gln Val P he Phe Gly Pro Ala Leu
                165                 170                 175

Asp Ala Val Arg Gly Ser Leu Lys Leu Thr A sn Leu Ser Ile Ala Met
            180                 185                 190

Ser Gly Val Tyr Val Cys Lys Ala Gln Asn A rg Val Gly Phe Ala Lys
        195                 200                 205

Cys Asn Val Thr Leu Asp Val Met Thr Gly S er Lys Ala Ala Val Val
    210                 215                 220

Ala Gly Ala Val Val Gly Thr Phe Val Gly L eu Val Leu Ile Ala Gly
```

-continued

```
225                 230                 235                 240

Leu Val Leu Leu Tyr Gln Arg Arg Ser Lys T hr Leu Glu Glu Leu Ala
                245                 250                 255

Asn Asp Ile Lys Glu Asp Ala Ile Ala Pro A rg Thr Leu Pro Trp Thr
            260                 265                 270

Lys Gly Ser Asp Thr Ile Ser Lys Asn Gly T hr Leu Ser Ser Val Thr
        275                 280                 285

Ser Ala Arg Ala Leu Arg Pro Pro Lys Ala A la Pro Pro Arg Pro Gly
    290                 295                 300

Thr Phe Thr Pro Thr Pro Ser Val Ser Ser G ln Ala Leu Ser Ser Pro
305                 310                 315                 320

Arg Leu Pro Arg Val Asp Glu Pro Pro Pro G ln Ala Val Ser Leu Thr
                325                 330                 335

Pro Gly Gly Val Ser Ser Ser Ala Leu Ser A rg Met Gly Ala Val Pro
            340                 345                 350

Val Met Val Pro Ala Gln Ser Gln Ala Gly S er Leu Val
        355                 360                 365
```

<210> SEQ ID NO 41
<211> LENGTH: 29
<212> TYPE: PRT
<213> ORGANISM: Mus musculus

<400> SEQUENCE: 41

```
Met Ile Leu Gln Ala Gly Thr Pro Glu Thr S er Leu Leu Arg Val Leu
  1               5                  10                  15

Phe Leu Gly Leu Ser Thr Leu Ala Ala Phe S er Arg Ala
             20                  25
```

<210> SEQ ID NO 42
<211> LENGTH: 249
<212> TYPE: PRT
<213> ORGANISM: Mus musculus

<400> SEQUENCE: 42

```
Met Ile Leu Gln Ala Gly Thr Pro Glu Thr S er Leu Leu Arg Val Leu
  1               5                  10                  15

Phe Leu Gly Leu Ser Thr Leu Ala Ala Phe S er Arg Ala Gln Met Glu
             20                  25                  30

Leu His Val Pro Pro Gly Leu Asn Lys Leu G lu Ala Val Glu Gly Glu
        35                  40                  45

Glu Val Val Leu Pro Ala Trp Tyr Thr Met A la Arg Glu Glu Ser Trp
     50                  55                  60

Ser His Pro Arg Glu Val Pro Ile Leu Ile T rp Phe Leu Glu Gln Glu
 65                  70                  75                  80

Gly Lys Glu Pro Asn Gln Val Leu Ser Tyr I le Asn Gly Val Met Thr
                 85                  90                  95

Asn Lys Pro Gly Thr Ala Leu Val His Ser I le Ser Ser Arg Asn Val
            100                 105                 110

Ser Leu Arg Leu Gly Ala Leu Gln Glu Gly A sp Ser Gly Thr Tyr Arg
        115                 120                 125

Cys Ser Val Asn Val Gln Asn Asp Glu Gly L ys Ser Ile Gly His Ser
    130                 135                 140

Ile Lys Ser Ile Glu Leu Lys Val Leu Val P ro Pro Ala Pro Pro Ser
145                 150                 155                 160

Cys Ser Leu Gln Gly Val Pro Tyr Val Gly T hr Asn Val Thr Leu Asn
```

-continued

```
                165                 170                 175

Cys Lys Ser Pro Arg Ser Lys Pro Thr Ala Gln Tyr Gln Trp Glu Arg
            180                 185                 190

Leu Ala Pro Ser Ser Gln Val Phe Phe Gly Pro Ala Leu Asp Ala Val
        195                 200                 205

Arg Gly Ser Leu Lys Leu Thr Asn Leu Ser Ile Ala Met Ser Gly Val
    210                 215                 220

Tyr Val Cys Lys Ala Gln Asn Arg Val Gly Phe Ala Lys Cys Asn Val
225                 230                 235                 240

Thr Leu Asp Val Met Thr Gly Ser Lys
                245


<210> SEQ ID NO 43
<211> LENGTH: 355
<212> TYPE: PRT
<213> ORGANISM: Mus musculus
<220> FEATURE:
<221> NAME/KEY: SITE
<222> LOCATION: (355)
<223> OTHER INFORMATION: Xaa=unknown amino acid

<400> SEQUENCE: 43

Met Gly Pro Ser Thr Pro Leu Leu Ile Leu Phe Leu Leu Ser Trp Ser
  1               5                  10                  15

Gly Pro Leu Gln Gly Gln Gln His His Leu Val Glu Tyr Met Glu Arg
             20                  25                  30

Arg Leu Ala Ala Leu Glu Glu Arg Leu Ala Gln Cys Gln Asp Gln Ser
         35                  40                  45

Ser Arg His Ala Ala Glu Leu Arg Asp Phe Lys Asn Lys Met Leu Pro
     50                  55                  60

Leu Leu Glu Val Ala Glu Lys Glu Arg Glu Ala Leu Arg Thr Glu Ala
 65                  70                  75                  80

Asp Thr Ile Ser Gly Arg Val Asp Arg Leu Glu Arg Glu Val Asp Tyr
                 85                  90                  95

Leu Glu Thr Gln Asn Pro Ala Leu Pro Cys Val Glu Phe Asp Glu Lys
            100                 105                 110

Val Thr Gly Gly Pro Gly Thr Lys Gly Lys Gly Arg Arg Asn Glu Lys
        115                 120                 125

Tyr Asp Met Val Thr Asp Cys Gly Tyr Thr Ile Ser Gln Val Arg Ser
    130                 135                 140

Met Lys Ile Leu Lys Arg Phe Gly Gly Pro Ala Gly Leu Trp Thr Lys
145                 150                 155                 160

Asp Pro Leu Gly Gln Thr Glu Lys Ile Tyr Val Leu Asp Gly Thr Gln
                165                 170                 175

Asn Asp Thr Ala Phe Val Phe Pro Arg Leu Arg Asp Phe Thr Leu Ala
            180                 185                 190

Met Ala Ala Arg Lys Ala Ser Arg Val Arg Val Pro Phe Pro Trp Val
        195                 200                 205

Gly Thr Gly Gln Leu Val Tyr Gly Gly Phe Leu Tyr Phe Ala Arg Arg
    210                 215                 220

Pro Pro Gly Arg Pro Gly Gly Gly Gly Glu Met Glu Asn Thr Leu Gln
225                 230                 235                 240

Leu Ile Lys Phe His Leu Ala Asn Arg Thr Val Val Asp Ser Ser Val
                245                 250                 255

Phe Pro Ala Glu Gly Leu Ile Pro Pro Tyr Gly Leu Thr Ala Asp Thr
            260                 265                 270
```

-continued

Tyr Ile Asp Leu Ala Ala Asp Glu Glu Gly L eu Trp Ala Val Tyr Ala
275 280 285

Thr Arg Glu Asp Asp Arg His Leu Cys Leu A la Lys Leu Asp Pro Gln
290 295 300

Thr Leu Asp Thr Glu Gln Gln Trp Asp Thr P ro Cys Pro Arg Glu Asn
305 310 315 320

Ala Glu Ala Ala Phe Val Ile Cys Gly Thr L eu Tyr Val Val Tyr Asn
325 330 335

Thr Arg Pro Ala Ser Arg Ala Arg Ile Gln C ys Ser Phe Asp Ala Ser
340 345 350

Gly Pro Xaa
355

<210> SEQ ID NO 44
<211> LENGTH: 25
<212> TYPE: PRT
<213> ORGANISM: Mus musculus

<400> SEQUENCE: 44

Ala Ala Val Val Ala Gly Ala Val Val Gly T hr Phe Val Gly Leu Val
1 5 10 15

Leu Ile Ala Gly Leu Val Leu Leu Tyr
20 25

<210> SEQ ID NO 45
<211> LENGTH: 120
<212> TYPE: PRT
<213> ORGANISM: Mus musculus

<400> SEQUENCE: 45

Gln Arg Arg Ser Lys Thr Leu Glu Glu Leu A la Asn Asp Ile Lys Glu
1 5 10 15

Asp Ala Ile Ala Pro Arg Thr Leu Pro Trp T hr Lys Gly Ser Asp Thr
20 25 30

Ile Ser Lys Asn Gly Thr Leu Ser Ser Val T hr Ser Ala Arg Ala Leu
35 40 45

Arg Pro Pro Lys Ala Ala Pro Pro Arg Pro G ly Thr Phe Thr Pro Thr
50 55 60

Pro Ser Val Ser Ser Gln Ala Leu Ser Ser P ro Arg Leu Pro Arg Val
65 70 75 80

Asp Glu Pro Pro Pro Gln Ala Val Ser Leu T hr Pro Gly Gly Val Ser
85 90 95

Ser Ser Ala Leu Ser Arg Met Gly Ala Val P ro Val Met Val Pro Ala
100 105 110

Gln Ser Gln Ala Gly Ser Leu Val
115 120

<210> SEQ ID NO 46
<211> LENGTH: 1801
<212> TYPE: DNA
<213> ORGANISM: Homo sapiens

<400> SEQUENCE: 46
gtcgacccac gcgtccggcg gaggttgtgg ctgcaccgtg gtcctgggct t ggtcctggg 60 cttgatgcgt ctgtttgtcc gtccgtccgt ccgtcccgcc atggctgcgc c ggcgccctc 120 tccgtggacc ctttcgctgc tgctgttgtt gctactgccg tctccgggtg c ccatggcga 180

-continued gctgtgcagg cccttcggtg aagacaattc gatcccagag tcctgtcctg a cttctgttg 240 tggctcctgt tccagccaat actgctgctc tgacgtgctg aagaaaatcc a gtggaatga 300 ggaaatgtgc cctgagccag agtccagcag attttccgcc cacccggaga c accagaaca 360 gctgggttca gcgctgaagt atcagtccag tcttgacagt gacaacatgc c agggttcgg 420 agcgaccgtg gccatcggcc tgaccgtctt cgtggtgttt atcgctacca t cattgtgtg 480 ctttacctgc tcctgctgct gtctatataa gatgtgctgc cgcccacgac c tgtcgtgtc 540 caacaccaca actactaccg tggttcacac cgcttaccct cagcctcaac c tgtggcccc 600 cagctatcct ggaccaacat accagggcta ccatcccatg cccccccagc c aggaatgcc 660 agcagcaccc tacccaacgc agtaccctcc accctacctg gcccagccca c agggccacc 720 agcctatcat gagacgttgg ctggagccag ccagcctcca tacaacccgg c ctacatgga 780 tcccccaaag gcagttccct gagcctgccc ccagcctctt tggctaacat t tgattatgt 840 catgtgtgtg tgagtgctat gcagagttct ttactgctgt ctgtggtgcg t gtgccttgt 900 ctagacatgt ggcttcctct gctgatgacc aggtaggcac aaatcttacc a gtgctggtt 960 gggaccaatc tgtttcttc ctcacttgaa attgtaattt ctgaaatttc a agtaaatta 1020 aaaacaatag ggtaggaggt atttcccgct tcaccccaag gtgaccagcc a tagcctgcc 1080 acacatagga gagcaagctt tttgtgggtc catgtcctgc tttggggagt a gccagctag 1140 ctgctgctat gggtttattc ccagggcttg gctgcattta gctggacaga g aacaagggg 1200 cctcagtggc agtgggtcag tgactgatgt cagagcacac taggcagaga g ccccgtccg 1260 tctccatcag ctgtctgtct ggacggtccc actgtctttc ctgggactat g tagagggcc 1320 acatgtattc actattcagg ctccagtggc ttccaggcca ggggcctctg t ctactacac 1380 actctggttt ctccctacag tgtcttttta cgattagcca aacatattgc c tgttttttg 1440 tatccagatg tgtgataatt ggtgaggttg aaatccttgg ttcctggaga a caggaaacc 1500 tgacctctga cagtccgttt cccttgacac cagcttcata gaatacctga c tcctgtact 1560 acagtccagt ttgttccagt agcagggaca ccagggccag gggttatctg g accaagggt 1620 gggggtggag agcctggatg gtagctctgg accagatgtg aatgcctcca t attccctgt 1680 tggttcctgt ttcactggct gttttagttt tgtgttaatt ggtgtttctg a gcattcaaa 1740 ctccgcaccc tcgtttataa taaatgaata tttggaaaaa aaaaaaaaaa a aaaaaaaaa 1800 a 1801

<210> SEQ ID NO 47
<211> LENGTH: 735
<212> TYPE: DNA
<213> ORGANISM: Homo sapiens

<400> SEQUENCE: 47
atgcgtctgt ttgtccgtcc gtccgtccgt cccgccatgg ctgcgccggc g ccctctccg 60 tggacccttt cgctgctgct gttgttgcta ctgccgtctc cgggtgccca t ggcgagctg 120 tgcaggccct tcggtgaaga caattcgatc ccagagtcct gtcctgactt c tgttgtggc 180 tcctgttcca gccaatactg ctgctctgac gtgctgaaga aaatccagtg g aatgaggaa 240 atgtgccctg agccagagtc cagcagattt tccgcccacc cggagacacc a gaacagctg 300 ggttcagcgc tgaagtatca gtccagtctt gacagtgaca acatgccagg g ttcggagcg 360 accgtggcca tcggcctgac cgtcttcgtg gtgtttatcg ctaccatcat t gtgtgcttt 420 acctgctcct gctgctgtct atataagatg tgctgccgcc cacgacctgt c gtgtccaac 480

-continued

```
accacaacta ctaccgtggt tcacaccgct taccctcagc ctcaacctgt g gcccccagc    540

tatcctggac caacatacca gggctaccat cccatgcccc cccagccagg a atgccagca    600

gcaccctacc caacgcagta ccctccaccc tacctggccc agcccacagg g ccaccagcc    660

tatcatgaga cgttggctgg agccagccag cctccataca acccggccta c atggatccc    720

ccaaaggcag ttccc                                                     735
```

```
<210> SEQ ID NO 48
<211> LENGTH: 245
<212> TYPE: PRT
<213> ORGANISM: Homo sapiens

<400> SEQUENCE: 48

Met Arg Leu Phe Val Arg Pro Ser Val Arg P ro Ala Met Ala Ala Pro
  1               5                  10                  15

Ala Pro Ser Pro Trp Thr Leu Ser Leu Leu L eu Leu Leu Leu Leu Pro
             20                  25                  30

Ser Pro Gly Ala His Gly Glu Leu Cys Arg P ro Phe Gly Glu Asp Asn
         35                  40                  45

Ser Ile Pro Glu Ser Cys Pro Asp Phe Cys C ys Gly Ser Cys Ser Ser
     50                  55                  60

Gln Tyr Cys Cys Ser Asp Val Leu Lys Lys I le Gln Trp Asn Glu Glu
 65                  70                  75                  80

Met Cys Pro Glu Pro Glu Ser Ser Arg Phe S er Ala His Pro Glu Thr
                 85                  90                  95

Pro Glu Gln Leu Gly Ser Ala Leu Lys Tyr G ln Ser Ser Leu Asp Ser
            100                 105                 110

Asp Asn Met Pro Gly Phe Gly Ala Thr Val A la Ile Gly Leu Thr Val
        115                 120                 125

Phe Val Val Phe Ile Ala Thr Ile Ile Val C ys Phe Thr Cys Ser Cys
    130                 135                 140

Cys Cys Leu Tyr Lys Met Cys Cys Arg Pro A rg Pro Val Val Ser Asn
145                 150                 155                 160

Thr Thr Thr Thr Thr Val Val His Thr Ala T yr Pro Gln Pro Gln Pro
                165                 170                 175

Val Ala Pro Ser Tyr Pro Gly Pro Thr Tyr G ln Gly Tyr His Pro Met
            180                 185                 190

Pro Pro Gln Pro Gly Met Pro Ala Ala Pro T yr Pro Thr Gln Tyr Pro
        195                 200                 205

Pro Pro Tyr Leu Ala Gln Pro Thr Gly Pro P ro Ala Tyr His Glu Thr
    210                 215                 220

Leu Ala Gly Ala Ser Gln Pro Pro Tyr Asn P ro Ala Tyr Met Asp Pro
225                 230                 235                 240

Pro Lys Ala Val Pro
                245
```

```
<210> SEQ ID NO 49
<211> LENGTH: 38
<212> TYPE: PRT
<213> ORGANISM: Homo sapiens

<400> SEQUENCE: 49

Met Arg Leu Phe Val Arg Pro Ser Val Arg P ro Ala Met Ala Ala Pro
  1               5                  10                  15

Ala Pro Ser Pro Trp Thr Leu Ser Leu Leu L eu Leu Leu Leu Leu Pro
```

-continued

```
            20                  25                  30

Ser Pro Gly Ala His Gly
        35


<210> SEQ ID NO 50
<211> LENGTH: 207
<212> TYPE: PRT
<213> ORGANISM: Homo sapiens

<400> SEQUENCE: 50

Glu Leu Cys Arg Pro Phe Gly Glu Asp Asn Ser Ile Pro Glu Ser Cys
  1               5                  10                  15

Pro Asp Phe Cys Cys Gly Ser Cys Ser Ser Gln Tyr Cys Cys Ser Asp
            20                  25                  30

Val Leu Lys Lys Ile Gln Trp Asn Glu Glu Met Cys Pro Glu Pro Glu
        35                  40                  45

Ser Ser Arg Phe Ser Ala His Pro Glu Thr Pro Glu Gln Leu Gly Ser
     50                  55                  60

Ala Leu Lys Tyr Gln Ser Ser Leu Asp Ser Asp Asn Met Pro Gly Phe
 65                  70                  75                  80

Gly Ala Thr Val Ala Ile Gly Leu Thr Val Phe Val Val Phe Ile Ala
                 85                  90                  95

Thr Ile Ile Val Cys Phe Thr Cys Ser Cys Cys Cys Leu Tyr Lys Met
            100                 105                 110

Cys Cys Arg Pro Arg Pro Val Val Ser Asn Thr Thr Thr Thr Thr Val
        115                 120                 125

Val His Thr Ala Tyr Pro Gln Pro Gln Pro Val Ala Pro Ser Tyr Pro
    130                 135                 140

Gly Pro Thr Tyr Gln Gly Tyr His Pro Met Pro Pro Gln Pro Gly Met
145                 150                 155                 160

Pro Ala Ala Pro Tyr Pro Thr Gln Tyr Pro Pro Pro Tyr Leu Ala Gln
                165                 170                 175

Pro Thr Gly Pro Pro Ala Tyr His Glu Thr Leu Ala Gly Ala Ser Gln
            180                 185                 190

Pro Pro Tyr Asn Pro Ala Tyr Met Asp Pro Pro Lys Ala Val Pro
        195                 200                 205


<210> SEQ ID NO 51
<211> LENGTH: 85
<212> TYPE: PRT
<213> ORGANISM: Homo sapiens

<400> SEQUENCE: 51

Glu Leu Cys Arg Pro Phe Gly Glu Asp Asn Ser Ile Pro Glu Ser Cys
  1               5                  10                  15

Pro Asp Phe Cys Cys Gly Ser Cys Ser Ser Gln Tyr Cys Cys Ser Asp
            20                  25                  30

Val Leu Lys Lys Ile Gln Trp Asn Glu Glu Met Cys Pro Glu Pro Glu
        35                  40                  45

Ser Ser Arg Phe Ser Ala His Pro Glu Thr Pro Glu Gln Leu Gly Ser
     50                  55                  60

Ala Leu Lys Tyr Gln Ser Ser Leu Asp Ser Asp Asn Met Pro Gly Phe
 65                  70                  75                  80

Gly Ala Thr Val Ala
                 85
```

-continued

<210> SEQ ID NO 52
<211> LENGTH: 25
<212> TYPE: PRT
<213> ORGANISM: Homo sapiens

<400> SEQUENCE: 52

```
Ile Gly Leu Thr Val Phe Val Val Phe Ile A la Thr Ile Ile Val Cys
  1               5                  10                  15

Phe Thr Cys Ser Cys Cys Cys Leu Tyr
             20                  25
```

<210> SEQ ID NO 53
<211> LENGTH: 97
<212> TYPE: PRT
<213> ORGANISM: Homo sapiens

<400> SEQUENCE: 53

```
Lys Met Cys Cys Arg Pro Arg Pro Val Val S er Asn Thr Thr Thr Thr
  1               5                  10                  15

Thr Val Val His Thr Ala Tyr Pro Gln Pro G ln Pro Val Ala Pro Ser
             20                  25                  30

Tyr Pro Gly Pro Thr Tyr Gln Gly Tyr His P ro Met Pro Pro Gln Pro
         35                  40                  45

Gly Met Pro Ala Ala Pro Tyr Pro Thr Gln T yr Pro Pro Pro Tyr Leu
     50                  55                  60

Ala Gln Pro Thr Gly Pro Pro Ala Tyr His G lu Thr Leu Ala Gly Ala
 65                  70                  75                  80

Ser Gln Pro Pro Tyr Asn Pro Ala Tyr Met A sp Pro Pro Lys Ala Val
                 85                  90                  95

Pro
```

<210> SEQ ID NO 54
<211> LENGTH: 50
<212> TYPE: PRT
<213> ORGANISM: Homo sapiens

<400> SEQUENCE: 54

```
Cys Arg Pro Phe Gly Glu Asp Asn Ser Ile P ro Glu Ser Cys Pro Asp
  1               5                  10                  15

Phe Cys Cys Gly Ser Cys Ser Ser Gln Tyr C ys Cys Ser Asp Val Leu
             20                  25                  30

Lys Lys Ile Gln Trp Asn Glu Glu Met Cys P ro Glu Pro Glu Ser Ser
         35                  40                  45

Arg Phe
     50
```

<210> SEQ ID NO 55
<211> LENGTH: 56
<212> TYPE: PRT
<213> ORGANISM: Homo sapiens

<400> SEQUENCE: 55

```
Thr Val Phe Val Val Phe Ile Ala Thr Ile I le Val Cys Phe Thr Cys
  1               5                  10                  15

Ser Cys Cys Cys Leu Tyr Lys Met Cys Cys A rg Pro Arg Pro Val Val
             20                  25                  30

Ser Asn Thr Thr Thr Thr Thr Val Val His T hr Ala Tyr Pro Gln Pro
         35                  40                  45

Gln Pro Val Ala Pro Ser Tyr Pro
```

-continued 50 55

<210> SEQ ID NO 56
<211> LENGTH: 1858
<212> TYPE: DNA
<213> ORGANISM: Mus musculus

<400> SEQUENCE: 56

```
gtcgacccac gcgtccgcgc ggaggttgcg gcggcaccgt ggtcttgggc t tggtccgtc     60
tgttcgtccg tccgttggtc tgtcccgcca tggctgcgcc ggcgccctct c tgtggaccc    120
tattgctgct gctgttgctg ctgccgccgc ctccgggtgc ccatggtgag c tgtgcaggc    180
cctttggtga agacaattcg atcccagtgt tctgtcctga tttctgttgt g gttcctgtt    240
ccaaccaata ctgctgctcg gacgtgctga ggaaaatcca gtggaatgag g aaatgtgtc    300
ctgagccaga gtccagcaga ttttccaccc ccgcggagga gacacccgaa c atctgggtt    360
cagcgctgaa atttcgatcc agttttgaca gtgaccctat gtcagggttc g gagcgaccg    420
tcgccattgg cgtgaccatc tttgtggtgt ttattgccac tatcatcatc t gcttcacct    480
gctcctgctg ctgtctgtat aagatgtgct gcccccaacg ccctgtcgtg a ccaacacca    540
caactactac cgtggttcat gcccccttacc ctcagcctca acctcaacct g tggccccca    600
gctatcctgg accaacatac cagggctacc atcccatgcc ccccccagcc a ggaatgcca    660
gcagcaccct acccaacgca gtacccacca ccctacctgg cccagcccac a gggccgcca    720
ccctaccatg agtccttggc tggagccagc cagcctccat acaacccgac c tacatggat    780
tccctaaaga caattccctg aacctgcccc cagcctcttt ggctgccatt t atgtcgtgt    840
gtgagtgagt gatacgcaga gttctttact gctgtctgtg gtgtgtgtgc c ttgtctaga    900
catgtggctt cctctgctgt tgaccaggta ggcgcaagtc ttaccagtgt g ggtcgggac    960
caacctgttt tcttcctcac ttgaaattgt actttctgaa atttcaagca a attaaaaac   1020
aataaggtag gaggtatttc ccacgtcacc ccaaggtgac cagccatggc c tgtcatact   1080
taggagagca agctttttgc gggtacagag caggctttgg ggggtaacca g ctagctgct   1140
gctaggcctt tattcccagg gtttggctgc attggcagtg aggcaggtgg c tgggggtga   1200
caccaggtga caaggggact cagtggcagg gggtcacacc aggcagaaca c catacactc   1260
tccatcagct gtctgtctgg atgtcactgt ccttcccggg gctgtataga g ggccacatg   1320
tgttcactat tcaggctcca ctgggggaat tttcctacct ttgctggctt g gctcctgct   1380
cccaggccag ggacctcggt ctgtctacta cacactctgg tttctccctg c actgtcttt   1440
ttactgttag ccaaacattt tgcctgtttt ctgtctccag atgtgtgata a ttggtgtga   1500
ggttgaaatc cctggttcct ggaggacaga caacctgacc tccgactgtc a gtttccctt   1560
gacaccatct tcatagaaat acctgactcc tgtaccacag tccagtttgt c ccagtagca   1620
gggacaccaa ggccaatggg ttatctggac caaaggtggg gtggagggcc t agatggtat   1680
ctccggccca gatgtgaata cctccatatt ccctgttggt tcctgtttca c tggctgttt   1740
tagctttgtg ttgattggtg tttctgagca ttcagactcc gcaccctcat t tctaataaa   1800
tgcaacattg gaaaaaaaaa aaaaaaaaaa aaaaaaaaaa aaaaaaaagg g cggccgc     1858
```

<210> SEQ ID NO 57
<211> LENGTH: 639
<212> TYPE: DNA
<213> ORGANISM: Mus musculus

<400> SEQUENCE: 57

-continued

```
atggctgcgc cggcgccctc tctgtggacc ctattgctgc tgctgttgct g ctgccgccg     60

cctccgggtg cccatggtga gctgtgcagg ccctttggtg aagacaattc g atcccagtg    120

ttctgtcctg atttctgttg tggttcctgt tccaaccaat actgctgctc g gacgtgctg    180

aggaaaatcc agtggaatga ggaaatgtgt cctgagccag agtccagcag a ttttccacc    240

cccgcggagg agacacccga acatctgggt tcagcgctga aatttcgatc c agttttgac    300

agtgacccta tgtcagggtt cggagcgacc gtcgccattg gcgtgaccat c tttgtggtg    360

tttattgcca ctatcatcat ctgcttcacc tgctcctgct gctgtctgta t aagatgtgc    420

tgcccccaac gccctgtcgt gaccaacacc acaactacta ccgtggttca t gccccttac    480

cctcagcctc aacctcaacc tgtggccccc agctatcctg gaccaacata c cagggctac    540

catcccatgc cccccccagc caggaatgcc agcagcaccc tacccaacgc a gtacccacc    600

accctacctg gcccagccca cagggccgcc accctacca                          639
```

<210> SEQ ID NO 58
<211> LENGTH: 213
<212> TYPE: PRT
<213> ORGANISM: Mus musculus

<400> SEQUENCE: 58

```
Met Ala Ala Pro Ala Pro Ser Leu Trp Thr L eu Leu Leu Leu Leu Leu
  1               5                  10                  15

Leu Leu Pro Pro Pro Pro Gly Ala His Gly G lu Leu Cys Arg Pro Phe
             20                  25                  30

Gly Glu Asp Asn Ser Ile Pro Val Phe Cys P ro Asp Phe Cys Cys Gly
         35                  40                  45

Ser Cys Ser Asn Gln Tyr Cys Cys Ser Asp V al Leu Arg Lys Ile Gln
     50                  55                  60

Trp Asn Glu Glu Met Cys Pro Glu Pro Glu S er Ser Arg Phe Ser Thr
 65                  70                  75                  80

Pro Ala Glu Glu Thr Pro Glu His Leu Gly S er Ala Leu Lys Phe Arg
                 85                  90                  95

Ser Ser Phe Asp Ser Asp Pro Met Ser Gly P he Gly Ala Thr Val Ala
            100                 105                 110

Ile Gly Val Thr Ile Phe Val Val Phe Ile A la Thr Ile Ile Ile Cys
        115                 120                 125

Phe Thr Cys Ser Cys Cys Cys Leu Tyr Lys M et Cys Cys Pro Gln Arg
    130                 135                 140

Pro Val Val Thr Asn Thr Thr Thr Thr Thr V al Val His Ala Pro Tyr
145                 150                 155                 160

Pro Gln Pro Gln Pro Gln Pro Val Ala Pro S er Tyr Pro Gly Pro Thr
                165                 170                 175

Tyr Gln Gly Tyr His Pro Met Pro Pro Pro A la Arg Asn Ala Ser Ser
            180                 185                 190

Thr Leu Pro Asn Ala Val Pro Thr Thr Leu P ro Gly Pro Ala His Arg
        195                 200                 205

Ala Ala Thr Leu Pro
    210
```

<210> SEQ ID NO 59
<211> LENGTH: 26
<212> TYPE: PRT
<213> ORGANISM: Mus musculus -continued

<400> SEQUENCE: 59

Met Ala Ala Pro Ala Pro Ser Leu Trp Thr L eu Leu Leu Leu Leu Leu
1 5 10 15

Leu Leu Pro Pro Pro Pro Gly Ala His Gly
20 25

<210> SEQ ID NO 60
<211> LENGTH: 187
<212> TYPE: PRT
<213> ORGANISM: Mus musculus

<400> SEQUENCE: 60

Glu Leu Cys Arg Pro Phe Gly Glu Asp Asn S er Ile Pro Val Phe Cys
1 5 10 15

Pro Asp Phe Cys Cys Gly Ser Cys Ser Asn G ln Tyr Cys Cys Ser Asp
20 25 30

Val Leu Arg Lys Ile Gln Trp Asn Glu Glu M et Cys Pro Glu Pro Glu
35 40 45

Ser Ser Arg Phe Ser Thr Pro Ala Glu Glu T hr Pro Glu His Leu Gly
50 55 60

Ser Ala Leu Lys Phe Arg Ser Ser Phe Asp S er Asp Pro Met Ser Gly
65 70 75 80

Phe Gly Ala Thr Val Ala Ile Gly Val Thr I le Phe Val Val Phe Ile
85 90 95

Ala Thr Ile Ile Ile Cys Phe Thr Cys Ser C ys Cys Cys Leu Tyr Lys
100 105 110

Met Cys Cys Pro Gln Arg Pro Val Val Thr A sn Thr Thr Thr Thr Thr
115 120 125

Val Val His Ala Pro Tyr Pro Gln Pro Gln P ro Gln Pro Val Ala Pro
130 135 140

Ser Tyr Pro Gly Pro Thr Tyr Gln Gly Tyr H is Pro Met Pro Pro Pro
145 150 155 160

Ala Arg Asn Ala Ser Ser Thr Leu Pro Asn A la Val Pro Thr Thr Leu
165 170 175

Pro Gly Pro Ala His Arg Ala Ala Thr Leu P ro
180 185

<210> SEQ ID NO 61
<211> LENGTH: 86
<212> TYPE: PRT
<213> ORGANISM: Mus musculus

<400> SEQUENCE: 61

Glu Leu Cys Arg Pro Phe Gly Glu Asp Asn S er Ile Pro Val Phe Cys
1 5 10 15

Pro Asp Phe Cys Cys Gly Ser Cys Ser Asn G ln Tyr Cys Cys Ser Asp
20 25 30

Val Leu Arg Lys Ile Gln Trp Asn Glu Glu M et Cys Pro Glu Pro Glu
35 40 45

Ser Ser Arg Phe Ser Thr Pro Ala Glu Glu T hr Pro Glu His Leu Gly
50 55 60

Ser Ala Leu Lys Phe Arg Ser Ser Phe Asp S er Asp Pro Met Ser Gly
65 70 75 80

Phe Gly Ala Thr Val Ala
85

-continued

<210> SEQ ID NO 62
<211> LENGTH: 25
<212> TYPE: PRT
<213> ORGANISM: Mus musculus

<400> SEQUENCE: 62

Ile Gly Val Thr Ile Phe Val Val Phe Ile A la Thr Ile Ile Ile Cys
1 5 10 15

Phe Thr Cys Ser Cys Cys Cys Leu Tyr
20 25

<210> SEQ ID NO 63
<211> LENGTH: 76
<212> TYPE: PRT
<213> ORGANISM: Mus musculus

<400> SEQUENCE: 63

Lys Met Cys Cys Pro Gln Arg Pro Val Val T hr Asn Thr Thr Thr Thr
1 5 10 15

Thr Val Val His Ala Pro Tyr Pro Gln Pro G ln Pro Gln Pro Val Ala
20 25 30

Pro Ser Tyr Pro Gly Pro Thr Tyr Gln Gly T yr His Pro Met Pro Pro
35 40 45

Pro Ala Arg Asn Ala Ser Ser Thr Leu Pro A sn Ala Val Pro Thr Thr
50 55 60

Leu Pro Gly Pro Ala His Arg Ala Ala Thr L eu Pro
65 70 75

<210> SEQ ID NO 64
<211> LENGTH: 50
<212> TYPE: PRT
<213> ORGANISM: Mus musculus

<400> SEQUENCE: 64

Cys Pro Asp Phe Cys Cys Gly Ser Cys Ser A sn Gln Tyr Cys Cys Ser
1 5 10 15

Asp Val Leu Arg Lys Ile Gln Trp Asn Glu G lu Met Cys Pro Glu Pro
20 25 30

Glu Ser Ser Arg Phe Ser Thr Pro Ala Glu G lu Thr Pro Glu His Leu
35 40 45

Gly Ser
50

<210> SEQ ID NO 65
<211> LENGTH: 56
<212> TYPE: PRT
<213> ORGANISM: Mus musculus

<400> SEQUENCE: 65

Cys Phe Thr Cys Ser Cys Cys Cys Leu Tyr L ys Met Cys Cys Pro Gln
1 5 10 15

Arg Pro Val Val Thr Asn Thr Thr Thr Thr T hr Val Val His Ala Pro
20 25 30

Tyr Pro Gln Pro Gln Pro Gln Pro Val Ala P ro Ser Tyr Pro Gly Pro
35 40 45

Thr Tyr Gln Gly Tyr His Pro Met
50 55

<210> SEQ ID NO 66
<211> LENGTH: 1927

-continued

<212> TYPE: DNA
<213> ORGANISM: Homo sapiens
<220> FEATURE:
<221> NAME/KEY: modified_base
<222> LOCATION: all "n" positions
<223> OTHER INFORMATION: n=a, c, g, or t

<400> SEQUENCE: 66

```
ccccgcctcc aaagctaacc ctcgggcttg aggggaagan gctgactgta c gttccttct     60

actctggcac cactctccag gctgccatgg ggcccagcac ccctctcctc a tcttgttcc    120

ttttgtcatg gtcgggaccc ctccaaggac agcagcacca ccttgtggag t acatggaac    180

gccgactagc tgctttagag gaacggctgg cccagtgcca ggaccagagt a gtcggcatg    240

ctgctgagct gcgggacttc aagaacaaga tgctngccac tgctggaggt g gcagagaag    300

gagcgggagg cactcagaac tgaggccgac accatctccg ggagagtgga t cgtctggag    360

cgggaggtag actatctgga gacccagaac ccagctctgc cctgtgtaga g tttgatgag    420

aaggttgact ggaggccctg ggaccaaagg caagggaaga aggaatgaga a gtacgatat    480

ggtgacagac tgtggctaca caatctctca agtgagatca atgaagattc t gaagcgatt    540

tggtggccca gctggtctat ggaccaagga tccactgggg caaacagaga a gatctacgt    600

gttagatggg acacagaatg acacagcctt tgtcttccca aggctgcgtg a cttcaccct    660

tgccatggct gcccggaaag cttcccgagt ccgggtgccc ttcccctggg t aggcacagg    720

gcagctggta tatggtggct ttctttattt tgctcggagg cctcctggaa g acctggtgg    780

aggtggtgag atggagaaca ctttgcagct aatcaaattc cacctggcaa a ccgaacagt    840

ggtggacagc tcagtattcc cagcagaggg gctgatcccc ccctacggct t gacagcaga    900

cacctacatc gacctggcag ctgatgagga aggtctttgg gctgtctatg c cacccggga    960

ggatgacagg cacttgtgtc tggccaagtt agatccacag acactggaca c agagcagca   1020

gtgggacaca ccatgtccca gagagaatgc tgaggctgcc tttntcatct g tgggaccct   1080

ctatgtcgtc tataacaccc gtcctgccag tcgggcccgc atccagtgct c ctttgatgc   1140

cagcggaccc tgacccctga acgggcagca ctcccttatt ttccccgcag a tatggtgcc   1200

catgccagcc tccgctataa cccccgagaa cgccagctct atgcctggga t gatcgctac   1260

cagattgtct ataagctgga gatgaggaag aaagaggagg aggtttgagg a gctagcctt   1320

gttttttgca tctttctcac tcccatacat ttatattata tccccactaa a tttcttgtt   1380

cctcattctt caaatgtggg ccagttgtgg ctcaaatcct ctatattttt a gccaatggc   1440

aatcaaattc tttcagctcc tttgtttcat acggaactcc agatcctgag t aatcctttt   1500

agagcccgaa gagtcaaaac cctcaatgtt ccctcctgct ctcctgcccc a tgtcaacaa   1560

atttcaggct aaggatgccc cagacccagg gctctaacct tgtatgcggg c aggcccagg   1620

gagcaggcag cagtgttctt cccctcagag tgacttgggg agggagaaat a ggaggagac   1680

gtccagctct gtcctctctt cctcactcct ccccttcagtg tcctcaggaa c aggactttc   1740

tccacattgt tttgtattgc aacattttgc attaaaaagg aaaatccana a aaaaaaaaa   1800

aaaaaaaaaa aaaaaaaaaa aaaaaaaaaa aaaaaaaaaa aaaaaaaaaa a aaaaaaaaa   1860

aaactgcggc cgctgtccct tctgtcgtct tctcgcagcc gtacccttct g tcgtcttct   1920

cgcagcc                                                             1927
```

<210> SEQ ID NO 67
<211> LENGTH: 319
<212> TYPE: PRT

-continued

<213> ORGANISM: Homo sapiens

<400> SEQUENCE: 67

Met Val Gly Lys Met Trp Pro Val Leu Trp T hr Leu Cys Ala Val Arg
1 5 10 15

Val Thr Val Asp Ala Ile Ser Val Glu Thr P ro Gln Asp Val Leu Arg
20 25 30

Ala Ser Gln Gly Lys Ser Val Thr Leu Pro C ys Thr Tyr His Thr Ser
35 40 45

Thr Ser Ser Arg Glu Gly Leu Ile Gln Trp A sp Lys Leu Leu Leu Thr
50 55 60

His Thr Glu Arg Val Val Ile Trp Pro Phe S er Asn Lys Asn Tyr Ile
65 70 75 80

His Gly Glu Leu Tyr Lys Asn Arg Val Ser I le Ser Asn Asn Ala Glu
85 90 95

Gln Ser Asp Ala Ser Ile Thr Ile Asp Gln L eu Thr Met Ala Asp Asn
100 105 110

Gly Thr Tyr Glu Cys Ser Val Ser Leu Met S er Asp Leu Glu Gly Asn
115 120 125

Thr Lys Ser Arg Val Arg Leu Leu Val Leu V al Pro Pro Ser Lys Pro
130 135 140

Glu Cys Gly Ile Glu Gly Glu Thr Ile Ile G ly Asn Asn Ile Gln Leu
145 150 155 160

Thr Cys Gln Ser Lys Glu Gly Ser Pro Thr P ro Gln Tyr Ser Trp Lys
165 170 175

Arg Tyr Asn Ile Leu Asn Gln Glu Gln Pro L eu Ala Gln Pro Ala Ser
180 185 190

Gly Gln Pro Val Ser Leu Lys Asn Ile Ser T hr Asp Thr Ser Gly Tyr
195 200 205

Tyr Ile Cys Thr Ser Ser Asn Glu Glu Gly T hr Gln Phe Cys Asn Ile
210 215 220

Thr Val Ala Val Arg Ser Pro Ser Met Asn V al Ala Leu Tyr Val Gly
225 230 235 240

Ile Ala Val Gly Val Val Ala Ala Leu Ile I le Ile Gly Ile Ile Ile
245 250 255

Tyr Cys Cys Cys Cys Arg Gly Lys Asp Asp A sn Thr Glu Asp Lys Glu
260 265 270

Asp Ala Arg Pro Asn Arg Glu Ala Tyr Glu G lu Pro Pro Glu Gln Leu
275 280 285

Arg Glu Leu Ser Arg Glu Arg Glu Glu Glu A sp Asp Tyr Arg Gln Glu
290 295 300

Glu Gln Arg Ser Thr Gly Arg Glu Ser Pro A sp His Leu Asp Gln
305 310 315

<210> SEQ ID NO 68
<211> LENGTH: 2793
<212> TYPE: DNA
<213> ORGANISM: Homo sapiens

<400> SEQUENCE: 68 ctacccottt gtgagcagtc taggactttg tacacctgtt aagtagggag a aggcagggg 60 aggtggctgg tttaagggga acttgaggga agtagggaag actcctcttg g gacctttgg 120 agtaggtgac acatgagccc agccccagct cacctgccaa tccagctgag g agctcacct 180 gccaatccag ctgaggctgg gcagaggtgg gtgagaagag ggaaaattgc a gggacctcc 240

-continued

```
agttgggcca ggccagaagc tgctgtagct ttaaccagac agctcagacc t gtctggagg    300
ctgccagtga caggttaggt ttagggcaga gaagaagcaa gaccatggtg g ggaagatgt    360
ggcctgtgtt gtggacactc tgtgcagtca gggtgaccgt cgatgccatc t ctgtggaaa    420
ctccgcagga cgttcttcgg gcttcgcagg gaaagagtgt caccctgccc t gcacctacc    480
acacttccac ctccagtcga gagggactta ttcaatggga taagctcctc c tcactcata    540
cggaaagggt ggtcatctgg ccgttttcaa acaaaaacta catccatggt g agctttata    600
agaatcgcgt cagcatatcc aacaatgctg agcagtccga tgcctccatc a ccattgatc    660
agctgaccat ggctgacaac ggcacctacg agtgttctgt ctcgctgatg t cagacctgg    720
agggcaacac caagtcacgt gtccgcctgt tggtcctcgt gccaccctcc a aaccagaat    780
gcggcatcga gggagagacc ataattggga acaacatcca gctgacctgc c aatcaaagg    840
agggctcacc aacccctcag tacagctgga agaggtacaa catcctgaat c aggagcagc    900
ccctggccca gccagcctca ggtcagcctg tctccctgaa gaatatctcc a cagacacat    960
cgggttacta catctgtacc tccagcaatg aggaggggac gcagttctgc a acatcacgg   1020
tggccgtcag atctccctcc atgaacgtgg ccctgtatgt gggcatcgcg g tgggcgtgg   1080
ttgcagccct cattatcatt ggcatcatca tctactgctg ctgctgccga g ggaaggacg   1140
acaacactga agacaaggag gatgcaaggc cgaaccggga agcctatgag g agccaccag   1200
agcagctaag agaactttcc agagagaggg aggaggagga tgactacagg c aagaagagc   1260
agaggagcac tgggcgtgaa tccccggacc acctcgacca gtgacaggcc a gcagcagag   1320
ggcggcggag gaagggttag ggttcattc tcccgcttcc tggcctccct t ctcctttct   1380
aagccctgtt ctcctgtccc tccatcccag acattgatgg ggacatttct t ccccagtgt   1440
cagctgtggg gaacatggct ggcctggtaa gggggtccct gtgctgatcc t gctgacctc   1500
actgtcctgt gaagtaaccc ctcctggctg tgacacctgg tgcgggcctg g ccctcactc   1560
aagaccaggc tgcagcctcc acttccctcg tagttggcag gagctcctgg a agcacagcg   1620
ctgagcatgg ggcgctccca ctcagaactc tccagggagg cgatgccagc c ttgggggt   1680
gggggctgtc ctgctcacct gtgtgcccag cacctggagg ggcaccaggt g gagggtttg   1740
cactccacac atctttcttg aatgaatgaa agaataagtg agtatgcttg g gccctgcat   1800
tggcctggcc tccagctccc actccctttc caacctcact tcccgtagct g ccagtatgt   1860
tccaaaccct cctgggaagg ccacctccca ctcctgctgc acaggccctg g ggagctttt   1920
gcccacacac tttccatctc tgcctgtcaa tatcgtacct gtccctccag g cccatctca   1980
aatcacaagg atttctctaa ccctatccta attgtccaca tacgtggaaa c aatcctgtt   2040
actctgtccc acgtccaatc atgggccaca aggcacagtc ttctgagcga g tgctctcac   2100
tgtattagag cgccagctcc ttggggcagg gcctgggcct catggctttt g ctttccctg   2160
aagccctagt agctggcgcc catcctagtg ggcacttaag cttaattggg g aaactgctt   2220
tgattggttg tgccttccct tctctggtct ccttgagatg atcgtagaca c agggatgat   2280
tcccacccaa acccacgtat tcattcagtg agttaaacac gaattgattt a aagtgaaca   2340
cacacaaggg agcttgcttg cagatggtct gagttcttgt gtcctggtaa t tcctctcca   2400
ggccagaata attggcatgt ctcctcaacc cacatggggt tcctggttgt t cctgcatcc   2460
cgatacctca gccctggccc tgcccagccc atttgggctc tggttttctg g tggggctgt   2520
cctgctgccc tcccacagcc tccttctgtt tgtcgagcat ttcttctact c ttgagagct   2580
```

-continued

```
caggcagcgt tagggctgct taggtctcat ggaccagtgg ctggtctcac c caactgcag   2640

tttactattg ctatcttttc tggatgatca gaaaaataat tccataaatc t attgtctac   2700

ttgcgatttt ttaaaaaatg tatattttta tatatattgt taaatccttt g cttcattcc   2760

aaatgctttc agtaataata aaattgtggg tgg                                2793
```

<210> SEQ ID NO 69
<211> LENGTH: 52
<212> TYPE: PRT
<213> ORGANISM: Homo sapiens

<400> SEQUENCE: 69

```
Lys Thr Ala Leu Gly Glu Leu Leu Lys Pro L eu Asn Ser Glu Tyr Gly
  1               5                  10                  15

Lys Val Ala Pro Gly Trp Gly Thr Thr Pro L eu Met Gly Val Phe Met
             20                  25                  30

Ala Leu Phe Ala Val Phe Leu Leu Ile Ile L eu Glu Ile Tyr Asn Ser
         35                  40                  45

Ser Val Leu Leu
     50
```

<210> SEQ ID NO 70
<211> LENGTH: 1832
<212> TYPE: DNA
<213> ORGANISM: Homo sapiens
<220> FEATURE:
<221> NAME/KEY: modified_base
<222> LOCATION: all "n" positions
<223> OTHER INFORMATION: n=a, c, g, or t

<400> SEQUENCE: 70

```
tgtggctgac gtcatctgga ggagatttgc tttctttttc tccaaaaggg g aggaaattg     60

aaactgcagt ggcccacgat gggaagaggg gaaagcccag gggtacagga g gcctctggg    120

tgaaggcaga ggctaacatg gggttcggag cgaccttggc cgttggctga c catctttgt    180

gctgtctgtc gtcactatca tcatctgctt cacctgctcc tgctgctgcc t ttacaagac    240

gtgccgccga ccacgtccgg ttgtcaccac caccacatcc accactgtgg t gcatgcccc    300

ttatcctcag cctccaagtg tgccgcccag ctaccctgga ccaagctacc a gggctacca    360

caccatgccg cctcagccag ggatgccagc agcaccctac ccaatgcagt a cccaccacc    420

ttacccagcc cagcccatgg gcccaccggc ctaccacgag accctggctg g aggagcagc    480

cgcgccctam cccgscagcc agcctcctta caacccggcc tacatggatg c ccgaagcgg    540

ccctctgagc attccctggc ctctytggct gccacttggt tatgttgtgt g tgtgcgtra    600

gtggtgtgca ggcgcggttc cttacgcccc atgtgtgctg tgtgtgtcca g gcacggttc    660

cttacgcccc atgtgtgctg tgtgtgtcct gcctgtatat gtggcttcct c tgatgctga    720

caagtgggga acaatccttg ccagagtggg ctgggaccag actttgttct c ttcctcacc    780

tgaaattatg cttcctaaaa tctcaagcca aactcaaaga atggggtggt g gggggcacc    840

ctgtgaggtg gcccctgaga ggtgggggcc tctccagggc acatctggag t tcttctcca    900

gcttacccta gggtgaccaa gtagggcctg tcacaccagg gtggcgcast t tctgtgtga    960

tgcagatgtg tcctggtttc ggcagcgtag ccagctgctg cttgaggcca t ggctcgtcc   1020

ccggagttgg gggtacccgt tgcagagcca gggacatgat gcaggcgaag y ttgggatct   1080

ggccaagttg gactttgatc ctttgggcag atgtcccatt gctccctgga g cctgtcatg   1140

cctgttgggg atcaggcagc ctcctgatgc cagaacacct caggcagagc c ctactcagc   1200
```

-continued

```
tgtacctgtc tgcctggact gtcccctgtc cccgcatctc ccctgggacc a gctggaggg   1260

ccacatgcac acacagccta gctgccccca gggagctctg ctgcccttgc t ggccctgcc   1320

cttcccacag gtgagcaggg ctcctgtcca ccagcacact cagttctctt c cctgcagtg   1380

ttttcatttt attttagcca aacattttgc ctgttttctg tttcaaacat g atagttgat   1440

atgagactga aacccctggg ttgtggaggg aaattggctc agagatggac a acctggcaa   1500

ctgtgagtcc ctgcttcccg acaccagcct catggaatat gcaacaactc c tgtacccca   1560

gtccacggtg ttctggcagc agggacacct gggccaatgg gccatctgga c caaaggtgg   1620

ggtgtggggc cctggatggc agctctggcc cagacatgaa tacctcgtgt t cctcctccc   1680

tctattactg tttcaccaga gctgtcttag ctcaaatctg ttgtgtttct g agtctaggg   1740

tctgtacact tgtttataat aaatgcaatc gtttnggaaa aaaaananaa a aaaaaaagg   1800

ggsggcgctc taaaaggatn ccccnaaggg gg                              1832


<210> SEQ ID NO 71
<211> LENGTH: 51
<212> TYPE: PRT
<213> ORGANISM: Mus musculus

<400> SEQUENCE: 71

Ser Pro Arg Ser Lys Pro Thr Ala Gln Tyr G ln Trp Glu Arg Leu Ala
  1               5                  10                  15

Pro Ser Ser Gln Val Phe Phe Gly Pro Ala L eu Asp Ala Val Arg Gly
             20                  25                  30

Ser Leu Lys Leu Thr Asn Leu Ser Ile Ala M et Ser Gly Val Tyr Val
         35                  40                  45

Cys Lys Ala
     50


<210> SEQ ID NO 72
<211> LENGTH: 2557
<212> TYPE: DNA
<213> ORGANISM: Homo sapiens

<400> SEQUENCE: 72

gaattccggg agaagtgacc agagcaattt ctgcttttca cagggcgggt t tctcaacgg     60

tgacttgtgg gcagtgcctt ctgctgagcg agtcatggcc cgaaggcaga a ctaactgtg    120

cctgcagtct tcactctcag gatgcagccg aggtgggccc aaggggccac g atgtggctt    180

ggagtcctgc tgacccttct gctctgttca agccttgagg gtcaagaaaa c tctttcaca    240

atcaacagtg ttgacatgaa gagcctgccg gactggacgg tgcaaaatgg g aagaacctg    300

accctgcagt gcttcgcgga tgtcagcacc acctctcacg tcaagcctca g caccagatg    360

ctgttctata aggatgacgt gctgttttac aacatctcct ccatgaagag c acagagagt    420

tattttattc ctgaagtccg gatctatgac tcagggacat ataaatgtac t gtgattgtg    480

aacaacaaag agaaaaccac tgcagagtac cagctgttgg tggaaggagt g cccagtccc    540

agggtgacac tggacaagaa agaggccatc caaggtggga tcgtgagggt c aactgttct    600

gtcccagagg aaaaggcccc aatacacttc acaattgaaa aacttgaact a aatgaaaaa    660

atggtcaagc tgaaaagaga gaagaattct cgagaccaga attttgtgat a ctggaattc    720

cccgttgagg aacaggaccg cgttttatcc ttccgatgtc aagctaggat c atttctggg    780

atccatatgc agacctcaga atctaccaag agtgaactgg tcaccgtgac g gaatccttc    840
```

-continued

```
tctacaccca agttccacat cagccccacc ggaatgatca tggaaggagc t cagctccac    900

attaagtgca ccattcaagt gactcacctg gcccaggagt ttccagaaat c ataattcag    960

aaggacaagg cgattgtggc ccacaacaga catggcaaca aggctgtgta c tcagtcatg   1020

gccatggtgg agcacagtgg caactacacg tgcaaagtgg agtccagccg c atatccaag   1080

gtcagcagca tcgtggtcaa cataacagaa ctattttcca agcccgaact g gaatcttcc   1140

ttcacacatc tggaccaagg tgaaagactg aacctgtcct gctccatccc a ggagcacct   1200

ccagccaact tcaccatcca gaaggaagat acgattgtgt cacagactca a gatttcacc   1260

aagatagcct caaagtcgga cagtgggacg tatatctgca ctgcaggtat t gacaaagtg   1320

gtcaagaaaa gcaacacagt ccagatagtc gtatgtgaaa tgctctccca g cccaggatt   1380

tcttatgatg cccagtttga ggtcataaaa ggacagacca tcgaagtccg t tgcgaatcg   1440

atcagtggaa ctttgcctat ttcttaccaa cttttaaaaa caagtaaagt t ttggagaat   1500

agtaccaaga actcaaatga tcctgcggta ttcaaagaca accccactga a gacgtcgaa   1560

taccagtgtg ttgcagataa ttgccattcc catgccaaaa tgttaagtga g gttctgagg   1620

gtgaaggtga tagccccggt ggatgaggtc cagatttcta tcctgtcaag t aaggtggtg   1680

gagtctggag aggacattgt gctgcaatgt gctgtgaatg aaggatctgg t cccatcacc   1740

tataagtttt acagagaaaa agagggcaaa cccttctatc aaatgacctc a aatgccacc   1800

caggcatttt ggaccaagca gaaggctagc aaggaacagg agggagagta t tactgcaca   1860

gccttcaaca gagccaacca cgcctccagt gtccccagaa gcaaaatact g acagtcaga   1920

gtcattcttg ccccatggaa gaaaggactt attgcagtgg ttatcatcgg a gtgatcatt   1980

gctctcttga tcattgcggc caaatgttat tttctgagga aagccaaggc c aagcagatg   2040

ccagtggaaa tgtccaggcc agcagtacca cttctgaact ccaacaacga g aaaatgtca   2100

gatcccaata tggaagctaa cagtcattac ggtcacaatg acgatgtcag a aaccatgca   2160

atgaaaccaa taaatgataa taaagagcct ctgaactcag acgtgcagta c acggaagtt   2220

caagtgtcct cagctgagtc tcacaaagat ctaggaaaga aggacacaga g acagtgtac   2280

agtgaagtcc ggaaagctgt ccctgatgcc gtggaaagca gatactctag a acggaaggc   2340

tcccttgatg gaacttagac agcaaggcca gatgcacatc cctggaagga c atccatgtt   2400

ccgagaagaa cagataatcc ctgtatttca agacctctgt gcacttattt a tgaacctgc   2460

cctgctccca cagaacacag caattcctca ggctaagctg ccggttctta a atccatcct   2520

gctaagttaa tgttgggtag aaagagatac agagggg                           2557


<210> SEQ ID NO 73
<211> LENGTH: 738
<212> TYPE: PRT
<213> ORGANISM: Homo sapiens

<400> SEQUENCE: 73

Met Gln Pro Arg Trp Ala Gln Gly Ala Thr M et Trp Leu Gly Val Leu
  1               5                  10                  15

Leu Thr Leu Leu Leu Cys Ser Ser Leu Glu G ly Gln Glu Asn Ser Phe
             20                  25                  30

Thr Ile Asn Ser Val Asp Met Lys Ser Leu P ro Asp Trp Thr Val Gln
         35                  40                  45

Asn Gly Lys Asn Leu Thr Leu Gln Cys Phe A la Asp Val Ser Thr Thr
     50                  55                  60

Ser His Val Lys Pro Gln His Gln Met Leu P he Tyr Lys Asp Asp Val
```

-continued 65 70 75 80

Leu Phe Tyr Asn Ile Ser Ser Met Lys Ser T hr Glu Ser Tyr Phe Ile
85 90 95

Pro Glu Val Arg Ile Tyr Asp Ser Gly Thr T yr Lys Cys Thr Val Ile
100 105 110

Val Asn Asn Lys Glu Lys Thr Thr Ala Glu T yr Gln Leu Leu Val Glu
115 120 125

Gly Val Pro Ser Pro Arg Val Thr Leu Asp L ys Lys Glu Ala Ile Gln
130 135 140

Gly Gly Ile Val Arg Val Asn Cys Ser Val P ro Glu Glu Lys Ala Pro
145 150 155 160

Ile His Phe Thr Ile Glu Lys Leu Glu Leu A sn Glu Lys Met Val Lys
165 170 175

Leu Lys Arg Glu Lys Asn Ser Arg Asp Gln A sn Phe Val Ile Leu Glu
180 185 190

Phe Pro Val Glu Glu Gln Asp Arg Val Leu S er Phe Arg Cys Gln Ala
195 200 205

Arg Ile Ile Ser Gly Ile His Met Gln Thr S er Glu Ser Thr Lys Ser
210 215 220

Glu Leu Val Thr Val Thr Glu Ser Phe Ser T hr Pro Lys Phe His Ile
225 230 235 240

Ser Pro Thr Gly Met Ile Met Glu Gly Ala G ln Leu His Ile Lys Cys
245 250 255

Thr Ile Gln Val Thr His Leu Ala Gln Glu P he Pro Glu Ile Ile Ile
260 265 270

Gln Lys Asp Lys Ala Ile Val Ala His Asn A rg His Gly Asn Lys Ala
275 280 285

Val Tyr Ser Val Met Ala Met Val Glu His S er Gly Asn Tyr Thr Cys
290 295 300

Lys Val Glu Ser Ser Arg Ile Ser Lys Val S er Ser Ile Val Val Asn
305 310 315 320

Ile Thr Glu Leu Phe Ser Lys Pro Glu Leu G lu Ser Ser Phe Thr His
325 330 335

Leu Asp Gln Gly Glu Arg Leu Asn Leu Ser C ys Ser Ile Pro Gly Ala
340 345 350

Pro Pro Ala Asn Phe Thr Ile Gln Lys Glu A sp Thr Ile Val Ser Gln
355 360 365

Thr Gln Asp Phe Thr Lys Ile Ala Ser Lys S er Asp Ser Gly Thr Tyr
370 375 380

Ile Cys Thr Ala Gly Ile Asp Lys Val Val L ys Lys Ser Asn Thr Val
385 390 395 400

Gln Ile Val Val Cys Glu Met Leu Ser Gln P ro Arg Ile Ser Tyr Asp
405 410 415

Ala Gln Phe Glu Val Ile Lys Gly Gln Thr I le Glu Val Arg Cys Glu
420 425 430

Ser Ile Ser Gly Thr Leu Pro Ile Ser Tyr G ln Leu Leu Lys Thr Ser
435 440 445

Lys Val Leu Glu Asn Ser Thr Lys Asn Ser A sn Asp Pro Ala Val Phe
450 455 460

Lys Asp Asn Pro Thr Glu Asp Val Glu Tyr G ln Cys Val Ala Asp Asn
465 470 475 480

Cys His Ser His Ala Lys Met Leu Ser Glu V al Leu Arg Val Lys Val
485 490 495

-continued

```
Ile Ala Pro Val Asp Glu Val Gln Ile Ser I le Leu Ser Ser Lys Val
            500                 505                 510

Val Glu Ser Gly Glu Asp Ile Val Leu Gln C ys Ala Val Asn Glu Gly
        515                 520                 525

Ser Gly Pro Ile Thr Tyr Lys Phe Tyr Arg G lu Lys Glu Gly Lys Pro
    530                 535                 540

Phe Tyr Gln Met Thr Ser Asn Ala Thr Gln A la Phe Trp Thr Lys Gln
545                 550                 555                 560

Lys Ala Ser Lys Glu Gln Glu Gly Glu Tyr T yr Cys Thr Ala Phe Asn
                565                 570                 575

Arg Ala Asn His Ala Ser Ser Val Pro Arg S er Lys Ile Leu Thr Val
            580                 585                 590

Arg Val Ile Leu Ala Pro Trp Lys Lys Gly L eu Ile Ala Val Val Ile
        595                 600                 605

Ile Gly Val Ile Ile Ala Leu Leu Ile Ile A la Ala Lys Cys Tyr Phe
    610                 615                 620

Leu Arg Lys Ala Lys Ala Lys Gln Met Pro V al Glu Met Ser Arg Pro
625                 630                 635                 640

Ala Val Pro Leu Leu Asn Ser Asn Asn Glu L ys Met Ser Asp Pro Asn
                645                 650                 655

Met Glu Ala Asn Ser His Tyr Gly His Asn A sp Asp Val Arg Asn His
            660                 665                 670

Ala Met Lys Pro Ile Asn Asp Asn Lys Glu P ro Leu Asn Ser Asp Val
        675                 680                 685

Gln Tyr Thr Glu Val Gln Val Ser Ser Ala G lu Ser His Lys Asp Leu
    690                 695                 700

Gly Lys Lys Asp Thr Glu Thr Val Tyr Ser G lu Val Arg Lys Ala Val
705                 710                 715                 720

Pro Asp Ala Val Glu Ser Arg Tyr Ser Arg T hr Glu Gly Ser Leu Asp
                725                 730                 735

Gly Thr
```

<210> SEQ ID NO 74
<211> LENGTH: 601
<212> TYPE: DNA
<213> ORGANISM: Rattus norvegicus
<220> FEATURE:
<221> NAME/KEY: modified_base
<222> LOCATION: all “n” positions
<223> OTHER INFORMATION: n=a, c, g, or t

<400> SEQUENCE: 74

```
gnnnnnnagg tntanagncn cctttacncc gccgcggacg cgtgggcgga c gcgtggggt     60

gctgtggagc aagaagcaac ccgaagctag gagtctgtca gcgagggcag g ggctgcctg    120

gttggggtag gagtgggagc agggccagca ggagggtctg aggaagccat t caaagcgag    180

cagctgggag agctggggag ccgggaaggg cctacagact acaagagagg a tcctggcgt    240

ctgggcctcc tgggtcatca ccatgaggcc acttcttgcc ctgctgcttc t gggtctggc    300

atcaggctct cctcctctgg acgacaacaa gatccccagc ctgtgtcccg g gcagcccgg    360

cctcccaggc acaccaggcc accacggcag ccaaggcctg cctggccgtg a cggccgtga    420

tggccgcgac ggtgcacccg gagctccggg agagaaaggc gagggcggga g accgggact    480

acctgggcca cgtngggagc ccgggccgcg tggagaggca ggacctgtgg g ggctatcgg    540

gcctggnggg gaatgctcgg tgccccacga tcagcttcag tgccaagcga t cagaaagcc    600
```

```
c                                                                  601

<210> SEQ ID NO 75
<211> LENGTH: 732
<212> TYPE: DNA
<213> ORGANISM: Rattus norvegicus
<220> FEATURE:
<221> NAME/KEY: modified_base
<222> LOCATION: all "n" positions
<223> OTHER INFORMATION: n=a, c, g, or t

<400> SEQUENCE: 75

gngngttnnn ttccncctcc gacttaaggc tgccatgggg cccagtgctc c tctgctcct      60

cttcttcctt ttgtcatggc cgggacccct tcagggacag cagcaccacc t tgtggagta     120

catggaacgc cgactagctg ccttagagga gcggctggca cagtgccagg a tcagagcag    180

tcggcatgct gctgagcttc gggacttcaa aaacaagatg ctgcctctac t ggaggtggc    240

agagaaggag cgggaaacac tcagaaccga ggcagacagc atttcaggaa g agtggaccg    300

tcttgaacgg gaagtagact acctggagac acagaaccca gctttgccct g tgtagaact    360

ggatgagaag gtgactggag gccctggaac caaaggcaag ggccggagaa a tgagaaata   420

cgatatggtg acagactgta gctacacaat ctctcaggtg aggtcaatga a gatcctgaa    480

gcggtttggt ggctcagctg gcctatggac caaggatcca ctggggccag c anagaagat   540

ctacgtgtta gacggnacgc agaacgacac ggccttcgtt ttccganggt g cgtgactta    600

ccctcaccat ggctgccgca aagttccgaa tcgggtgccc ttncctgggt a gnacaagaa    660

aactggtgtn tgtggcttcc tttttatctc aangcntctg gaggaacttg n anggggggn   720

nggtggnaaa at                                                          732
```